(12) United States Patent
Casarez et al.

(10) Patent No.: US 8,476,225 B2
(45) Date of Patent: Jul. 2, 2013

(54) ANTIVIRAL COMPOUNDS

(75) Inventors: Anthony Casarez, Princeton, NJ (US); Mingzhe Ji, Union City, CA (US); Choung U. Kim, San Carlos, CA (US); Xiaoning C. Sheng, Foster City, CA (US); Qiaoyin Wu, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 211 days.

(21) Appl. No.: 12/958,086

(22) Filed: Dec. 1, 2010

(65) Prior Publication Data
US 2011/0135604 A1 Jun. 9, 2011

Related U.S. Application Data

(60) Provisional application No. 61/266,890, filed on Dec. 4, 2009.

(51) Int. Cl.
*A61K 38/00* (2006.01)
(52) U.S. Cl.
USPC .......................................... 514/3.7
(58) Field of Classification Search
None
See application file for complete search history.

(56) References Cited

U.S. PATENT DOCUMENTS
8,163,693 B2    4/2012   Chen et al.

FOREIGN PATENT DOCUMENTS
| | | |
|---|---|---|
| EP | 2272858 A2 | 1/2011 |
| WO | WO-2006020276 A2 | 2/2006 |
| WO | WO-2007009109 A2 | 1/2007 |
| WO | WO-2008005565 A2 | 1/2008 |
| WO | WO-2009005676 A2 | 1/2009 |
| WO | WO-2009005677 A2 | 1/2009 |

OTHER PUBLICATIONS

Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*

* cited by examiner

*Primary Examiner* — Thomas Heard

(57) ABSTRACT

The invention is related to anti-viral compounds, compositions containing such compounds, and therapeutic methods that include the administration of such compounds, as well as to processes and intermediates useful for preparing such compounds.

45 Claims, No Drawings

ANTIVIRAL COMPOUNDS

This application is filed under 35 U.S.C. 111 (a) claiming the benefit under 35 U.S.C. 119(e) of U.S. provisional application 61/266,890 filed Dec. 4, 2009 which is herein incorporated by reference in its entirety for all purposes.

FIELD OF THE INVENTION

The invention relates generally to compounds with HCV inhibitory activity.

BACKGROUND OF THE INVENTION

Hepatitis C is recognized as a chronic viral disease of the liver which is characterized by liver disease. Although drugs targeting the liver are in wide use and have shown effectiveness, toxicity and other side effects have limited their usefulness. Inhibitors of HCV are useful to limit the establishment and progression of infection by HCV as well as in diagnostic assays for HCV.

There is a need for new HCV therapeutic agents.

SUMMARY OF THE INVENTION

In one embodiment the invention provides a compound of formula 1

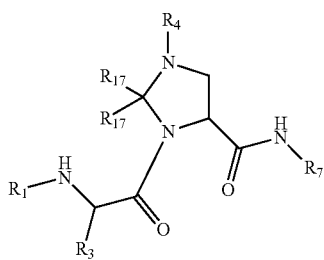

1 or a racemate, enantiomer, solvate, polymorph or salt thereof; wherein;

$R_1$ is $R_2$—, $R_2$—C(O)—, $R_2$—O—C(O)— or $R_2$—N(H)—C(O)—

$R_2$ is optionally substituted $C_1$-$C_8$ alkyl, optionally substituted $C_3$-$C_{10}$ cycloalkyl, optionally substituted $C_7$-$C_{14}$ cycloalkyl alkyl, optionally substituted aryl, optionally substituted arylalkyl, optionally substituted heterocycle or optionally substituted heterocyclylalkyl;

$R_3$ is optionally substituted $C_1$-$C_8$ alkyl, optionally substituted $C_3$-$C_{10}$ cycloalkyl, optionally substituted $C_7$-$C_{14}$ cycloalkylalkyl, optionally substituted heterocyclylalkyl, or optionally substituted heterocycle, or $R_3$ and $R_8$, along with the atoms that connect them, form a 12 to 18 membered saturated, partially unsaturated or unsaturated heterocycle wherein the 12 to 18 membered saturated, partially unsaturated or unsaturated heterocycle may be optionally substituted with $C_1$-$C_6$ alkyl, $C_1$-$C_6$-haloalkyl, halo, oxo and cyano and wherein 0, 1, 2, or 3 carbon atoms of $R_3$ can be replaced by O, N, or S;

$R_4$ is $R_6$—, $R_6$—$R_5$—, $R_6$—W—, $R_6$—W—C(O)—, $R_6$—C(O)—, $R_6$—C(O)—W—, $R_6$—W—O—C(O)—, $R_6$—S(O)$_m$—, $R_6$—W—S(O)$_m$—, $R_6$—N(H)—C(O)—, $R_6$—N(H)—S(O)$_m$—, $R_6$—$R_5$—S(O)$_m$— or $R_6$—N(H)—$R_5$—;

$R_5$ is optionally substituted arylene or optionally substituted heteroarylene;

$R_6$ is optionally substituted $C_3$-$C_{10}$ cycloalkyl, optionally substituted aryl or optionally substituted heterocycle;

m is 0, 1 or 2

W is $C_1$-$C_4$ alkylene, $C_2$-$C_4$ alkenylene, or $C_1$-$C_4$alkynylene wherein the $C_1$-$C_4$ alkylene, $C_2$-$C_4$ alkenylene, or $C_1$-$C_4$alkynylene may be optionally substituted with $C_1$-$C_3$-alkyl, $C_1$-$C_3$-haloalkyl, cyano or halo;

$R_7$ is:

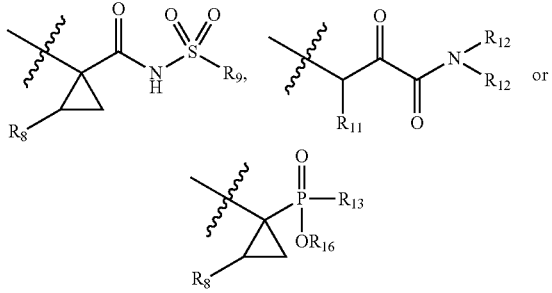

$R_8$ is $C_1$-$C_4$ alkyl, $C_2$-$C_4$ alkenyl or $C_2$-$C_4$ alkynyl wherein the $C_1$-$C_4$ alkyl, $C_2$-$C_4$ alkenyl or $C_2$-$C_4$ alkynyl may be optionally substituted with halo or cyano;

$R_9$ is $R_{10}$, $R_{10}$—NH— or $R_{10}$—O—

$R_{10}$ is $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl may be optionally substituted with $C_1$-$C_2$-alkyl, $C_1$-$C_2$-haloalkyl, cyano or halo;

$R_{11}$ is $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl may be optionally substituted with $C_1$-$C_2$-alkyl, $C_1$-$C_4$-alkylthio, cyano or halo;

each $R_{12}$ is independently H, $C_1$-$C_6$ alkyl, $C_3$-$C_7$ cycloalkyl or $C_4$-$C_9$ cycloalkylalkyl wherein the $C_1$-$C_6$ alkyl, $C_3$-$C_7$ cycloalkyl or $C_4$-$C_9$ cycloalkylalkyl may be optionally substituted with $C_1$-$C_2$-alkyl, $C_1$-$C_2$ haloalkyl cyano or halo;

$R_{13}$ is H, OH, OR$_{14}$, $C_1$-$C_4$ alkyl, $C_3$-$C_7$ cycloalkyl, $C_4$-$C_{12}$ cycloalkylalkyl, aryl, arylalkyl, heterocycle or heterocyclylalkyl wherein the $C_1$-$C_4$ alkyl, $C_3$-$C_7$ cycloalkyl, $C_4$-$C_{12}$ cycloalkylalkyl, aryl, arylalkyl, heterocycle or heterocyclylalkyl may be optionally substituted with $C_1$-$C_2$-alkyl, $C_1$-$C_2$-haloalkyl cyano or halo;

$R_{14}$ is $R_{15}$—, $R_{15}$—C(O)—, $R_{15}$—O—C(O)—, $R_{15}$—O—C(O)—X—

$R_{15}$ is $C_1$-$C_6$ alkyl, $C_3$-$C_7$ cycloalkyl, $C_7$-$C_{12}$ cycloalkylalkyl, aryl, arylalkyl, heterocycle, heterocyclylalkyl wherein the $C_1$-$C_6$ alkyl, $C_3$-$C_7$ cycloalkyl, $C_7$-$C_{12}$ cycloalkylalkyl may be optionally substituted with $C_1$-$C_2$-alkyl, $C_1$-$C_2$-haloalkyl, cyano or halo;

X is $C_1$-$C_5$ alkylene or $C_3$-$C_6$ spiroalkylene;

$R_{16}$ is H, $R_{17}$—C(O)—, $R_{17}$—O—C(O)— or $R_{17}$—O—C(O)—X—;

each $R_{17}$ is independently H, $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl may be optionally substituted with $C_1$-$C_2$-alkyl, $C_1$-$C_2$-haloalkyl cyano or halo, or two $R_{17}$ may, along with the carbon they are attached to, form a 3-6 membered spirocyclic carbocycle or heterocycle wherein any carbon of said carbocycle or heterocycle may be substituted with $C_1$-$C_2$-alkyl, $C_1$-$C_2$-haloalkyl, cyano or halo and any nitrogen of said heterocycle may be substituted with $C_1$-$C_2$-alkyl, $C_1$-$C_2$-haloalkyl, $C_3$-$C_5$ cycloalkyl or $C_1$-$C_3$ acyl, or, taken together, two instances of $R_{17}$ together with the carbon they are attached to form a carbonyl group;

In one embodiment of the invention $R_7$ is

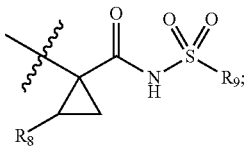

In one embodiment of the invention $R_9$ is $R_{10}$, $R_{10}$—NH— or $R_{10}$—O—;

In one embodiment of the invention $R_9$ is $R_{10}$;

In one embodiment of the invention $R_1$ is $R_2$—O—C(O)—;

In one embodiment of the invention $R_2$ is optionally substituted $C_1$-$C_8$ alkyl, optionally substituted $C_3$-$C_{10}$ cycloalkyl or optionally substituted $C_7$-$C_{14}$ cycloalkylalkyl, In one embodiment of the invention each of $R_{17}$ is independently H or substituted alkyl, In one embodiment of the invention $R_4$ is

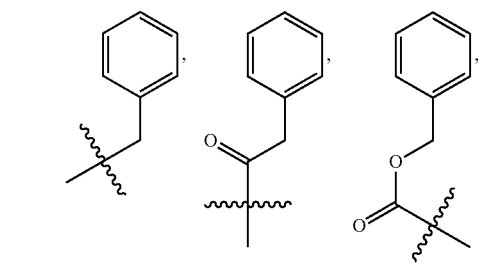

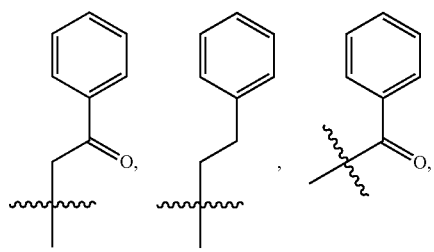

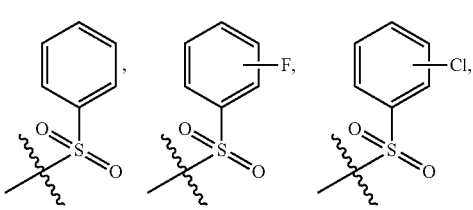

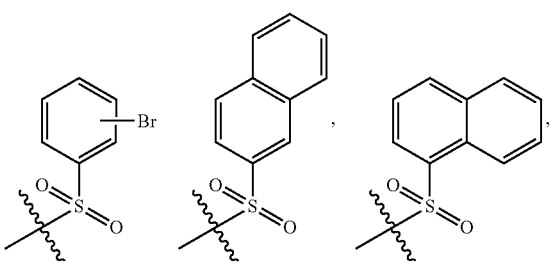

-continued

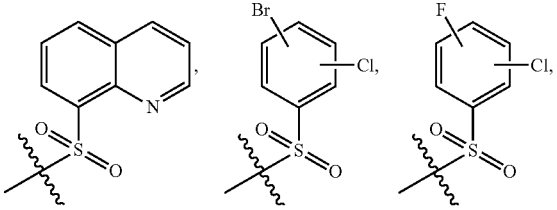

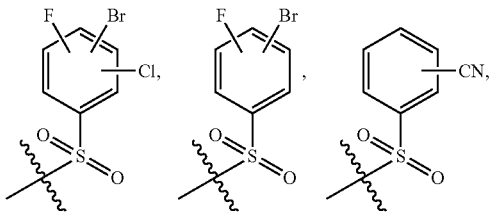

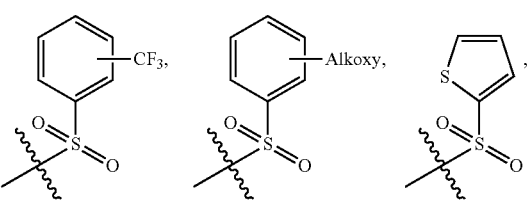

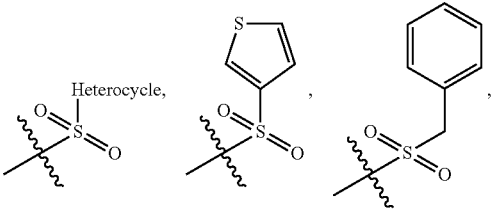

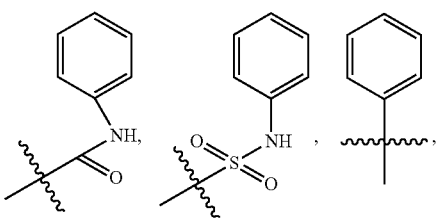

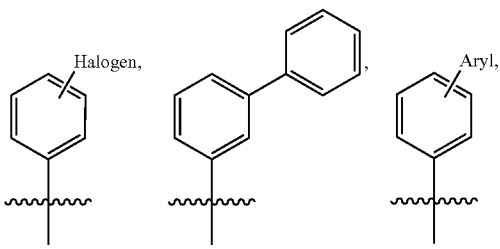

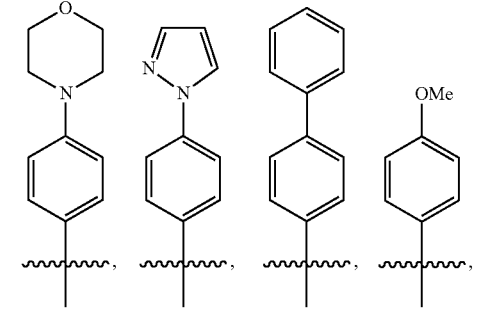

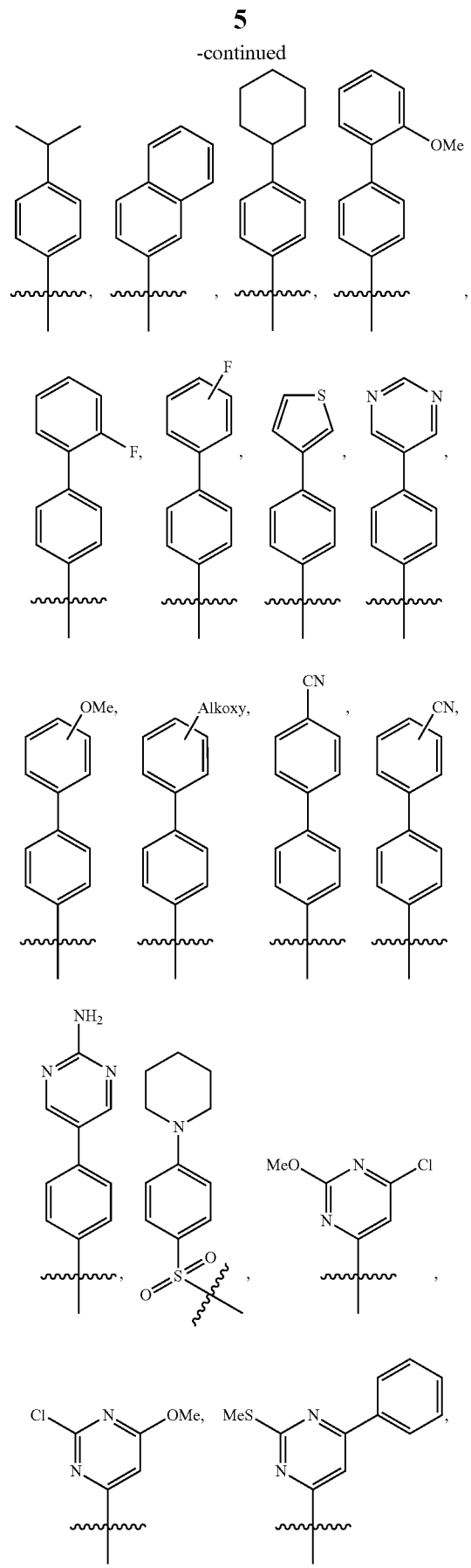
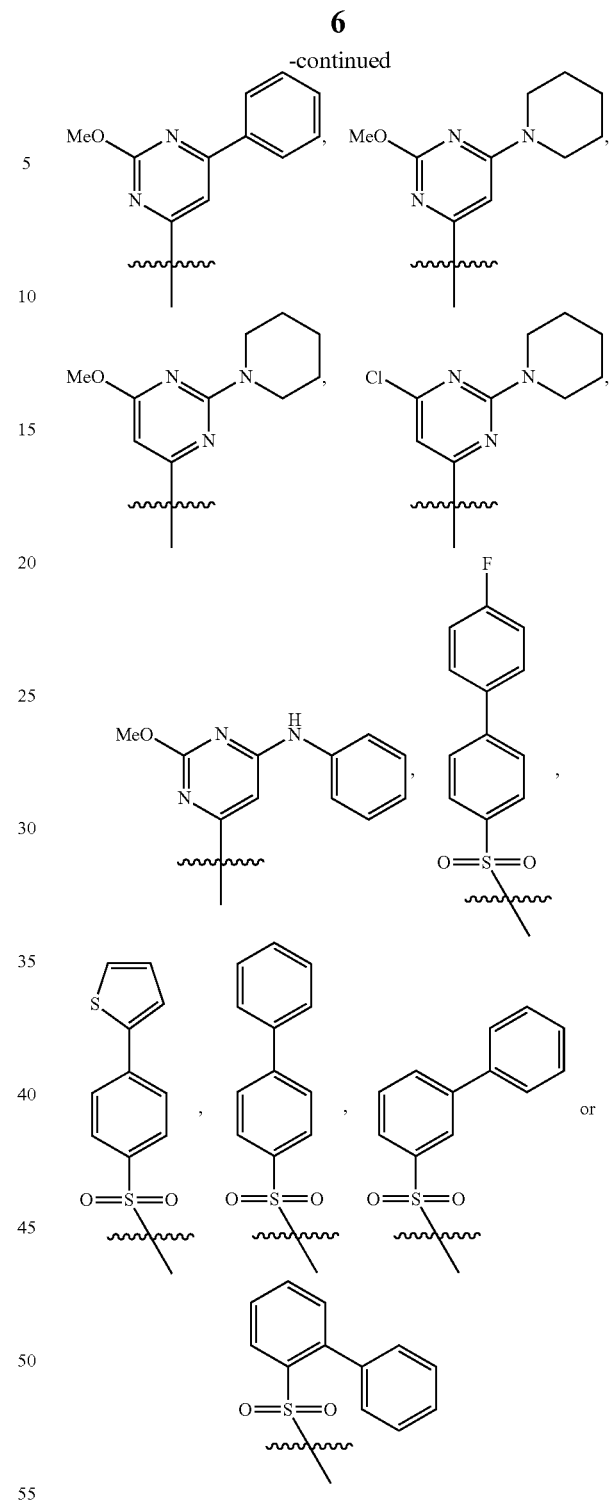

In one embodiment of the invention $R_1$ is cyclopentyloxycarbonyl, t-butyloxycarbonyl, or 2,2,2-trifluoro-1,1-dimethylethyloxycarbonyl.

In one embodiment of the invention $R_2$ is cyclopentyl, t-butyl or 2,2,2-trifluoro-1,1-dimethylethyl.

In one embodiment of the invention $R_3$ is t-butyl.

In one embodiment of the invention $R_3$ and $R_8$ together form a $C_6$ to $C_8$ alkylene, wherein the alkylene may be optionally unsaturated.

In one embodiment of the invention $R_3$ and $R_8$ together form

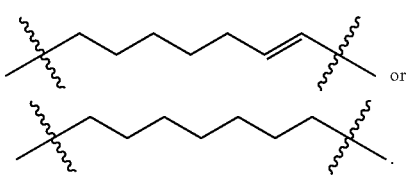

In one embodiment of the invention $R_4$ is $R_6$-alkylene-, $R_6$-alkylene-C(O)—, $R_6$—C(O)-alkylene-, $R_6$—C(O)—, $R_6$—S(O)$_2$—, $R_6$-alkylene-S(O)$_2$—, $R_6$—NH—C(O)—, $R_6$—NH—S(O)$_2$—, $R_6$—, $R_6$—$R_5$—, $R_6$—$R_5$—S(O)$_2$—, or $R_6$—NH—$R_5$—.

In one embodiment of the invention $R_5$ is

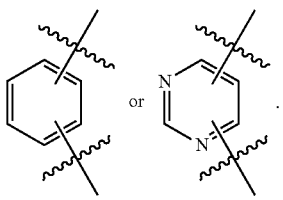

In one embodiment of the invention $R_6$ is

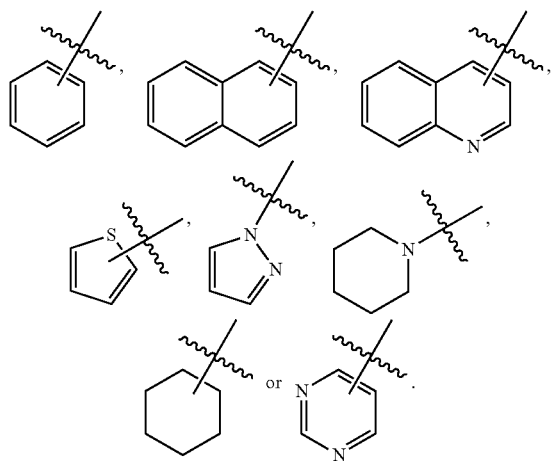

In one embodiment of the invention $R_7$ is

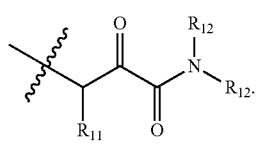

In one embodiment of the invention $R_7$ is

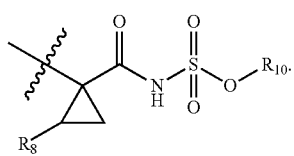

In one embodiment of the invention $R_7$ is

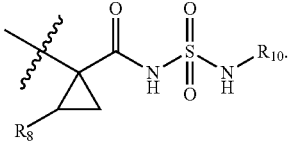

In one embodiment of the invention $R_7$ is

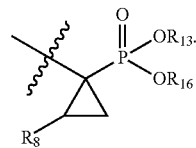

In one embodiment of the invention $R_8$ is ethyl or ethylene.

In one embodiment of the invention $R_9$ is $R_{10}$.

In one embodiment of the invention $R_{10}$ is cyclopropyl or 1-methylcyclopropyl.

In one embodiment of the invention $R_{11}$ is cyclobutylmethyl or n-propyl.

In one embodiment of the invention $R_{12}$ is H or cyclopropyl.

In one embodiment of the invention $R_{13}$ is alkyl, optionally substituted alkyl, optionally substituted arylalkyl or optionally substituted heterocyclylalkyl.

In one embodiment of the invention $R_{16}$ is H, $R_{17}$—C(O)—, $R_{17}$—O—C(O)— or $R_{17}$—O—C(O)—X—;

In one embodiment of the invention $R_{17}$ is alkyl, optionally substituted alkyl, optionally substituted aryl, optionally substituted heterocycle, optionally substituted arylalkyl or optionally substituted heterocyclylalkyl.

Examples of compounds provided by the invention are:

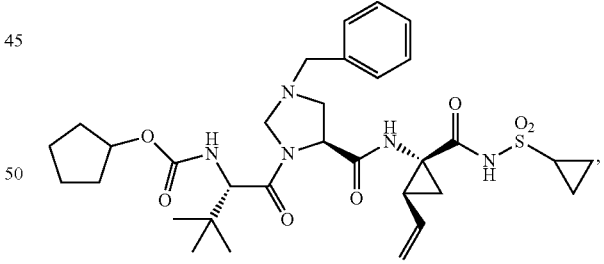

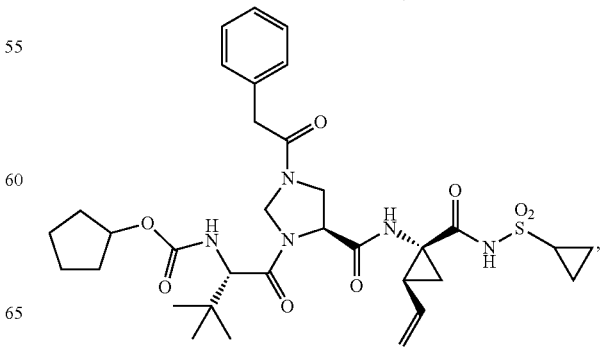

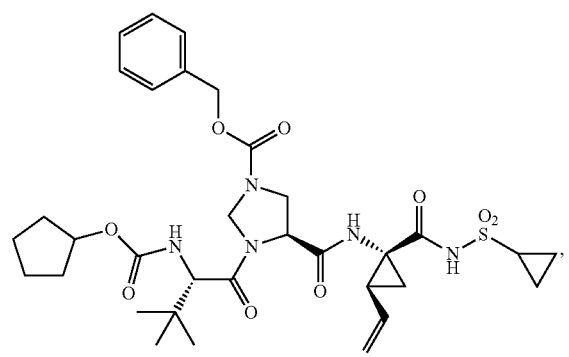
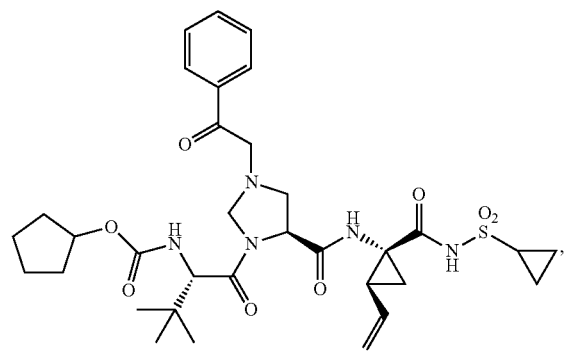
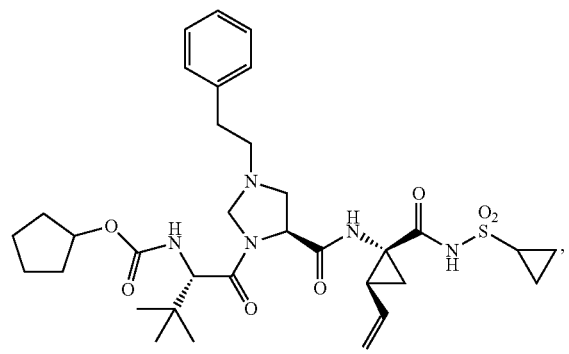
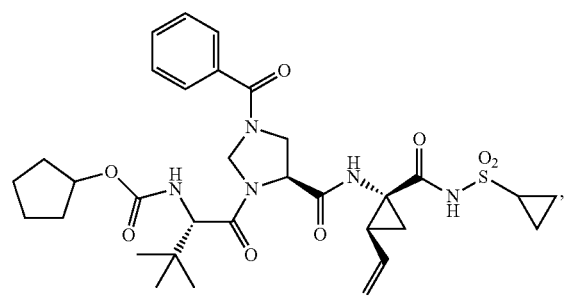
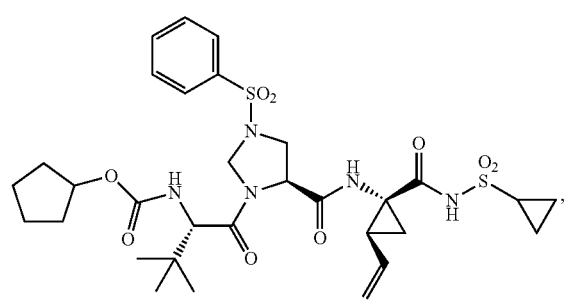
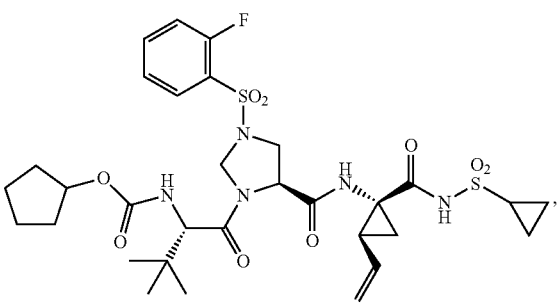
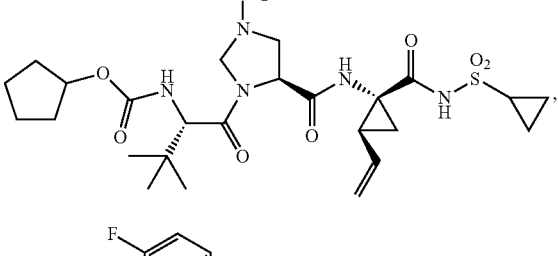
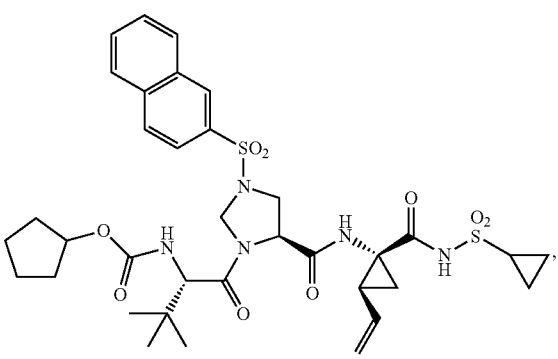
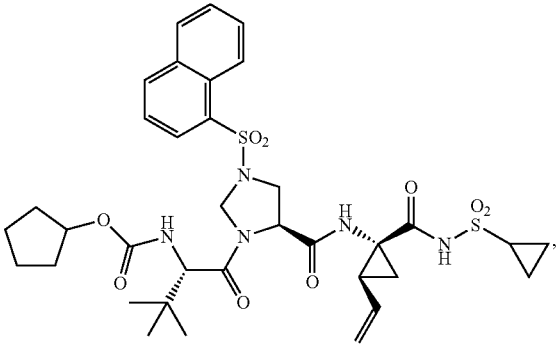

11
-continued
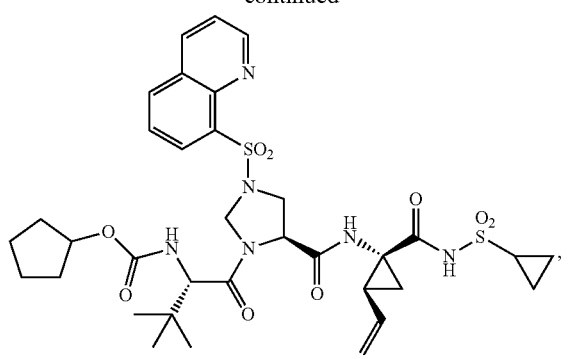
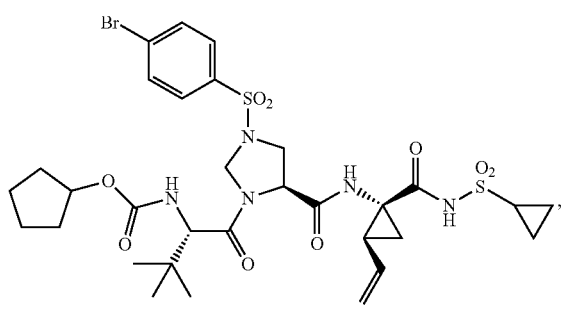
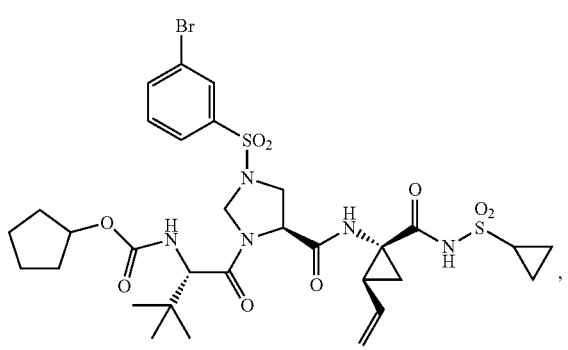
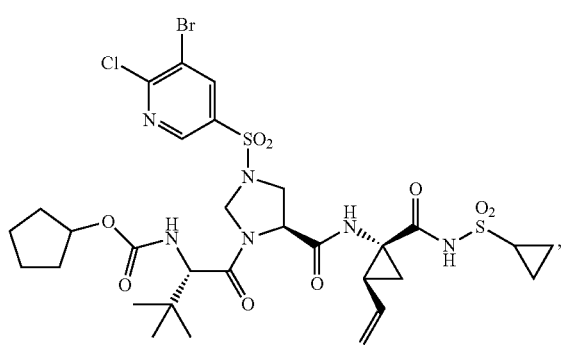
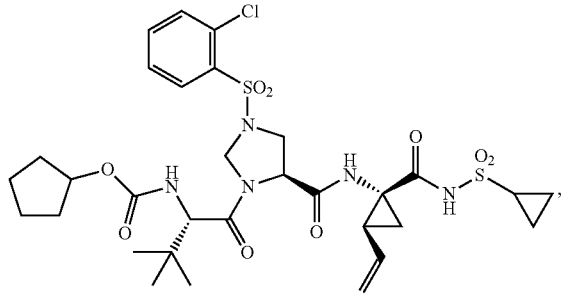
12
-continued
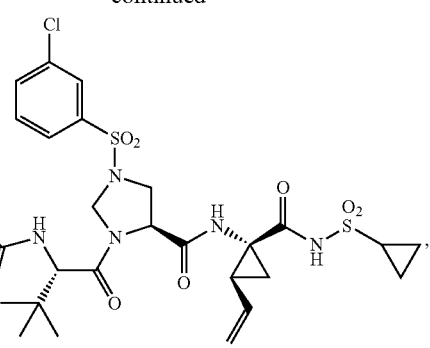
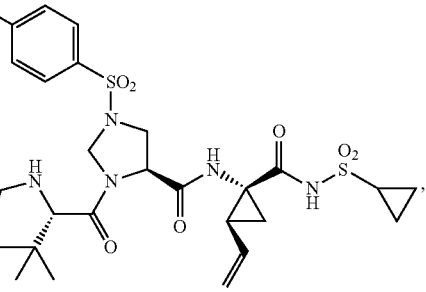
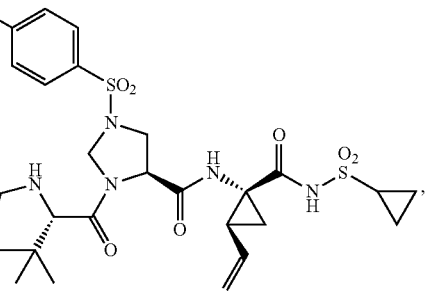
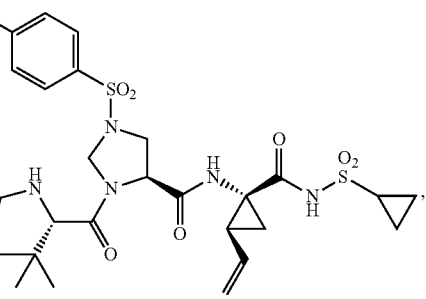
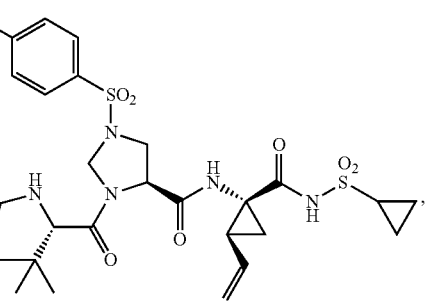

13
-continued
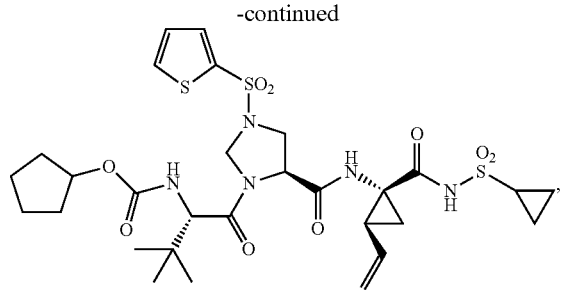
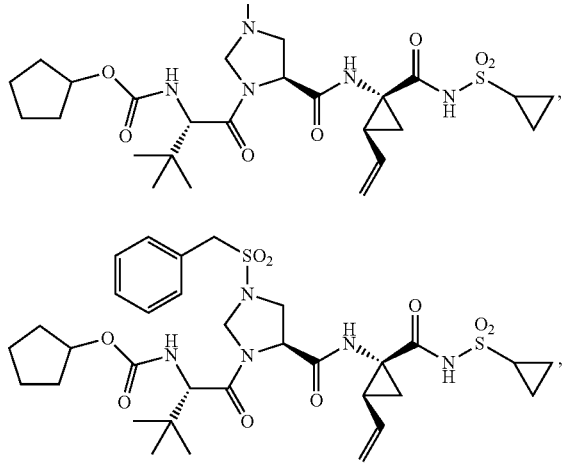
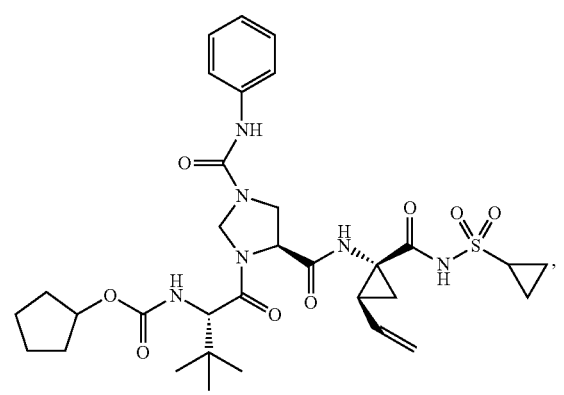
14
-continued
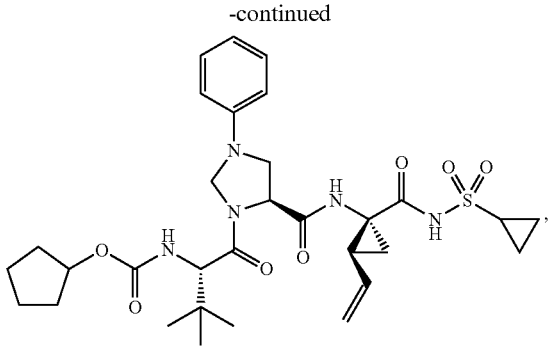
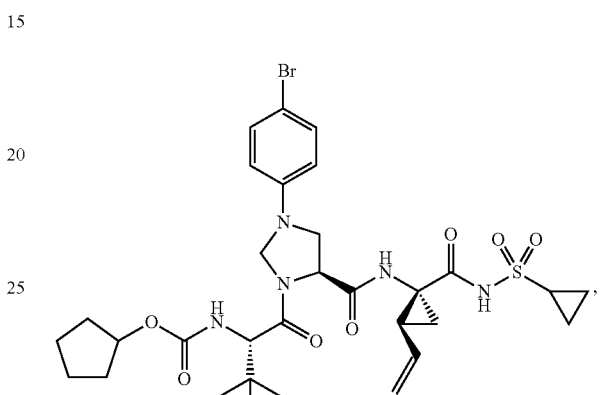
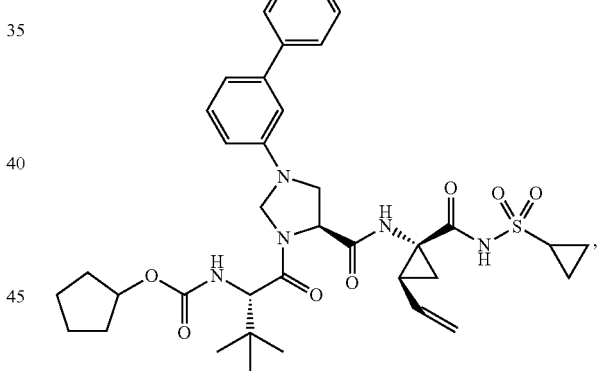
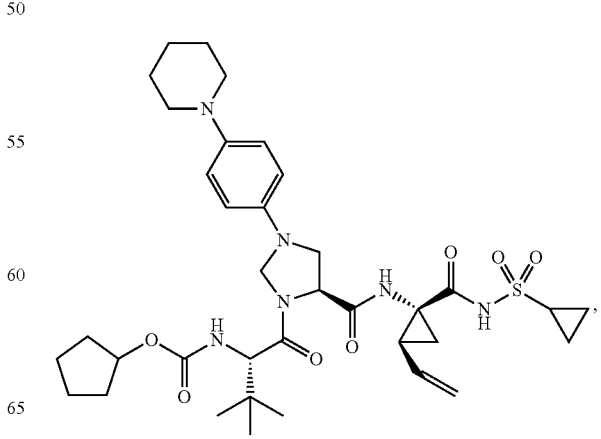

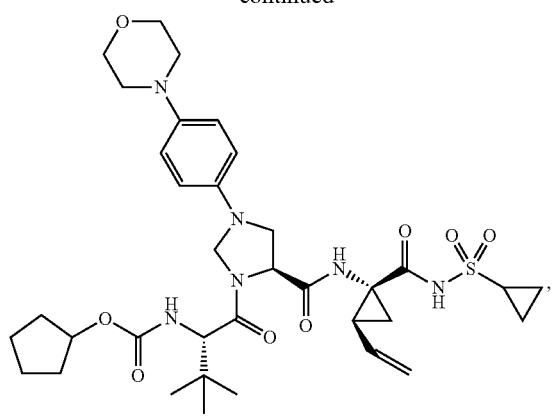
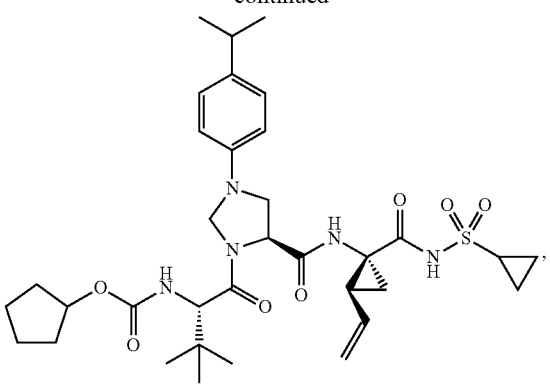
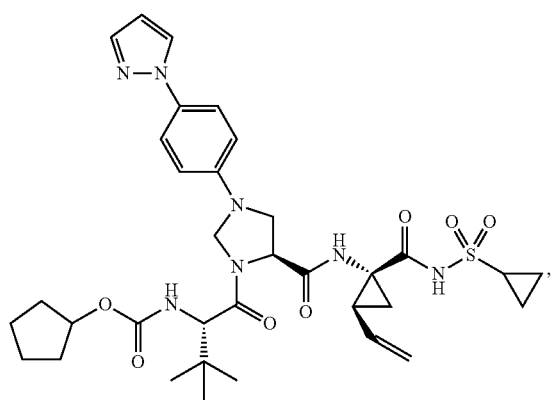
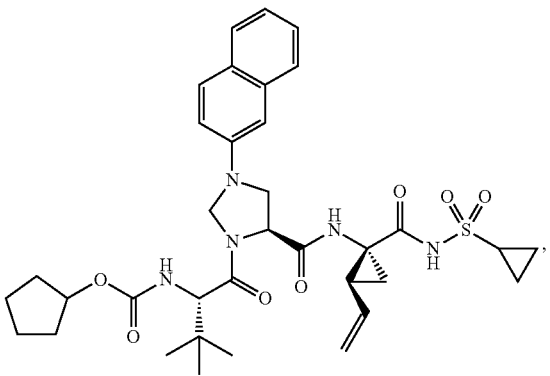
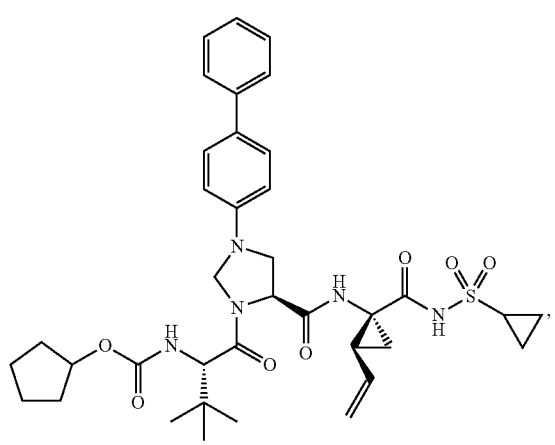
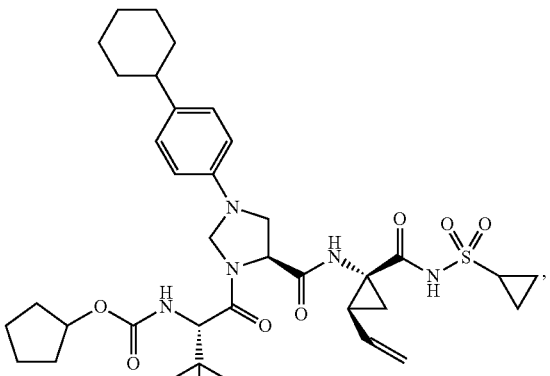
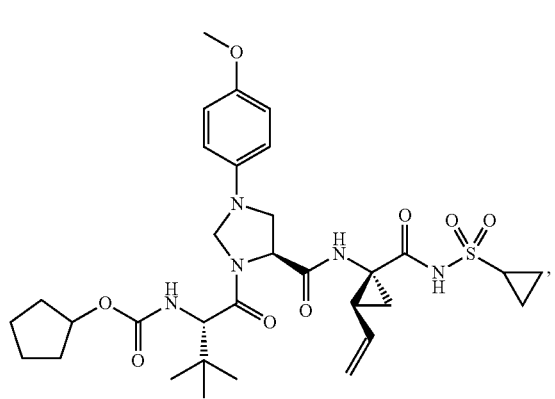
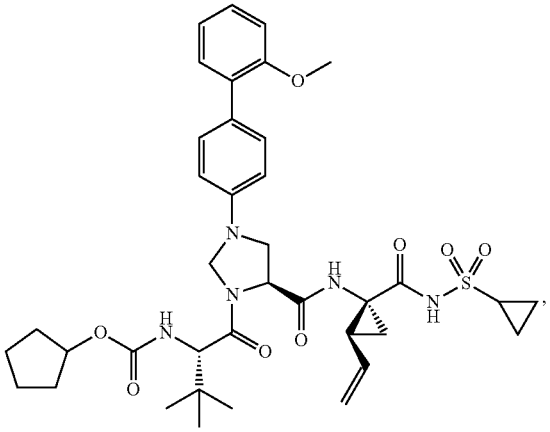

17
-continued
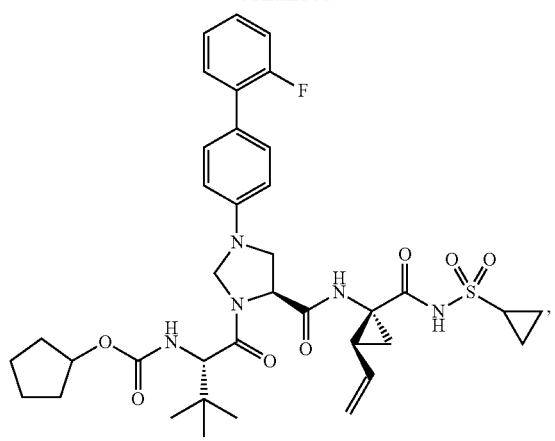
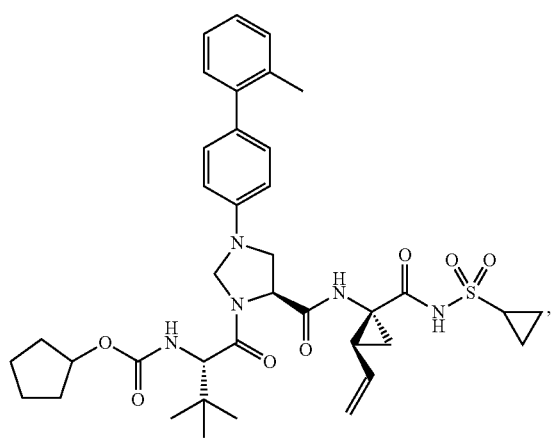
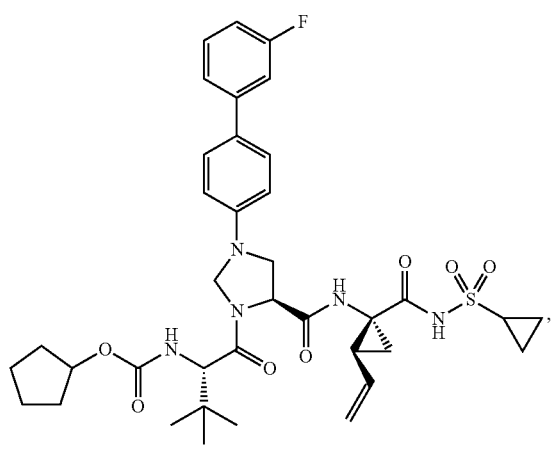
18
-continued
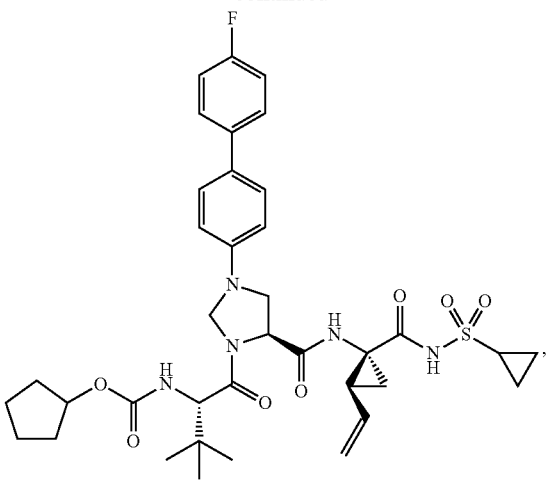
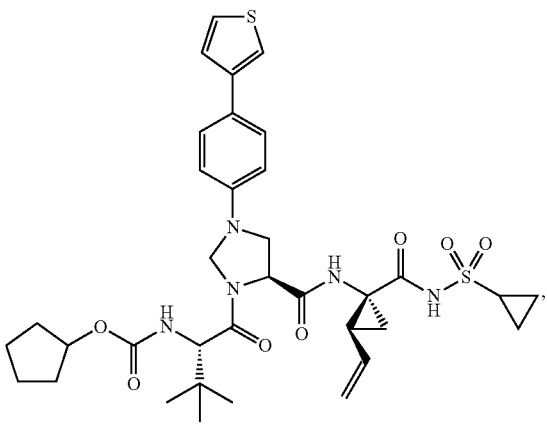
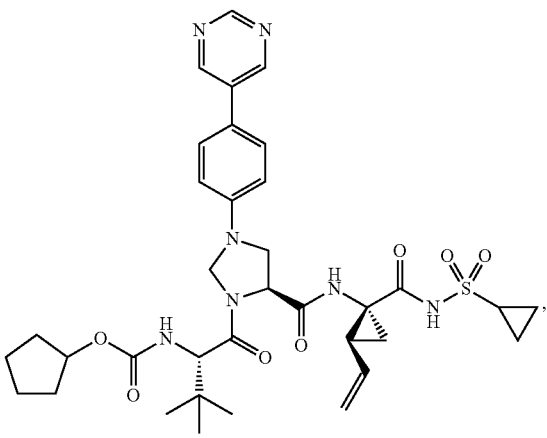

19
-continued
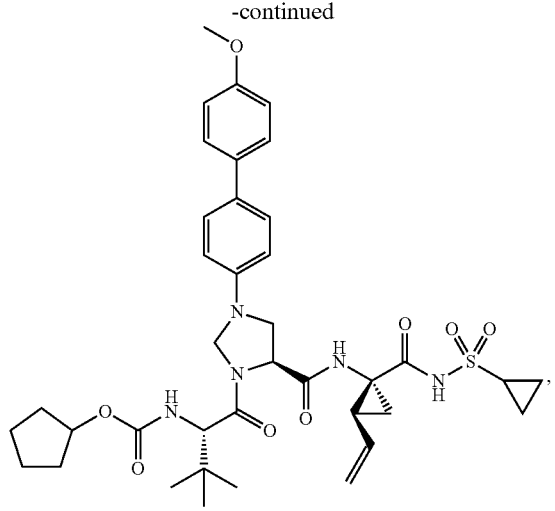
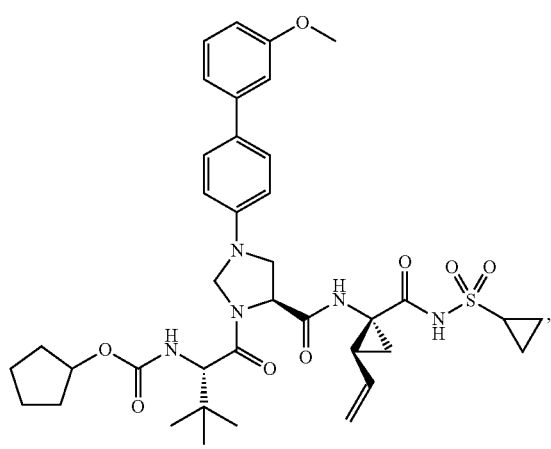
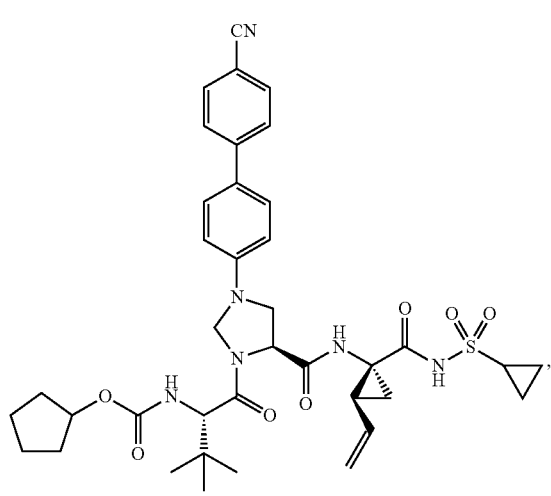
20
-continued
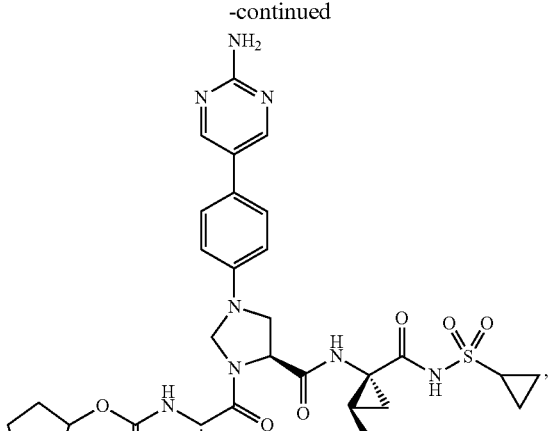
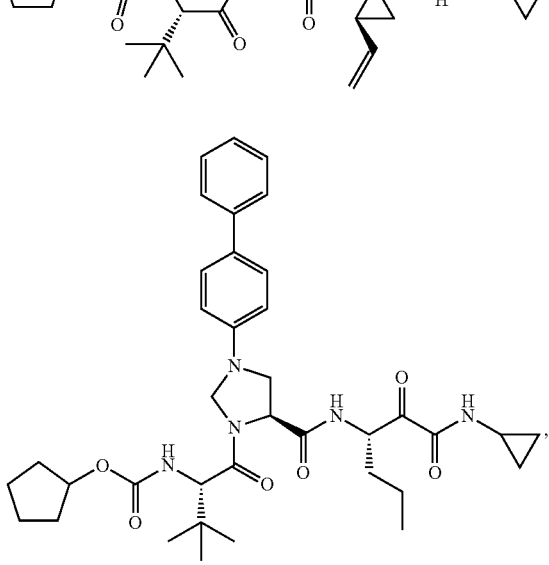
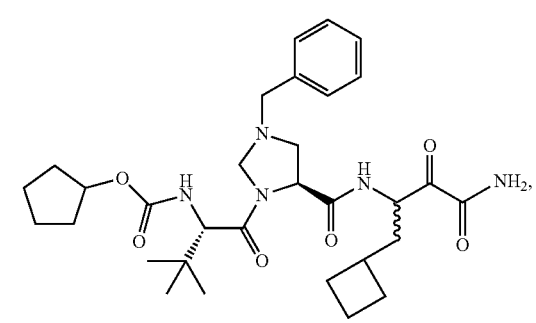

21
-continued
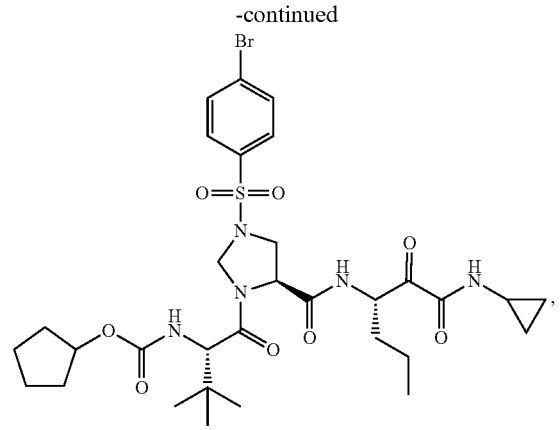
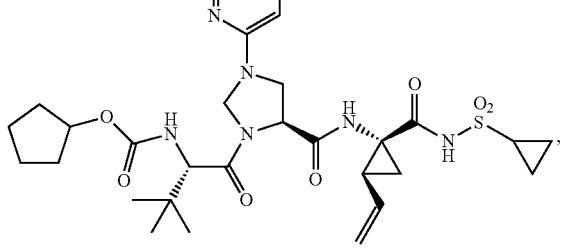
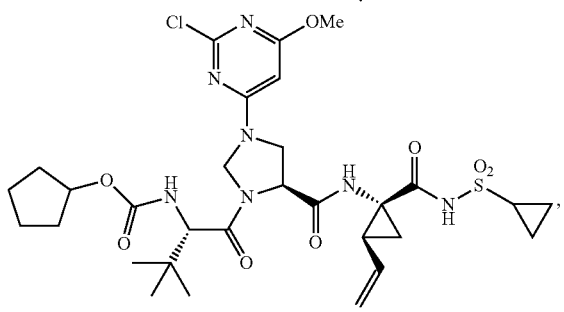
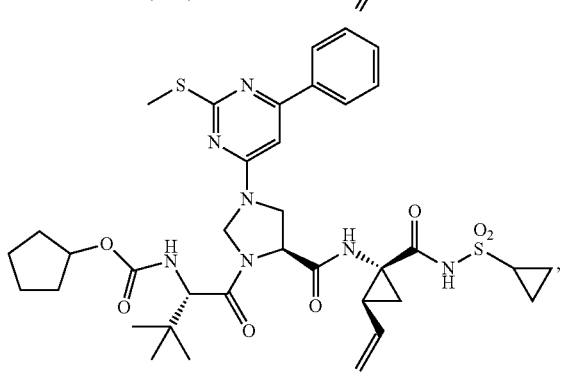
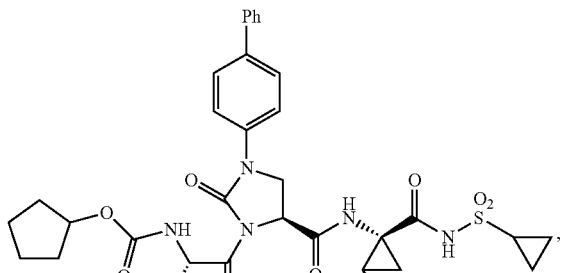
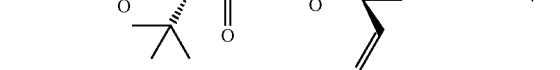
22
-continued
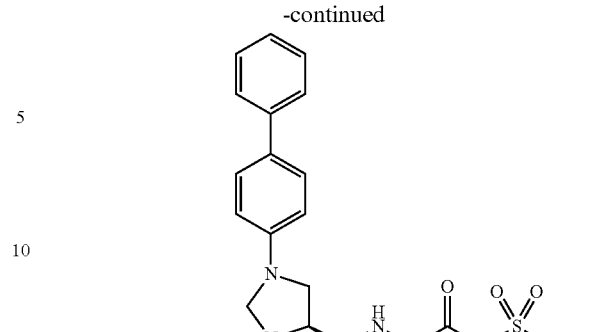
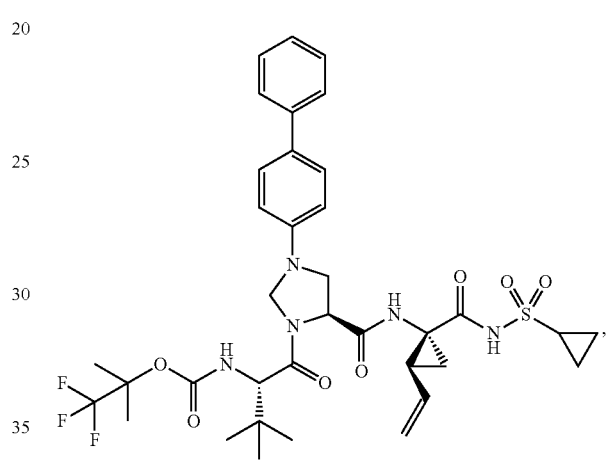
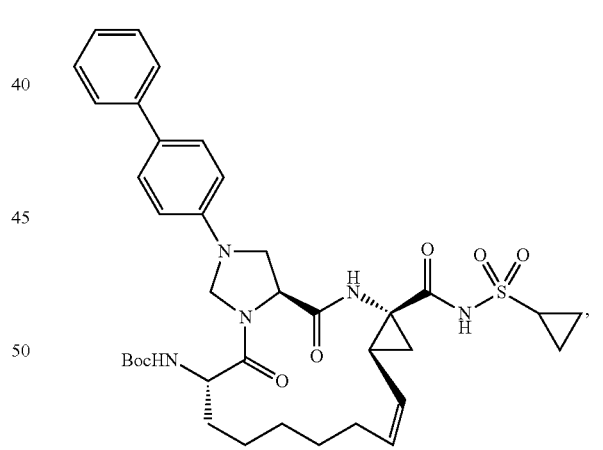
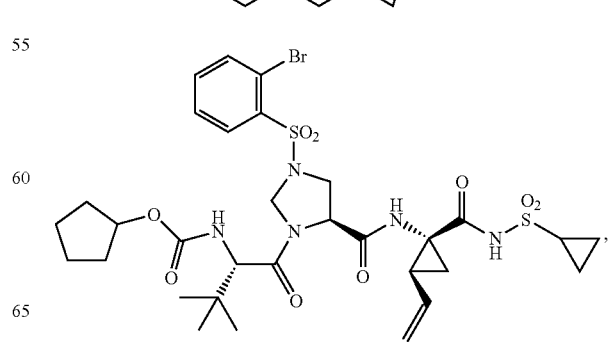
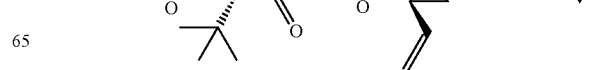

-continued
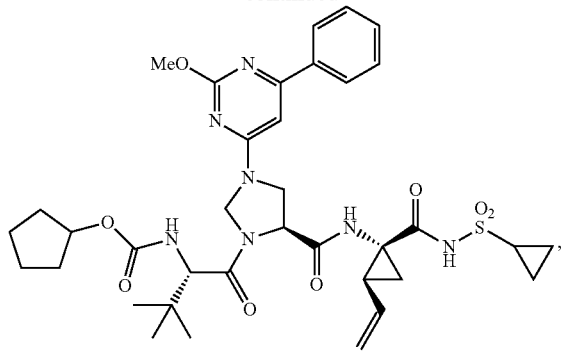
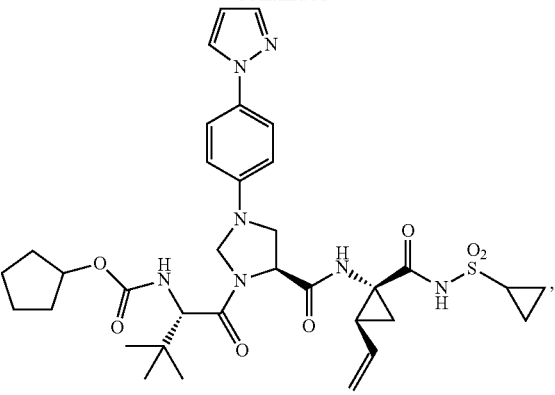
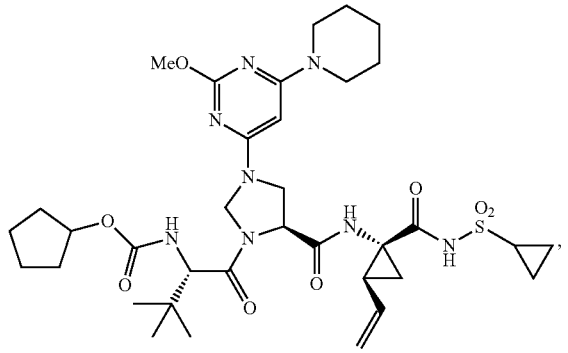
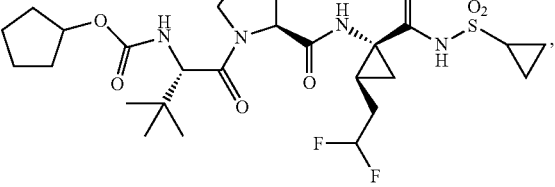
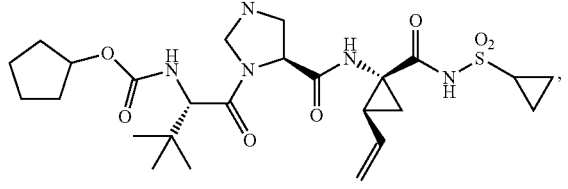
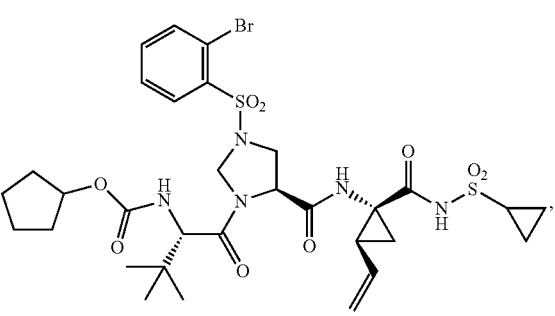
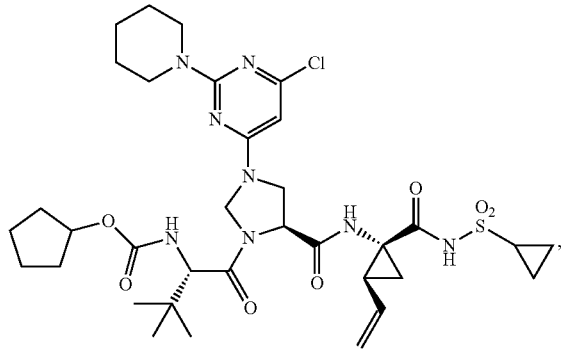
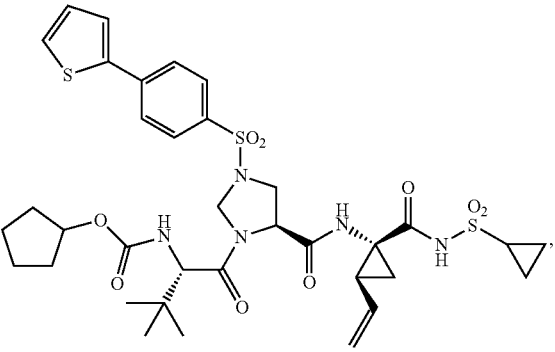

-continued

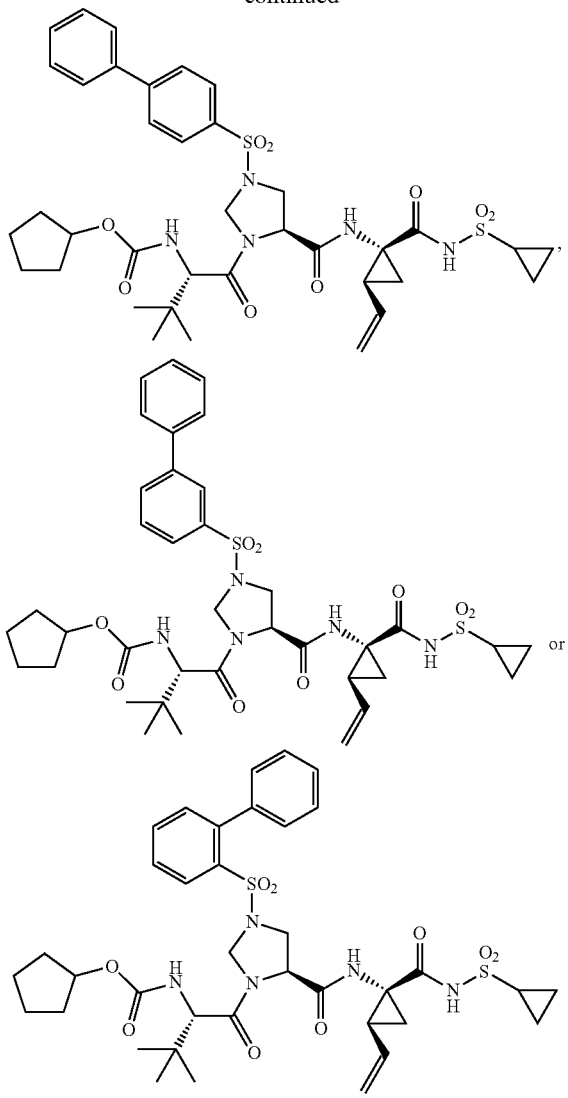

or

In one embodiment the invention is a compound or synthetic method described herein.

The present invention also provides pharmaceutical compositions comprising a compound of the invention and at least one pharmaceutically acceptable carrier.

The present invention also provides a pharmaceutical composition for use in treating HCV infection.

The present invention also provides a pharmaceutical composition comprising a compound of the invention and further comprising a nucleoside analog.

The present invention also provides a pharmaceutical composition comprising a compound of the invention and further comprising an interferon or pegylated interferon.

The present invention also provides a pharmaceutical composition and a nucleoside analogue selected from ribavirin, viramidine levovirin, a L-nucleoside, and isatoribine and a-interferon or pegylated interferon.

The present invention also provides a method of treating hepatitis C infection, said method comprising administering to an individual a pharmaceutical composition which comprises a therapeutically effective amount of a compound of the invention.

The present invention also provides a method of inhibiting HCV, comprising administering to a mammal afflicted with HCV infection, an amount of a compound of the invention, effective to inhibit HCV replication.

The present invention also provides a compound of the invention for use in medical therapy (preferably for use in inhibiting HCV replication or treating an HCV infection), as well as the use of a compound of the invention for the manufacture of a medicament useful for inhibiting HCV replication or the treatment of HCV infection in a mammal.

The present invention also provides synthetic processes and novel intermediates disclosed herein which are useful for preparing compounds of the invention. Some of the compounds of the invention are useful to prepare other compounds of the invention.

In another aspect the invention provides a compound of formula I, or a pharmaceutically acceptable salt or prodrug thereof, for use in the prophylactic or therapeutic treatment of HCV infection.

In another aspect the invention provides a method of inhibiting HCV replication in a sample comprising treating the sample with a compound of the invention.

In one embodiment the invention provides a compound having improved inhibitory or pharmacokinetic properties, including enhanced activity against development of viral resistance, improved oral bioavailability, greater potency or extended effective half-life in vivo. Certain compounds of the invention may have fewer side effects, less complicated dosing schedules, or be orally active.

The present invention provides for methods of treating HCV infection wherein each method includes the step of administering to a human being suffering from HCV infection a therapeutically effective amount of a compound of this invention or a salt, hydrate, or polymorph thereof. Typical dosages include 0.1 mg to 10 mg, 10 mg to 100 mg, 100 mg to 1000 mg or 1000 mg to 10 g.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compounds of the Invention

The compounds of the invention exclude compounds heretofore known. However it is within the invention to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "$R^1$", then it will be understood that the groups may be the same or different, i.e., each group is independently selected.

"Alkyl" means a $C_1$-$C_{18}$ hydrocarbon containing normal, secondary, tertiary or cyclic carbon atoms. Examples include, but are not limited to methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —CH₂CH(CH₃)₂), 2-butyl (s-Bu, s-butyl, —CH(CH₃)CH₂CH₃), 2-methyl-2-propyl (t-Bu, t-butyl, —C(CH₃)₃), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)₂CH(CH₃)₂), 3-methyl-1-butyl (—CH₂CH₂CH(CH₃)₃), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), and 3,3-dimethyl-2-butyl (—CH(CH₃)C(CH₃)₃).

"Alkenyl" means a $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—CH═CH₂), allyl (—CH₂CH═CH₂), cyclopentenyl (—C₅H₇), and 5-hexenyl (—CH₂CH₂CH₂CH₂CH═CH₂).

"Alkynyl" means a $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH₂C≡CH), "Alkylene" means a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" means an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—).

"Alkynylene" means an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, naphthalene, anthracene, biphenyl, and the like.

"Arylalkyl" means an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Heterocyclylalkyl" means an acyclic alkyl radical in which one of the hydrogen atoms bonded to a carbon atom, typically a terminal or $sp^3$ carbon atom, is replaced with an heterocycle radical.

The term "polycarbocycle" means a saturated or unsaturated polycyclic ring system having from about 6 to about 25 carbon atoms and having two or more rings (e.g. 2, 3, 4, or 5 rings). The rings can be fused and/or bridged to form the polycyclic ring system. For example, the term includes bicyclo [4,5], [5,5], [5,6] or [6,6] ring systems, as well as the following bridged ring systems:

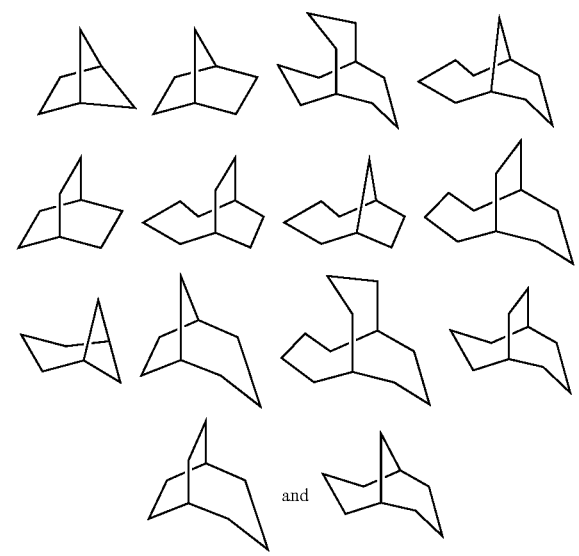

(i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" means a polycarbocycle as defined herein, wherein one or more carbon atoms is replaced with a heteroatom (e,g, O, S, S(O), S(O)₂, N⁺(O⁻)$R_x$, or N$R_x$); wherein each $R_x$ is independently H, (C1-10)alkyl, (C2-10)alkenyl, (C2-10)alkynyl, (C1-10)alkanoyl, S(O)₂N$R_n$$R_p$, S(O)₂$R_x$, or (C1-10)alkoxy, wherein each (C1-10)alkyl, (C2-10)alkenyl, (C2-10)alkynyl, (C1-10)alkanoyl, and (C1-10)alkoxy is optionally substituted with one or more halo).

The term "optionally substituted" in reference to a particular moiety of the compound of formula I, (e.g., an optionally substituted aryl group) refers to a moiety having 0, 1, 2, or more substituents.

The symbol "════" means that a bond is a single or double bond. In a non-limiting example,

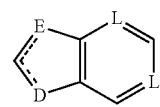

can be

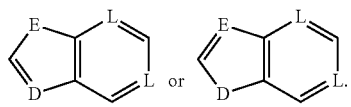

"Haloalkyl" means an alkyl group substituted with one or more halogens (e.g. F, Cl, Br, or I). Representative examples of haloalkyl include trifluoromethyl, 2,2,2-trifluoroethyl, and 2,2,2-trifluoro-1-(trifluoromethyl)ethyl.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (O, N, P or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

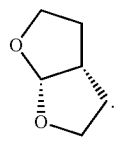

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6 pyrimidinyl 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo [4,5], [5,5], [5,6] or [6,6] system, or 9 or 10 ring atoms arranged as a bicyclo [5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term optionally substituted alkyl means an alkyl group said alkyl group is substituted with 0, 1, 2, 3, 4 or 5 substituents selected from halogen, cyano, azido, amino, nitro, sulfonamide, alkylsulfonyl or carboxamido.

The term optionally substituted $C_1$-$C_8$ alkyl means an alkyl group comprising from 1 to 8 carbon atoms, wherein said alkyl group is substituted with 0, 1, 2, 3, 4 or 5 substituents selected from F, Cl, Br, I, —R, —OR, —SR, —NRR, —CF$_3$, —CCl$_3$, —OCF$_3$, —CN, —N$_3$, —NO$_2$, —N(R)C(=O)R, —C(=O)R, —OC(=O)R, —C(O)OR, —C(=O)NRR, —S(=O)R, —S(=O)$_2$OR, —S(=O)$_2$R, —OS(=O)$_2$OR, —S(=O)$_2$NRR, wherein each R is independently —H, alkyl, aryl, arylalkyl, or heterocycle.

The term optionally substituted cycloalkyl means a cycloalkyl group comprising wherein said cycloalkyl group is substituted with 0, 1, 2, 3, 4 or 5 substituents selected from F, Cl, Br, I, —R, —OR, —SR, —NRR, —CF$_3$, —CCl$_3$, —OCF$_3$, —CN, —N$_3$, —NO$_2$, —N(R)C(=O)R, —C(=O) R, —OC(=O)R, —C(O)OR, —C(=O)NRR, —S(=O)R, —S(=O)$_2$OR, —S(=O)$_2$R, —OS(=O)$_2$OR, —S(=O)$_2$ NRR, wherein each R is independently —H, alkyl, aryl, arylalkyl, or heterocycle.

The term optionally substituted $C_3$-$C_{10}$ cycloalkyl means an cycloalkyl group comprising from 3 to 10 carbon atoms, wherein said cycloalkyl group is substituted with 0, 1, 2, 3, 4 or 5 substituents selected from F, Cl, Br, I, —R, —OR, —SR, —NR$_2$, —CF$_3$, —CCl$_3$, —OCF$_3$, —CN, —N$_3$, —NO$_2$, —N(R)C(=O)R, —C(=O)R, —OC(=O)R, —C(O)OR, —C(=O)NRR, —S(=O)R, —S(=O)$_2$OR, —S(=O)$_2$R, —OS(=O)$_2$OR, —S(=O)$_2$NRR, wherein each R is independently —H, alkyl, aryl, arylalkyl, or heterocycle.

The term optionally substituted cycloalkylalkyl means a cycloalkyl group, wherein said cycloalkylalkyl group is substituted with 0, 1, 2, 3, 4 or 5 substituents selected from F, Cl, Br, I, —R, —OR, —SR, —NRR, —CF$_3$, —CCl$_3$, —OCF$_3$, —CN, —N$_3$, —NO$_2$, —N(R)C(=O)R, —C(=O)R, —OC (=O)R, —C(O)OR, —C(=O)NRR, —S(=O)R, —S $-(=O)_2OR$, $-S(=O)_2R$, $-OS(=O)_2OR$, $-S(=O)_2NRR$, wherein each R is independently $-H$, alkyl, aryl, arylalkyl, or heterocycle.

The term optionally substituted $C_7$-$C_{14}$ cycloalkylalkyl means an cycloalkyl group comprising from 7 to 14 carbon atoms, wherein said cycloalkylalkyl group is substituted with 0, 1, 2, 3, 4 or 5 substituents selected from F, Cl, Br, I, $-R$, $-OR$, $-SR$, $-NRR$, $-CF_3$, $-CCl_3$, $-OCF_3$, $-CN$, $-N_3$, $-NO_2$, $-N(R)C(=O)R$, $-C(=O)R$, $-OC(=O)R$, $-C(O)OR$, $-C(=O)NRR$, $-S(=O)R$, $-S(=O)_2OR$, $-S(=O)_2R$, $-OS(=O)_2OR$, $-S(=O)_2NRR$, wherein each R is independently $-H$, alkyl, aryl, arylalkyl, or heterocycle.

The term optionally substituted aryl means an aryl group, wherein said aryl group is substituted with 0, 1, 2, 3, 4 or 5 substituents selected from optionally substituted alkyl, optionally substituted cycloalkyl, optionally substituted cycloalkylalkyl, optionally substituted arylalkyl, optionally substituted heterocyclylalkyl, F, Cl, Br, I, $-R$, $-OR$, $-SR$, $-NRR$, $-CF_3$, $-CCl_3$, $-OCF_3$, $-CN$, $-N_3$, $-NO_2$, $-N(R)C(=O)R$, $-C(=O)R$, $-OC(=O)R$, $-C(O)OR$, $-C(=O)NRR$, $-S(=O)R$, $-S(=O)_2OR$, $-S(=O)_2R$, $-OS(=O)_2OR$, $-S(=O)_2NRR$, wherein each R is independently $-H$, alkyl, aryl, arylalkyl, or heterocycle.

The term optionally substituted arylalkyl means an arylalkyl group, wherein said arylalkyl group is substituted with 0, 1, 2, 3, 4 or 5 substituents selected from optionally substituted alkyl, optionally substituted cycloalkyl, optionally substituted cycloalkylalkyl, optionally substituted arylalkyl, optionally substituted heterocyclylalkyl, F, Cl, Br, I, $-R$, $-OR$, $-SR$, $-NRR$, $-CF_3$, $-CCl_3$, $-OCF_3$, $-CN$, $-N_3$, $-NO_2$, $-N(R)C(=O)R$, $-C(=O)R$, $-OC(=O)R$, $-C(O)OR$, $-C(=O)NRR$, $-S(=O)R$, $-S(=O)_2OR$, $-S(=O)_2R$, $-OS(=O)_2OR$, $-S(=O)_2NRR$, wherein each R is independently $-H$, alkyl, aryl, arylalkyl, or heterocycle.

The term optionally substituted heterocycle means a heterocycle group, wherein said heterocycle group is substituted with 0, 1, 2, 3, 4 or 5 substituents selected from optionally substituted alkyl, optionally substituted cycloalkyl, optionally substituted cycloalkylalkyl, optionally substituted arylalkyl, optionally substituted heterocyclylalkyl, F, Cl, Br, I, $-R$, $-OR$, $-SR$, $-NRR$, $-CF_3$, $-CCl_3$, $-OCF_3$, $-CN$, $-N_3$, $-NO_2$, $-N(R)C(=O)R$, $-C(=O)R$, $-OC(=O)R$, $-C(O)OR$, $-C(=O)NRR$, $-S(=O)_2OR$, $-S(=O)_2R$, $-OS(=O)_2OR$, $-S(=O)_2NRR$, wherein each R is independently $-H$, alkyl, aryl, arylalkyl, or heterocycle.

The term optionally substituted heterocyclylalkyl means a heterocyclylalkyl group, wherein said heterocyclylalkyl group is substituted with 0, 1, 2, 3, 4 or 5 substituents selected from optionally substituted alkyl, optionally substituted cycloalkyl, optionally substituted cycloalkylalkyl, optionally substituted arylalkyl, optionally substituted heterocyclylalkyl, aryl, heterocycle, halogen, cyano, azido, amino, nitro, sulfonamide, alkylsulfonyl or carboxamido.

The term arylene means a divalent aryl group

The term optionally substituted arylene means an arylene group, wherein said arylene group is substituted with 0, 1, 2, 3, 4 or 5 substituents selected from optionally substituted alkyl, optionally substituted cycloalkyl, optionally substituted cycloalkylalkyl, optionally substituted arylalkyl, optionally substituted heterocyclylalkyl, aryl, heterocycle, halogen, cyano, azido, amino, nitro, sulfonamide, alkylsulfonyl or carboxamido.

The term heteroarylene means a divalent heterocycle.

The term $C_3$-$C_6$ spiroalkylene means a divalent $C_3$-$C_6$ cycloalkyl group wherein both valencies occur on the same carbon.

The term optionally substituted heteroarylene means a heteroarylene group, wherein said heteroarylene group is substituted with 0, 1, 2, 3, 4 or 5 substituents selected from optionally substituted alkyl, optionally substituted cycloalkyl, optionally substituted cycloalkylalkyl, optionally substituted arylalkyl, optionally substituted heterocyclylalkyl, aryl, heterocycle, halogen, cyano, azido, amino, nitro, sulfonamide, alkylsulfonyl or carboxamido.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Prodrugs

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, or inside a cell, by hydrolysis, enzymatic cleavage, or by some other process inside the organism (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^x$ and acyloxymethyl carbonates —$CH_2OC(=O)OR^x$ where $R^x$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group will be dependent upon the chemistry of the reaction to be protected against (e.g., acidic, basic, oxidative, reductive or other conditions) and the intended direction of the synthesis. The protecting groups do not need to be, and generally are not, the same if the compound is substituted with multiple protecting groups. In general, protecting groups will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Whenever a compound described herein is substituted with more than one of the same designated group, e.g., "$R^1$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of HCV. Accordingly, the invention relates to methods of detecting HCV protease in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (1) that comprises or that is bound or linked to one or more detectable labels.

Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of HCV activation in animals or in man.

However, in screening compounds capable of inhibiting HCV it should be kept in mind that the results of enzyme assays may not always correlate with cell culture assays. Thus, a cell based assay should typically be the primary screening tool.

Screens for HCV Protease Inhibitors

Compounds of the invention are screened for inhibitory activity against HCV protease by any of the conventional techniques for evaluating enzyme activity. Within the context of the invention, typically compounds are first screened for inhibition of HCV in vitro and compounds showing inhibitory activity are then screened for activity in vivo. One such screen is described in the following reference: Taliani M, Bianchi E, Narjes F, Fossatelli M, Urbani A, Steinkuhler C, et al. A continuous assay of hepatitis C virus protease based on resonance energy transfer depsipeptide substrates. Anal Biochem 1996; 240 (1):60-7.

Pharmaceutical Formulations

The compounds of this invention are typically formulated with conventional carriers and excipients, which will be selected in accord with ordinary practice. Tablets typically will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-dial or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infection.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Another aspect of the present invention includes use of a compound of the present invention for the manufacture of a medicament for the treatment of an HCV viral infection. Another aspect includes a compound for use in treating a viral infection. In one embodiment of each aspect of use and compound, the treatment results in one or more of a reduction in viral load or clearance of viral RNA.

Another aspect of the present invention includes a method for treating or preventing HCV comprising administering a compound of the present invention. Another aspect includes the use of a compound of the present invention for the manufacture of a medicament for the treatment or prevention of HCV.

Combination Therapy

Active ingredients of the invention can also be used in combination with other active ingredients. Such combinations are selected based on the condition to be treated, cross-reactivities of ingredients and pharmaco-properties of the combination. Typically, the active ingredients of this invention will be combined with other agents having anti-HCV activity, but may also be combined with agents having immunomodulatory activity as well.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients which are used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Suitable active therapeutic agents or ingredients which can be combined with the compounds of formula 1 can include:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738 GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib).

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034 SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib).

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of formula I and additional active therapeutic agents may be selected to treat patients infected with HCV and other conditions such as HIV infections. Accordingly, the compounds of formula I may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albufcron, 12) ribavirin analogs, e.g., rebetol, copegus, levovirin, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, G1-5005, ANA-975 (isatoribine), XTL-6865, ANA 971, NOV-205, tarvacin, EHC-18, and NIM811, 19) pharmacokinetic enhancers, e.g., BAS-100 and SPI452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV—inhibitory activity of their own.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry*. In 9 Volumes, Barry M. Trost, Editor-in-Chief (Pergamon Press, New York, 1993 printing).

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be $-100°$ C. to $200°$ C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about $20°$ C.), although for metal hydride reductions frequently the temperature is reduced to $0°$ C. to $-100°$ C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01 M to 10M, typically 0.1M to 1M), temperatures ($-100°$ C. to $250°$ C., typically $-78°$ C. to $150°$ C., more typically $-78°$ C. to $100°$ C., still more typically $0°$ C. to $100°$ C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113, 3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wiley, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (–) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

SCHEMES AND EXAMPLES

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention.

Compounds which are representative of the invention, along with their activities as inhibitors of HCV protease ($IC_{50}$) and HCV replication are listed in Table 1.

TABLE 1

| Structure | Example | IC50 (μM) |
|---|---|---|
| 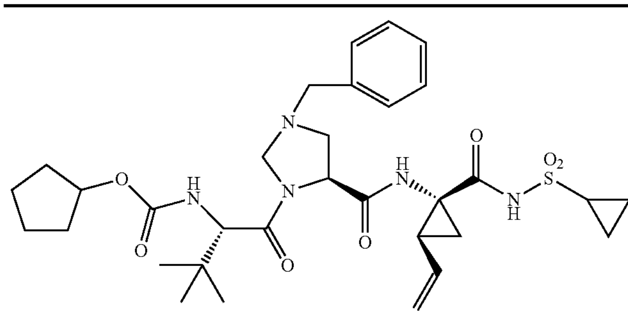 | 1 | 0.195 |
| 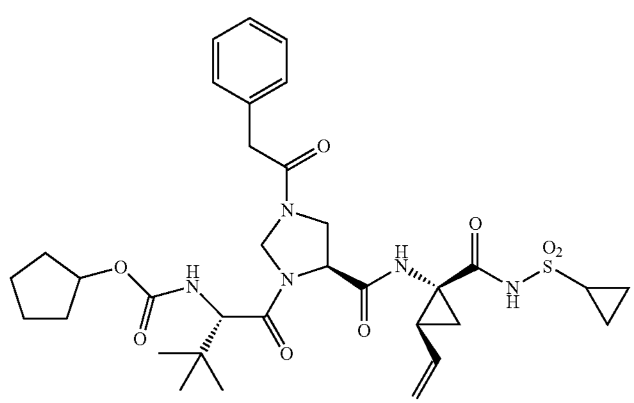 [SMILES: C=C[C@@H]1C[C@]1(NC(=O)[C@@H]1CN(C(=O)Cc2ccccc2)CN1C(=O)[C@@H](NC(=O)OC1CCCC1)C(C)(C)C)C(=O)NS(=O)(=O)C1CC1] | 2 | 0.49 |

TABLE 1-continued

| Structure | Example | IC50 (μM) |
|---|---|---|
| 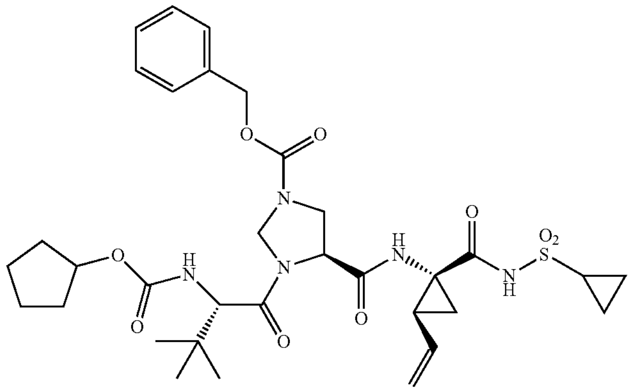 [SMILES: C=C[C@@H]1C[C@]1(NC(=O)[C@@H]1CN(C(=O)OCc2ccccc2)CN1C(=O)[C@@H](NC(=O)OC1CCCC1)C(C)(C)C)C(=O)NS(=O)(=O)C1CC1] | 3 | 0.057 |
| 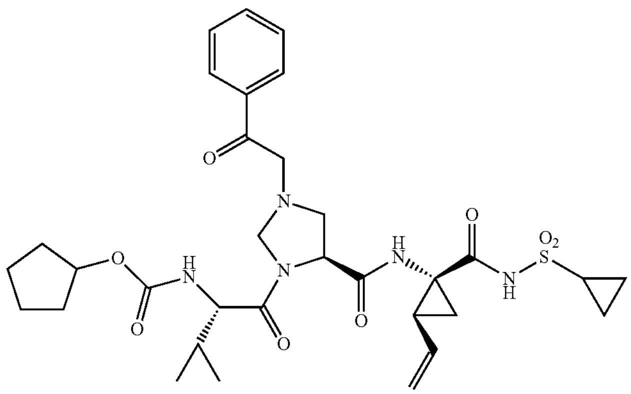 [SMILES: C=C[C@@H]1C[C@]1(NC(=O)[C@@H]1CN(CC(=O)c2ccccc2)CN1C(=O)[C@@H](NC(=O)OC1CCCC1)C(C)C)C(=O)NS(=O)(=O)C1CC1] | 4 | 0.021 |
| 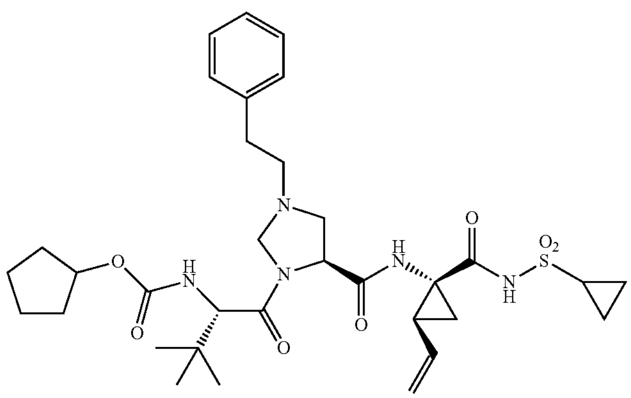 [SMILES: C=C[C@@H]1C[C@]1(NC(=O)[C@@H]1CN(CCc2ccccc2)CN1C(=O)[C@@H](NC(=O)OC1CCCC1)C(C)(C)C)C(=O)NS(=O)(=O)C1CC1] | 5 | 0.013 |
| 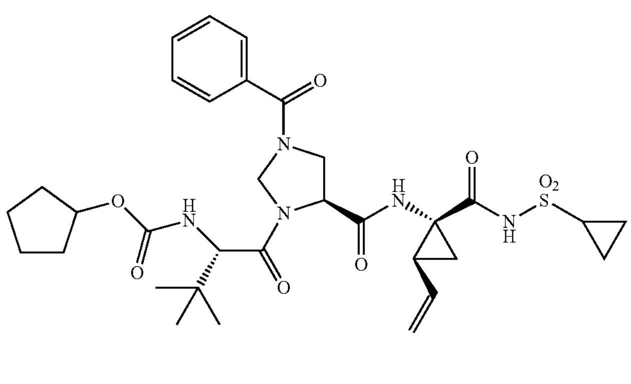 [SMILES: C=C[C@@H]1C[C@]1(NC(=O)[C@@H]1CN(C(=O)c2ccccc2)CN1C(=O)[C@@H](NC(=O)OC1CCCC1)C(C)(C)C)C(=O)NS(=O)(=O)C1CC1] | 6 | 0.403 |

TABLE 1-continued

| Structure | Example | IC50 (μM) |
|---|---|---|
| 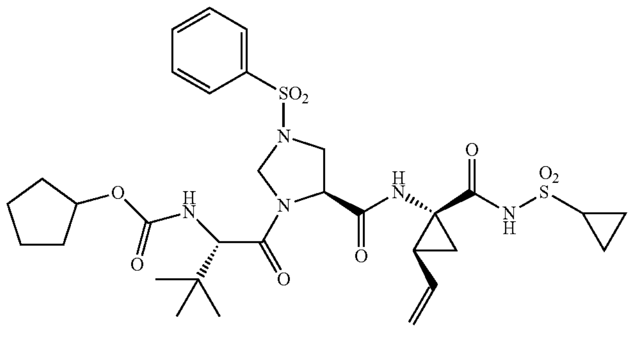 [SMILES: C=C[C@@H]1C[C@]1(NC(=O)[C@@H]1CN(S(=O)(=O)c2ccccc2)CN1C(=O)[C@@H](NC(=O)OC1CCCC1)C(C)(C)C)C(=O)NS(=O)(=O)C1CC1] | 7 | 0.005 |
| 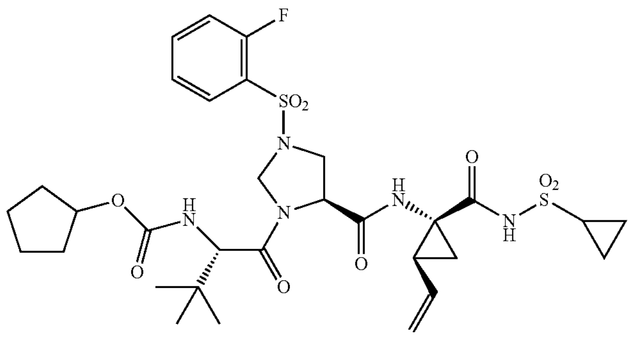 [SMILES: C=C[C@@H]1C[C@]1(NC(=O)[C@@H]1CN(S(=O)(=O)c2ccccc2F)CN1C(=O)[C@@H](NC(=O)OC1CCCC1)C(C)(C)C)C(=O)NS(=O)(=O)C1CC1] | 8 | 0.011 |
| 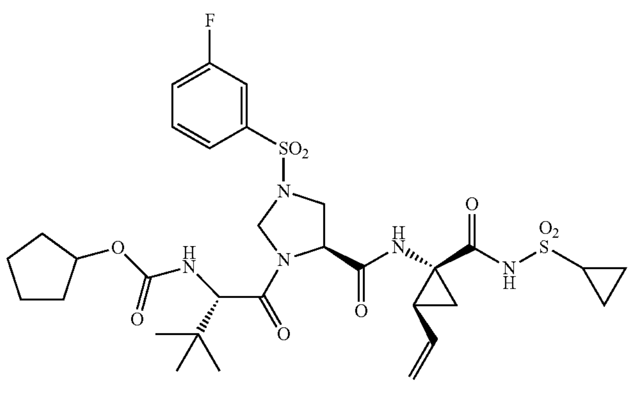 | 9 | 0.014 |
| 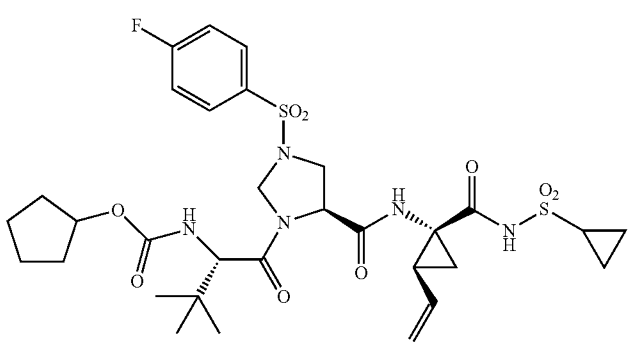 [SMILES: C=C[C@@H]1C[C@]1(NC(=O)[C@@H]1CN(S(=O)(=O)c2ccc(F)cc2)CN1C(=O)[C@@H](NC(=O)OC1CCCC1)C(C)(C)C)C(=O)NS(=O)(=O)C1CC1] | 10 | 0.004 |

TABLE 1-continued

| Structure | Example | IC50 (μM) |
|---|---|---|
| 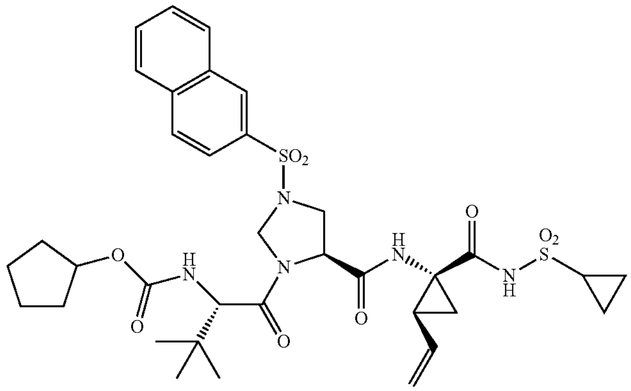 [SMILES: C=C[C@@H]1C[C@]1(NC(=O)[C@@H]1CN(S(=O)(=O)c2ccc3ccccc3c2)CN1C(=O)[C@@H](NC(=O)OC1CCCC1)C(C)(C)C)C(=O)NS(=O)(=O)C1CC1] | 11 | 0.022 |
| 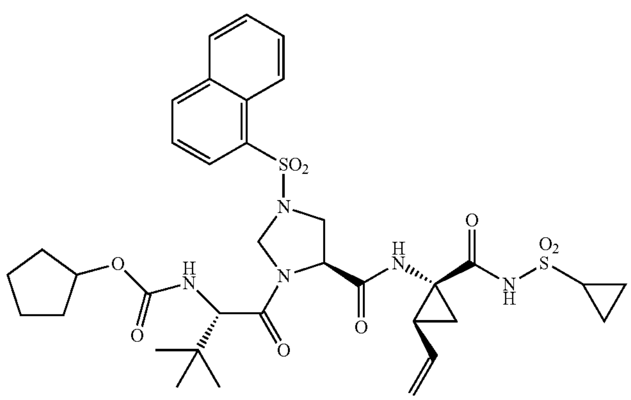 [SMILES: C=C[C@@H]1C[C@]1(NC(=O)[C@@H]1CN(S(=O)(=O)c2cccc3ccccc23)CN1C(=O)[C@@H](NC(=O)OC1CCCC1)C(C)(C)C)C(=O)NS(=O)(=O)C1CC1] | 12 | 0.17 |
| 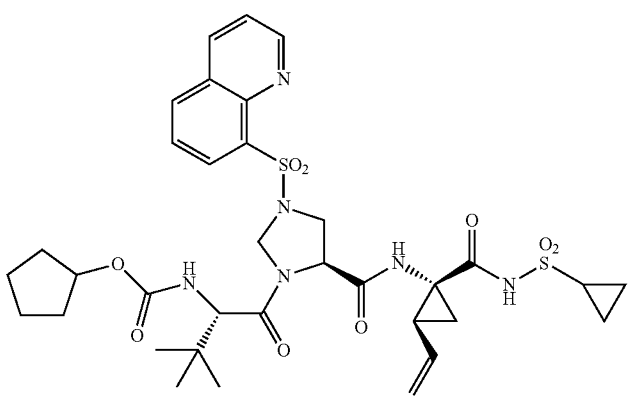 | 13 | 0.16 |
| 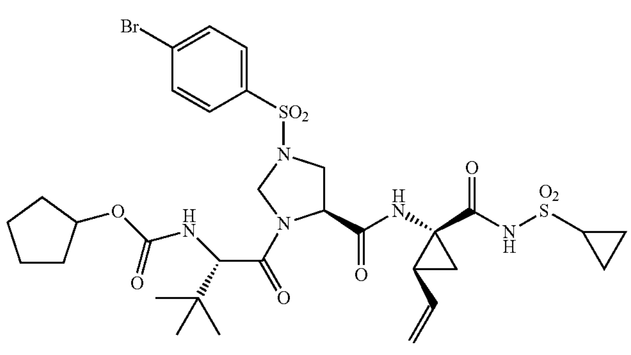 [SMILES: C=C[C@@H]1C[C@]1(NC(=O)[C@@H]1CN(S(=O)(=O)c2ccc(Br)cc2)CN1C(=O)[C@@H](NC(=O)OC1CCCC1)C(C)(C)C)C(=O)NS(=O)(=O)C1CC1] | 14 | 0.002 |

TABLE 1-continued
| Structure | Example | IC50 (μM) |
|---|---|---|
| 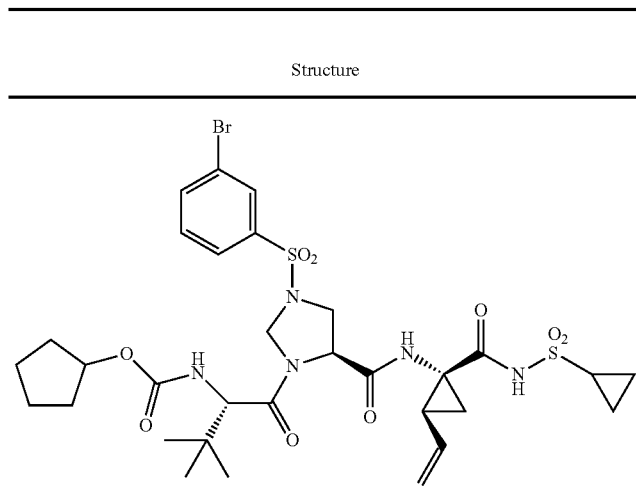 | 15 | 0.032 |
| 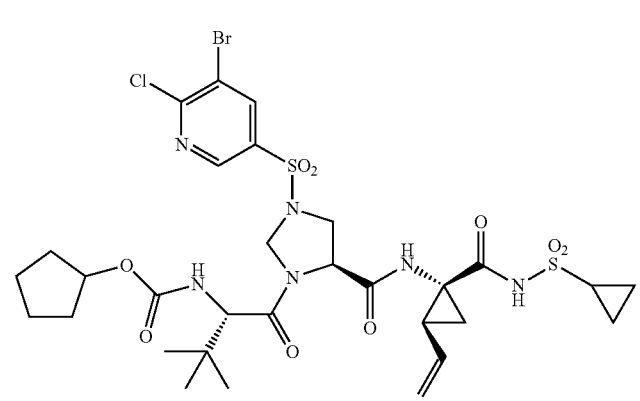 [SMILES: C=C[C@@H]1C[C@]1(NC(=O)[C@@H]1CN(S(=O)(=O)c2cnc(Cl)c(Br)c2)CN1C(=O)[C@@H](NC(=O)OC1CCCC1)C(C)(C)C)C(=O)NS(=O)(=O)C1CC1] | 16 | 0.068 |
| 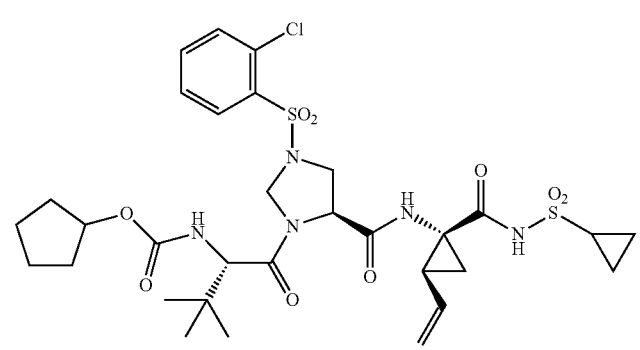 | 17 | 0.016 |
| 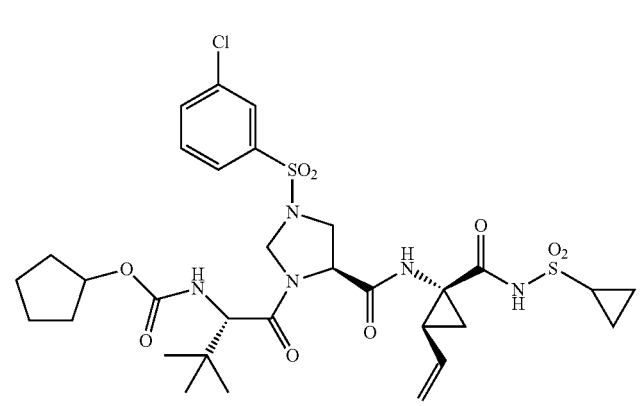 | 18 | 0.028 |

TABLE 1-continued
| Structure | Example | IC50 (μM) |
|---|---|---|
| 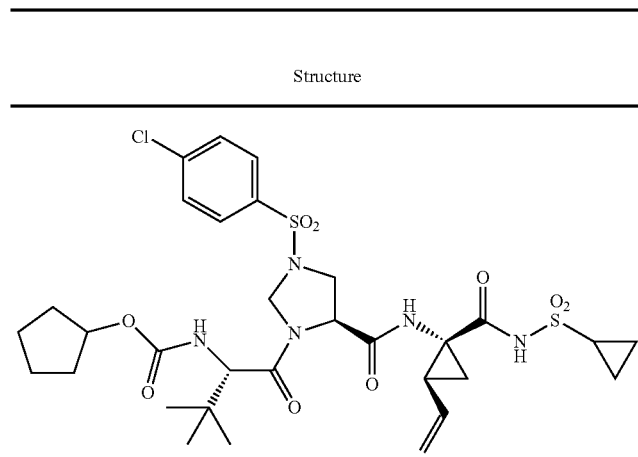 | 19 | 0.002 |
| 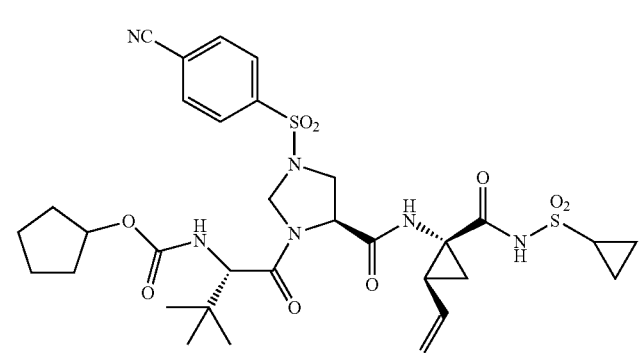 [SMILES: C=C[C@@H]1C[C@]1(NC(=O)[C@@H]1CN(S(=O)(=O)c2ccc(Cl)cc2)CN1C(=O)[C@@H](NC(=O)OC1CCCC1)C(C)(C)C)C(=O)NS(=O)(=O)C1CC1] | 20 | 0.006 |
| 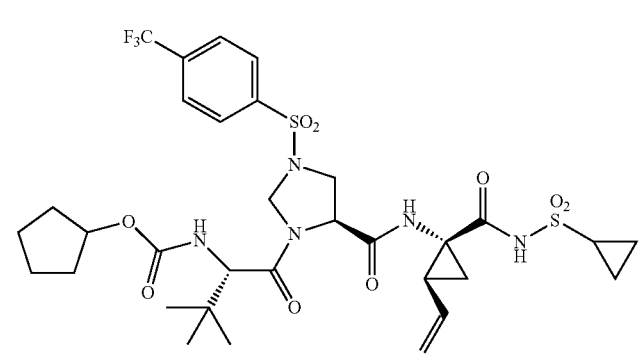 | 21 | 0.004 |
| 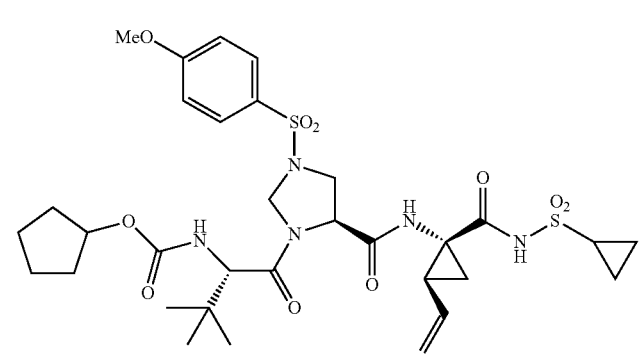 [SMILES: C=C[C@@H]1C[C@]1(NC(=O)[C@@H]1CN(S(=O)(=O)c2ccc(OC)cc2)CN1C(=O)[C@@H](NC(=O)OC1CCCC1)C(C)(C)C)C(=O)NS(=O)(=O)C1CC1] | 22 | 0.002 |

TABLE 1-continued
| Structure | Example | IC50 (μM) |
|---|---|---|
| 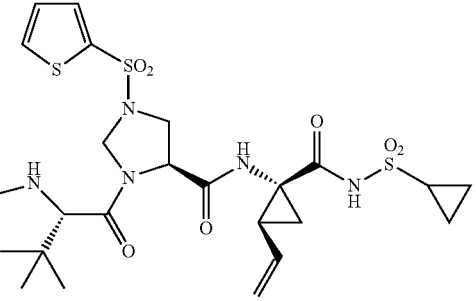 | 23 | 0.006 |
| 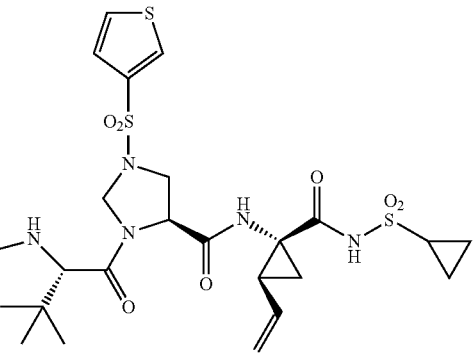 | 24 | 0.003 |
| 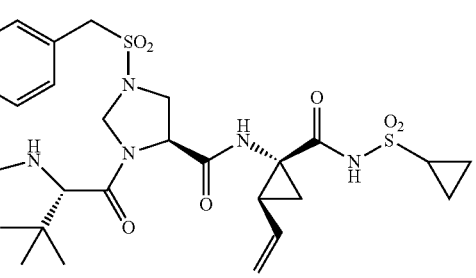 | 25 | 0.014 |
| 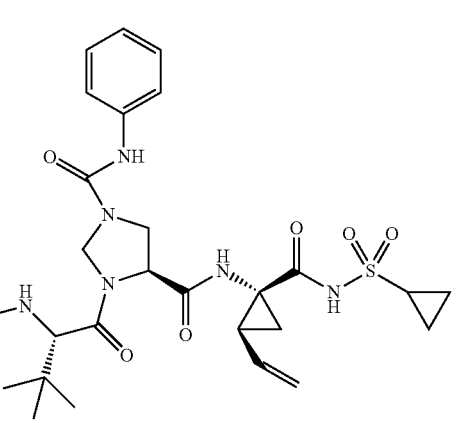 | 26 | 0.64 |

TABLE 1-continued

| Structure | Example | IC50 (μM) |
|---|---|---|
| 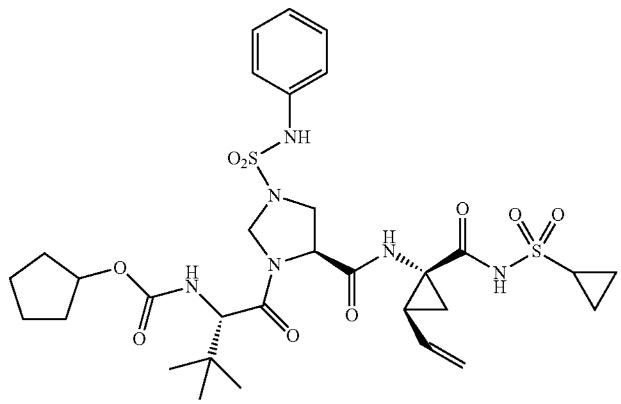 [SMILES: C=C[C@@H]1C[C@]1(NC(=O)[C@@H]1CN(S(=O)(=O)Nc2ccccc2)CN1C(=O)[C@@H](NC(=O)OC1CCCC1)C(C)(C)C)C(=O)NS(=O)(=O)C1CC1] | 27 | 0.061 |
| 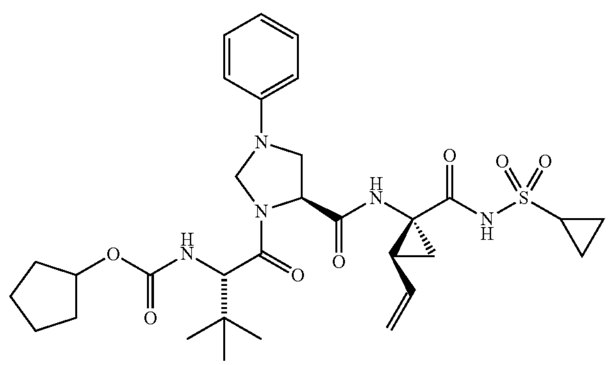 [SMILES: C=C[C@@H]1C[C@]1(NC(=O)[C@@H]1CN(c2ccccc2)CN1C(=O)[C@@H](NC(=O)OC1CCCC1)C(C)(C)C)C(=O)NS(=O)(=O)C1CC1] | 28 | 0.019 |
| 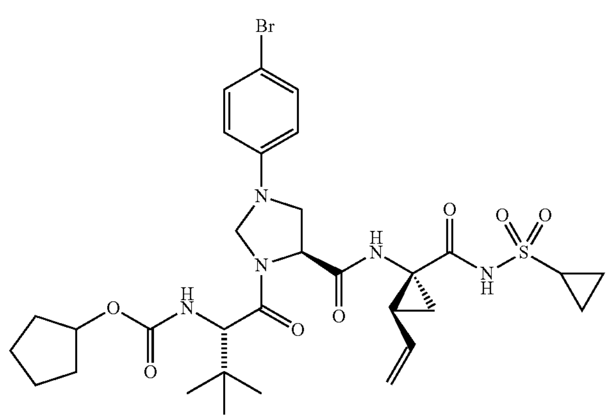 [SMILES: C=C[C@@H]1C[C@]1(NC(=O)[C@@H]1CN(c2ccc(Br)cc2)CN1C(=O)[C@@H](NC(=O)OC1CCCC1)C(C)(C)C)C(=O)NS(=O)(=O)C1CC1] | 29 | 0.041 |

TABLE 1-continued

| Structure | Example | IC50 (μM) |
|---|---|---|
| 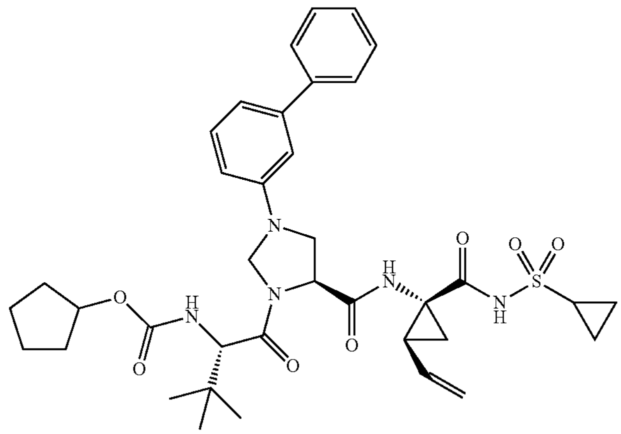 [SMILES: C=C[C@@H]1C[C@]1(NC(=O)[C@@H]1CN(c2cccc(-c3ccccc3)c2)CN1C(=O)[C@@H](NC(=O)OC1CCCC1)C(C)(C)C)C(=O)NS(=O)(=O)C1CC1] | 30 | 0.013 |
| 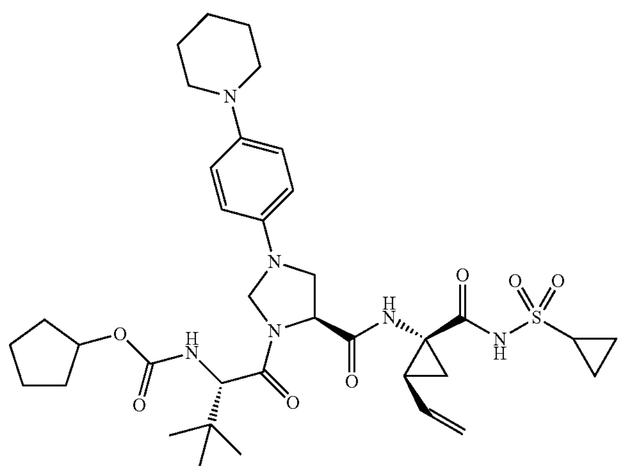 [SMILES: C=C[C@@H]1C[C@]1(NC(=O)[C@@H]1CN(c2ccc(N3CCCCC3)cc2)CN1C(=O)[C@@H](NC(=O)OC1CCCC1)C(C)(C)C)C(=O)NS(=O)(=O)C1CC1] | 31 | 0.009 |
| 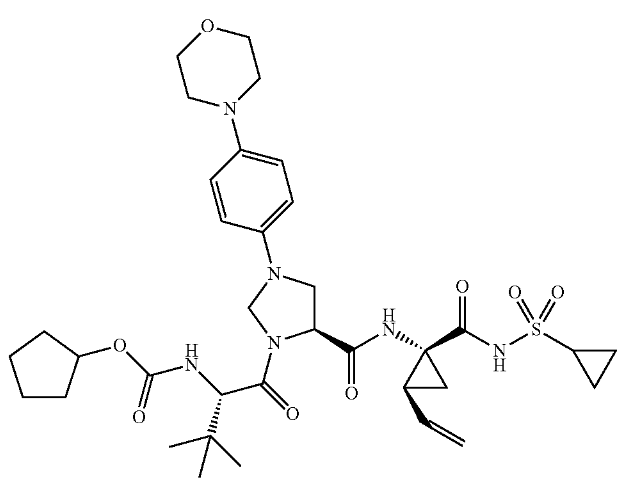 [SMILES: C=C[C@@H]1C[C@]1(NC(=O)[C@@H]1CN(c2ccc(N3CCOCC3)cc2)CN1C(=O)[C@@H](NC(=O)OC1CCCC1)C(C)(C)C)C(=O)NS(=O)(=O)C1CC1] | 32 | 0.01 |

TABLE 1-continued

| Structure | Example | IC50 (μM) |
|---|---|---|
| 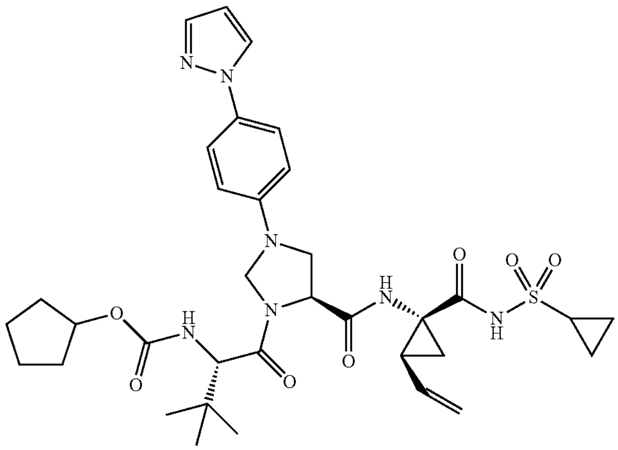 [SMILES: C=C[C@@H]1C[C@]1(NC(=O)[C@@H]1CN(c2ccc(-n3cccn3)cc2)CN1C(=O)[C@@H](NC(=O)OC1CCCC1)C(C)(C)C)C(=O)NS(=O)(=O)C1CC1] | 33 | 0.009 |
| 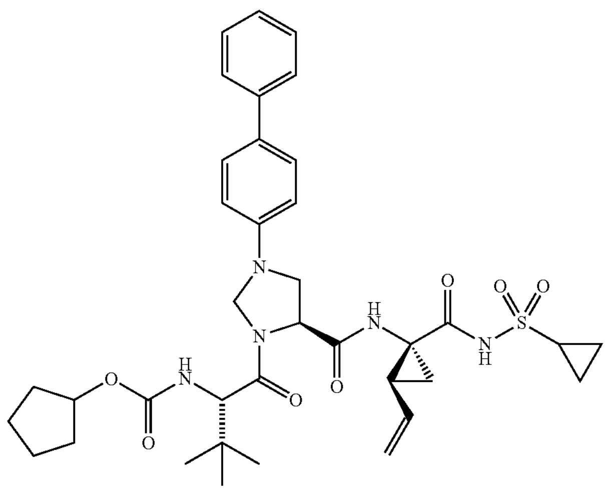 [SMILES: C=C[C@@H]1C[C@]1(NC(=O)[C@@H]1CN(c2ccc(-c3ccccc3)cc2)CN1C(=O)[C@@H](NC(=O)OC1CCCC1)C(C)(C)C)C(=O)NS(=O)(=O)C1CC1] | 34 | 0.002 |
| 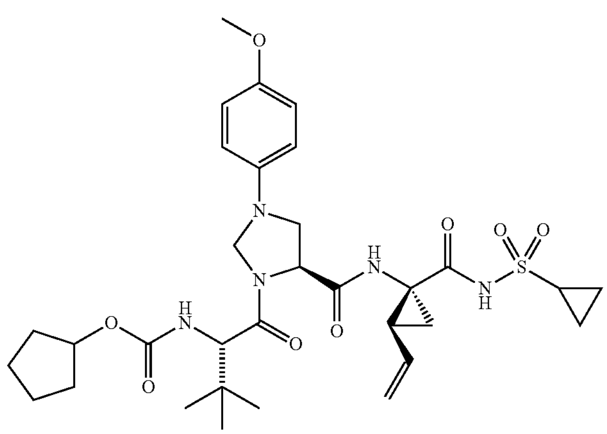 [SMILES: C=C[C@@H]1C[C@]1(NC(=O)[C@@H]1CN(c2ccc(OC)cc2)CN1C(=O)[C@@H](NC(=O)OC1CCCC1)C(C)(C)C)C(=O)NS(=O)(=O)C1CC1] | 35 | 0.012 |

TABLE 1-continued

| Structure | Example | IC50 (μM) |
|---|---|---|
| 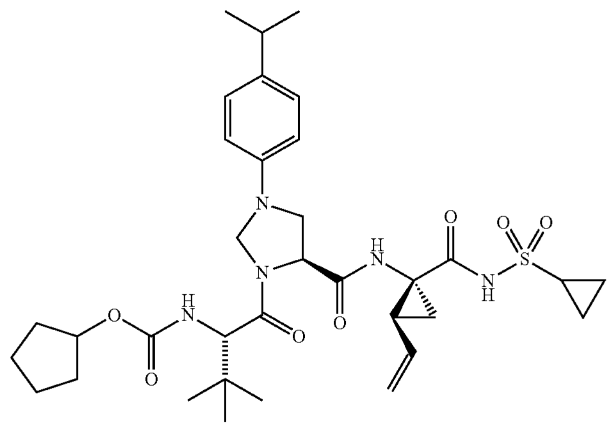 [SMILES: C=C[C@@H]1C[C@]1(NC(=O)[C@@H]1CN(c2ccc(C(C)C)cc2)CN1C(=O)[C@@H](NC(=O)OC1CCCC1)C(C)(C)C)C(=O)NS(=O)(=O)C1CC1] | 36 | 0.016 |
| 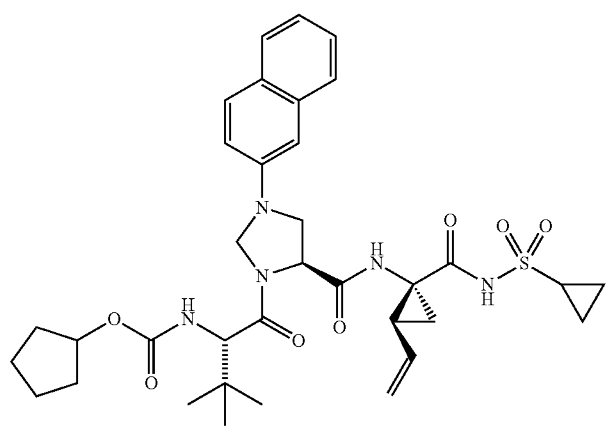 [SMILES: C=C[C@@H]1C[C@]1(NC(=O)[C@@H]1CN(c2ccc3ccccc3c2)CN1C(=O)[C@@H](NC(=O)OC1CCCC1)C(C)(C)C)C(=O)NS(=O)(=O)C1CC1] | 37 | 0.012 |
| 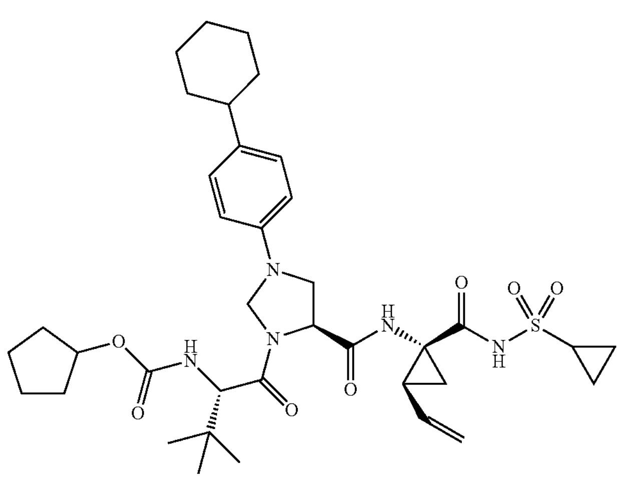 [SMILES: C=C[C@@H]1C[C@]1(NC(=O)[C@@H]1CN(c2ccc(C3CCCCC3)cc2)CN1C(=O)[C@@H](NC(=O)OC1CCCC1)C(C)(C)C)C(=O)NS(=O)(=O)C1CC1] | 38 | 0.005 |

TABLE 1-continued

| Structure | Example | IC50 (μM) |
|---|---|---|
| 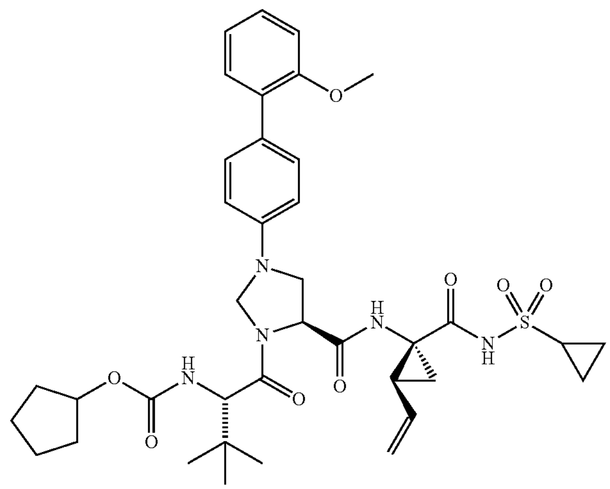 [SMILES: C=C[C@@H]1C[C@]1(NC(=O)[C@@H]1CN(c2ccc(-c3ccccc3OC)cc2)CN1C(=O)[C@@H](NC(=O)OC1CCCC1)C(C)(C)C)C(=O)NS(=O)(=O)C1CC1] | 39 | 0.021 |
| 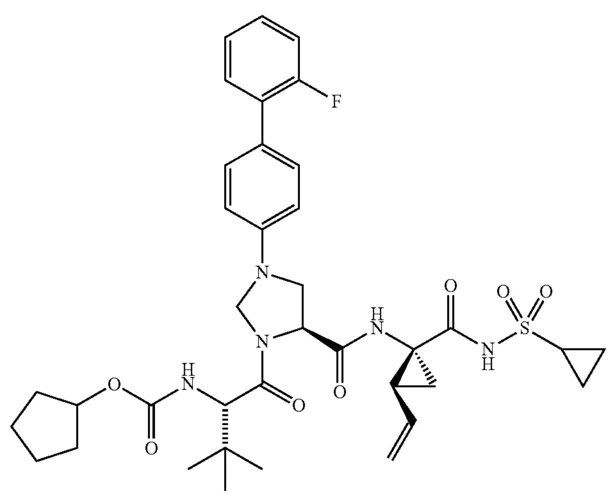 [SMILES: C=C[C@@H]1C[C@]1(NC(=O)[C@@H]1CN(c2ccc(-c3ccccc3F)cc2)CN1C(=O)[C@@H](NC(=O)OC1CCCC1)C(C)(C)C)C(=O)NS(=O)(=O)C1CC1] | 40 | 0.034 |
| 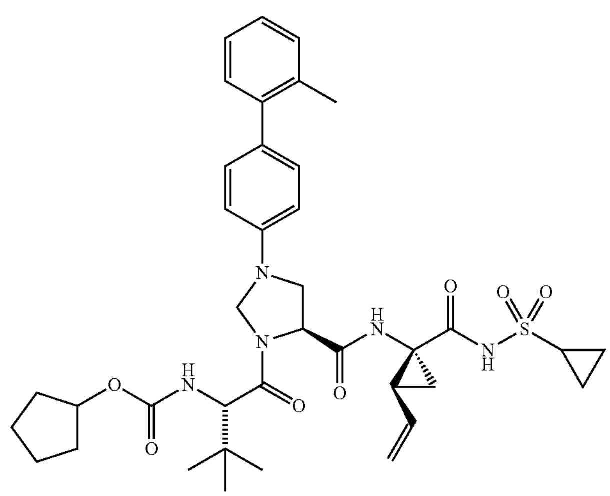 [SMILES: C=C[C@@H]1C[C@]1(NC(=O)[C@@H]1CN(c2ccc(-c3ccccc3C)cc2)CN1C(=O)[C@@H](NC(=O)OC1CCCC1)C(C)(C)C)C(=O)NS(=O)(=O)C1CC1] | 41 | 0.039 |

TABLE 1-continued

| Structure | Example | IC50 (μM) |
|---|---|---|
| 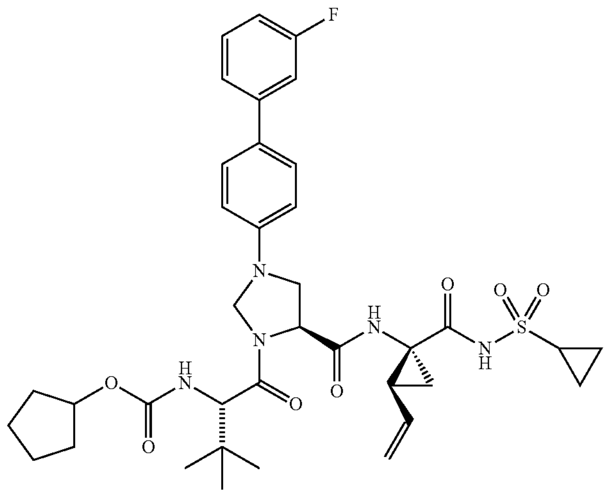 [SMILES: C=C[C@@H]1C[C@]1(NC(=O)[C@@H]1CN(c2ccc(-c3cccc(F)c3)cc2)CN1C(=O)[C@@H](NC(=O)OC1CCCC1)C(C)(C)C)C(=O)NS(=O)(=O)C1CC1] | 42 | 0.082 |
| 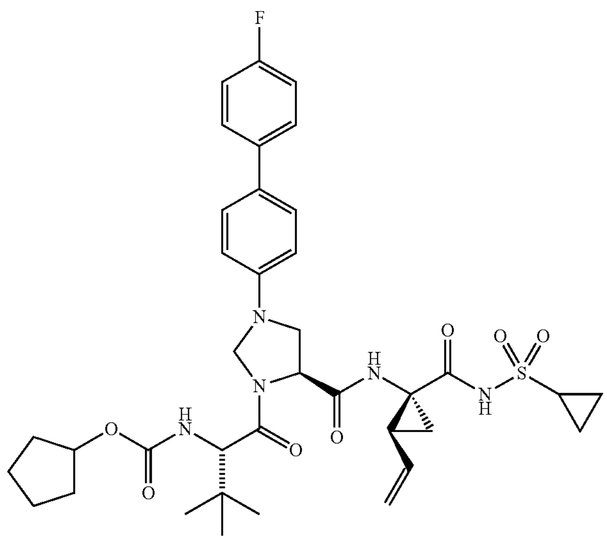 [SMILES: C=C[C@@H]1C[C@]1(NC(=O)[C@@H]1CN(c2ccc(-c3ccc(F)cc3)cc2)CN1C(=O)[C@@H](NC(=O)OC1CCCC1)C(C)(C)C)C(=O)NS(=O)(=O)C1CC1] | 43 | 0.045 |
| 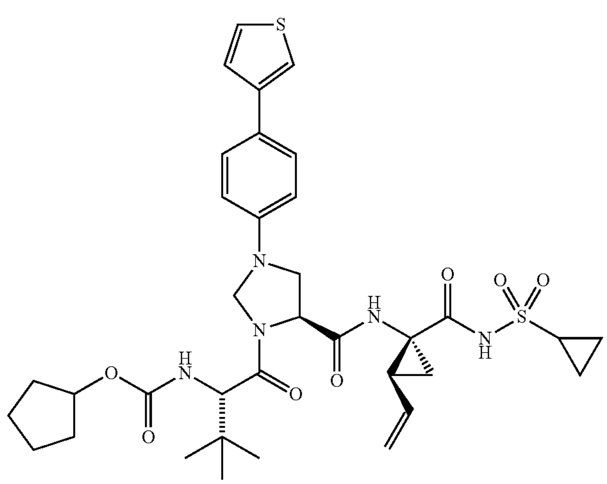 [SMILES: C=C[C@@H]1C[C@]1(NC(=O)[C@@H]1CN(c2ccc(-c3ccsc3)cc2)CN1C(=O)[C@@H](NC(=O)OC1CCCC1)C(C)(C)C)C(=O)NS(=O)(=O)C1CC1] | 44 | 0.04 |

TABLE 1-continued

| Structure | Example | IC50 (μM) |
|---|---|---|
| 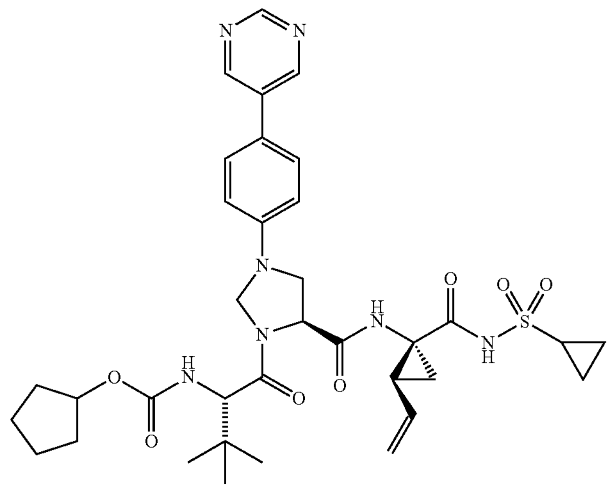 [SMILES: C=C[C@@H]1C[C@]1(NC(=O)[C@@H]1CN(c2ccc(-c3cncnc3)cc2)CN1C(=O)[C@@H](NC(=O)OC1CCCC1)C(C)(C)C)C(=O)NS(=O)(=O)C1CC1] | 45 | 45 |
| 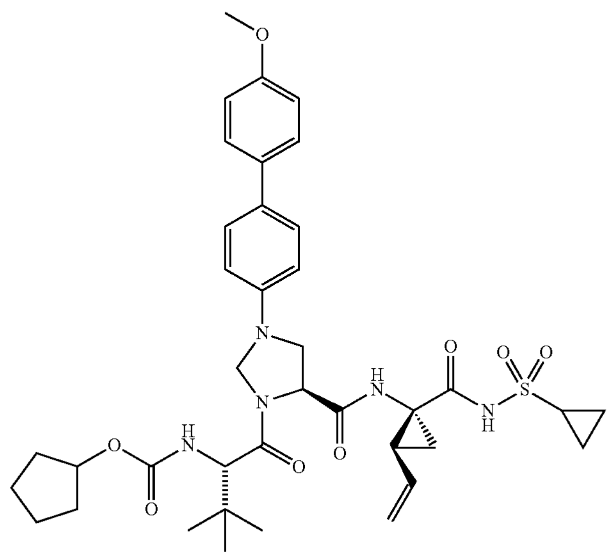 [SMILES: C=C[C@@H]1C[C@]1(NC(=O)[C@@H]1CN(c2ccc(-c3ccc(OC)cc3)cc2)CN1C(=O)[C@@H](NC(=O)OC1CCCC1)C(C)(C)C)C(=O)NS(=O)(=O)C1CC1] | 46 | 0.066 |
| 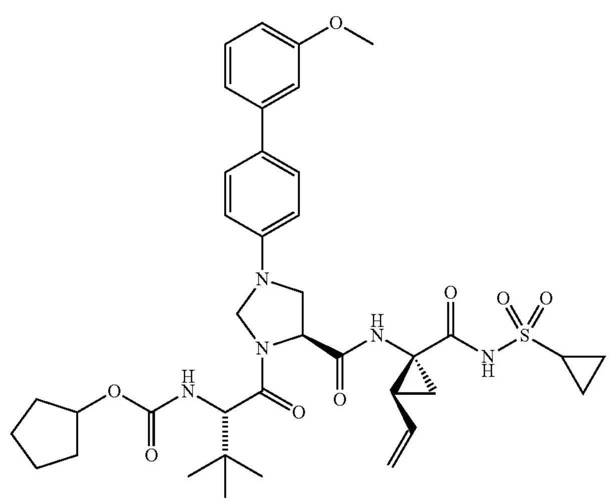 [SMILES: C=C[C@@H]1C[C@]1(NC(=O)[C@@H]1CN(c2ccc(-c3cccc(OC)c3)cc2)CN1C(=O)[C@@H](NC(=O)OC1CCCC1)C(C)(C)C)C(=O)NS(=O)(=O)C1CC1] | 47 | 0.11 |

TABLE 1-continued
| Structure | Example | IC50 (μM) |
|---|---|---|
| 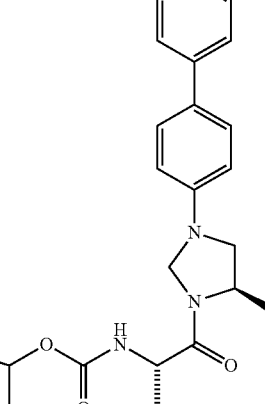 | 48 | 0.028 |
| 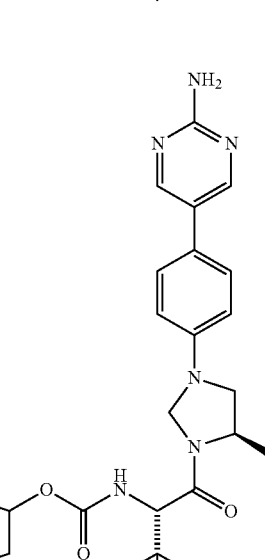 | 49 | 16 |
| 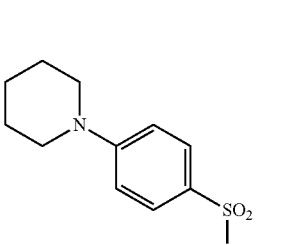 | 50 | 0.003 |

TABLE 1-continued
| Structure | Example | IC50 (μM) |
|---|---|---|
| 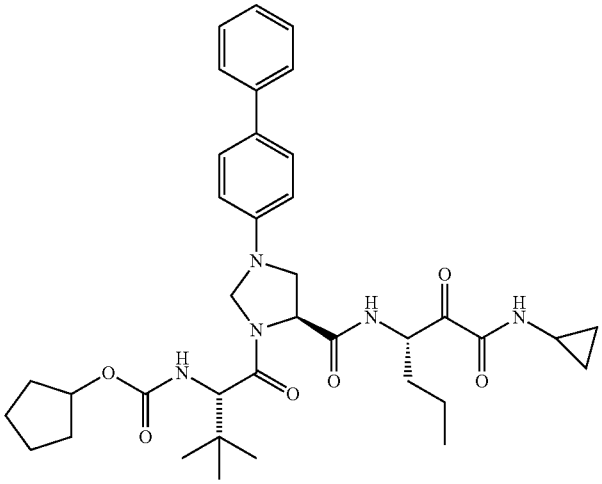 [SMILES: CCC[C@H](NC(=O)[C@@H]1CN(c2ccc(-c3ccccc3)cc2)CN1C(=O)[C@@H](NC(=O)OC1CCCC1)C(C)(C)C)C(=O)C(=O)NC1CC1] | 51 | 0.94 |
| 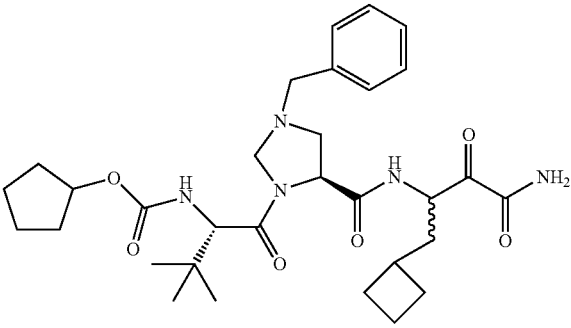 [SMILES: CC(C)(C)[C@H](NC(=O)OC1CCCC1)C(=O)N1CN(Cc2ccccc2)C[C@H]1C(=O)NC(CC1CCC1)C(=O)C(N)=O] | 52 | 4.2 |
| 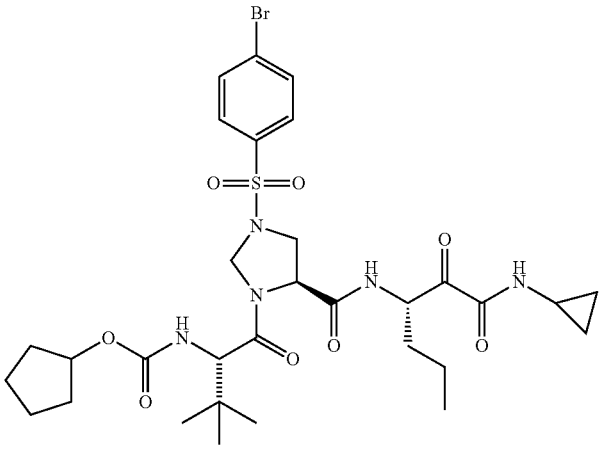 [SMILES: CCC[C@H](NC(=O)[C@@H]1CN(S(=O)(=O)c2ccc(Br)cc2)CN1C(=O)[C@@H](NC(=O)OC1CCCC1)C(C)(C)C)C(=O)C(=O)NC1CC1] | 53 | 0.5 |

TABLE 1-continued

| Structure | Example | IC50 (μM) |
|---|---|---|
| 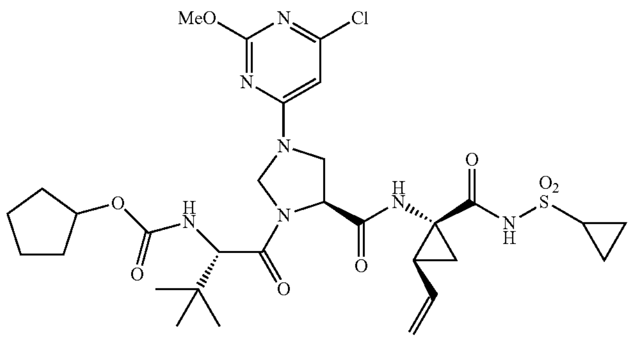 [SMILES: C=C[C@@H]1C[C@]1(NC(=O)[C@@H]1CN(c2cc(Cl)nc(OC)n2)CN1C(=O)[C@@H](NC(=O)OC1CCCC1)C(C)(C)C)C(=O)NS(=O)(=O)C1CC1] | 54 | 1 |
| 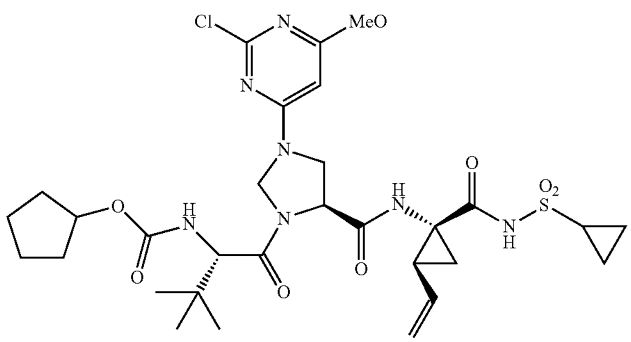 [SMILES: C=C[C@@H]1C[C@]1(NC(=O)[C@@H]1CN(c2cc(OC)nc(Cl)n2)CN1C(=O)[C@@H](NC(=O)OC1CCCC1)C(C)(C)C)C(=O)NS(=O)(=O)C1CC1] | 55 | 1.09 |
| 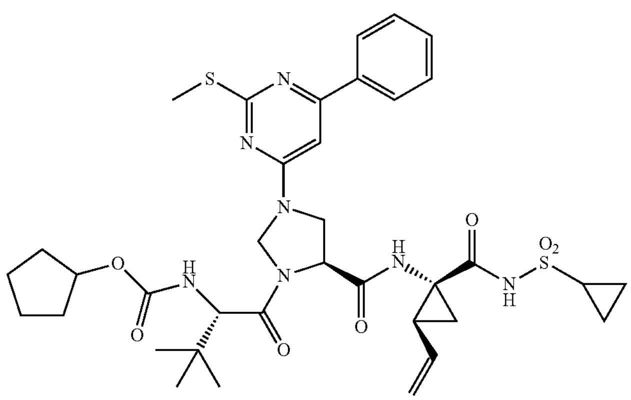 [SMILES: C=C[C@@H]1C[C@]1(NC(=O)[C@@H]1CN(c2cc(-c3ccccc3)nc(SC)n2)CN1C(=O)[C@@H](NC(=O)OC1CCCC1)C(C)(C)C)C(=O)NS(=O)(=O)C1CC1] | 56 | 3.4 |
| 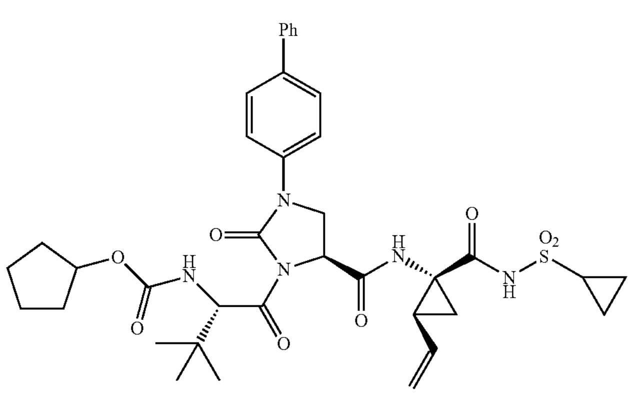 [SMILES: C=C[C@@H]1C[C@]1(NC(=O)[C@@H]1CN(c2ccc(-c3ccccc3)cc2)C(=O)N1C(=O)[C@@H](NC(=O)OC1CCCC1)C(C)(C)C)C(=O)NS(=O)(=O)C1CC1] | 57 | 0.61 |

TABLE 1-continued
| Structure | Example | IC50 (μM) |
|---|---|---|
| 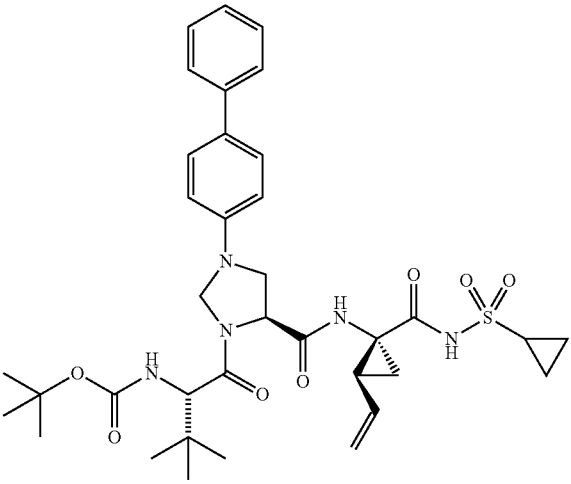 [SMILES: C=C[C@@H]1C[C@]1(NC(=O)[C@@H]1CN(c2ccc(-c3ccccc3)cc2)CN1C(=O)[C@@H](NC(=O)OC(C)(C)C)C(C)(C)C)C(=O)NS(=O)(=O)C1CC1] | 58 | 0.005 |
| 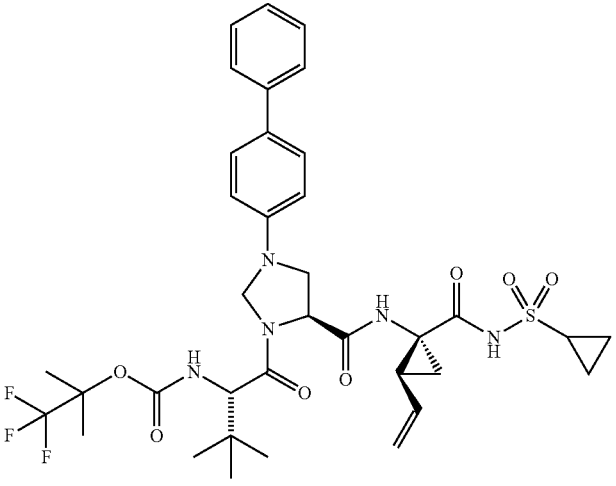 [SMILES: C=C[C@@H]1C[C@]1(NC(=O)[C@@H]1CN(c2ccc(-c3ccccc3)cc2)CN1C(=O)[C@@H](NC(=O)OC(C)(C)C(F)(F)F)C(C)(C)C)C(=O)NS(=O)(=O)C1CC1] | 59 | 0.002 |
| 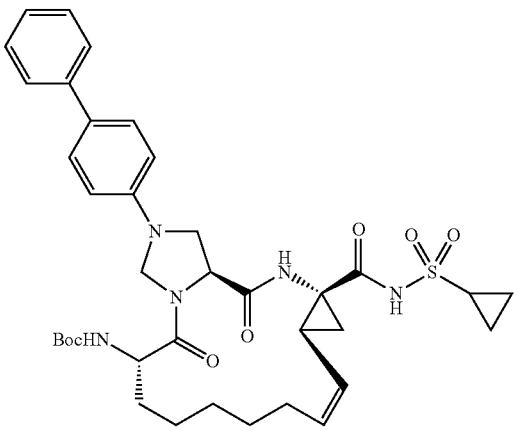 [SMILES: CC(C)(C)OC(=O)N[C@H]1CCCCC/C=C\[C@@H]2C[C@@]2(C(=O)NS(=O)(=O)C2CC2)NC(=O)[C@@H]2CN(c3ccc(-c4ccccc4)cc3)CN2C1=O] | 60 | 0.002 |

TABLE 1-continued

| Structure | Example | IC50 (μM) |
|---|---|---|
| 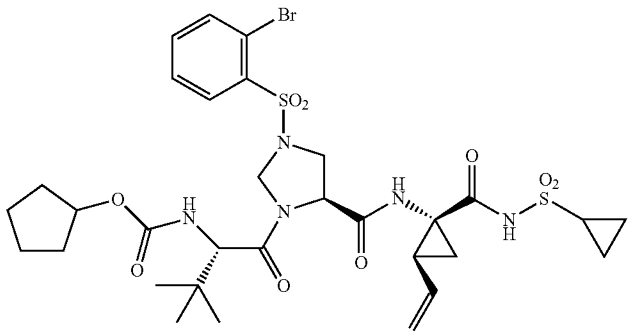 [SMILES: C=C[C@@H]1C[C@]1(NC(=O)[C@@H]1CN(S(=O)(=O)c2ccccc2Br)CN1C(=O)[C@@H](NC(=O)OC1CCCC1)C(C)(C)C)C(=O)NS(=O)(=O)C1CC1] | 61 | 0.02 |
| 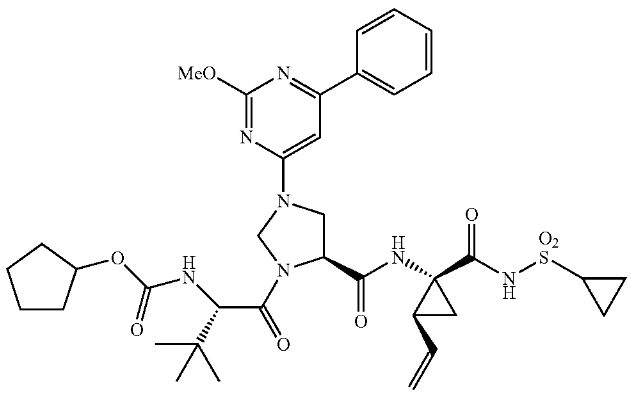 [SMILES: C=C[C@@H]1C[C@]1(NC(=O)[C@@H]1CN(c2cc(-c3ccccc3)nc(OC)n2)CN1C(=O)[C@@H](NC(=O)OC1CCCC1)C(C)(C)C)C(=O)NS(=O)(=O)C1CC1] | 62 | 1.42 |
| 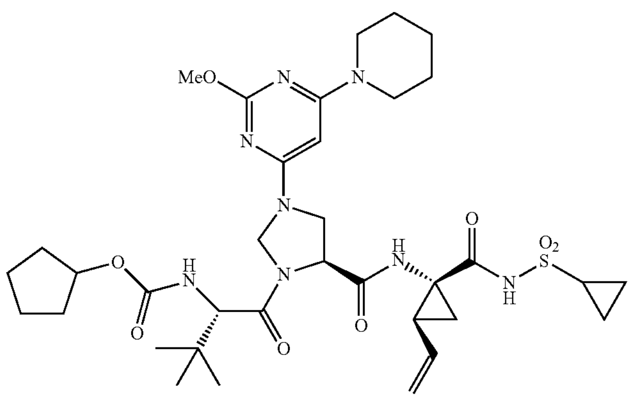 [SMILES: C=C[C@@H]1C[C@]1(NC(=O)[C@@H]1CN(c2cc(N3CCCCC3)nc(OC)n2)CN1C(=O)[C@@H](NC(=O)OC1CCCC1)C(C)(C)C)C(=O)NS(=O)(=O)C1CC1] | 63 | 1.43 |
| 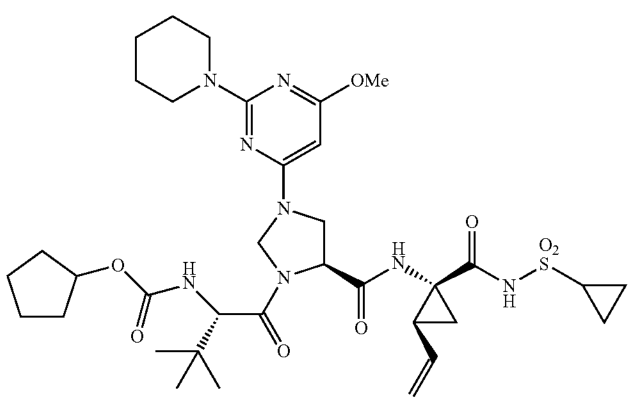 [SMILES: C=C[C@@H]1C[C@]1(NC(=O)[C@@H]1CN(c2cc(OC)nc(N3CCCCC3)n2)CN1C(=O)[C@@H](NC(=O)OC1CCCC1)C(C)(C)C)C(=O)NS(=O)(=O)C1CC1] | 64 | 1.15 |

TABLE 1-continued

| Structure | Example | IC50 (μM) |
|---|---|---|
| 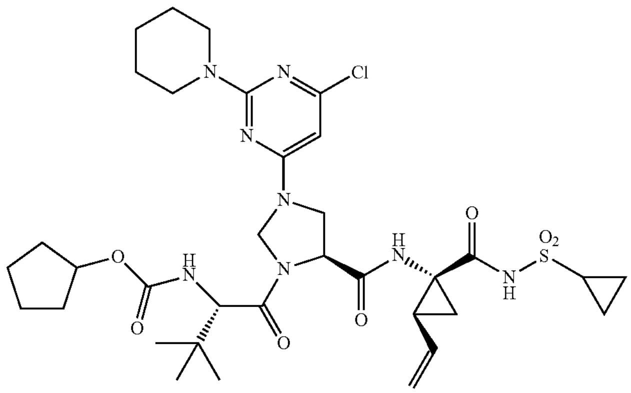 [SMILES: C=C[C@@H]1C[C@]1(NC(=O)[C@@H]1CN(c2cc(Cl)nc(N3CCCCC3)n2)CN1C(=O)[C@@H](NC(=O)OC1CCCC1)C(C)(C)C)C(=O)NS(=O)(=O)C1CC1] | 65 | 0.95 |
| 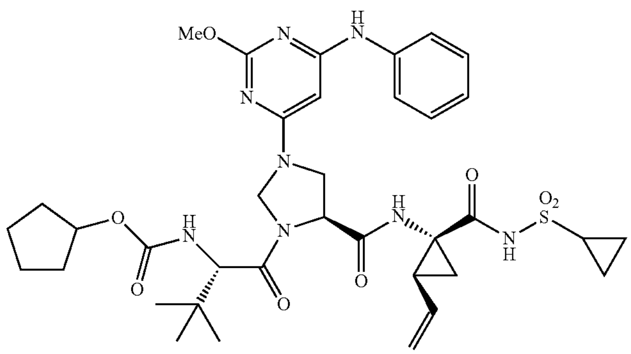 [SMILES: C=C[C@@H]1C[C@]1(NC(=O)[C@@H]1CN(c2cc(Nc3ccccc3)nc(OC)n2)CN1C(=O)[C@@H](NC(=O)OC1CCCC1)C(C)(C)C)C(=O)NS(=O)(=O)C1CC1] | 66 | 0.61 |
| 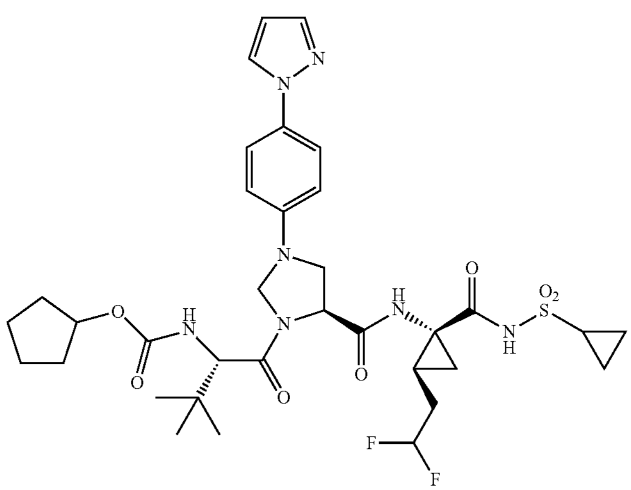 [SMILES: CC(C)(C)[C@H](NC(=O)OC1CCCC1)C(=O)N1CN(c2ccc(-n3cccn3)cc2)C[C@H]1C(=O)N[C@]1(C(=O)NS(=O)(=O)C2CC2)C[C@H]1CC(F)F] | 67 | |

TABLE 1-continued

| Structure | Example | IC50 (μM) |
|---|---|---|
| 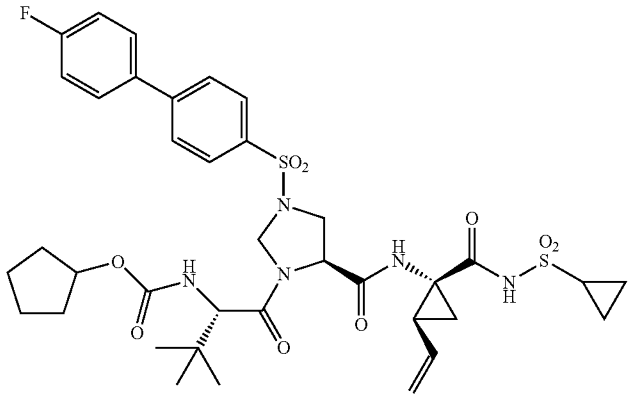 [SMILES: C=C[C@@H]1C[C@]1(NC(=O)[C@@H]1CN(S(=O)(=O)c2ccc(-c3ccc(F)cc3)cc2)CN1C(=O)[C@@H](NC(=O)OC1CCCC1)C(C)(C)C)C(=O)NS(=O)(=O)C1CC1] | 68 | |
| 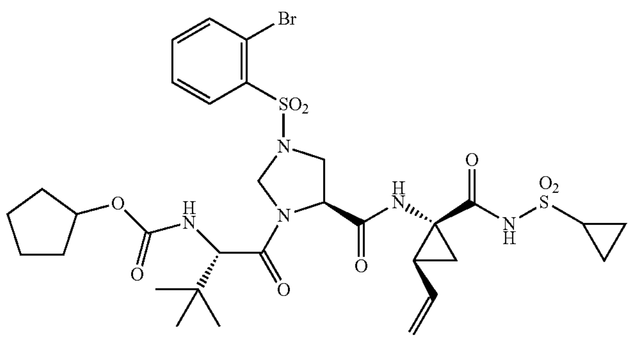 | 69 | |
| 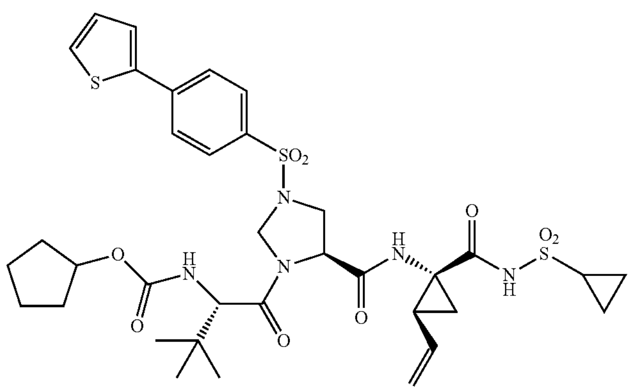 [SMILES: C=C[C@@H]1C[C@]1(NC(=O)[C@@H]1CN(S(=O)(=O)c2ccc(-c3cccs3)cc2)CN1C(=O)[C@@H](NC(=O)OC1CCCC1)C(C)(C)C)C(=O)NS(=O)(=O)C1CC1] | 70 | |
| 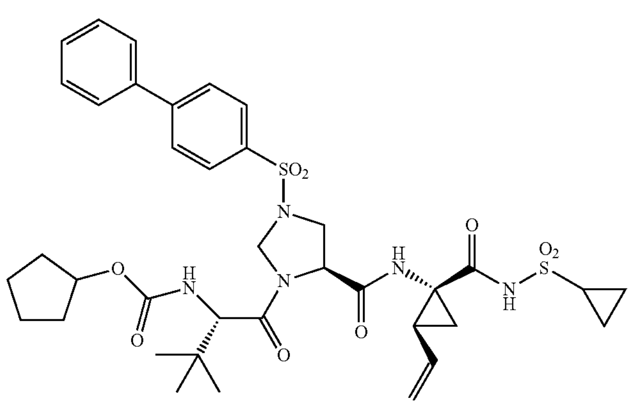 [SMILES: C=C[C@@H]1C[C@]1(NC(=O)[C@@H]1CN(S(=O)(=O)c2ccc(-c3ccccc3)cc2)CN1C(=O)[C@@H](NC(=O)OC1CCCC1)C(C)(C)C)C(=O)NS(=O)(=O)C1CC1] | 71 | |

TABLE 1-continued
| Structure | Example | IC50 (μM) |
|---|---|---|
| 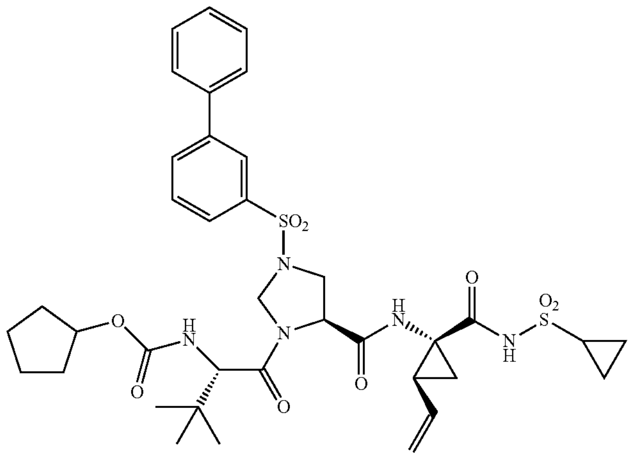 [SMILES: C=C[C@@H]1C[C@]1(NC(=O)[C@@H]1CN(S(=O)(=O)c2cccc(-c3ccccc3)c2)CN1C(=O)[C@@H](NC(=O)OC1CCCC1)C(C)(C)C)C(=O)NS(=O)(=O)C1CC1] | 72 | |
| 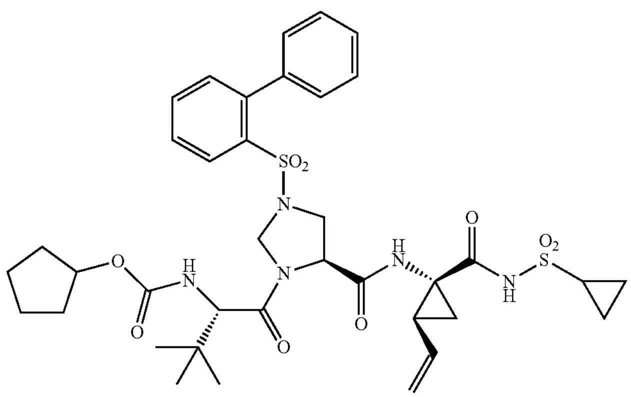 [SMILES: C=C[C@@H]1C[C@]1(NC(=O)[C@@H]1CN(S(=O)(=O)c2ccccc2-c2ccccc2)CN1C(=O)[C@@H](NC(=O)OC1CCCC1)C(C)(C)C)C(=O)NS(=O)(=O)C1CC1] | 73 | |
EXAMPLES
Section A: Preparation of Intermediates
1. Preparation of 1-Benzyl-3-(2-cyclopentyloxycarbonylamino-3,3-dimethyl-butyryl)-imidazolidine-4-carboxylic acid methyl ester
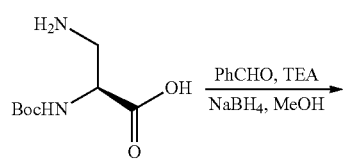
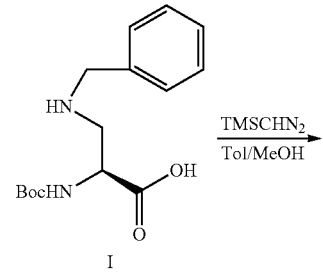
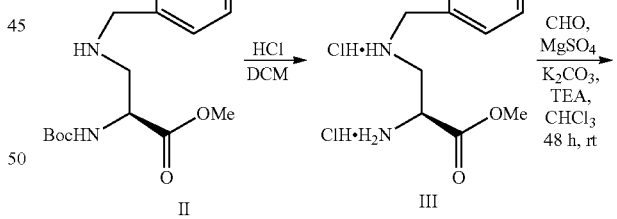
-continued
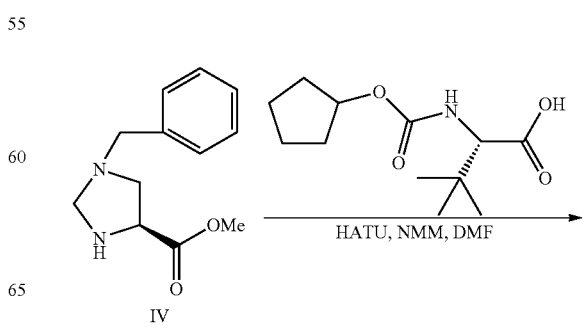

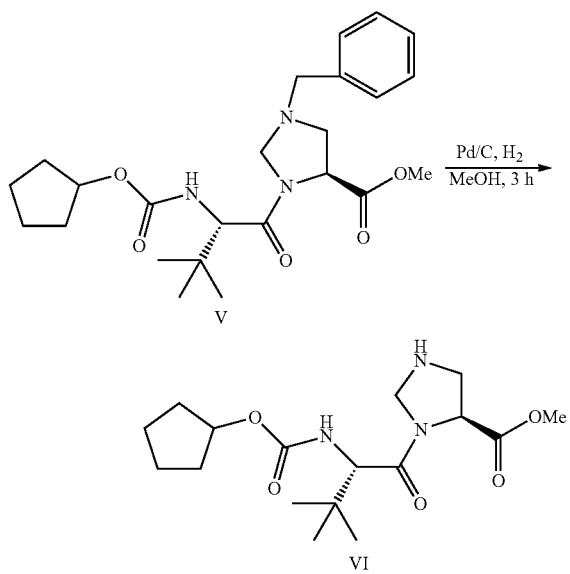

Step 1:

To a suspension of Boc-DAP-OH (5.0 g, 24.5 mmol) in MeOH (50 mL) at room temperature was added benzaldehyde (5.2 g, 49.0 mmol) and TEA (10.2 ml, 73.5 mmol) and the solution was stirred at room temperature for 1 h. The reaction mixture was cooled to 0° C. and solid NaBH$_4$ (4.65 g, 73.5 mmol) was added. After stirring the reaction mixture for 40 minutes, solvent was removed under vacuum and the residue was dissolved in NaOH (0.1N) and extracted with Et$_2$O (3×) where the organic layer was discarded. The aqueous layer was adjusted to pH=6 by HCl (10%) and extracted with CHCl$_3$. The organic layer was washed with brine, dried over MgSO$_4$, and coned in vacuo. The crude solid I (6.1 g) was used directly without purification. LCMS (M+1)=295.00

Step 2:

To a solution of acid I (6.1 g, 21 mmol) in toluene (20 mL) and MeOH (40 mL) at 0° C. was added TMSCHN$_2$ (17 mL, 2N in Hexane, 33 mmol). After stirring the reaction mixture for 15 minutes, solvent and excess amount of TMSCHN$_2$ were removed under vacuum. The crude compound was purified by silica gel chromatography to provide 3.73 g of II in 49% yield over two steps.

$^1$H NMR (300 MHz, CDCl$_3$) d: 8.33-7.23 (m, 5H), 5.52 (d, 1H), 4.40 (dd, 1H), 3.76 (d, 2H), 3.72 (s, 1H), 2.97 (d, 2H), 1.45 (s, 9H) LCMS (M+1)=309.17.

Step 3:

To a solution of compound II (3.73 g, 12.10 mmol) in DCM (20 ml) was added HCl (4N in dioxane, 60 ml, 240 mmol). After stirring at room temperature for 4 hours the reaction mixture was concentrated under vacuum to afford 3.0 g product III in 92% yield.

$^1$H NMR (300 MHz, CD$_3$OD) d: 7.63 (d, 2H), 7.46 (m, 3H), 4.65 (dd, 1H), 4.39 (s, 2H), 3.92 (s, 3H), 3.76 (m, 1H), 3.58 (m, 1H), 3.35 (d, 2H)

LCMS (M+1)=209.07

Step 4:

To a solution of compound III (2.0 g, 7.1 mmol) in CHCl$_3$ (20 ml) was added, in the following order, paraformaldehyde (0.21 g, 7.1 mmol), MgSO$_4$ (2.0 g), K$_2$CO$_3$ (2.0 g) and TEA (3.9 ml, 142.0 mmol). The mixture was stirred for 48 hours at room temperature then filtered and concentrated in vacuo to provide crude xx g of IV in xx % yield.

Step 5:

To a solution of IV in DMF (15 ml) was added 2-cyclopentyloxycarbonylamino-3,3-dimethyl-butyric acid (2.6 g, 11 mmol), HATU (6.7 g, 17.6 mmol), and NMM (3.9 ml, 35.5 mmol). The mixture was stirred at rt overnight then diluted with EtOAc and washed with 2N HCl, 2% LiCl, satd NaHCO$_3$, brine, dried over MgSO$_4$, and concentrated in vacuo. The crude residue was purified by silica-gel chromatography to afford 2.35 g of V as a white solid in 74% yield.

$^1$H NMR (300MHz, CDCl$_3$) d: 7.32 (m, 5H), 5.33 (d, 1H), 5.06 (bs, 1H), 4.60 (m, 2H), 4.36 (d, 1H), 4.12 (m, 1H), 3.69 (m, 5H), 3.21 (m, 1H), 2.95 (m, 1H), 1.828-1.555 (m, 8H), 1.03 (s, 9H)

LCMS (M+1)=446.20.

Step 6:

To a solution of benzyl azaproline V (200 mg, 0.45 mmol) in MeOH (5 mL) was added 10% Pd/C (40 mg). The resulting mixture was evacuated and purged with H$_2$ (3×) and stirred at rt for 2 hours. The mixture was filtered and concentrated in vacuo, affording 159 mg of amine VI as a white solid in 100% yield.

$^1$H NMR (300 MHz, CD3OD) d5.02 (s, 1H), 4.50 (d, 1H), 4.40 (dd, 1H), 4.15 (d, 1H), 3.73 (s, 3H), 3.48 (m, 1H), 3.09 (m, 1H), 1.85-1.60 (m, 8H), 1.06 (s, 9H)

LCMS (M+1)=356

2. Preparation of cyclopropanesulfonic acid (1-amino-2-vinyl-cyclopropanecarbonyl)-amide hydrochloride salt

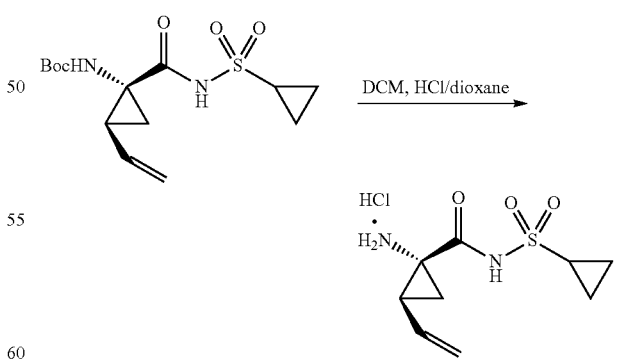

Vinylcyclopropylacylsulfonamide (57 mg, 0.17 mmol) was dissolved in DCM (850 μL) and HCl (4 N in dioxane, 850 μL) was slowly added. After 2 h at rt the solution was concentrated in vacuo and the crude amine salt was used directly in a subsequent reaction. LCMS (M+1): 230.85

Section B: Preparation of Compounds

Example 1

Preparation of Compound 1

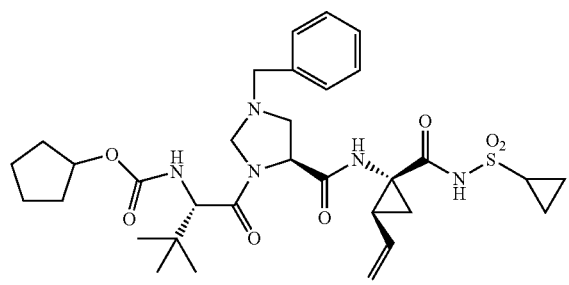

Compound 1

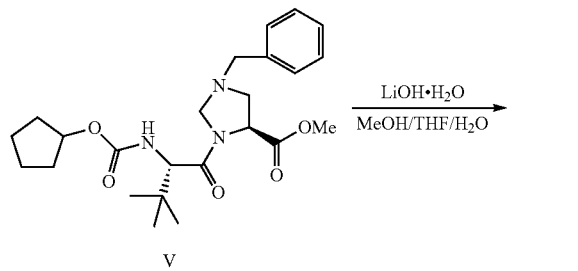

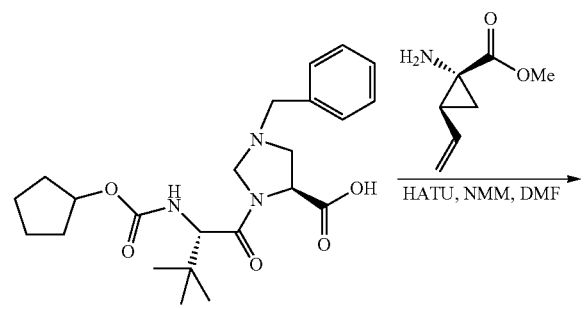

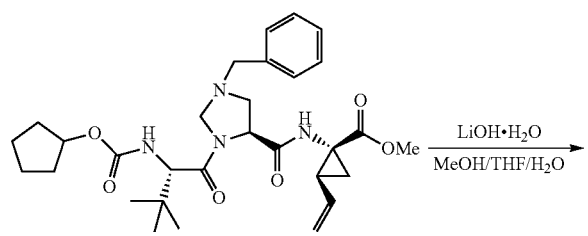

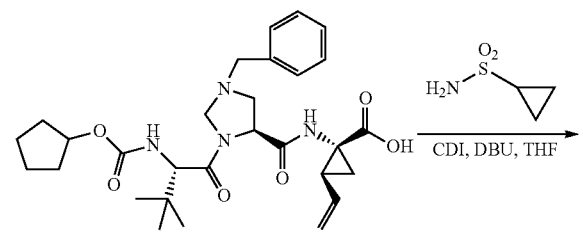

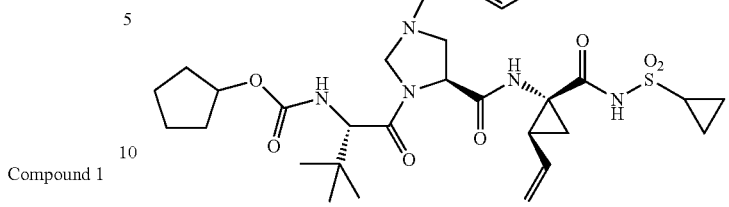

Step 1:

To a solution of methyl ester V (0.42 g, 0.95 mmol) in MeOH (2.0 mL)/THF (2.0 mL) was added LiOH (200 mg, 8.35 mmol) as a solution in H$_2$O (2.0 mL). After stirring at rt for 3 h, the organic solvent was removed in vacuo, and the residue was diluted with EtOAc and the pH adjusted to 2 by HCl (1N). The aqueous phase was extracted with EtOAc and the combined organic phases were washed with brine, dried over Na$_2$SO$_4$, and concentrated in vacuo, affording 400 mg of carboxylic acid VII as a white solid in 98% yield. LCMS (M+1)=432.24.

Step 2:

Acid (0.4 g, 0.92 mmol) was dissolved in DMF (3 ml), amine (0.30 g, 1.7 mmol), HATU (0.9 g, 2.3 mmol) were added, followed by the addition NMM (0.52 ml, 4.8 mmol). The resulting reaction mixture was stirred at room temperature for overnight. The crude reaction solution was diluted with EtOAc and washed with 1N HCl, 5% LiOH, sat. NaHCO$_3$, brine, dried over MgSO$_4$, filtered, and concentrated. The crude material was purified by flash column chromatograph to give a white solid (0.28 g, 0.518 mmol, 56% yield).

$^1$H NMR (300 MHz, CDCl$_3$) d 7.25-7.29 (m, 5H), 5.72 (m, 1H), 5.31-5.07 (m, 3H), 4.53 (m, 2H), 4.31 (d, 1H), 4.14 (d, 1H), 3.74-3.65 (m, 5H), 3.45 (m, 1H), 2.09 (m, 1H), 1.89-1.57 (m, 9H), 1.43 (m, 1H), 1.01 (s, 9H)

LC/MS=555.33 (M$^+$+1)

Step 3:

Methyl ester hydrolysis was carried out by the same procedure as described for step 1.

LC/MS=541.29 (M$^+$+1)

Step 4:

To a solution of acid (68 mg, 0.13 mmol) in THF (2 ml) was added CDI (54 mg, 0.34 mmol). The resulting solution was heated in a microwave at 100° C. for 20 minutes. The reaction mixture was taken out off the microwave and cooled to room temperature. To this reaction mixture was added acylsulonamide (62.5 mg, 0.5 mmol) and DBU (51.8 mg, 0.34 mmol). After stirring at room temperature for 1 h, the mixture was diluted with EtOAc and washed with 0.05 N HCl, dried over MgSO$_4$, filtered, and concentrated. The crude material was purified by preparative HPLC to yield 54 mg (0.084 mmol, 64% yield) of the desired product, Compound I as a white solid.

$^1$H NMR (300 MHz, CDCl$_3$) d 7.43 (m, 5H), 5.80-5.40 (m, 4H), 5.24 (dd, 1H), 5.17-5.03 (m, 3H), 4.81-4.70 (m, 2H), 4.19-4.08 (m, 2H), 3.66 (m, 1H), 3.40 (m, 1H), 2.93 (m, 1H), 1.92-1.56 (m, 10H), 1.39 (m, 2H), 1.08-0.9 (m, 2H), 1.01 (s, 9H)

LC/MS=644.20 (M$^+$+1)

Example 2

Preparation of Compound 2

Compound 2

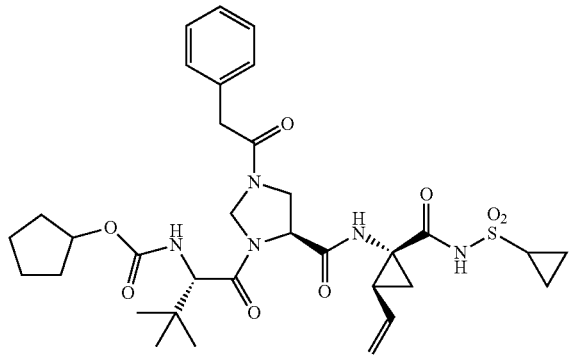

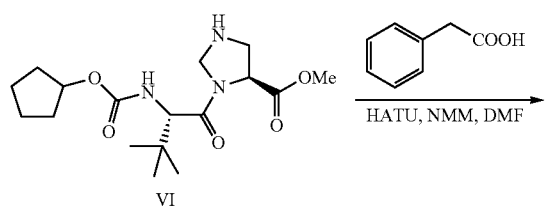

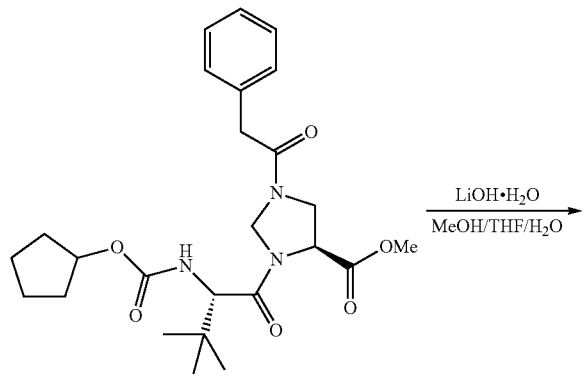

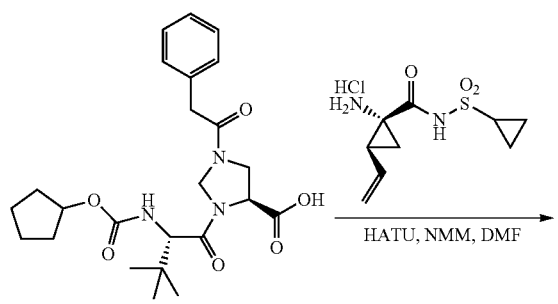

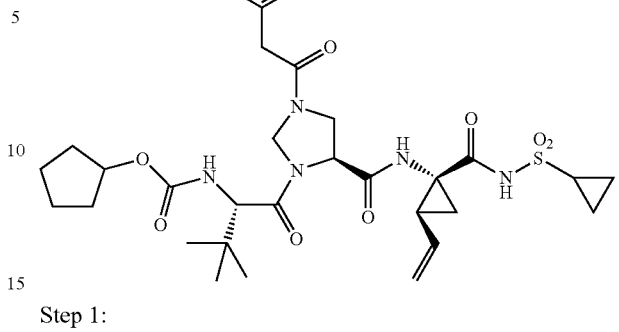

Step 1:
To a solution of amine VI (159 mg, 0.45 mmol) in DMF (2 ml) was added Phenyl-acetic acid (130 mg, 0.97 mmol), HATU (500 mg, 1.2 mmol) and NMM (190 mg, 1.94 mmol). The resulting reaction mixture was stirred at room temperature overnight. The reaction mixture was diluted with EtOAc and washed with 1N HCl, 5% LiOH, sat. NaHCO$_3$, brine, dried over MgSO$_4$, filtered and concentrated. The residue was purified by flash chromatograph to give ester as a white solid (178 mg, 0.38 mmol, 84%).
LC/MS=474.20 (M$^+$+1)

Step 2:
Methyl ester hydrolysis was carried out by the same procedure as described in Example 1, Step 1.

Step 3:
To a solution of product from Step 2 (90 mg, 0.195 mmol) in DMF (2 ml) was added amine (70 mg, 0.235 mmol), HATU (190 mg, 0.5 mmol) and NMM (100 mg, 1.0 mmol). The resulting solution was stirred at room temperature for two hours. The reaction mixture was purified directly by preparative HPLC to give Compound 2 (60 mg, 0.09 mmol, 46% yield) as a white solid.

$^1$H NMR (300 MHz, CD3OD) d 7.34-7.26 (m, 5H), 5.73-5.64 (m, 1H), 5.62-5.38 (dd, 1H), 5.31 (d, 1H), 5.14 (d, 1H), 5.05 (bs, 1H), 4.67 (m, 1H) 4.57 (m, 1H), 4.12-4.04 (m, 2H), 4.02-3.75 (m, 2H), 2.92 (m, 1H), 2.20 (m, 1H), 1.87-1.60 (m, 9H), 1.37 (m, 1H), 1.22 (m, 2H), 1.05 (s, 9H), 1.06-1.03 (m, 2H)
LC/MS=672.20 (M$^+$+1)

Example 3

Preparation of Compound 3

Compound 3

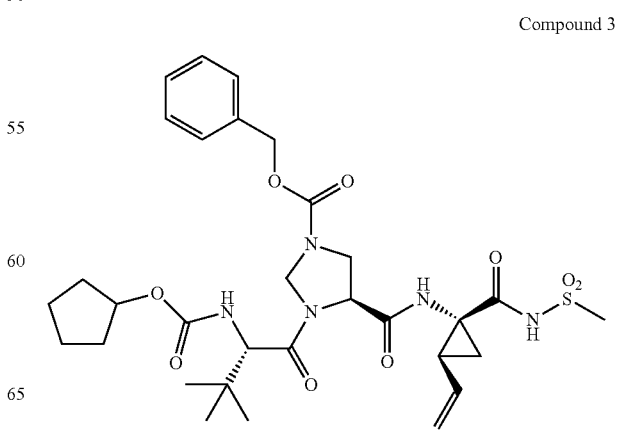

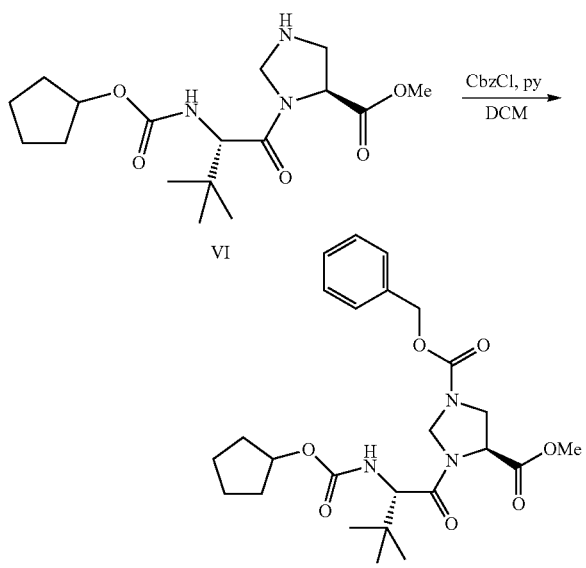

To a solution of VI (80 mg, 0.24 mmol) in DCM (2 ml) cooled at 0° C. was added pyridine (35.5 mg, 0.35 mmol), CbzCl (55 mg, 0.324 mmol). The reaction mixture was stirred at room temperature for 3 hours. The reaction mixture was diluted with EtOAc and washed with $NaHCO_3$, brine, dried over $MgSO_4$, filtered and concentrated. The residue was purified by flash chromatograph to give desired product (100 mg, 0.2 mmol, 83% yield) as white solid $^1$H NMR (300 MHz, CD3OD) d 7.36 (m, 5H), 5.28 (m, 1H), 5.15 (m, 3H), 5.01 (bs, 1H), 4.92-4.81 (m, 2H), 4.11-4.08 (m, 1H), 3.84 (m, 1H), 3.70 (s, 3H), 1.82-1.58 (m, 8H), 1.05 (s, 9H)

LC/MS=490.00 ($M^+$+1)

Compound 3 was prepared from product obtained above using the same procedures described in Example 2 (Step 2 and Step 3) for Compound 2.

$^1$H NMR (300 MHz, CD3OD) d 7.37 (m, 5H), 5.70-5.64 (m, 1H), 5.33-5.28 (m, 2H), 5.18-5.12 (m, 3H), 5.02 (s, 1H), 5.57 (m, 1H), 4.10 (s, 1H), 3.90 (m, 1H), 3.65 (m, 1H), 2.94 (m, 1H), 2.22 (m, 1H), 1.89-1.59 (m, 9H), 1.35 (m, 1H), 1.22 (m, 2H), 1.05 (s, 9H), 1.20-1.00 (m, 2H)

LC/MS=687.93 ($M^+$+1)

Example 4

Preparation of Compound 4

Compound 4

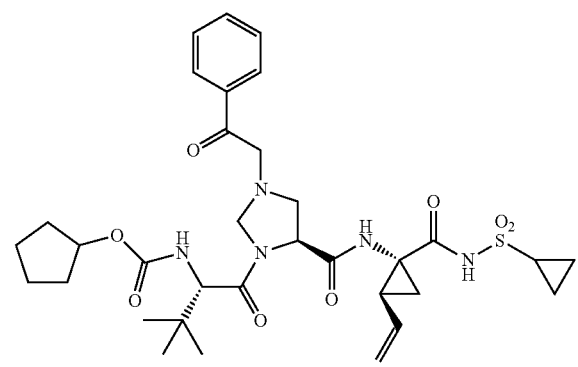

To a solution of azaproline VI (95 mg, 0.267 mmol) in THF (2 ml) cooled at 0° C. was added $Cs_2CO_3$ (261 mg, 0.801 mmol), and followed by the addition of 2-Bromo-1-phenyl-ethanone (53 mg, 0.267 mmol) solution in THF. After the addition, the reaction mixture was stirred at room temperature for overnight. The reaction mixture was purified directly by preparative HPLC to give amine (80 mg, 0.17 mmol, 64% yield) as a white solid.

LC/MS=474.00 ($M^+$+1)

Compound 4 was prepared from product obtained above using the same procedures described in Example 2 (Step 2 and Step 3) for Compound 2.

$^1$H NMR (300 MHz, CD3OD) d 8.03 (m, 2H), 7.67 (m, 1H), 7.56 (m, 2H), 5.73 (m, 1H), 5.37-5.28 (m, 2H), 5.15 (m, 1H), 4.85 (m, 1H), 4.78-4.75 (m, 2H), 4.66 (m, 1H), 4.09 (S, 1H), 3.84 (m, 1H), 3.47 (m, 1H), 2.95 (m, 1H), 2.23 (m, 1H), 1.88 (m, 1H), 1.70-1.46 (m, 8H), 1.43 (m, 1H), 1.22 (m, 2H), 1.09-1.04 (m, 2H), 1.09 (s, 9H)

LC/MS=672.13 ($M^+$+1)

Example 5

Preparation of Compound 5

Compound 5

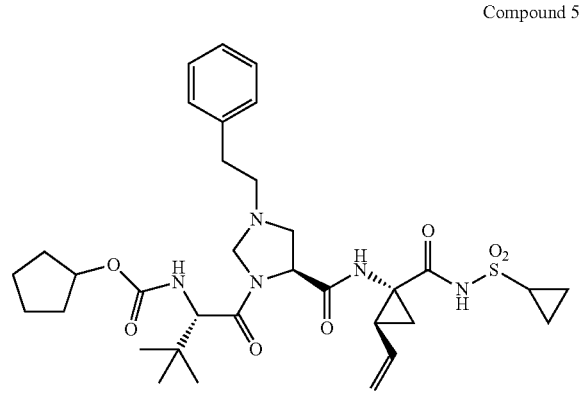 [SMILES: C=C[C@@H]1C[C@]1(NC(=O)[C@@H]1CN(CCc2ccccc2)CN1C(=O)[C@@H](NC(=O)OC1CCCC1)C(C)(C)C)C(=O)NS(=O)(=O)C1CC1]

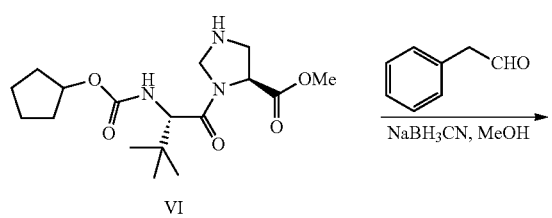
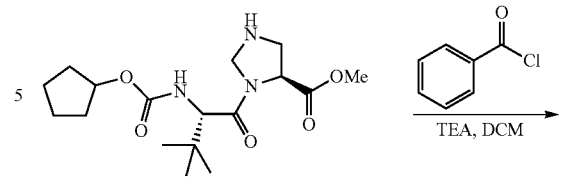

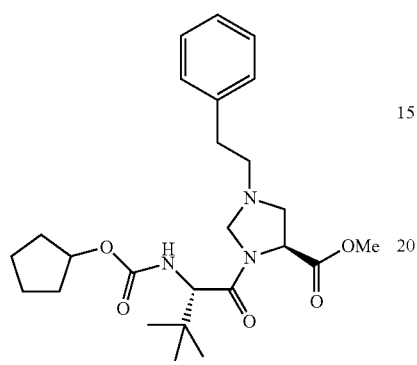

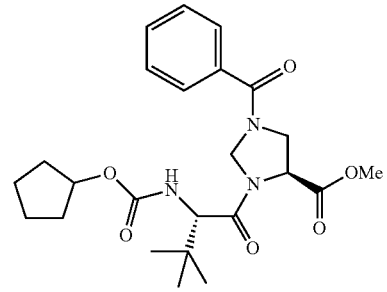

To a solution of azaproline VI (98 mg, 0.27 mmol) in MeOH (2 ml) was added Phenyl-acetaldehyde (99 mg, 0.83 mmol), and followed by the addition of NaBH₃CN (50 mg, 0.80 mmol). The resulting solution was stirred at room temperature overnight. Crude reaction was purified by preparative HPLC to give desired product as a white solid (80 mg, 0.17 mmol, 63% yield).

Compound 5 was prepared from product obtained above using the same procedures described in Example 2 (Step 2 and Step 3) for compound 2.

¹H NMR (300MHz, CD3OD) d 7.32 (m, 5H), 5.73 (m, 1H), 5.33-5.28 (m, 2H), 5.15 (m, 1H), 5.04 (bs, 1H), 4.63 (d, 2H), 4.56 (dd, 1H), 4.13 (s, 1H), 3.80 (m, 1H), 3.37-3.27 (m, 3H), 3.03-2.92 (m, 3H), 2.22 (m, 1H), 1.91-1.61 (m, 9H), 1.43 (m, 1H), 1.22 (m, 2H), 1.09-1.05 (m, 2H), 1.04 (s, 9H)

LC/MS=659.33 (M⁺+1)

To a solution of azaproline VI (140 mg, 0.39 mmol) in DCM (1 ml) cooled at 0° C. was added TEA (50 mg, 0.51 mmol), then followed by the addition of Benzoyl chloride (66 mg, 0.47 mmol). The resulting solution was stirred at room temperature overnight. The reaction mixture was diluted with EtOAc and washed with NaHCO₃, brine and dried over Na₂CO₃, filtered and concentrated. The residue was purified by flash chromatography to give ester as a white solid (140 mg, 0.305 mmol, 78% yield).

¹H NMR (300 MHz, CD3OD) d 7.55 (m, 5H), 5.45 (m, 1H), 5.12-4.99 (m, 2H), 4.84 (m, 2H), 4.30-4.01 (m, 2H), 3.72 (s, 3H), 1.84-1.60 (m, 8H), 1.00 (s, 9H)

LC/MS 460.00 (M⁺+1)

Compound 6 was prepared from product obtained above using the same procedures described in Example 2 (Step 2 and Step 3) for compound 2.

¹H NMR (300 MHz, CD3OD) d 7.56 (m, 5H), 5.74-5.63 (m, 1H), 5.61-5.26 (m, 3H), 5.15-5.02 (m, 2H), 4.58 (m, 1H), 4.25-3.72 (m, 3H), 2.94 (m, 1H), 2.18 (m, 1H), 1.86-1.60 (m, 9H), 1.50-1.20 (m, 3H), 1.20-1.00 (m, 2H), 1.04 (s, 9H)

LC/MS=658.00 (M⁺+1)

Example 6

Preparation of Compound 6

Example 7

Preparation of Compound 7

Compound 6

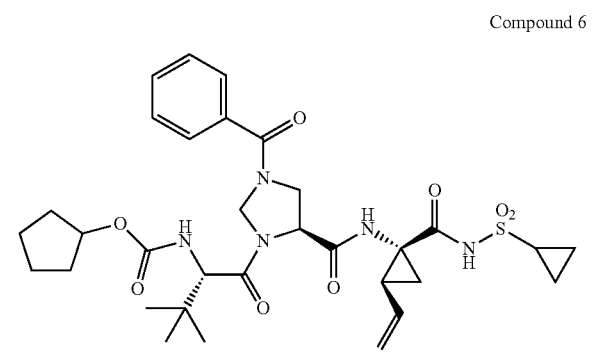 [SMILES: C=C[C@@H]1C[C@]1(NC(=O)[C@@H]1CN(C(=O)c2ccccc2)CN1C(=O)[C@@H](NC(=O)OC1CCCC1)C(C)(C)C)C(=O)NS(=O)(=O)C1CC1]

Compound 7

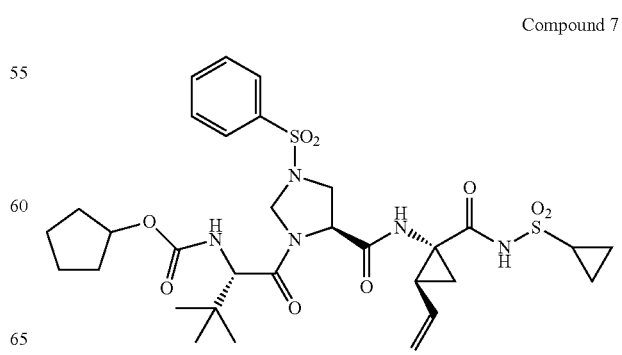

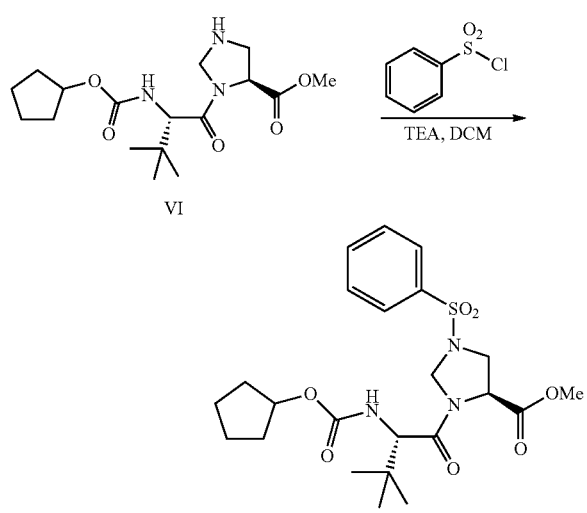

To a solution of azaproline VI (78 mg, 0.22 mmol) in DCM (1 ml) cooled at 0° C. was added TEA (29 mg, 0.28 mmol) and Benzenesulfonyl chloride (46 mg, 0.26 mmol). The resulting reaction mixture was stirred at room temperature overnight. The reaction mixture was diluted with EtOAc and washed with NaHCO$_3$, brine and dried over Na$_2$CO$_3$, filtered and concentrated. The crude material was purified by flash chromatography to give desired product as a white solid (80 mg, 0.16 mmol, 73% yield).

$^1$H NMR (300 MHz, CD3OD) d 7.93-7.87 (m, 2H), 7.72-7.54 (m, 3H), 5.51 (d, 1H), 5.15 (bs, 1H), 4.94 (d, 1H), 4.13-4.04 (m, 2H), 3.91-3.86 (m, 1H), 3.62 (s, 3H), 3.58 (m, 1H), 1.91-1.61 (m, 8H), 1.00 (s, 9H)

LC/MS=496.20 (M$^+$+1)

Compound 7 was prepared from product obtained above using the same procedures described in Example 2 (Step 2 and Step 3) for compound 2.

$^1$H NMR (300 MHz, CD3OD) d 7.91 (m, 2H), 7.72 (m, 1H), 7.57 (m, 2H), 5.72-5.61 (m, 2H), 5.27 (m, 1H), 5.19 (bs, 1H), 5.11 (m, 1H), 4.84 (m, 1H), 4.18-4.11 (m, 2H), 3.54 (dd, 1H), 3.37 (m, 1H), 2.89 (m, 1H), 2.16 (m, 1H), 1.95-1.66 (m, 9H), 1.38 (m, 1H), 1.19 (m, 2H), 1.03 (m, 2H), 1.00 (s, 9H)

LC/MS=694.00 (M$^+$+1)

Compounds 8-25 were prepared using the process described in Example 7 but using the appropriate building blocks.

| CPD # | Structure | LCMS |
|---|---|---|
| 8 | 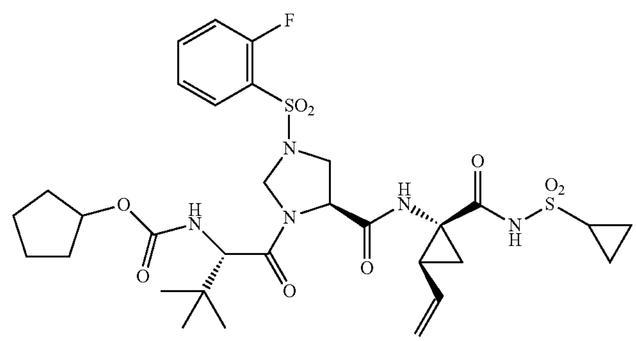 | 712.07 |
| 9 | 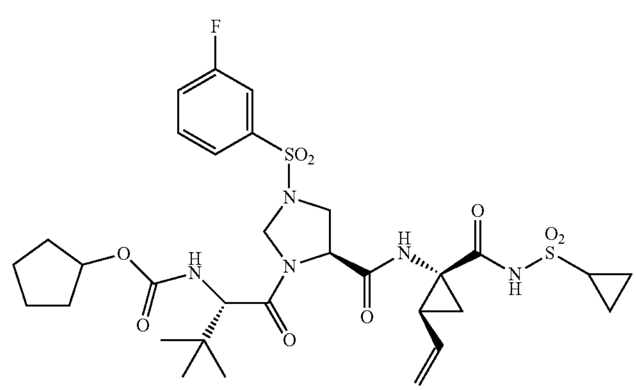 [SMILES: C=C[C@@H]1C[C@]1(NC(=O)[C@@H]1CN(S(=O)(=O)c2cccc(F)c2)CN1C(=O)[C@@H](NC(=O)OC1CCCC1)C(C)(C)C)C(=O)NS(=O)(=O)C1CC1] | 712.07 |

-continued
| CPD # | Structure | LCMS |
|---|---|---|
| 10 | 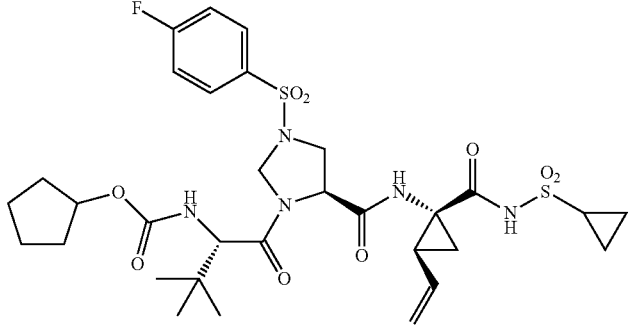 | 712.07 |
| 11 | 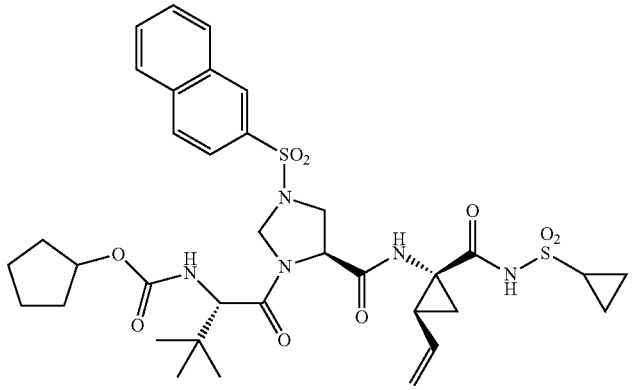 [SMILES: C=C[C@@H]1C[C@]1(NC(=O)[C@@H]1CN(S(=O)(=O)c2ccc3ccccc3c2)CN1C(=O)[C@@H](NC(=O)OC1CCCC1)C(C)(C)C)C(=O)NS(=O)(=O)C1CC1] | 743.93 |
| 12 | 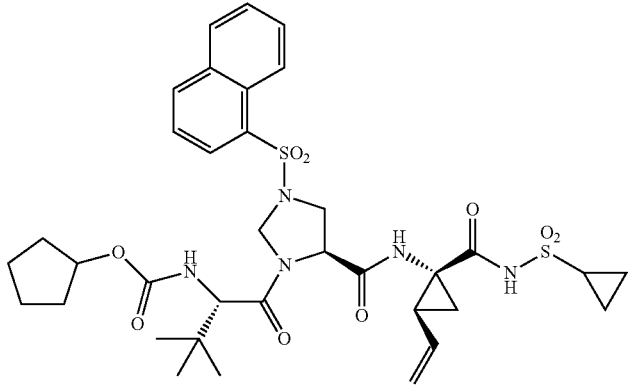 [SMILES: C=C[C@@H]1C[C@]1(NC(=O)[C@@H]1CN(S(=O)(=O)c2cccc3ccccc23)CN1C(=O)[C@@H](NC(=O)OC1CCCC1)C(C)(C)C)C(=O)NS(=O)(=O)C1CC1] | 743.93 |
| 13 | 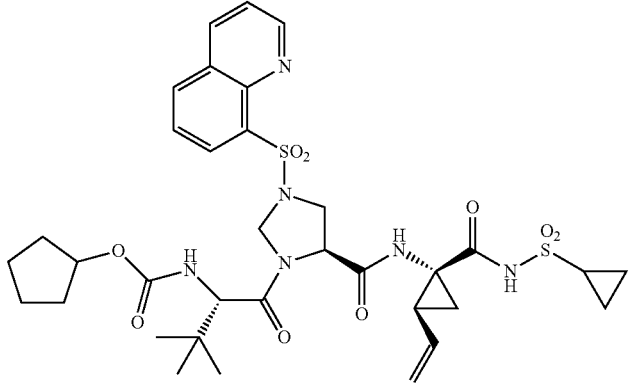 [SMILES: C=C[C@@H]1C[C@]1(NC(=O)[C@@H]1CN(S(=O)(=O)c2cccc3cccnc23)CN1C(=O)[C@@H](NC(=O)OC1CCCC1)C(C)(C)C)C(=O)NS(=O)(=O)C1CC1] | 745.02 |

-continued

| CPD # | Structure | LCMS |
|---|---|---|
| 14 | 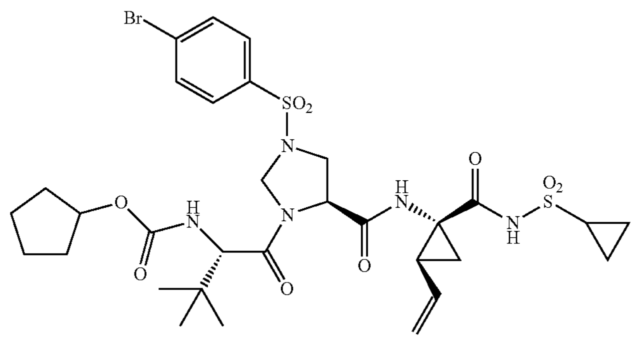 | 773.92 |
| 15 | 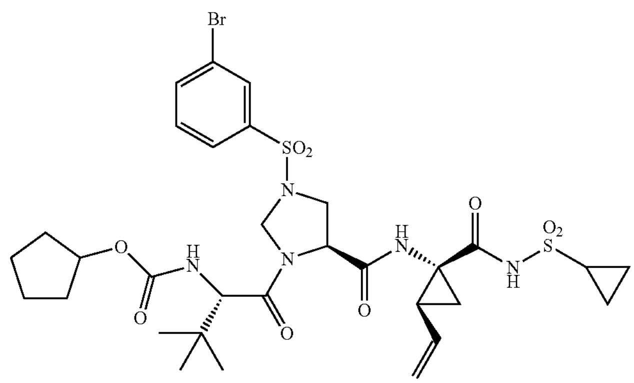 | 773.92 |
| 16 | 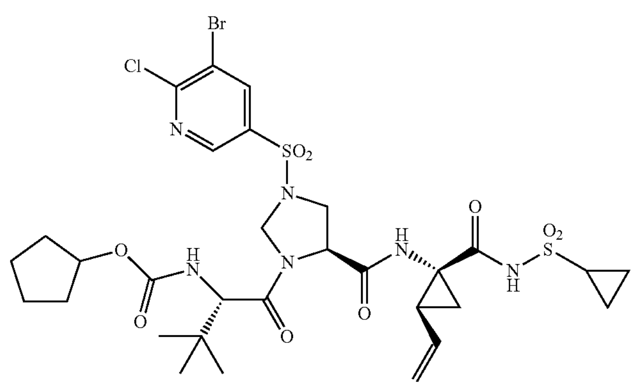 [SMILES: C=C[C@@H]1C[C@]1(NC(=O)[C@@H]1CN(S(=O)(=O)c2cnc(Cl)c(Br)c2)CN1C(=O)[C@@H](NC(=O)OC1CCCC1)C(C)(C)C)C(=O)NS(=O)(=O)C1CC1] | 804.93 |
| 17 | 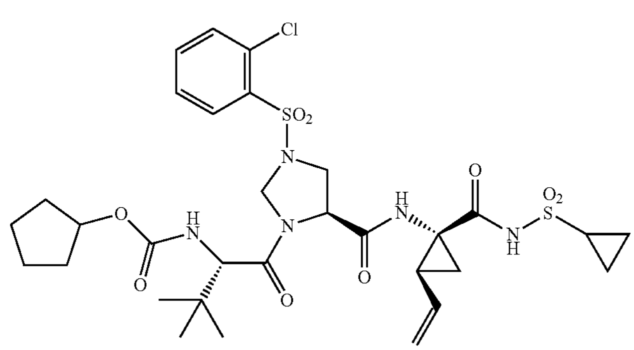 [SMILES: C=C[C@@H]1C[C@]1(NC(=O)[C@@H]1CN(S(=O)(=O)c2ccccc2Cl)CN1C(=O)[C@@H](NC(=O)OC1CCCC1)C(C)(C)C)C(=O)NS(=O)(=O)C1CC1] | 728.07 |

| CPD # | Structure | LCMS |
|---|---|---|
| 18 | 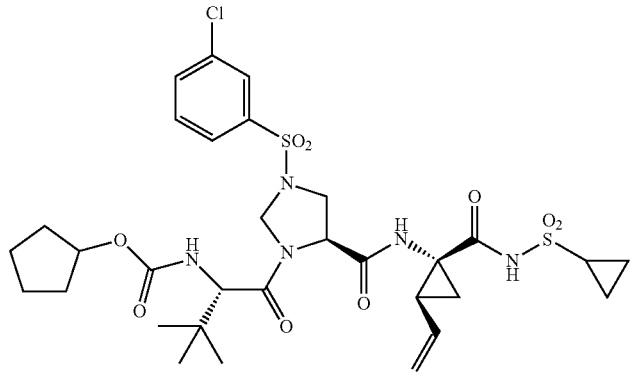 | 728.07 |
| 19 | 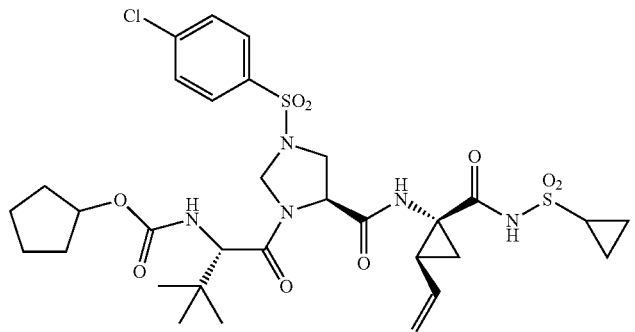 [SMILES: C=C[C@@H]1C[C@]1(NC(=O)[C@@H]1CN(S(=O)(=O)c2ccc(Cl)cc2)CN1C(=O)[C@@H](NC(=O)OC1CCCC1)C(C)(C)C)C(=O)NS(=O)(=O)C1CC1] | 728.07 |
| 20 | 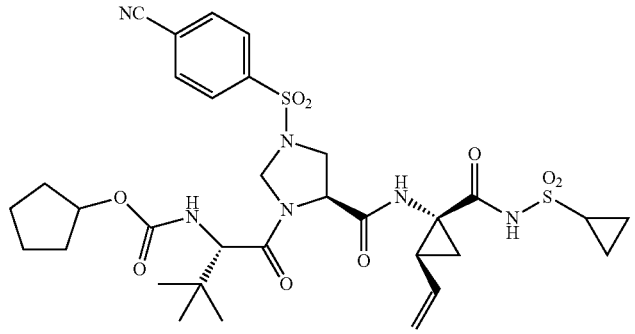 | 719.02 |
| 21 | 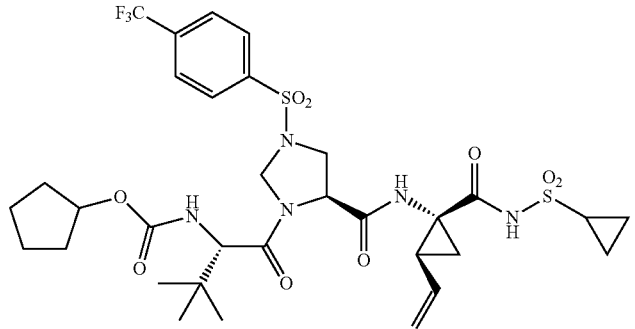 [SMILES: C=C[C@@H]1C[C@]1(NC(=O)[C@@H]1CN(S(=O)(=O)c2ccc(C(F)(F)F)cc2)CN1C(=O)[C@@H](NC(=O)OC1CCCC1)C(C)(C)C)C(=O)NS(=O)(=O)C1CC1] | 762.24 |

-continued
| CPD # | Structure | LCMS |
|---|---|---|
| 22 | 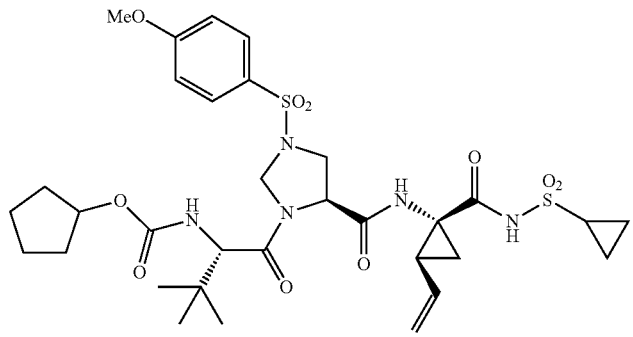 [SMILES: C=C[C@@H]1C[C@]1(NC(=O)[C@@H]1CN(S(=O)(=O)c2ccc(OC)cc2)CN1C(=O)[C@@H](NC(=O)OC1CCCC1)C(C)(C)C)C(=O)NS(=O)(=O)C1CC1] | 724.04 |
| 23 | 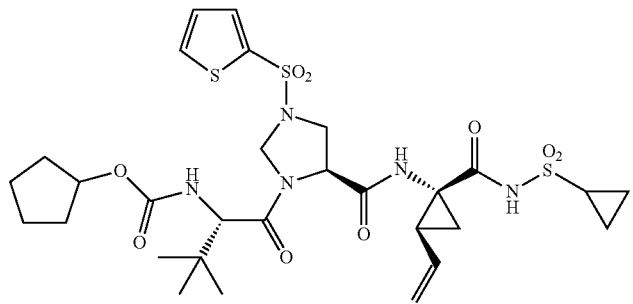 [SMILES: C=C[C@@H]1C[C@]1(NC(=O)[C@@H]1CN(S(=O)(=O)c2cccs2)CN1C(=O)[C@@H](NC(=O)OC1CCCC1)C(C)(C)C)C(=O)NS(=O)(=O)C1CC1] | 700.01 |
| 24 | 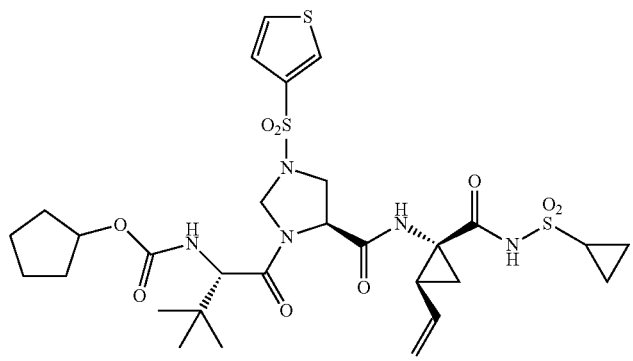 [SMILES: C=C[C@@H]1C[C@]1(NC(=O)[C@@H]1CN(S(=O)(=O)c2ccsc2)CN1C(=O)[C@@H](NC(=O)OC1CCCC1)C(C)(C)C)C(=O)NS(=O)(=O)C1CC1] | 700.01 |
| 25 | 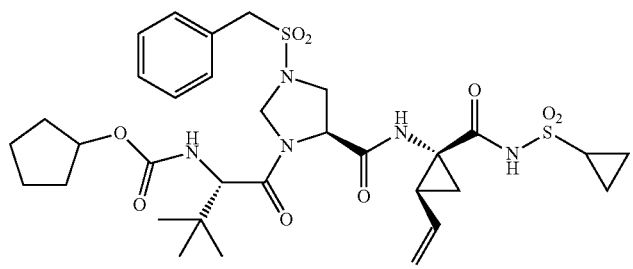 [SMILES: C=C[C@@H]1C[C@]1(NC(=O)[C@@H]1CN(S(=O)(=O)Cc2ccccc2)CN1C(=O)[C@@H](NC(=O)OC1CCCC1)C(C)(C)C)C(=O)NS(=O)(=O)C1CC1] | 708.04 |

Example 26

Preparation of Compound 26

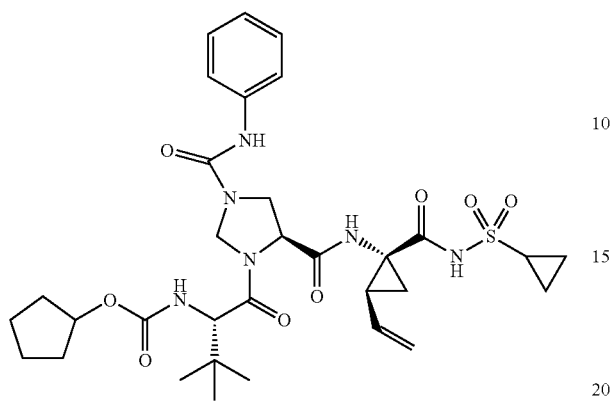

Compound 26

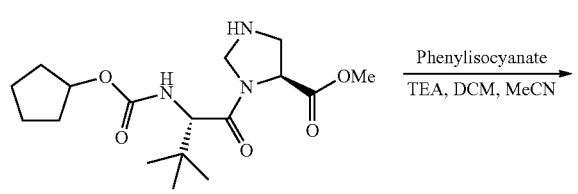

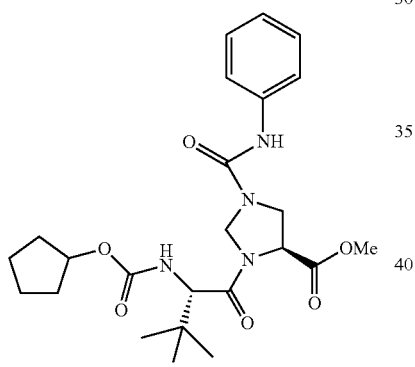

To a solution of azaproline VI (20.0 mg, 0.056 mmol) and TEA (9.5 pt, 0.068 mmol) in DCM (400 μL)/MeCN (750 μL) was added phenylisocyanate (7.3 μL, 0.067 mmol). The solution was stirred at rt for 16 h then concentrated in vacuo. The crude residue was purified by silica gel chromatography (ethyl acetate-hexanes) to afford 18.9 mg of phenylurea in 71% yield. LCMS (M+1): 474.84.

To a solution of phenylisocyanate (18.9 mg, 0.040 mmol) in THF (150 μL) and MeOH (150 μL) was added LiOH aq (1.5 M, 133 μL, 0.20 mmol) dropwise. After 1 h at rt, the resulting suspension was diluted with H₂O and acidified to pH=2. The aqueous was extracted with ethylacetate (5 mL×3). The combined organic layers were washed with brine (7 mL), dried over MgSO₄, and concentrated in vacuo to afford 17.5 mg of acid in 95% crude yield.

Cyclopropylacylsulfonamide hydrochloride (0.048 mmol) was dissolved in DCM (400 μL) and crude carboxylic acid was added (17.5 mg, 0.038 mmol) followed by HATU (29.2 mg, 0.077 mmol) and the slurry was cooled to 0° C. To the slurry was added N-methylmopholine (21 μL, 0.191 mmol) dropwise. The mixture was slowly warmed to rt and allowed to stir an additional 16 h before the volatiles were removed in vacuo. The crude residue was dissolved in DMF and purified directly by reverse-phase preparative HPLC (Column: Phemomenex Gemini 5u, C18, 110A, 75×30 mm, Gradient: 30-95% acetonitrile-water with 0.1% TFA) affording 15.1 mg of Compound 26 in 59% yield. LCMS (M+1): 672.91.

Example 27

Preparation of Compound 27

Compound 27

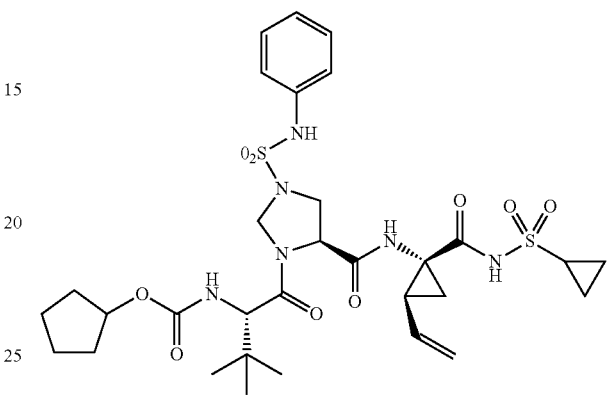

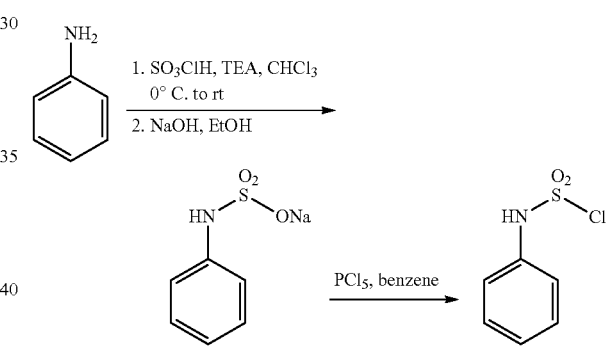

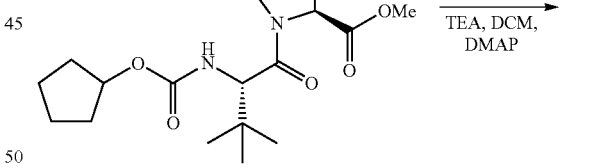

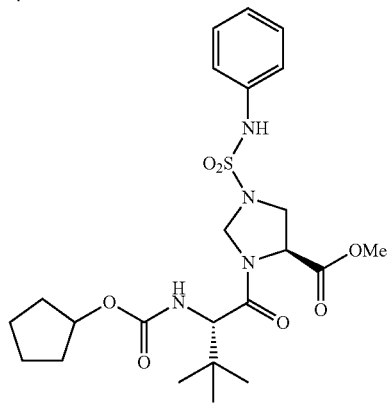

Step 1:

A solution of aniline (3.0 mL, 32.9 mmol) and TEA (41.0 mL, 294.2 mmol) in chloroform (65 mL) was cooled to −9° C. and chlorosulfonic acid (2.17 mL, 32.5 mmol) was added drop-wise, ensuring to maintain the internal temperature below −2° C. The solution was stirred an additional hour at −2° C. before it was concentrated in vacuo. The crude residue was dissolved in NaOH aq (1 N, 65.8 mL) then concentrated in vacuo. The resulting solid was suspended in boiling EtOH and the insoluble solids were filtered off via syringe filter. The volatiles were removed in vacuo to afford 5.54 g of solid sodium N-phenylsulfamate. To a flask charged with benzene (7.0 mL) was added sodium N-phenylsulfamate (405 mg, 2.08 mmol) followed by Phosphorus pentachloride (434 mg, 2.08 mmol). The mixture was refluxed for 20 h then cooled to rt. The suspension was filtered and filtrate was concentrated in vacuo affording 385 mg of crude sulfamoylchloride.

Step 2:

To a cooled (0° C.) solution of azaproline VI (52 mg, 0.15 mmol), TEA (200 μL, 1.43 mmol), and DMAP (catalytic) in DCM (700 μL) was added a solution of phenylsulfamoylchloride (97.4 mg, 0.508 mmol) in DCM (700 μL) drop-wise. The solution was slowly warmed to rt and allowed to stir for an additional 16 h, whereupon it was diluted with DCM (5 mL) and washed with HCl (0.5 N, 2 mL). The aqueous layer was extracted with DCM (3 mL×2) and the combined organic layers were washed with brine (5 mL), dried over MgSO$_4$ and concentrated in vacuo. The crude residue was purified via silica gel chromatography (ethylacetate-hexanes) to afford 43 mg of sulfonylurea in 58% yield. LCMS (M+1): 510.85

Step 3:

To a solution of sulfonylurea (105.7 mg, 0.207 mmol) in THF (700 μL) and MeOH (700 μL) was added LiOH aq (1.5 M, 690 μL, 1.03 mmol) dropwise. After 2 h at rt, the resulting suspension was diluted with H$_2$O and acidified to pH=1. The aqueous layer was extracted with ethylacetate (5 mL×3), and the combined organic layers were washed with brine (7 mL), dried over MgSO$_4$, and concentrated in vacuo to afford 100.3 mg of acid in 98% crude yield. The cyclopropyl-acylsulfonamide hydrochloride was prepared following the general procedure for boc-group deprotection using cyclopropylacylsulfonamide (85.4 mg, 0.258 mmol), DCM (1.3 mL) and HCl/dioxane (4 M, 1.3 mL). The solution was concentrated in vacuo and the crude amine hydrochloride was coupled directly to the sulfonylurea carboxylic acid. The general procedure for peptide coupling was followed using sulfonylurea carboxylic acid (100.3 mg, 0.202 mmol), cyclopropyl-acyl sulfonamide hydrochloride (0.258 mmol), HATU (154.8 mg, 0.407 mmol), NMM (135 μL, 1.23 mmol) and DCM (2.0 mL). The crude residue was dissolved in DMF and purified directly by reverse-phase preparative HPLC (Column: Phemomenex Gemini 5u, C18, 110A, 75×30 mm, Gradient: 30-95% acetonitrile-water with 0.1% TFA) affording 25.3 mg of Compound 27 in 18% yield. LCMS (M+1): 708.86.

Example 28

Preparation of Compound 28

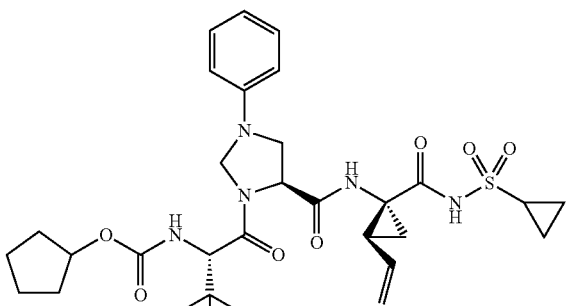

Compound 28

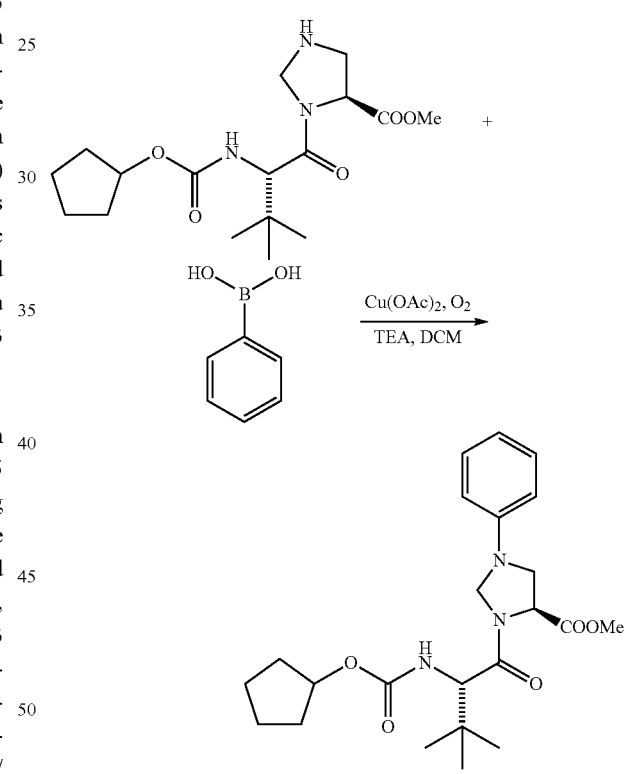

A solution of intermediate VI (31 mg, 0.087 mmol) and molecular sieve (300 mg) in CH$_2$Cl$_2$ (5 mL) stirred at room temperature as copper (II) acetate (34.8 mg, 0.19 mmol) phenylboronic acid (42 mg, 0.35 mmol) and triethylamine (0.3 mL) were added. Meanwhile, dry air was sucked to the reaction solution slowly by using vacuum. After stirring overnight, the reaction solution was quenched by adding 10% NH$_4$OH (aq) solution (20 mL) and stirred for 4 hours. After separation, the organic layer was washed by 0.5 N HCl (aq), brine and dried by Na$_2$SO$_4$. After concentration, the crude was purified with a CombiFlash Chromatography System to afford desired ester (21 mg, 53%).

LC/MS=432 (M$^+$+1)

Compound 28 was prepared from product obtained above using the same procedures described in Example 2 (Step 2 and Step 3) for Compound 2.

$^1$H NMR (300 MHz, CD$_3$OD): δ 9.18 (s, 1H), 7.27 (t, J=7.8 Hz, 2H), 6.85 (t, J=7.5 Hz, 1H), 6.78 (t, 7.8 Hz, 2H), 5.80-5.68 (m, 1H), 5.35-5.30 (m, 2H), 5.15 (d, J=11.4 Hz, 1H), 5.05 (bs, 1H), 4.92 (m, 1H), 4.60 (t, J=6.9 Hz, 1H), 4.32 (s, 1H), 3.84 (t, J=8.7 Hz, 1H), 2.98-2.91 (m, 1H), 2.32-2.23 (m, 1H), 1.92-1.1.60 (m, 10H), 1.45-1.40 (m, 1H), 1.30-1.22(m, 2H), 1.09 (s, 9H) 1.15-1.03 (m, 3H).

LC/MS=630 (M$^+$+1)

Example 29

Preparation of Compound 29

Compound 29

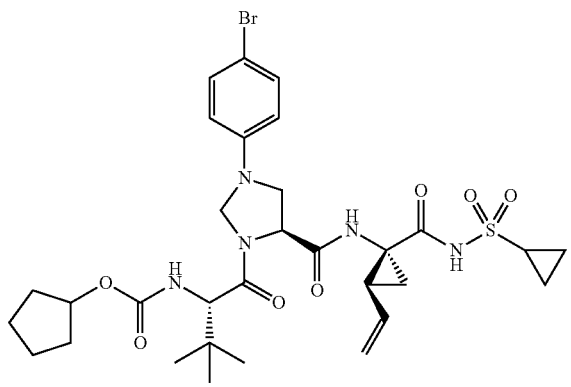

Compound 29 was prepared as described in the general procedure for example 28 by using 4-bromophenylboronic acid.

$^1$H NMR (300 MHz, CD$_3$OD): δ 7.37 (d, J=8.4 Hz, 2H), 7.11 (d, J=9.0 Hz, 1H), 6.70 (d, J=9.0 Hz, 2H), 5.80-5.68 (m, 1H), 5.35-5.30 (m, 2H), 5.15 (d, J=11.4 Hz, 1H), 5.04 (bs, 1H), 4.92 (m, 1H), 4.63 (t, J=6.9 Hz, 1H), 4.29 (d, J=9.0 Hz, 1H), 3.84 (t, J=8.7 Hz, 1H), 2.98-2.92 (m, 1H), 2.32-2.23 (m, 1H), 1.92-1.1.60 (m, 10H), 1.46-1.41 (m, 1H), 1.30-1.22 (m, 2H), 1.09 (s, 9H) 1.17-1.04 (m, 3H).

LC/MS=709 (M$^+$+1)

Example 30

Preparation of Compound 30

Compound 30

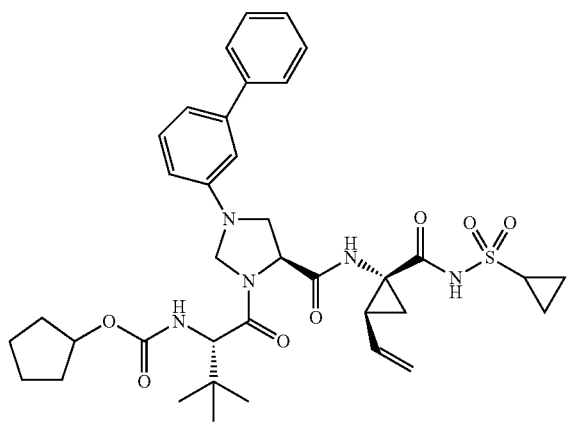

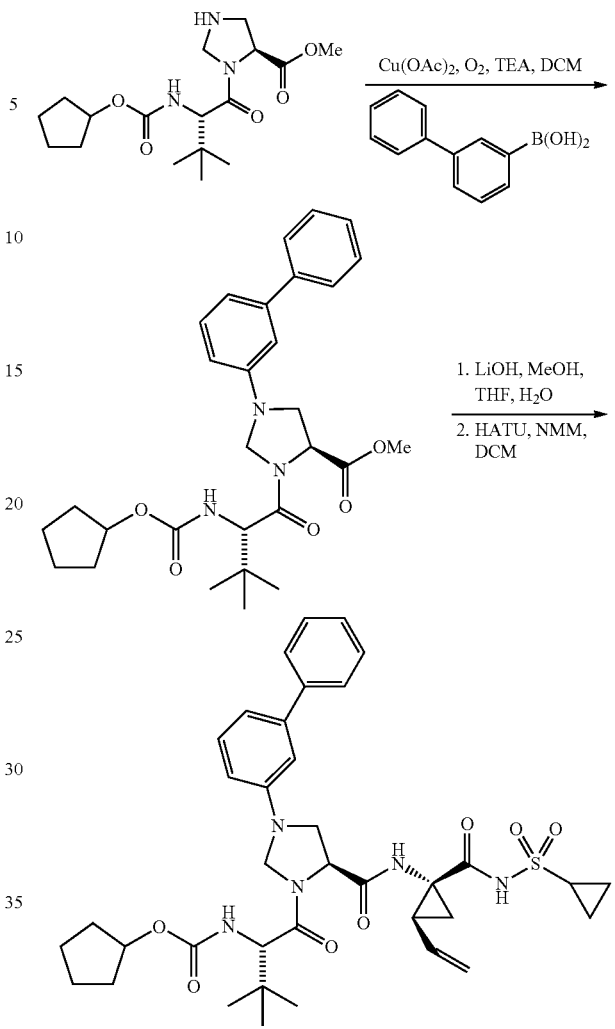

Step 1:

Azaproline VI (102 mg, 0.286 mmol) was dissolved in DCM (2.8 mL) followed by the addition of TEA (120 µL, 0.861 mmol), 3-biphenylboronic acid (172 mg, 0.869 mmol), molecular sieves (4 Å, 333 mg) and Cu(OAc)$_2$ (104 mg, 0.571 mmol). A balloon of O$_2$ was placed on top and the mixture was stirred at rt for 20 h followed by addition of NH$_3$ in MeOH (2N, 4.3 nit, 8.6 mmol). The mixture was concentrated in vacuo, slurried in DCM, filtered, and reconcentrated. The crude residue was purified via silica gel chromatography (ethylacetate-hexanes) to afford 113 mg of azaproline product in 78% yield.

LCMS (M+1): 508.07.

Step 2:

To a solution of azaproline obtained above (129 mg, 0.256 mmol) in THF (800 µL) and MeOH (800 µL) was added LiOH aq (1.5 M, 787 µL, 1.18 mmol) drop-wise. After 1.2 h at rt, the resulting suspension was diluted with H$_2$O and acidified to pH=1. The aqueous was extracted with ethylacetate (10 mL×3), and the combined organic layers were washed with brine (10 mL), dried over MgSO$_4$, and concentrated in vacuo to afford 118 mg of acid in 94% crude yield. The general procedure for peptide coupling was followed using azaproline carboxylic acid (118 mg, 0.240 mmol), cyclopropyl-acylsulfonamide hydrochloride (0.288 mmol), HATU (183 mg, 0.481 mmol), NMM (132 µL, 1.20 mmol), and DCM (2.4 mL). The crude residue was purified via silica gel chromatography (ethylacetate-hexanes) to afford 136 mg of Compound 30 in 80% yield.

$^1$H NMR (300 MHz, CD$_3$OD) δ: 7.63 (d, J=7.5 Hz, 2H), 7.43 (dd, J=6.9, 7.5 Hz, 2H), 7.38-7.29 (m, 2H), 7.18-7.07 (m, 2H), 6.98 (s, 1H), 6.78 (d, J=7.2 Hz, 1H), 5.84-5.68 (m, 1H), 5.43-5.38 (m, 1H), 5.32 (d, J=16.8 Hz, 1H), 5.14 (d, J=9.9 Hz, 1H), 5.04 (bs, 1H), 4.95 (bs, 1H), 4.67-4.59 (m, 1H), 4.35 (d, J=9.0 Hz, 1H), 3.96-3.88 (m, 1H), 3.02-2.90 (m, 1H), 2.35-2.23 (m, 1H), 1.94-1.51 (m, 11H), 1.49-1.40 (m, 1H), 1.45-1.19 (m, 2H), 1.02 (s, 9H); LCMS (M+1): 706.08.

Example 31

Preparation of Compound 31

Compound 31

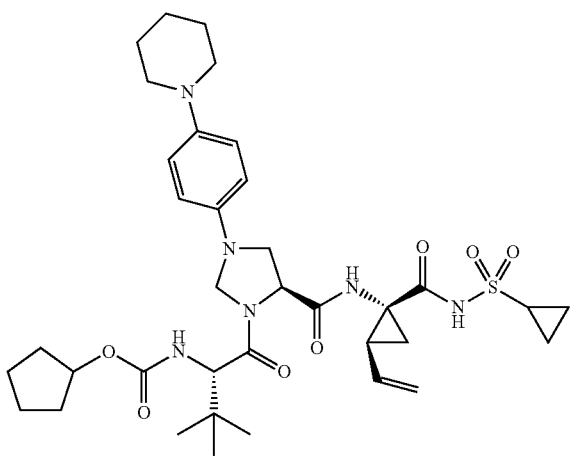

The procedure for the preparation of compound 30 was followed using azaproline VI (221 mg, 0.622 mmol), DMF (6.2 mL), 4-(piperidinyl)phenylboronic acid hydrochloride (300 mg, 1.24 mmol), Cs$_2$CO$_3$ (814, 2.50 mmol), molecular sieves (4 Å, 734 mg), Cu(OAc)$_2$ (226 mg, 1.24 mmol), O$_2$ (1 atm), and NH$_3$ in MeOH (2N, 10.0 mL, 20 mmol). The resulting mixture after quench was coned in vacuo and partitioned between H$_2$O (50 mL) and ethylacetate (70 mL). The organic layer was drawn off and the aqueous layer extracted with ethylacetate (70 mL×2). The combined organic layers were washed with LiCl (5% aq, 40 mL), brine (40 mL), dried over Na$_2$SO$_4$ and coned in vacuo. The crude residue was purified via silica gel chromatography (ethylacetate-hexanes) to afford 62 mg of azaproline product in 19% yield.

LCMS (M+1): 515.19.

Compound 31 was prepared from product obtained above using the procedures described in Example 30, Step 2 and 3, LiOH (1.5 N, 450 μL, 0.675 mmol), THF (450 μL), and MeOH (450 μL) providing carboxylic acid in quantitative yield which was coupled directly with vinyl cyclopropane amine hydrochloride (0.174 mmol), HATU (102 mg, 0.268 mmol), NMM (74 μL, 0.67 mmol), and DCM (1.4 mL) providing 34 mg of compound 31 in 36% yield.

$^1$H NMR (300 MHz, CD$_3$OD) δ: 7.54 (d, J=8.4 Hz, 2H), 7.19 (d, J=7.5 Hz, 1H), 6.93 (d, J=9.0 Hz, 2H), 5.80-5.66 (m, 1H), 5.32 (d, J=16.5 Hz, 2H), 5.16 (d, J=10.2 Hz, 1H), 5.09-4.97 (m, 2H), 4.31-4.24 (m, 1H), 4.00-3.89 (m, 1H), 3.65-3.52 (m, 4H), 3.49-3.80 (m, 1H), 3.02-2.90 (m, 1H), 2.27 (dt, J=9.0, 8.4 Hz, 1H), 2.09-1.97 (m, 4H), 1.96-1.48 (m, 13H), 1.47-1.37 (m, 1H), 1.28-1.20 (m, 2H), 1.09 (s, 9H); LCMS (M+1): 713.22.

Example 32

Preparation of Compound 32

Compound 32

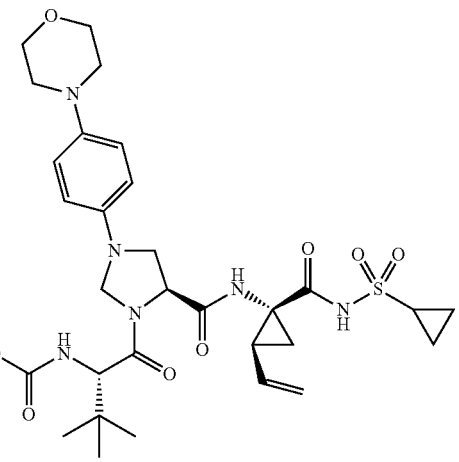

The procedure for the preparation of compound 30 was followed using azaproline VI (152 mg, 0.427 mmol), DMF (4.4 mL), 4-(morpholino)phenylboronic acid (177 mg, 0.857 mmol), K$_2$CO$_3$ (237, 1.71), molecular sieves (4 Å, 507 mg), Cu(OAc)$_2$ (158 mg, 0.869 mmol), and O$_2$ (1 atm), and NH$_3$ in MeOH (2N, 7.0 mL, 14 mmol). The crude residue was purified via silica gel chromatography (ethylacetate-hexanes) affording 53 mg of azaproline product in 24% yield. LCMS (M+1): 517.17.

Compound 32 was prepared from product obtained above using the procedures described in Example 30, Step 2 and 3, LiOH (1.5 N, 340 μL, 0.510 mmol), THF (340 μL), and MeOH (340 μL) providing 49 mg of carboxylic acid in 95% yield which was coupled directly with vinyl cyclopropane amine hydrochloride (0.121 mmol), HATU (76 mg, 0.20 mmol), NMM (53 μL, 0.48 mmol), and DCM (1.0 mL). The crude residue was purified via silica gel chromatography (ethylacetate-hexanes) affording 34 mg of compound 32 in 49% yield.

$^1$H NMR (300 MHz, CD$_3$OD) δ: 7.59-7.25 (m, 2H), 7.05-6.73 (m, 2H), 5.82-5.67 (m, 1H), 5.33 (d, J=16.8 Hz, 1H), 5.15 (d, J=5.15 Hz, 1H), 5.03 (bs, 1H), 4.73-4.60 (m, 1H), 4.27 (s, 1H), 3.40 (bs, 5H), 3.64-3.35 (m, 4H), 3.02-2.90 (m, 1H), 2.27 (dt, J=9.3, 8.4 Hz, 1H), 1.96-1.52 (m, 11H), 1.42 (dd, =9.3, 5.7 Hz, 1H), 1.24 (bs, 2H), 1.09 (s, 9H); LCMS (M+1): 715.17.

Example 33

Preparation of Compound 33

Compound 33

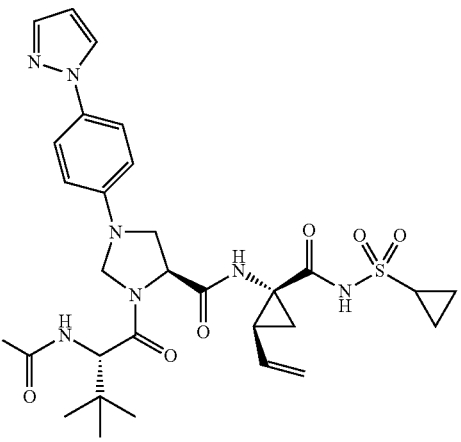

The procedure for the preparation of compound 30 was followed using azaproline VI (106 mg, 0.299 mmol), DCM (3.0 mL), 4-(pyrazole)phenylboronic acid (116 mg, 0.619 mmol), TEA (125 µL, 0.897 mmol), molecular sieves (4 Å, 345 mg), Cu(OAc)$_2$ (114 mg, 0.628 mmol), O$_2$ (1 atm), and NH$_3$ in MeOH (2N, 5.0 mL, 10 mmol). The crude residue was purified via silica gel chromatography (ethylacetate-hexanes) affording 91 mg of azaproline product in 61% yield. LCMS (M+1): 498.06.

Compound 33 was prepared from product obtained above using the procedures described in Example 30, Step 2 and 3, LiOH (1.5 N, 608 µL, 0.915 mmol), THF (610 µL), and MeOH (610 µL) providing 85 mg of carboxylic acid in 97% yield. Carboxylic acid (41 mg, 0.085 mmol) was coupled directly with vinylcyclopropane amine hydrochloride (0.121 mmol), HATU (67 mg, 0.18 mmol), NMM (47 µL, 0.43 mmol), and DCM (1.0 mL). The crude residue was purified via silica gel chromatography (ethylacetate-hexanes) affording 43 mg of compound 33 in 72% yield.

$^1$H NMR (300 MHz, CD$_3$OD) δ: 8.08 (d, J=2.1 Hz, 1H), 7.68 (s, 1H), 7.62 (d, J=8.7 Hz, 2H), 7.14 (d, J=8.7 Hz, 1H), 6.91 (d, J=8.7 Hz, 2H), 6.54-6.47 (m, 1H), 5.82-5.68 (m, 1H), 5.33 (d, J=17.1 Hz, 2H), 5.16 (d, J=10.2 Hz, 1H), 5.05 (bs, 1H), 4.70-4.63 (m, 1H), 4.31 (d, J=8.4 Hz, 1H), 4.03-3.90 (m, TH), 3.75-3.61 (m, 2H), 3.02-2.91 (m, 1H), 2.29 (dt, J=9.1, 8.4 Hz, 1H), 1.93-1.54 (m, 9H), 1.45 (dd, J=9.3, 5.4 Hz, 1H), 1.40-1.23 (m, 4H), 1.03 (s, 9H); LCMS (M+1):696.14.

Example 34

Preparation of Compound 34

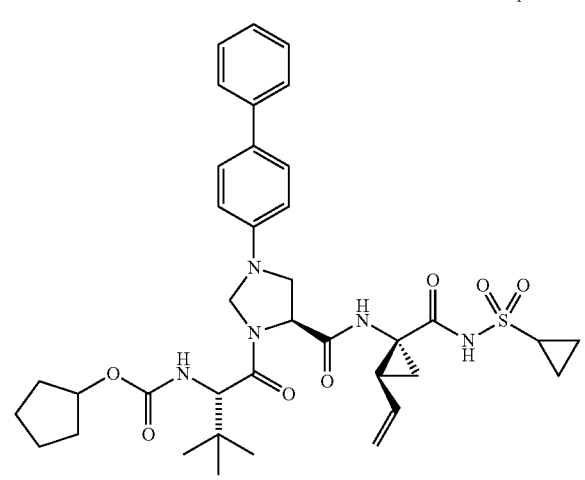

Compound 34

Compound 34 was prepared as described in the general procedure for example 28 by using 4-biphenylboronic acid.

$^1$H NMR (300 MHz, CD$_3$OD) δ: 9.17 (s, 1H), 7.56 (m, 4H), 7.41 (t, J=8.1 Hz, 2H), 7.26 (m, 1H) 6.86 (d, J=8.4 Hz, 2H), 5.80-5.69 (m, 1H), 5.36-5.30 (m, 2H), 5.15 (d, J=11.1 Hz, 1H), 5.05 (bs, 1H), 4.92 (m, 1H), 4.60 (t, J=6.9 Hz, 1H), 4.33 (s, 1H), 3.87 (t, J=8.4 Hz, 1H), 2.99-2.91 (m, 1H), 2.33-2.24 (m, 1H), 1.92-1.160 (m, 10H), 1.47-1.42 (m, 1H), 1.30-1.22 (m, 2H), 1.10 (s, 9H) 1.15-1.03 (m, 3H); LCMS (M+1): 706.

Example 35

Preparation of Compound 35

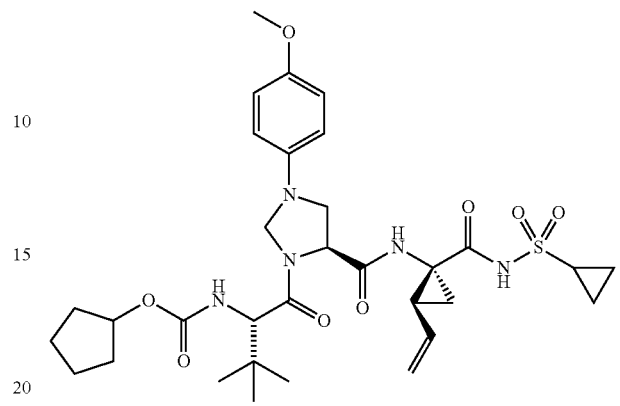

Compound 35

Compound 35 was prepared as described in the general procedure for example 28 by using 4-methoxyphenylboronic acid.

$^1$H NMR (300 MHz, CD$_3$OD): δ 9.21 (s, 1H), 6.89 (d, J=8.4 Hz, 2H), 6.79 (d, J=8.4 Hz, 2H), 5.80-5.68 (m, 1H), 5.35-5.30 (m, 2H), 5.15 (d, J=11.4 Hz, 1H), 5.04 (bs, 1H), 4.92 (m, 1H), 4.63 (t, J=6.9 Hz, 1H), 4.29 (s, 1H), 3.84 (t, Hz, 1H), 3.75 (s, 3H), 2.99-2.94 (m, 1H), 2.32-2.23 (m, 1H), 1.92-1.1.60 (m, 10H), 1.46-1.41 (m, 1H), 1.30-1.22(m, 2H), 1.09 (s, 9H) 1.17-1.02 (m, 3H).

LC/MS=660 (M$^+$+1)

Example 36

Preparation of Compound 36

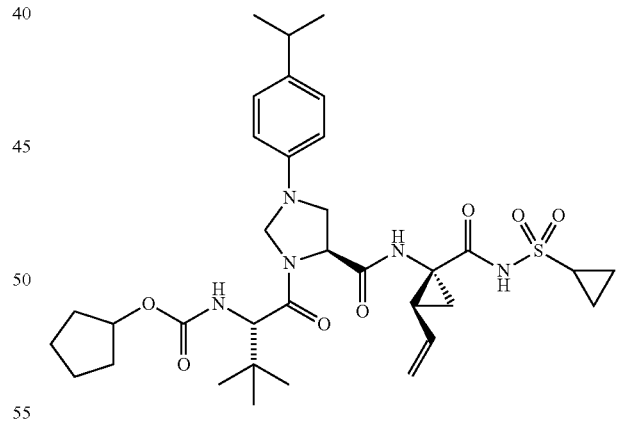

Compound 36

Compound 36 was prepared as described in the general procedure for example 28 by using 4-isopropylphenylboronic acid.

$^1$H NMR (300 MHz, CD$_3$OD): δ 7.15 (d, J=8.4 Hz, 2H), 6.75 (d, J=8.4 Hz, 2H), 5.80-5.68 (m, 1H), 5.35-5.30 (m, 2H), 5.15 (d, J=11.4 Hz, 1H), 5.04 (bs, 1H), 4.92 (m, 1H), 4.63 (t, J=6.9 Hz, 1H), 4.29 (d, J=9.0 Hz, 1H), 3.84 (t, J=8.7 Hz, 1H), 2.98-2.92 (m, 1H), 2.85-2.78 (m, 1H), 2.32-2.23 (m, 1H), 1.92-1.1.60 (m, 10H), 1.46-1.41 (m, 1H), 1.30-1.22(m, 8H), 1.09 (s, 9H) 1.17-1.04 (m, 3H).

LC/MS=672 (M$^+$+1)

Example 37

Preparation of Compound 37

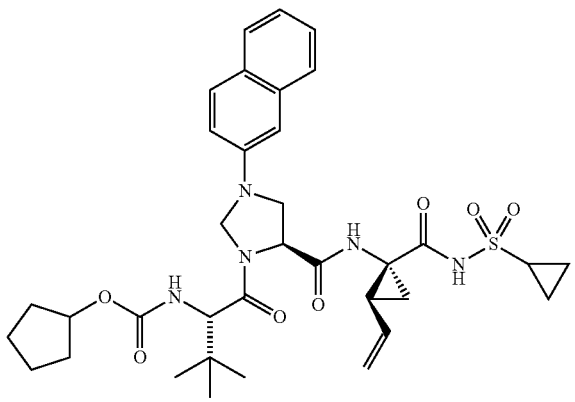

Compound 37

Compound 37 was prepared as described in the general procedure for example 28 by using 2-naphthaleneboronic acid.

$^1$H NMR (300 MHz, CD$_3$OD): δ 9.20 (s, 1H), 7.79-7.70 (m, 3H), 7.40 (t, J=7.2 Hz, 1H), 7.29-7.24 (m, 1H) 7.13 (d, J=8.1 Hz, 1H), 7.05 (s, 1H), 5.80-5.69 (m, TH), 5.36-5.30 (m, 2H), 5.15 (d, J=11.1 Hz, 1H), 5.05 (bs, 1H), 4.92 (m, 1H), 4.60 (t, J=6.9 Hz, 1H), 4.33 (s, 1H), 3.87 (t, J=8.4 Hz, 1H), 2.99-2.91 (m, 1H), 2.66-2.62 (m, 1H), 1.92-1.1.60 (m, 10H), 1.47-1.42 (m, 1H), 1.30-1.22(m, 2H), 1.10 (s, 9H) 1.15-1.03 (m, 3H).

LC/MS=680 (M$^+$+1)

Example 38

Preparation of Compound 38

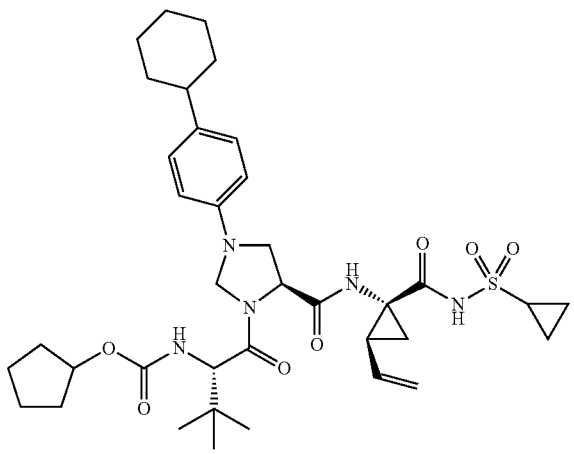

Compound 38

The procedure for the preparation of compound 30 was followed using azaproline VI (100 mg, 0.279 mmol), DCM (2.8 MI), TEA (120 μL, 0.861 mmol), 4-cylclohexylphenylboronic acid (172 mg, 0.840 mmol), molecular sieves (4 Å, 338 mg), Cu(OAc)$_2$ (101 mg, 0.557 mmol), O$_2$ (1 atm), and NH$_3$ in MeOH (2N, 4.0 mL, 8.0 mmol). The crude residue was purified via silica gel chromatography (ethylacetate-hexanes) affording 113 mg of azaproline product in 79% yield. LCMS (M+1): 514.11.

Compound 38 was prepared from product obtained above (126 mg, 0.247 mmol) using the procedures described in Example 30, Step 2 and 3, LiOH (1.5 N, 823 μL, 1.23 mmol), THF (850 μL), and MeOH (850 μL) providing 120 mg of carboxylic acid in 97% yield which was coupled directly with vinylcyclopropane amine hydrochloride (0.298 mmol), HATU (186 mg, 0.490 mmol), NMM (135 μL, 1.22 mmol), and DCM (2.4 mL). The crude residue was dissolved in DMF and purified directly by reverse-phase preparative HPLC (Column: Phemomenex Gemini 5u, C18, 110A, 75×30 mm, Gradient: 30-95% acetonitrile-water with 0.1% TFA) affording 43 mg of compound 38 in 21% yield. LCMS (M+1): 712.16.

Example 39

Preparation of Compound 39

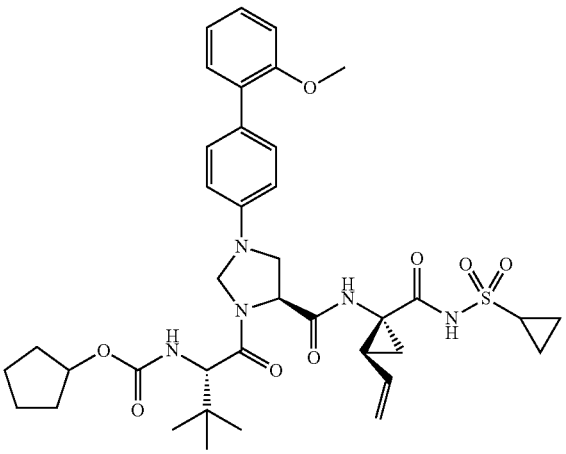

Compound 39

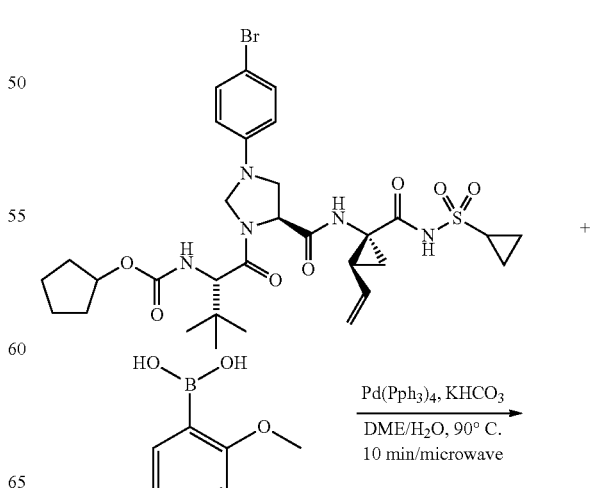

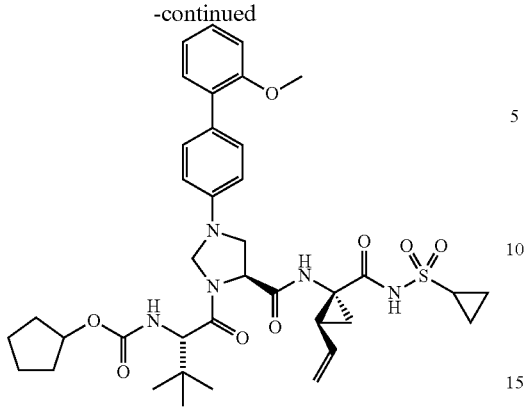

A solution of 29 (30 mg, 0.042 mmol), 2-methoxphenyl-boronic acid (7.3 mg, 0.050 mmol), tetrakis(triphenylphos-phine)palladium (0) (4.9 mg, 0.0042 mmol) and potassium bicarbonate (8.4 mg, 0.084 mmol) were dissolved in DME and H$_2$O (0.3 mL/0.13 mL) in a microwave tube. The reaction solution was heated to 90° C. for 10 minutes under microwave. After concentration, the crude was diluted with 1 mL DMF and purified by preparative HPLC to afford 39 (10 mg, 32%) as a white solid.

$^1$H NMR (300 MHz, CD$_3$OD): δ 9.04 (s, 1H), 7.44 (d, J=8.1 Hz, 2H), 7.26 (d, J=6.9 Hz, 1H), 7.05-6.98 (m, 2H), 6.81 (d, J=8.4 Hz, 2H), 5.69-5.61 (m, 1H), 5.37 (m, 1H), 5.22-5.13 (m, 2H), 5.06 (bs, 1H), 4.64 (t, J=6.9 Hz, 1H), 4.31 (s, 1H), 3.93 (t, J=8.7 Hz, 1H), 3.78 (s, 3H), 2.98-2.91 (m, 1H), 2.66-2.61 (m, 1H), 1.84-1.34 (m, 10H), 1.37-1.31 (m, 3H), 1.10 (s, 9H) 1.21-1.00 (m, 3H).

LC/MS=736 (M$^+$+1)

Example 40

Preparation of Compound 40

Compound 40

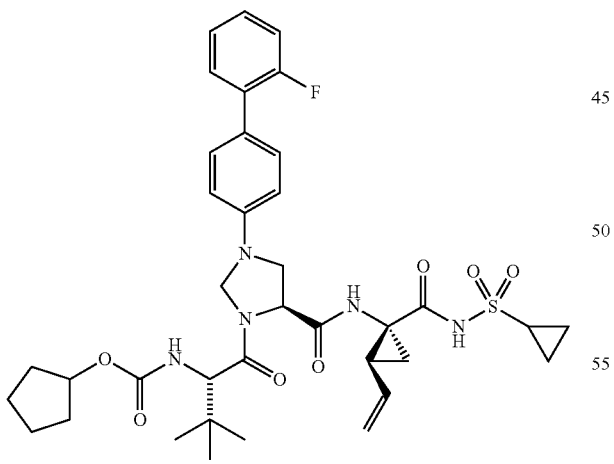

Compound 40 was prepared as described in the general procedure for example 39 by using 2-fluorophenylboronic acid.

$^1$H NMR (300 MHz, CD$_3$OD): δ 9.04 (s, 1H), 7.51-7.42 (m, 3H), 7.28-7.11 (m, 3H), 6.87 (d, J=9.0 Hz, 2H), 5.69-5.61 (m, 1H), 5.37 (m, 1H), 5.22-5.13 (m, 2H), 5.05 (bs, 1H), 4.66 (t, J=6.9 Hz, 1H), 4.31 (s, 1H), 3.95 (t, J=8.7 Hz, 1H), 2.98-2.91 (m, 1H), 2.66-2.61 (m, 1H), 1.84-1.34 (m, 10H), 1.37-1.31 (m, 3H), 1.10 (s, 9H) 1.21-1.00 (m, 3H).

LC/MS=724 (M$^+$+1)

Example 41

Preparation of Compound 41

Compound 41

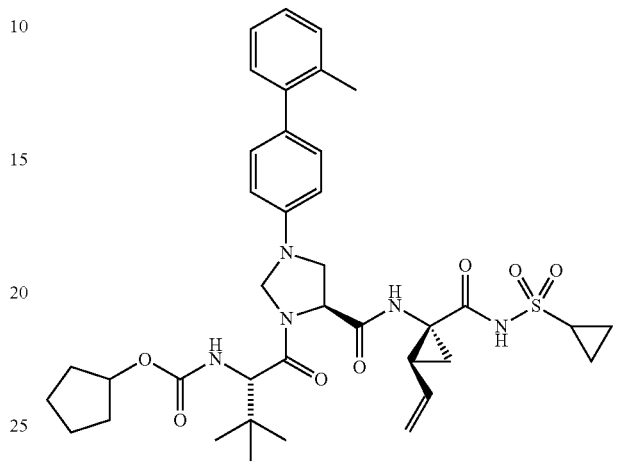

Compound 41 was prepared as described in the general procedure for example 39 by using 2-methylphenylboronic acid.

$^1$H NMR (300 MHz, CD$_3$OD): δ 9.05 (s, 1H), 7.26-7.18 (m, 6H), 6.86 (d, J=8.1 Hz, 2H), 5.69-5.61 (m, 1H), 5.38 (m, 1H), 5.22-5.13 (m, 2H), 5.05 (bs, 1H), 4.66 (t, J=6.9 Hz, 1H), 4.31 (s, 1H), 3.95 (t, J=8.7 Hz, 1H), 2.98-2.91 (m, 1H), 2.66-2.61 (m, 1H), 2.25 (m, 3H), 1.84-1.34 (m, 10H), 1.37-1.31 (m, 2H), 1.10 (s, 9H) 1.21-1.00 (m, 3H).

LC/MS=720 (M$^+$+1)

Example 42

Preparation of Compound 42

Compound 42

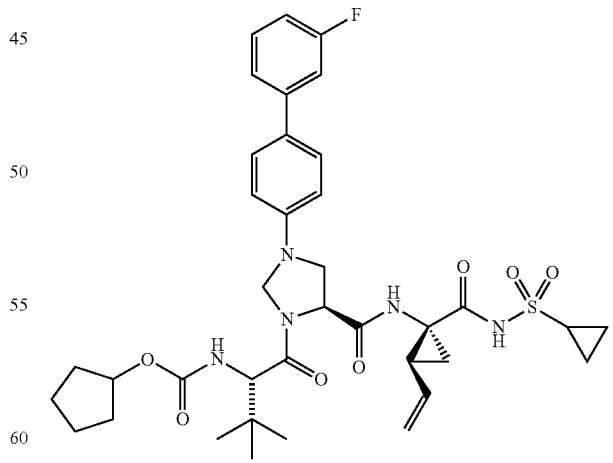

Compound 42 was prepared as described in the general procedure for example 39 by using 3-fluorophenylboronic acid.

$^1$H NMR (300 MHz, CD$_3$OD): δ 9.05 (s, 1H), 7.59 (d, J=8.4 Hz, 2H), 7.40 (m, 2H), 7.31 (d, J=9.3 Hz, 1H), 6.99 (m,

1H), 6.87 (d, J=8.7 Hz, 2H), 5.69-5.61 (m, 1H), 5.37 (m, 1H), 5.22-5.13 (m, 2H), 5.05 (bs, 1H), 4.67 (t, J=6.9 Hz, 1H), 4.30 (s, 1H), 3.94 (t, J=8.7 Hz, 1H), 2.98-2.91 (m, 1H), 2.68-2.60 (m, 1H), 1.84-1.34 (m, 10H), 1.37-1.31 (m, 3H), 1.10 (s, 9H) 1.21-1.00 (m, 3H).
LC/MS=724 (M$^+$+1)

Example 43

Preparation of Compound 43

Compound 43

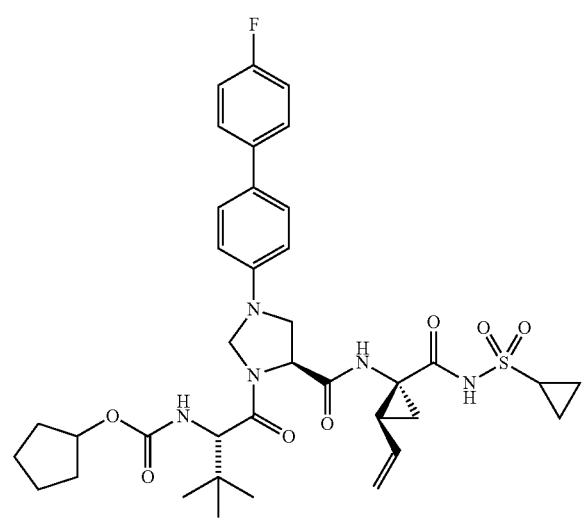

Compound 43 was prepared as described in the general procedure for example 39 by using 4-fluorophenylboronic acid.
$^1$H NMR (300 MHz, CD$_3$OD) δ: 9.04 (s, 1H), 7.60-7.52 (m, 4H), 7.13 (t, J=8.7 Hz, 2H), 6.86(d, J=8.4 Hz, 2H), 5.72-5.60 (m, 1H), 5.36 (m, 1H), 5.22-5.13 (m, 2H), 5.05 (bs, 1H), 4.65 (t, J=6.9 Hz, 1H), 4.31 (s, 1H), 3.93 (t, J=8.4 Hz, 1H), 2.99-2.92 (m, 1H), 2.65-2.60 (m, 1H), 1.84-1.34 (m, 10H), 1.37-1.31 (m, 3H), 1.10 (s, 9H) 1.21-1.05 (m, 3H); LC/MS=724 (M$^+$+1).

Example 44

Preparation of Compound 44

Compound 44

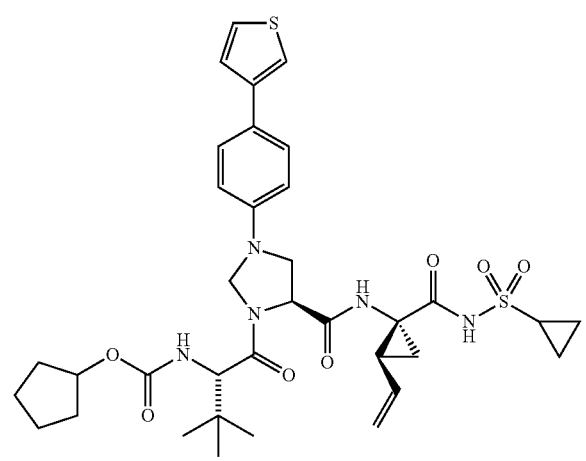

Compound 44 was prepared as described in the general procedure for example 39 by using thiophene-3-boronic acid.

$^1$H NMR (300 MHz, CD$_3$OD): δ 9.04 (s, 1H), 7.69 (d, J=7.5 Hz, 2H), 7.47-7.41 (m, 3H), 6.82 (d, J=8.9 Hz, 2H), 5.69-5.61 (m, 1H), 5.37 (m, 1H), 5.22-5.13 (m, 2H), 5.05 (bs, 1H), 4.66 (t, J=6.9 Hz, 1H), 4.31 (s, 1H), 3.95 (t, J=8.7 Hz, 1H), 2.98-2.91 (m, 1H), 2.66-2.61 (m, 1H), 1.84-1.34 (m, 10H), 1.37-1.31 (3n, 3H), 1.10 (s, 9H) 1.21-1.00 (m, 3H).
LC/MS=712 (M$^+$+1)

Example 45

Preparation of Compound 45

Compound 45

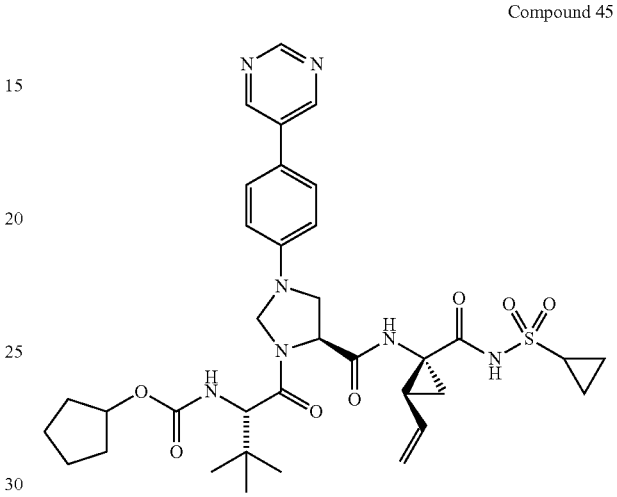

Compound 45 was prepared as described in the general procedure for example 39 by using pyrimidine-5-boronic acid.
$^1$H NMR (300 MHz, CD$_3$OD): δ 9.05 (m, 3H), 7.70 (d, J=8.7 Hz, 2H), 6.94 (d, J=8.7 Hz, 2H), 5.72-5.61 (m, 1H), 5.38 (m, 1H), 5.22-5.13 (m, 2H), 5.05 (bs, 1H), 4.66 (t, J=6.9 Hz, 1H), 4.31 (s, 1H), 3.97 (t, J=8.7 Hz, 1H), 2.98-2.91 (m, 1H), 2.66-2.61 (m, 1H), 1.84-1.34 (m, 10H), 1.37-1.31 (m, 3H), 1.10 (s, 9H) 1.21-1.00 (m, 3H).
LC/MS=708 (M$^+$+1)

Example 46

Preparation of Compound 46

Compound 46

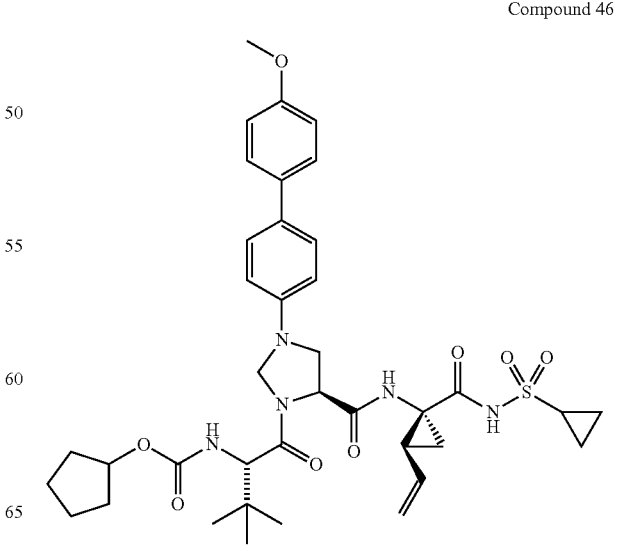

Compound 46 was prepared as described in the general procedure for example 39 by using 4-methoxyphenylboronic acid.

$^1$H NMR (300 MHz, CD$_3$OD): δ 9.03 (s, 1H), 7.53-7.48 (m, 4H), 6.97 (d, J=8.4 Hz, 2H), 6.84(d, J=8.4 Hz, 2H), 5.69-5.61 (m, 1H), 5.37 (m, 1H), 5.22-5.13 (m, 2H), 5.06 (bs, 1H), 4.64 (t, J=6.9 Hz, 1H), 4.31 (s, 1H), 3.92 (t, J=8.7 Hz, 1H), 3.82 (s, 3H), 2.98-2.91 (m, 1H), 2.66-2.61 (m, 1H), 1.84-1.34 (m, 10H), 1.37-1.31 (m, 3H), 1.10 (s, 9H) 1.21-1.00 (m, 3H).

LC/MS=736 (M$^+$+1)

Example 47

Preparation of Compound 47

Compound 47

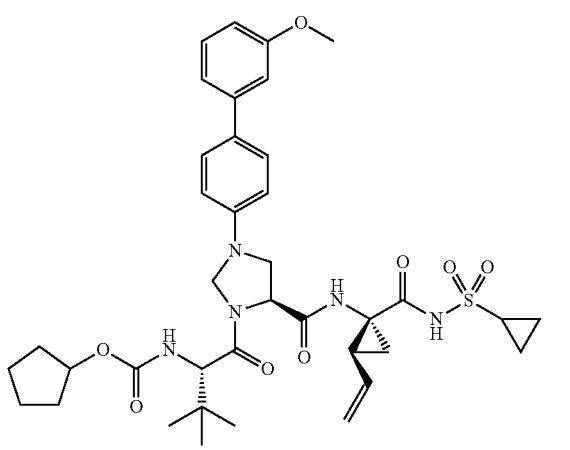

Compound 47 was prepared as described in the general procedure for example 39 by using 3-methoxyphenylboronic acid.

$^1$H NMR (300 MHz, CD$_3$OD): δ 9.04 (s, 1H), 7.59 (d, J=8.1 Hz, 2H), 7.35-7.29 (m, 2H), 7.18-7.09 (m, 2H), 6.82 (d, J=8.1 Hz, 2H), 5.69-5.61 (m, 1H), 5.37 (m, 1H), 5.22-5.13 (m, 2H), 5.06 (bs, 1H), 4.64 (t, J=6.9 Hz, 1H), 4.31 (s, 1H), 3.93 (t, J=8.7 Hz, 1H), 3.81 (s, 3H), 2.98-2.91 (m, 1H), 2.66-2.61 (m, 1H), 1.84-1.34 (m, 10H), 1.37-1.31 (m, 3H), 1.10 (s, 9H) 1.21-1.00 (m, 3H).

LC/MS=736 (M$^+$+1)

Example 48

Preparation of Compound 48

Compound 48

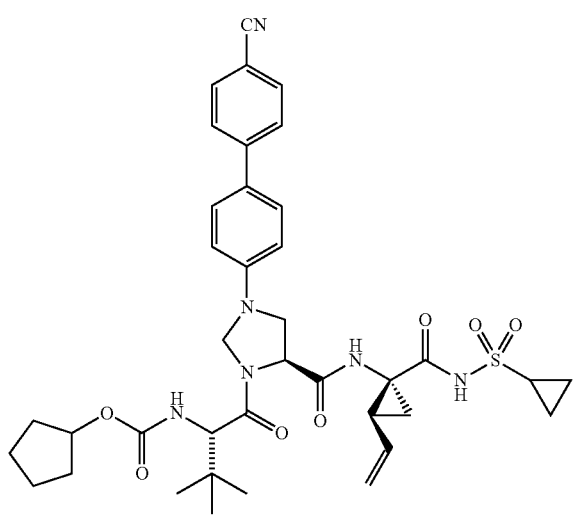

Compound 48 was prepared as described in the general procedure for example 39 by using 4-cyanophenylboronic acid.

$^1$H NMR (300 MHz, CD$_3$OD): δ 9.03 (s, 1H), 7.83-7.75 (m, 4H), 7.66 (d, J=8.4 Hz, 2H), 6.88(d, Hz, 2H), 5.72-5.61 (m, 1H), 5.37 (m, 1H), 5.22-5.13 (m, 2H), 5.06 (bs, 1H), 4.64 (t, J=6.9 Hz, 1H), 4.31 (s, 1H), 3.94 (t, J=8.7 Hz, 1H), 2.98-2.91 (m, 1H), 2.66-2.61 (m, 1H), 1.84-1.34 (m, 10H), 1.37-1.31 (m, 3H), 1.10 (s, 9H) 1.21-1.00 (m, 3H).

LC/MS=731 (M$^+$+1)

Example 49

Preparation of Compound 49

Compound 49

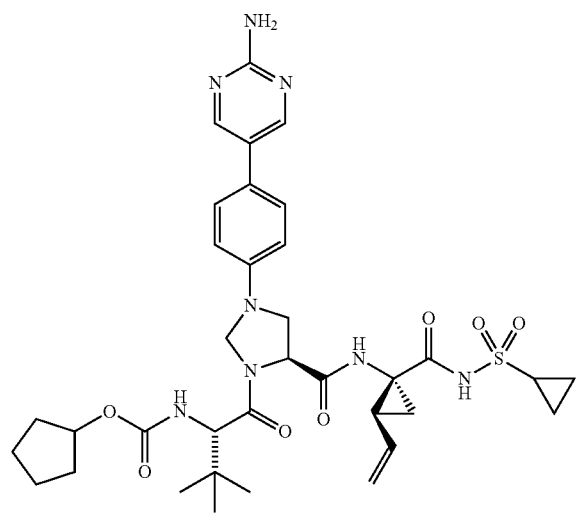

Compound 49 was prepared as described in the general procedure for example 39 by using 2-aminopyrimidine-5-boronic acid pinacol ester.

$^1$H NMR (300 MHz, CD$_3$OD): δ 9.05 (s, 1H), 8.72 (s, 2H), 7.57 (d, J=8.7 Hz, 2H), 6.90 (d, J=8.7 Hz, 2H), 5.76-5.60 (m, 1H), 5.38 (m, 1H), 5.22-5.13 (m, 2H), 5.05 (bs, 1H), 4.66 (t, J=6.9 Hz, 1H), 4.31 (s, 1H), 3.97 (t, J=8.7 Hz, 1H), 2.98-2.91 (m, 1H), 2.66-2.62 (m, 1H), 1.84-1.34 (m, 10H), 1.37-1.31 (m, 3H), 1.10 (s, 9H) 1.21-1.05 (m, 3H).

LC/MS=723 (M$^+$+1)

Example 50

Preparation of Compound 50

Compound 50

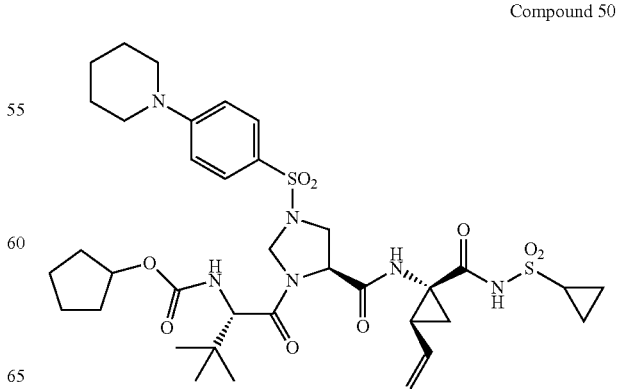

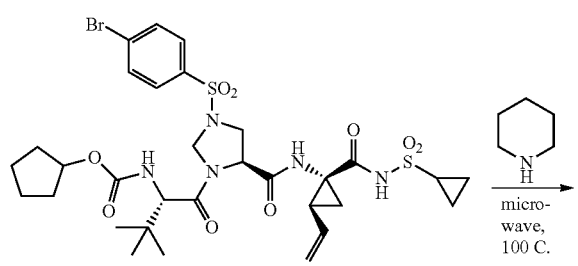
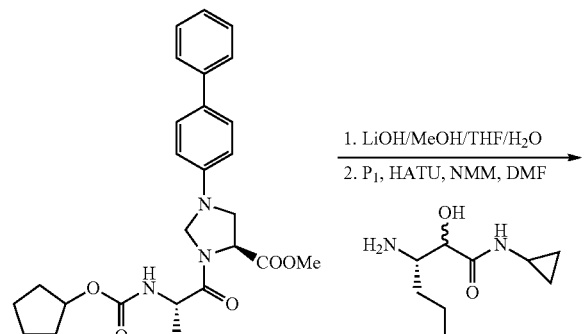
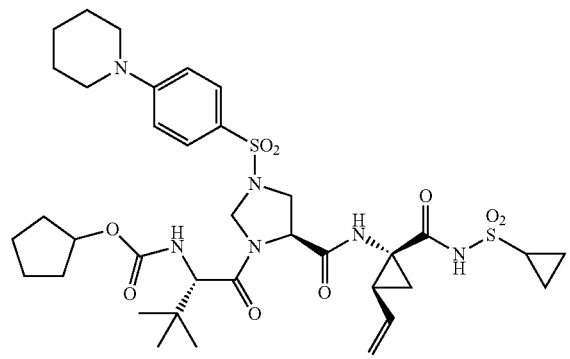
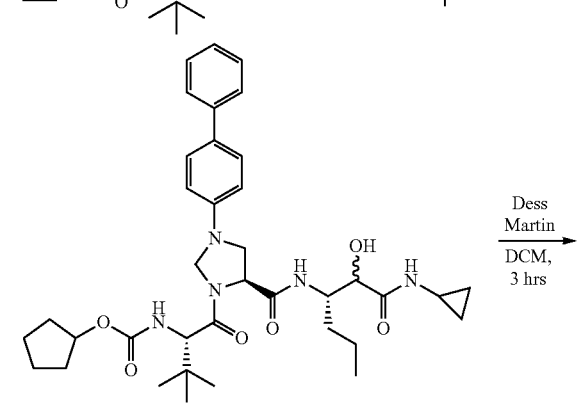
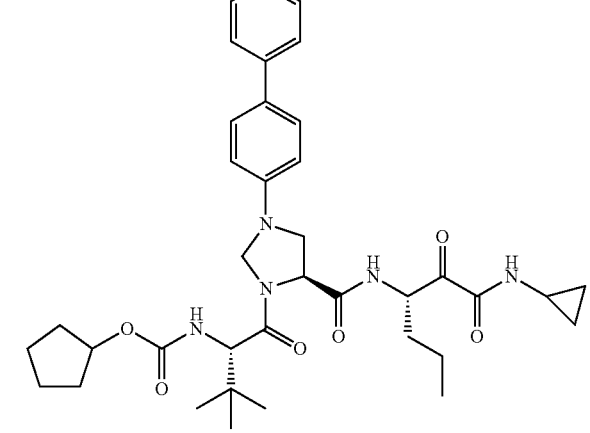
Compound 39 (30 mg, 0.042 mmol) was dissolved in neat Piperidine (0.5 ml), and the reaction mixture was heated at 100° C. in a microwave for 1 hour. The crude reaction material was purified by preparative HPLC to give Compound 50 (22 mg, 0.028 mmol) as a white solid.
LC/MS=777.06 (M$^+$+1)
Example 51
Preparation of Compound 51
Compound 51
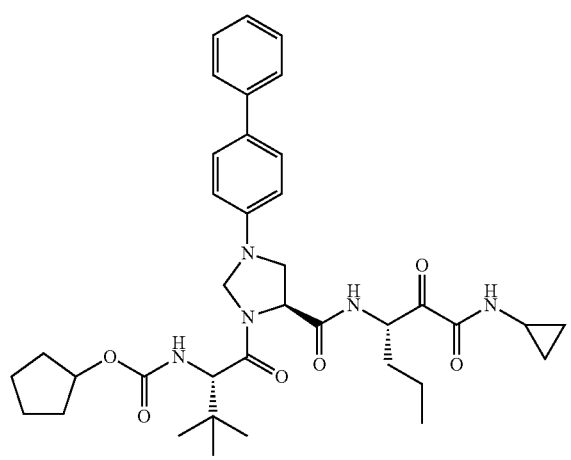
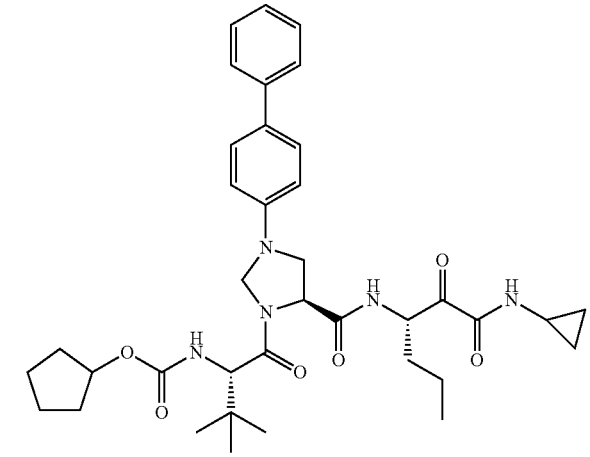
Ester (intermediate for Compound 34) (51 mg, 0.1 mmol) was dissolved in THF (1 mL), H$_2$O (1 mL), and MeOH (1 mL)

and LiOH.H$_2$O (42 mg, 1.0 mmol) was added. The reaction mixture was stirred at room temperature for 1 hour and diluted with EtOAc. The reaction mixture was acidified to pH=4 with 1 N HCl and separated. The aqueous layer was extracted with EtOAc (2×25 mL). The combined organic layers were washed with brine, dried with Na$_2$SO$_4$, concentrated and dried under vacuum to give 50 mg crude acid which was used for next step without further purification.

The acid (50 mg, 0.1 mmol) was suspended in 3 mL of DMF. HATU (76 mg, 0.2 mmol), P$_1$ (19 mg, 0.1 mmol) (for a synthesis see reference XXX) and NMM (55 mg, 0.5 mmol) were added. The reaction solution was stirred overnight at room temperature. The reaction solution was diluted with EtOAc and washed by 0.5 N HCl$_{(aq)}$, 5% LiCl$_{(aq)}$, sat. NaHCO$_{3(aq)}$ and brine, dried over Na$_2$SO$_4$ and concentrated. The residue was purified by a CombiFlash Chromatography System to afford desired alcohol (50 mg, 77%). LC/MS=662 (M$^+$+1)

Alcohol (50 mg, 0.076 mmol) and Dess-Martin periodinane (64 mg, 0.152 mmol) were dissolved in DCM (5 mL). After stirring 3 hours at room temperature, the reaction solution was diluted with DCM (20 mL) and washed by sat. Na$_2$S$_2$O$_3$. The organic layer was washed with sat. NaHCO$_3$, dried over Na$_2$SO$_4$, and concentrated. The residue was purified by preparative HPLC to provide Compound 51 (30 mg, 60%) as a white solid.

$^1$H NMR (300 MHz, CDCl$_3$): δ 7.56-7.50 (m, 4H), 7.41 (t, J=8.1 Hz, 2H), 7.26 (m, 1H) 6.92 (bs, 1H), 6.76 (d, J=8.4 Hz, 2H), 5.36-5.27 (m, 2H), 5.15 (m, 1H), 5.05-4.98 (m, 4H), 4.30 (m, 1H), 4.10 (m, 1H), 3.56-3.49 (m, 1H), 2.77 (m, 1H), 1.98-1.56 (m, 10H), 1.37-1.25 (m, 2H), 1.09 (s, 9H), 0.93-0.83 (m, 4H), 0.60 (m, 2H).

LC/MS=660 (M$^+$+1)

Example 52

Preparation of Compound 52

Compound 52

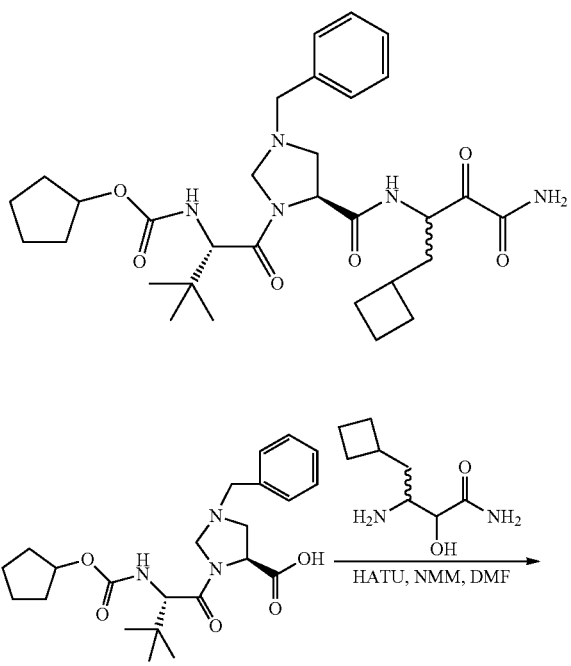

Step 1:
To a solution of acid (VII, 390 mg, 0.88 mmol, Example 1) in DMF (4 ml) was added HATU (840 mg, 2.2 mmol), NMM (360 mg, 3.52 mmol) and amine (xx mg, xx mmol) (synthesized according to WOXXXX). The reaction mixture was stirred at room temperature overnight. The mixture was diluted with EtOAc and washed with 1N HCl, 5% LiOH, sat. NaHCO$_3$, brine, dried over MgSO$_4$, filtered and concentrated. The crude material (white solid, 240 mg) was taken forward to next step without further purification.

Step 2:
Crude a-hydroxyl amide (50 mg) was dissolved in DCM under N$_2$, to the solution was added Dess-Martine periodinane. LC-MS showed complete conversion after 10 minutes. The mixture was cooled to 0° C. and diluted with EtOAc (5 ml), followed by the addition of sat. Na$_2$S$_2$CO$_3$ and sat. NaHCO$_3$. The solution was stirred at room temperature for 20 minutes; the organic phase was separated and washed with brine, dried over Na$_2$SO$_4$, filtered and concentrated. The residue was purified flash chromatography to give Compound 52 as a white solid.

LC/MS=584.33 (M$^+$+1)

Example 53

Preparation of Compound 53

Compound 53

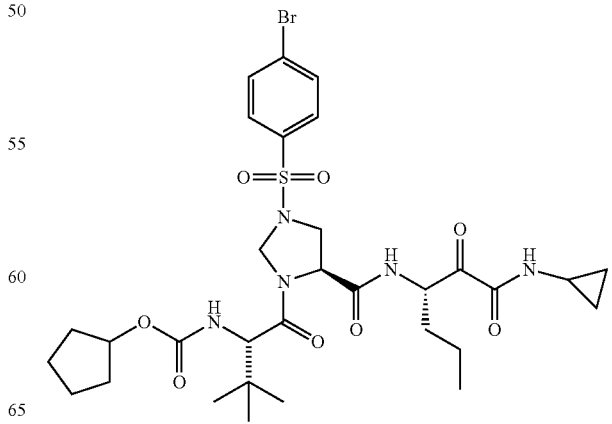

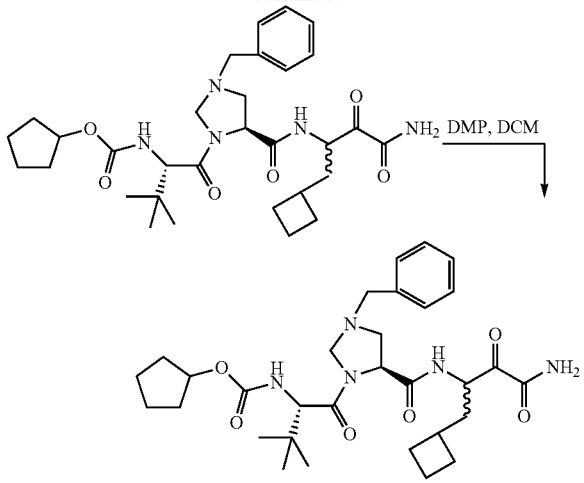

Compound 53 was prepared using the process described for Example 51 but using the starting material of Example 29.

$^1$H NMR (300 MHz, CD$_3$OD): δ 7.81 (d, J=8.7 Hz, 2H), 7.71 (d, J=8.1 Hz, 2H), 5.58-5.54 (m, 1H), 5.17-5.09 (m, 2H), 4.87-4.80 (m, 1H), 4.17-3.91 (m, 5H), 3.53-3.40 (m, 1H), 2.77-2.67 (m, 1H), 1.94-1.56 (m, 10H), 1.49-1.38 (m, 4H), 0.97 (s, 9H), 0.92-0.78 (m, 6H), 0.62-0.55 (m, 2H).

LC/MS=727 (M$^+$+1)

Example 54

Preparation of Compound 54

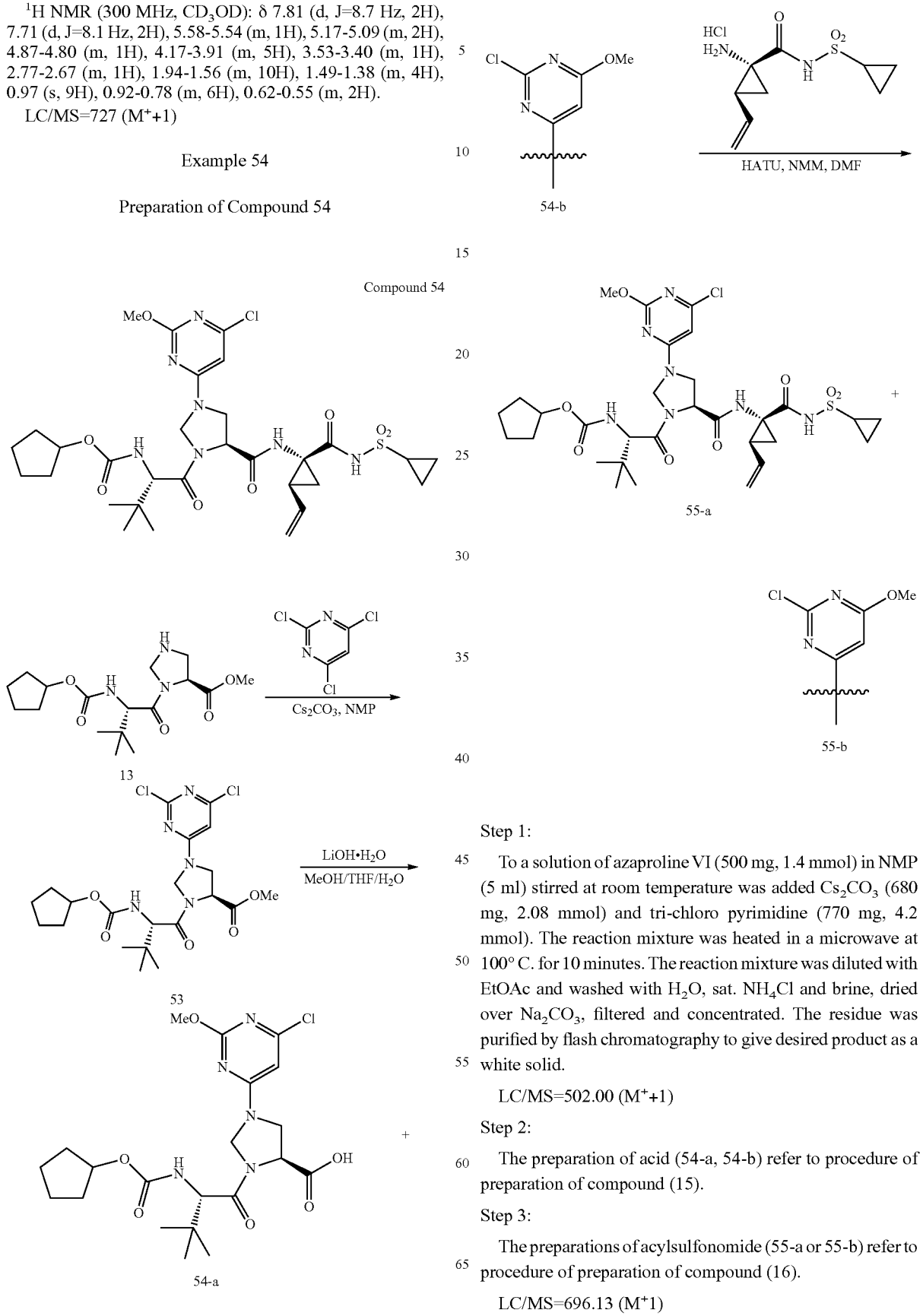

Step 1:

To a solution of azaproline VI (500 mg, 1.4 mmol) in NMP (5 ml) stirred at room temperature was added Cs$_2$CO$_3$ (680 mg, 2.08 mmol) and tri-chloro pyrimidine (770 mg, 4.2 mmol). The reaction mixture was heated in a microwave at 100° C. for 10 minutes. The reaction mixture was diluted with EtOAc and washed with H$_2$O, sat. NH$_4$Cl and brine, dried over Na$_2$CO$_3$, filtered and concentrated. The residue was purified by flash chromatography to give desired product as a white solid.

LC/MS=502.00 (M$^+$+1)

Step 2:

The preparation of acid (54-a, 54-b) refer to procedure of preparation of compound (15).

Step 3:

The preparations of acylsulfonomide (55-a or 55-b) refer to procedure of preparation of compound (16).

LC/MS=696.13 (M$^+$1)

Example 56

Preparation of Compound 56

Compound 56

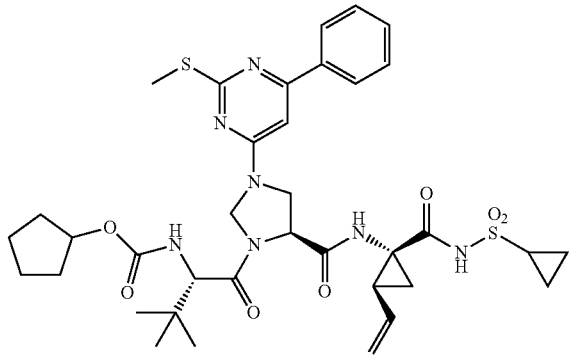

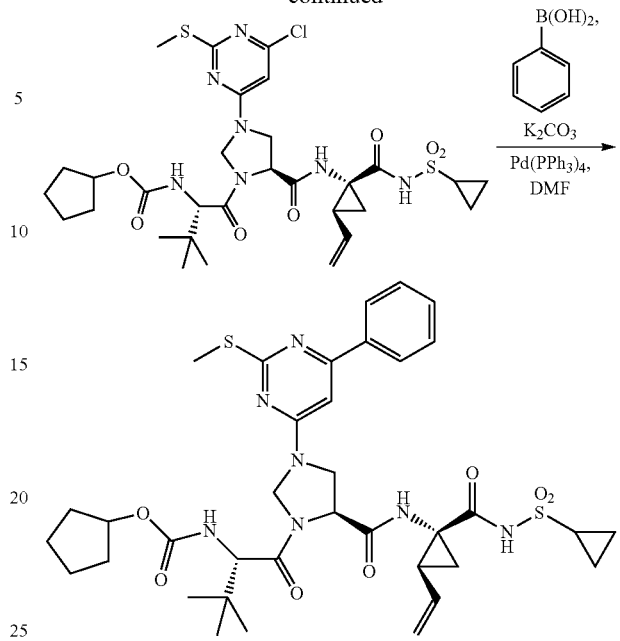

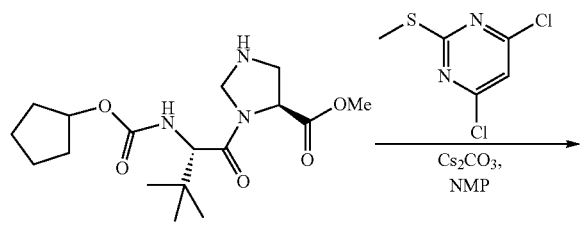

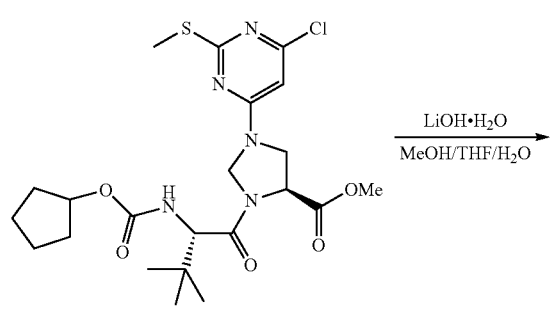

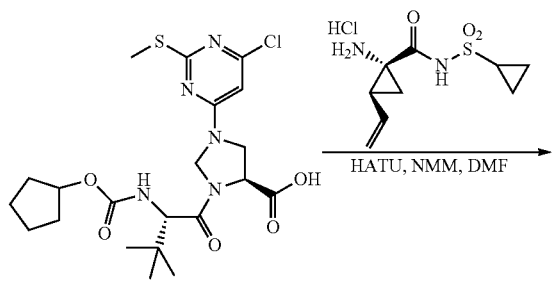

Step 1:

To a solution of azaproline VI (1.0 g, 2.8 mmol) in NMP (5 ml) was added $Cs_2CO_3$ (1.8 g, 5.5 mmol), 4,6-Dichloro-2-methylsulfanyl-pyrimidine (1.63 g, 8.4 mmol). The reaction mixture was heated at 90° C. for 5 hours. The reaction mixture was diluted with EtOAc and washed with $H_2O$, sat. $NH_4Cl$, sat $NaHCO_3$, brine, dried over $Na_2SO_4$, filtered and concentrated. The residue was purified by flash chromatography to give methyl ester (700 mg, 1.36 mmol) as a white solid.

$^1$H NMR (300 MHz, CD3OD) d 6.48 (s, 1H), 5.49 (d, 2H), 5.25 (d, 1H), 5.03 (m, 2H), 4.27 (m, 1H), 3.98 (m, 1H), 3.76 (s, 3H), 2.48 (s, 3H), 1.83-1.60 (m, 8H), 1.05 (s, 9H)

LC/MS=514.20 ($M^+$+1)

Step 2:

The methyl ester hydrolysis was carried out using the process as described for Example 1, Step 2.

Step 3:

Acylsulfonomide was prepared using the process described in Example 2, Step 3.

$^1$H NMR (300 MHz, CD3OD) d 6.47 (s, 1H), 5.72 (m, 1H), 5.49 (m, 1H), 5.32 (d, 1H), 5.23 (m, 1H), 5.15 (d, 1H), 5.05 (m, 1H), 4.74 (m, 1H), 4.25 (s, 1H), 4.07 (m, 1H), 3.72 (m, 1H), 2.95 (m, 1H), 2.53 (s, 3H), 2.27 (m, 1H), 1.91-1.60 (m, 9H), 1.42 (m, 1H), 1.23 (m, 1H), 1.08 (s, 9H), 1.20-1.00 (m, 2H)

LC/MS=726.20 ($M^+$+1)

Step 4:

To a solution of acylsulfonomide (50 mg, 0.07 mmol) in DMF (1 ml) was added phenylboronic acid (10 mg, 0.082 mmol), $K_2CO_3$ (12 mg, 0.087 mmol) and $Pd(PPh_3)_4$ (10 mg, 0.007 mmol). The reaction mixture was heated in a microwave at 130° C. for 40 minutes. The crude material was purified by preparative HPLC to give Compound 56 (10 mg, 0.013 mmol) as a light yellow solid.

LC/MS=754.32 ($M^+$+1)

Example 57
Preparation of Compound 57
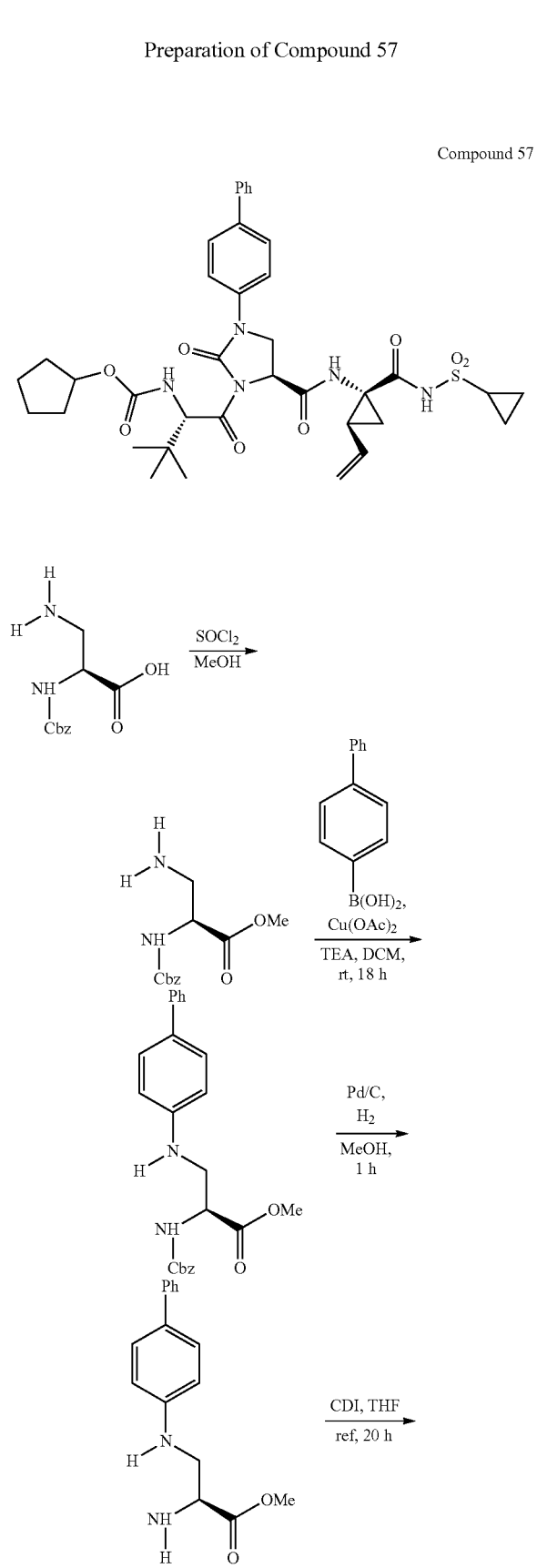
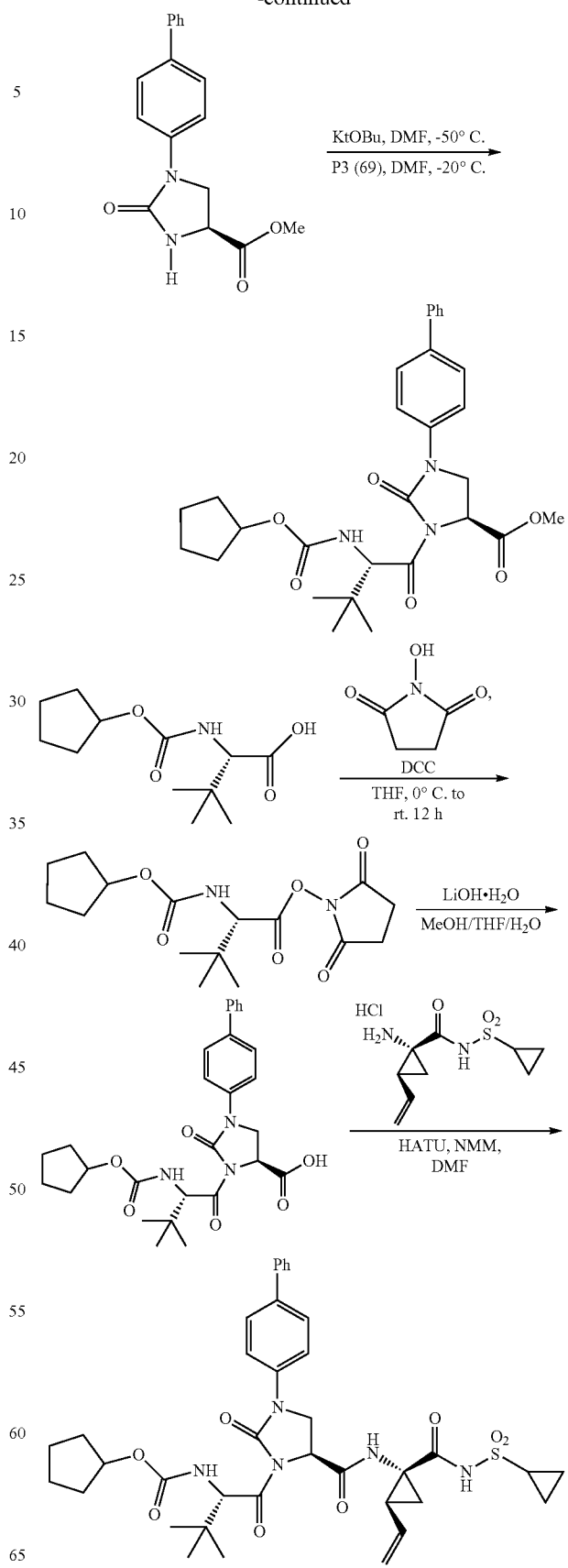

Step 1:

To a flask charged with MeOH (174 ml) was added SOCl₂ (10 g, 84 mmol) and the resulting solution was stirred at −10° C. for 40 minutes. Solid Cbz-Dap-OH (10 g, 41.9 mmol) was added to this solution. The reaction mixture was let to warm up to room temperature and stirred overnight. Solvent and excess amount of SOCl₂ was removed under vacuum to give crude methyl ester as its HCl salt (12.5 g, xx % yield).

$^1$H NMR (300 MHz, CDCl3) d 7.35 (m, 5H), 5.79 (m, 1H), 5.12 (s, 2H), 4.38 (m, 1H), 3.76 (s, 3H), 3.08 (m, 2H)

LC/MS=252.98 (M⁺+1)

Step 2:

To a solution of methyl ester (1.74 g, 6.9 mmol) in DCM (30 ml) was added boronic acid (2.7 g, 13.6 mmol), molecular sieves, TEA (2.09 g, 20.7 mmol) and Cu(OAc)². The resulting mixture was purged with O₂ three times and stirred under O₂ atmosphere for 24 hours. The reaction was quenched with 2N NH₃ in MeOH and concentrated in vacuo. The residue was re-dissolved in DCM, and filtered to remove the insoluble molecular sieves. The filtrate was concentrated and purified flash chromatography to give desired product (550 mg, XX % yield 1.36 mmol) as a white solid.

$^1$H NMR (300 MHz, CD3OD) d 7.47 (d, 2H), 7.38-7.15 (m, 10H), 6.69 (d, 2H), 5.05 (s, 2H), 4.51 (m, 1H), 3.65 (s, 3H), 3.61-3.44 (m, 2H)

LC/MS=270.97 (M⁺+1)

Step 3:

To a solution of amine (220 mg, 0.55 mmol) in MeOH (xx mL) was added 10% Pd/C (40 mg). The resulting mixture was purged with H₂ three times and stirred under H₂ atmosphere for 1 hours. The reaction mixture was filtered and the filtrate was concentrated under vacuum. Diamine (149 mg, xx % yield 0.55 mmol) was obtained as a white solid.

$^1$H NMR (300 MHz, CDCl3) d 7.59 (d, 2H), 7.50-7.40 (m, 4H), 6.77 (d, 2H), 3.78 (s, 3H), 3.78-3.76 (m, 1H), 3.56 (m, 1H), 3.28 (m, 1H)

LC/MS=405.09 (M⁺+1)

Step 4:

To a solution of diamine (149 mg, 0.55 mmol) in THF (2.0 ml) was added CDI (200 mg, 1.26 mmol). The reaction mixture was heated to reflux for 14 hours. Solvent was remover in vacuo. The residue was purified by preparative HPLC to give urea (125 mg, xx % yield 0.42 mmol).

$^1$H NMR (300 MHz, DMSO) d 7.65 (m, 6H), 7.43 (m, 2H), 7.32 (d, 1H), 4.44 (m, 1H), 4.18 (m, 1H), 3.95 (m, 1H), 3.72 (s, 1H)

LC/MS=297.15 (M⁺+1)

Step 5:

To solution of 2-Cyclopentyloxycarbonylamino-3,3-dimethyl-butyric acid (2.0 g, 8.2 mmol) in THF stirred at 0° C. was added N-hydroxysuccinimine (970 mg, 8.4 mmol) and followed by the addition of DCC (1.73 g, 8.4 mmol). The reaction mixture was slowly warded up to room temperature and stirred for 14 hours. The solid was filtered off and the filtrate was concentrated. The crude succinimide ester was used in the next step without purification.

To a solution of urea (90 mg, 0.304 mmol) in THF (3.0 ml) stirred at −50° C. was added K$^t$OBu (34 mg, 0.304 mmol) and warmed up to −20° C. over 20 minutes. To this mixture was added a slurry of the crude succinimide ester (0.103 g) in THF (1.0 ml) and warmed up to −10° C. over 20 minutes. The reaction was quenched with sat. NH₄Cl and extracted with EtOAc. The organic layer was separated, dried over Na₂SO₄ and concentrated. The crude material was purified by flash chromatography to give methyl ester (50 mg, xx % yield 0.09 mmol).

LC/MS=522.07 (M⁺+1) 544.32 (M⁺+Na)

Compound 57 was prepared from product obtained above using the same procedures described in Example 2 (Step 2 and Step 3) for compound 2.

$^1$H NMR (300 MHz, CD3OD) d 7.72-7.61 (m, 6H), 7.44 (m, 2H), 7.33 (d, 1H), 5.73(m, 1H), 5.33 (d, 1H), 5.16(d, 1H), 5.02 (m, 1H), 4.78 (m, 1H), 4.17 (m, 1H), 3.84 (m, 1H), 2.29 (m, 1H), 1.92 (m, 1H), 1.89-1.52 (m, 8H), 1.50 (m, 1H), 1.28 (m, 2H), 1.08 (s, 9H), 1.08-1.04 (m, 2H)

LC/MS=719.87 (M⁺+1) 742.18 (M⁺+Na)

Example 58

Preparation of Compound 58

Compound 58

Compound 58 was prepared using the process described in Example 34 but using Boc-L-tent-leucine as the building block.

$^1$H NMR (300 MHz, CD₃OD): δ 7.56 (m, 4H), 7.39 (t, J=7.5 Hz, 2H), 7.26 (m, 1H) 6.87 (d, J=8.4 Hz, 2H), 5.81-5.69 (m, 1H), 5.36-5.31 (m, 2H), 5.15 (d, J=11.1 Hz, 1H), 4.92 (m, 1H), 4.61 (t, J=6.9 Hz, 1H), 4.33 (s, 1H), 3.94 (t, J=8.4 Hz, 1H), 3.40-3.34 (m, 1H) 2.99-2.91 (m, 1H), 2.33-2.24 (m, 1H), 1.92-1.88 (m, 1H), 1.46 (s, 9H), 1.30-1.22(m, 2H), 1.10 (s, 9H), 1.15-1.06 (m, 3H).

LC/MS=694 (M⁺+1)

Example 59

Preparation of Compound 59

Compound 59

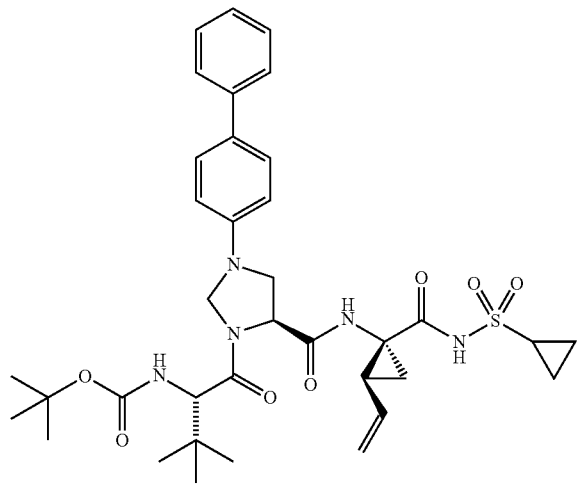
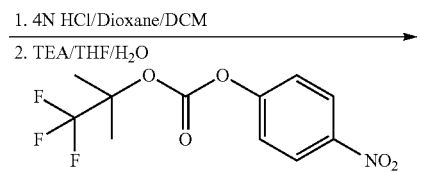

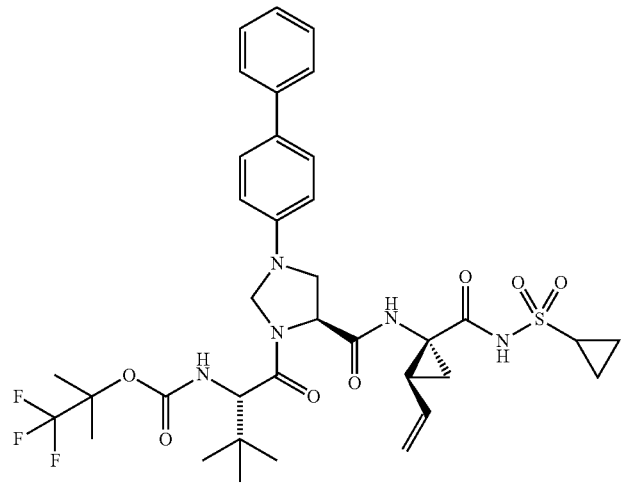

To a solution of Compound 58 (70 mg, 0.10 mmol) in DCM (0.5 mL) was added 4 N HCl in Dioxane (0.25 mL). The reaction mixture was stirred at room temperature for 1 h. After concentration, the crude was dissolved in THF (0.5 mL) and H$_2$O (0.1 mL). Triethylamine (21 mg, 0.20 mmol) and (1,1-dimethyl-2,2,2-trifluoroethyl)-4-nitrophenylcarbonate (44 mg, 0.15 mmol) were added to the reaction solution. After stirred overnight at room temperature, the reaction solution was diluted with EtOAc and washed by 0.5 N HCl$_{(aqu)}$, brine, dried by Na$_2$SO$_4$, filtered and concentrated. The residue was purified with a CombiFlash Chromatography System to afford Compounds 59 (38 mg, 50%).

$^1$H NMR (300 MHz, CD$_3$OD): δ 7.56 (m, 4H), 7.39 (t, J=7.5 Hz, 2H), 7.26 (m, 1H) 6.86 (d, J=9.0 Hz, 2H), 5.82-5.70 (m, 1H), 5.36-5.31 (m, 2H), 5.15 (d, J=11.1 Hz, 1H), 4.93 (m, 1H), 4.62 (t, J=7.2 Hz, 1H), 4.32 (d, J=8.7 Hz, 1H), 3.94 (t, J=8.7 Hz, 1H), 3.40-3.32 (m, 1H), 2.99-2.91 (m, 1H), 2.33-2.24 (m, 1H), 1.92-1.88 (m, 1H), 1.68 (d J=11.1 Hz, 6H), 1.48-1.43 (m, 1H), 1.30-1.22(m, 2H), 1.10 (s, 9H), 1.15-1.03 (m, 3H).

LC/MS=748 (M$^+$+1)

Example 60

Preparation of Compound 60

Compound 60

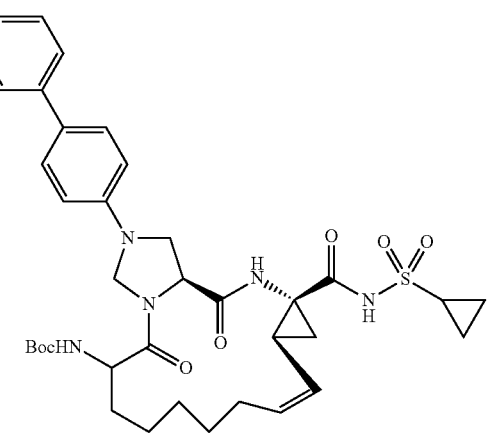

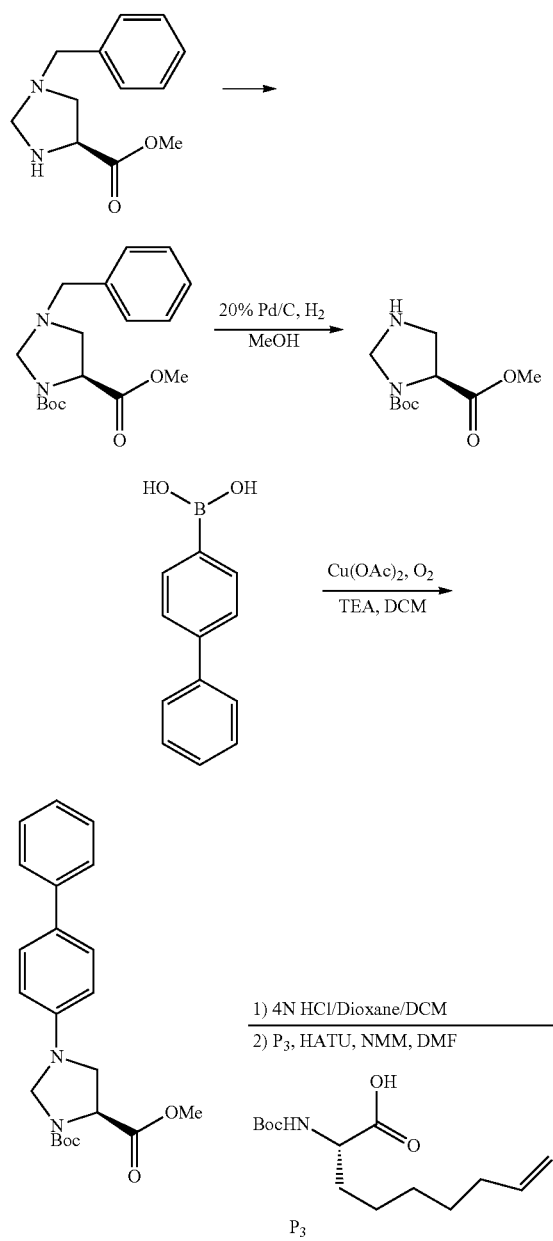
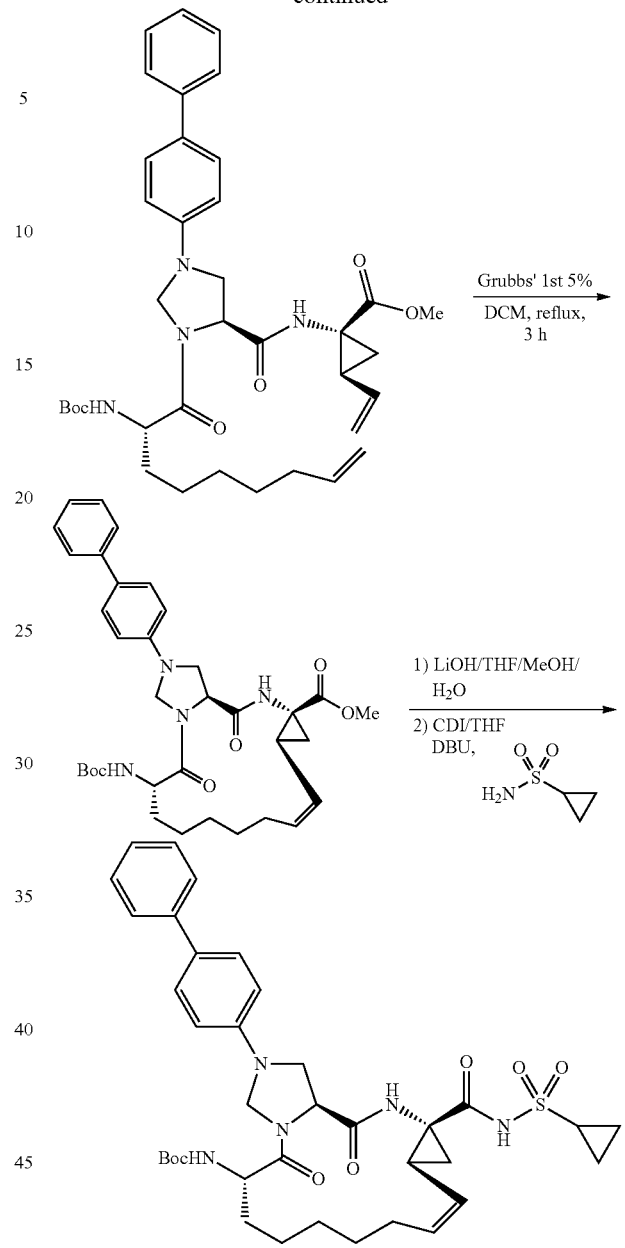
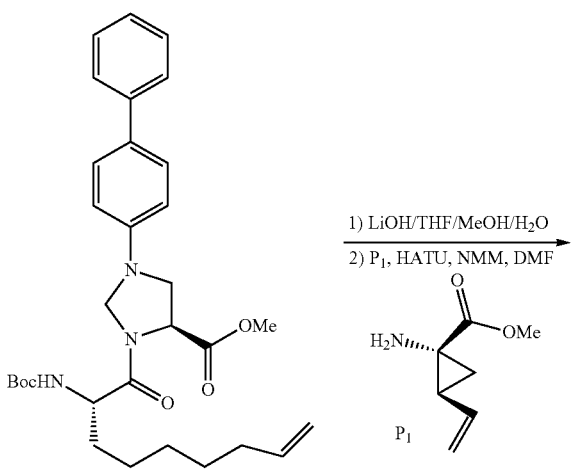

Step 1:

To a solution of Intermediate IV (10.2 g, 46.3 mmol) in DCM (200 ml) was added TEA (9.4 g, 92.6 mmol) at room temperature. The mixture was then cooled to 0° C. and was added (Boc)₂O (15.2 g, 69.5 mmol). The mixture was then warmed to room temperature and stirred for 1 hour. After concentration, the residue was diluted with EtOAc (500 mL), washed with aqu.1N HCl (100 mL) and aqu. sat. NaHCO₃ (200 mL). The organic layer was dried (Na₂SO₄) and concentrated in vacuo. The residue was purified by silica gel column Step 2:

A solution of 3-Benzyl-imidazolidine-1,5-dicarboxylic acid 1-tert-butyl ester 5-methyl ester (1.0 g, 3.12 mmol) in MeOH (20 mL) was added Pd/C (0.20 g) and stirred at room temperature under H₂ for two hours. The reaction mixture was filtered through celite. The filtrate was concentrated to afford Imidazolidine-1,5-dicarboxylic acid 1-tert-butyl ester 5-methyl ester (0.72 g, xx % yield) which was used for the next step directly.

LC/MS=231 (M$^+$+1)

Step 3:

A solution of Imidazolidine-1,5-dicarboxylic acid 1-tert-butyl ester 5-methyl ester (0.72 g, 3.12 mmol) and molecular sieve (3 g) in CH$_2$Cl$_2$ (100 mL) was stirred at room temperature as copper (II) acetate (1.25 g, 6.86 mmol), 4-biphenylboronic acid (2.47 g, 12.48 mmol) and triethylamine (10 mL) were added. Meanwhile, dry air was sucked into the reaction solution slowly by using vacuum. After stirring overnight, the reaction was quenched by adding 10% NH$_4$OH (aq) solution (20 mL) and stirred for 4 hours. After separation, the organic layer was washed by 0.5 N HCl (aq), brine, dried over Na$_2$SO$_4$, filtered and concentrated. After concentration, the crude was purified with a CombiFlash Chromatography System to afford desired ester (0.75 g, 63%).

LC/MS=383 (M$^+$+1)

Step 4:

A solution of ester (0.70 g, 1.83 mmol) in DCM (15 mL) was cooled to 0° C. and added 4 N HCl in dioxane (5 mL) slowly. The reaction solution was warmed to room temperature and stirred for 3 hours. After concentration, the crude was pumped under high vacuum for 1 hour. The crude was dissolved in DMF (10 mL) and followed by adding HATU (1.4 g, 3.66 mmol), NMM (0.93 g, 9.15 mmol) and P$_3$ (0.60 g, 2.2 mmol). The reaction solution was stirred at room temperature for 2 hours and diluted with EtOAc (100 mL). The organic layer was washed by 0.5 N HCl$_{(aqu)}$ (50 mL), 5% LiCl$_{(aqu)}$ (50 mL), brine (50 mL) and H$_2$O (50 mL) and dried by Na$_2$SO$_4$. After concentration, the crude was purified with a CombiFlash Chromatography System to afford desired dipeptide (0.51 g, 48%). LC/MS=536 (M$^+$+1)

Step 5:

To a solution of dipeptide (0.50 g, 0.935 mmol) in THF:H$_2$O (3 mL:3 mL) was added LiOH.H$_2$O (0.39 g, 9.35 mmol). The reaction mixture was stirred at room temperature for 1 h and diluted with EtOAc. The reaction mixture was acidified to pH=4 with 1 N HCl and separated. The aqueous layer was extracted with EtOAc (2×25 mL). The combined organic layers were washed with brine, dried with Na$_2$SO$_4$, concentrated and dried under vacuum to give 0.50 g crude acid which was used for next step without further purification.

Step 6:

To a solution of acid (0.49 g, 0.935 mmol) in 10 mL of DMF was added HATU (0.71 g, 1.87 mmol), amine (0.16 g, 1.12 mmol) and NMM (0.47 g, 4.86 mmol). The reaction mixture was stirred overnight at room temperature and diluted with EtOAc (100 mL). The organic layer was washed with 0.5 N HCl$_{(aqu)}$ (50 mL), 5% LiCl$_{(aqu)}$ (50 mL), brine (50 mL), dried over Na$_2$SO$_4$, filtered and concentrated. The residue was purified with a CombiFlash Chromatography System to afford tripeptide (0.40 g, 71%) as a white solid. LC/MS=645 (M$^+$+1)

Step 7:

Tripeptide (0.35 g, 0.54 mmol) was dissolved in CH$_2$Cl$_2$ (55 mL) and degassed with N7 for 20 minutes. Grubb's G1 catalyst (22 mg, 0.027 mmol) was added and degassed for an additional 20 minutes. The reaction mixture was heated to 45° C. for 3 hours and cooled to room temperature. After concentration, the crude was purified by combi-flash to give macrocylic tripeptide (0.24 g, 70%) as a white solid. LC/MS=617 (M$^+$+1)

Step 8:

Tripeptide methyl ester was converted the acylsulfonamid using the same procedures described in Example 2 (Step 2 and Step 3) for compound 2 to give Compound 60 (0.10 g, 47%) as a white solide.

$^1$H NMR (300 MHz, CD$_3$OD): δ 9.07 (s, 1H), 7.57 (m, 4H), 7.39 (t, J=8.1 Hz, 2H), 7.26 (m, 1H) 6.88 (d, J=8.4 Hz, 2H), 5.68 (m, 1H), 5.51 (m, 1H), 5.15 (bs, 1H), 4.87-4.78 (m, 2H), 4.27 (m, 1H), 4.00 (m, 1H), 3.61 (m, 1H), 2.91 (m, 1H), 2.56 (m, 1H), 2.34 (m, 1H), 1.90 (m, 2H), 1.75 (m, 1H), 1.66 (m, 2H), 1.51 (m, 3H), 1.43 (s, 9H), 1.29 (m, 3H), 1.09 (m, 2H) 1.00 (m, 1H).

LC/MS=706 (M$^+$+1)

Example 61

Preparation of Compound 61

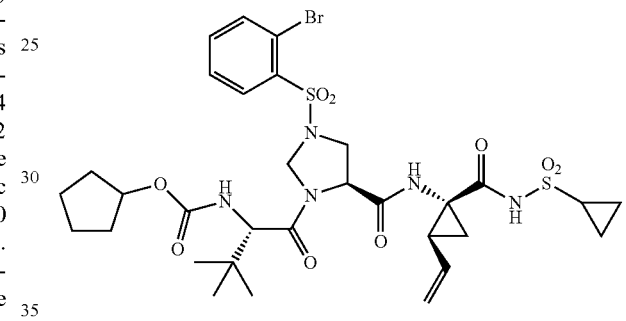

Compound 61

Compound 61 was prepared by using the same procedures described in Example 7 for compound 7.

LC/MS=773.92 (M$^+$+1)

Example 62

Preparation of Compound 62

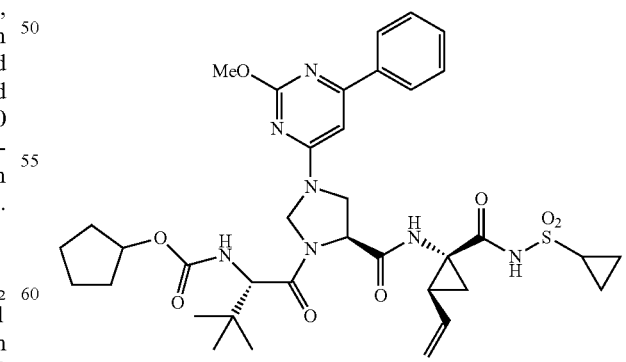

Compound 62

Compound 62 was prepared using the process described in Example 56 but using the appropriate building block.

LC/MS=738.90 (M$^+$+1)

Example 63
Preparation of Compound 63
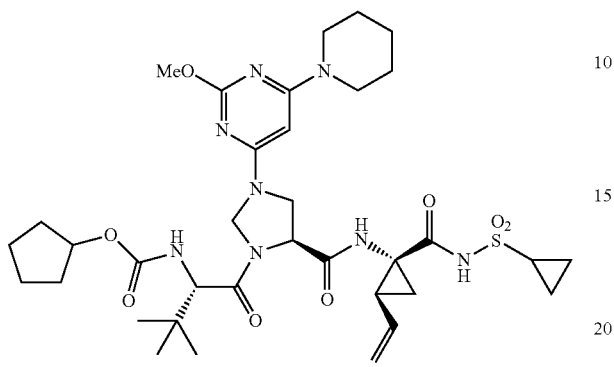
Compound 63
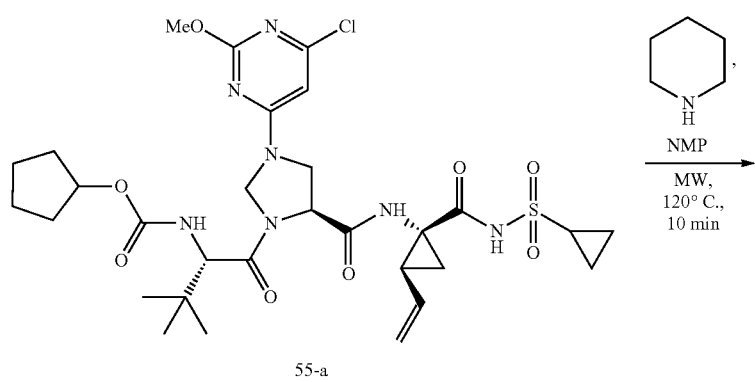
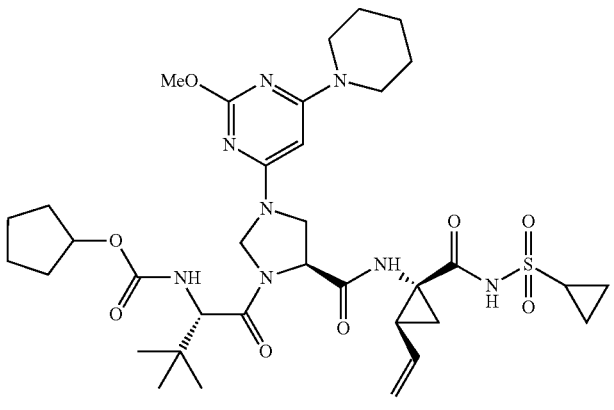
Compound 63 (60 mg, 0.086 mmol) was dissolved in NMP (0.6 ml) and followed by addition of Piperidine (0.3 ml), and the reaction mixture was heated at 100° C. in a microwave for 10 minutes. The crude reaction material was purified by preparative HPLC to give Compound 63 (55 mg, 0.071 mmol) as a white solid.
LC/MS=746.00 (M$^+$+1)

| CPD # | Structure | LCMS |
|---|---|---|
| 64 | 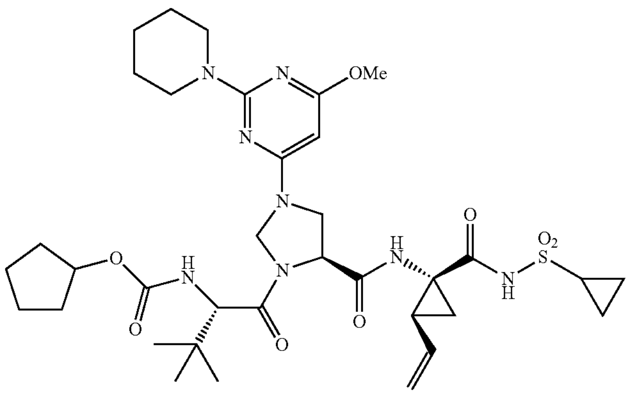 [SMILES: C=C[C@@H]1C[C@]1(NC(=O)[C@@H]1CN(c2cc(OC)nc(N3CCCCC3)n2)CN1C(=O)[C@@H](NC(=O)OC1CCCC1)C(C)(C)C)C(=O)NS(=O)(=O)C1CC1] | 746.00 |
| 65 | 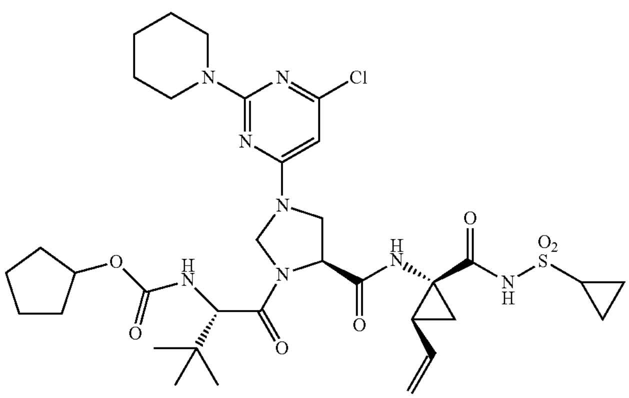 [SMILES: C=C[C@@H]1C[C@]1(NC(=O)[C@@H]1CN(c2cc(Cl)nc(N3CCCCC3)n2)CN1C(=O)[C@@H](NC(=O)OC1CCCC1)C(C)(C)C)C(=O)NS(=O)(=O)C1CC1] | 750.22 |
| 66 | 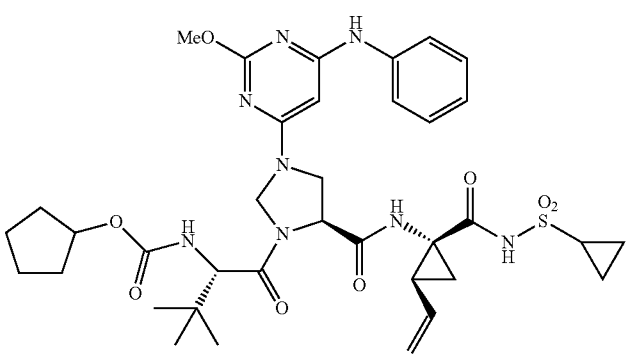 [SMILES: C=C[C@@H]1C[C@]1(NC(=O)[C@@H]1CN(c2cc(Nc3ccccc3)nc(OC)n2)CN1C(=O)[C@@H](NC(=O)OC1CCCC1)C(C)(C)C)C(=O)NS(=O)(=O)C1CC1] | 753.33 |

Compounds 64-66 were prepared using the process described in Example 63 but using the appropriate building blocks.
Example 67
Preparation of Compound 67
Compounds 67 was prepared using the process described in Example 33 but using the appropriate building blocks LC/MS=734 (M⁺+1)
Example 68
Preparation of Compound 68
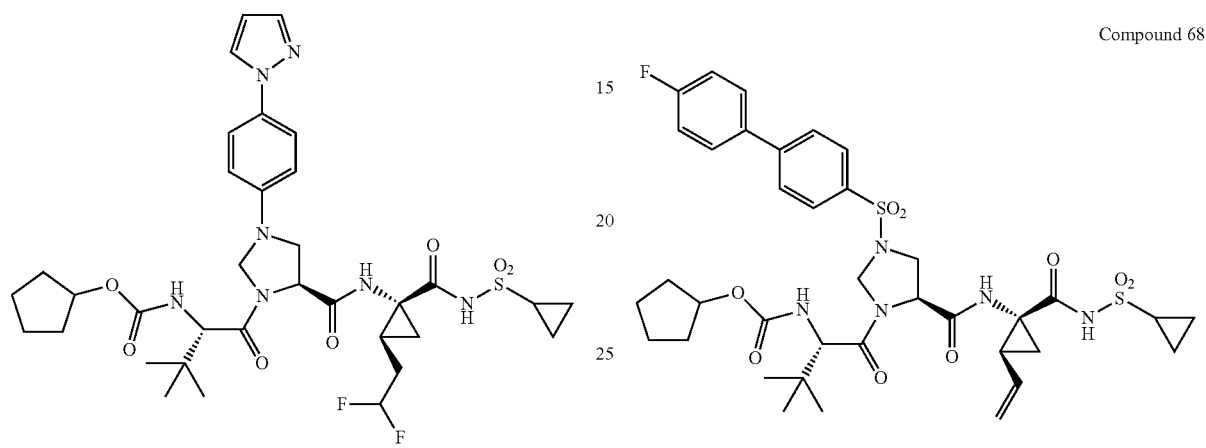
Compound 67
Compound 68
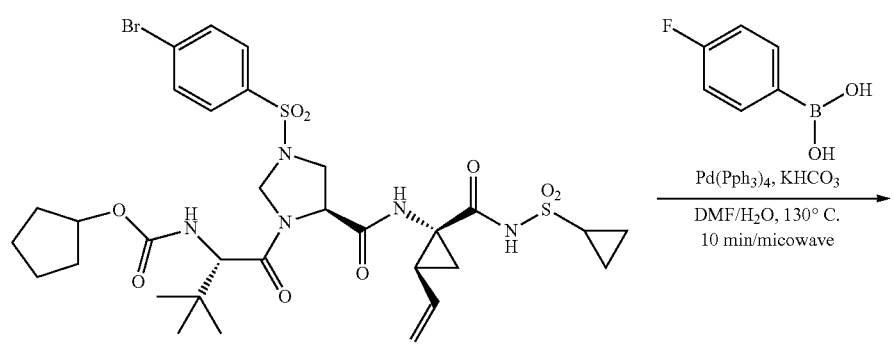
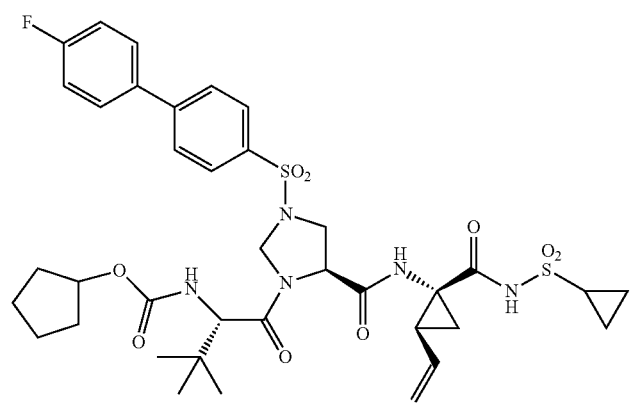

A solution of 14 (50 mg, 0.065 mmol), 4-florophenylboronic acid (11 mg, 0.078 mmol), tetrakis(triphenylphosphine)palladium (0) (7.5 mg, 0.0065 mmol) and potassium bicarbonate (13 mg, 0.13 mmol) were dissolved in DMF and $H_2O$ (0.5 mL/0.1 mL) in a microwave tube. The reaction solution was heated to 130° C. for 10 minutes under microwave. After concentration, the crude was diluted with 1 mL DMF and purified by preparative HPLC to afford 68 (15 mg, 30%) as a white solid.

LC/MS=788 ($M^+$+1)

A solution of 14 (50 mg, 0.065 mmol), thiophene-2-boronic acid (10 mg, 0.078 mmol), tetrakis(triphenylphosphine)palladium (0) (7.5 mg, 0.0065 mmol) and potassium bicarbonate (13 mg, 0.13 mmol) were dissolved in DMF and $H_2O$ (0.5 mL/0.1 mL) in a microwave tube. The reaction solution was heated to 130° C. for 10 minutes under microwave. After concentration, the crude was diluted with 1 mL DMF and purified by preparative HPLC to afford 69 (15 mg, 30%) as a white solid.

LC/MS=776 ($M^+$+1)

Example 69

Preparation of Compound 69

Example 70

Preparation of Compound 70

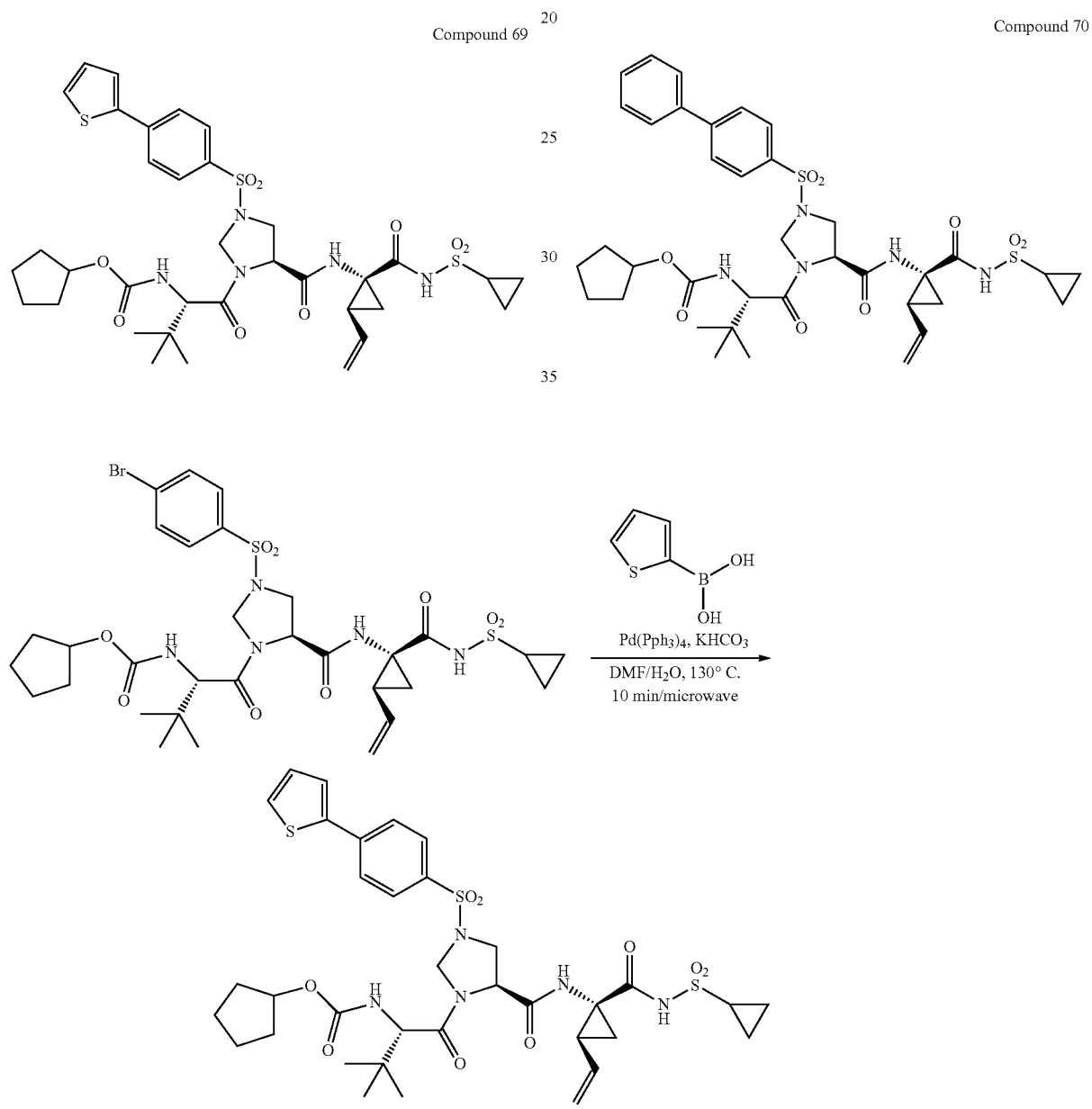

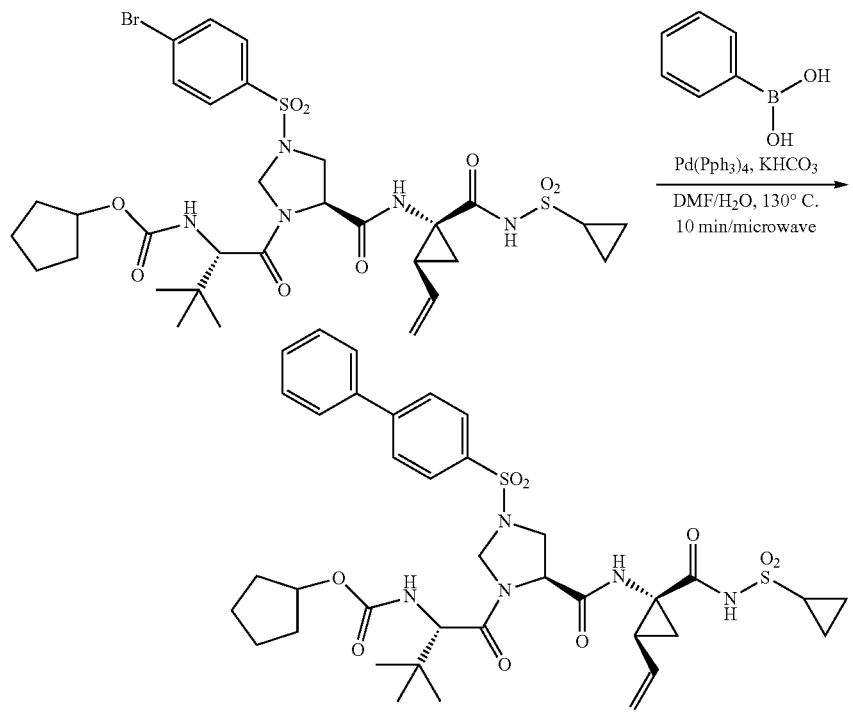

A solution of 14 (50 mg, 0.065 mmol), phenylboronic acid (10 mg, 0.078 mmol), tetrakis(triphenylphosphine)palladium (0) (7.5 mg, 0.0065 mmol) and potassium bicarbonate (13 mg, 0.13 mmol) were dissolved in DMF and $H_2O$ (0.5 mL/0.1 mL) in a microwave tube. The reaction solution was heated to 130° C. for 10 minutes under microwave. After concentration, the crude was diluted with 1 mL DMF and purified by preparative HPLC to afford 70 (9 mg, 18%) as a white solid.

LC/MS=770 ($M^+$+1)

Example 71

Preparation of Compound 71

Compound 71

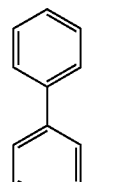
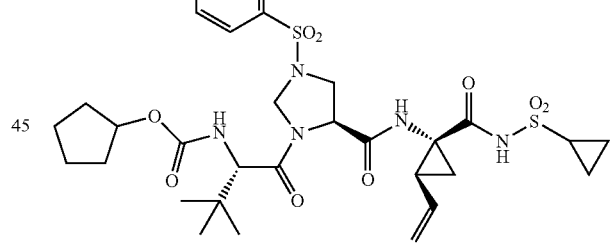

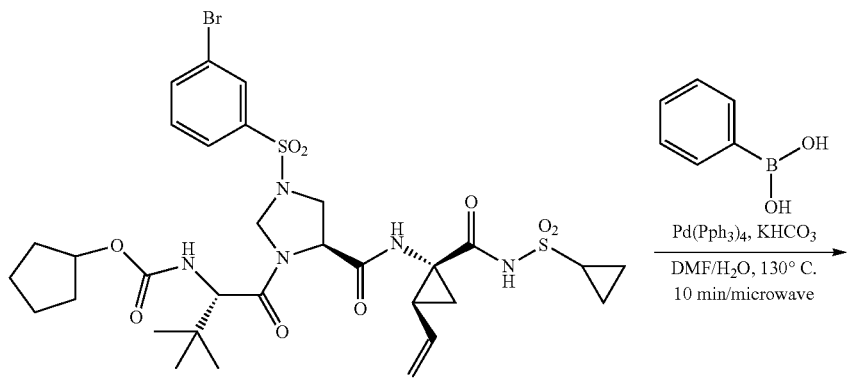

-continued

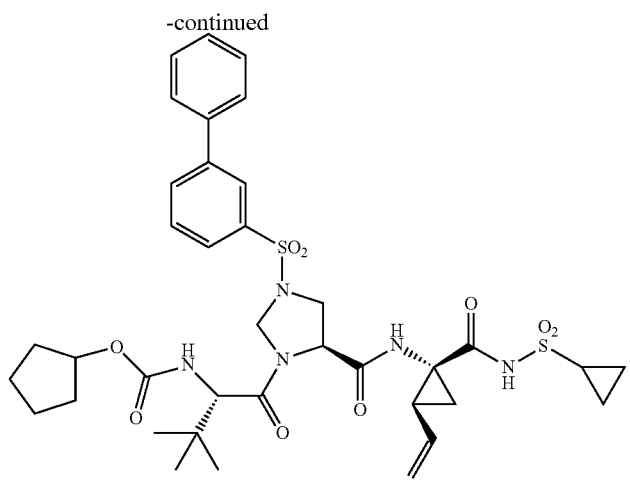

A solution of 15 (50 mg, 0.065 mmol), phenylboronic acid (1.0 mg, 0.078 mmol), tetrakis(triphenylphosphine)palladium (0) (7.5 mg, 0.0065 mmol) and potassium bicarbonate (13 mg, 0.13 mmol) were dissolved in DMF and H$_2$O (0.5 mL/0.1 mL) in a microwave tube. The reaction solution was heated to 130° C. for 10 minutes under microwave. After concentration, the crude was diluted with 1 mL DMF and purified by preparative HPLC to afford 71 (12 mg, 20%) as a white solid.

LC/MS=770 (M$^+$+1)

Example 72

Preparation of Compound 72

Compound 72

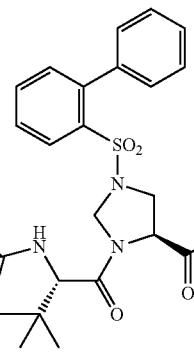

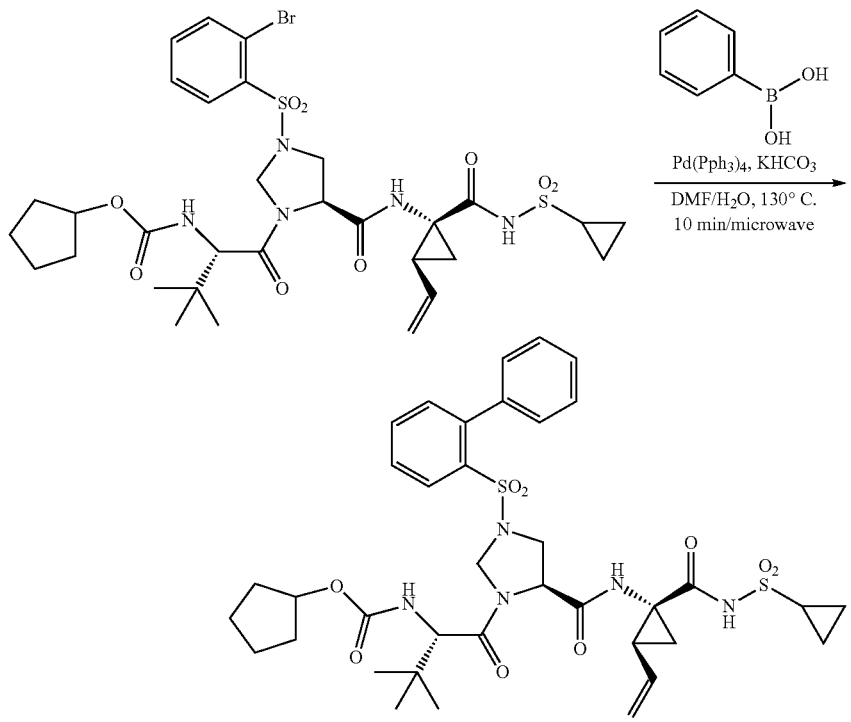

A solution of 61 (50 mg, 0.065 mmol), phenylboronic acid (10 mg, 0.078 mmol), tetrakis(triphenylphosphine)palladium (0) (7.5 mg, 0.0065 mmol) and potassium bicarbonate (13 mg, 0.13 mmol) were dissolved in DMF and H$_2$O (0.5 mL/0.1 mL) in a microwave tube. The reaction solution was heated to 130° C. for 10 minutes under microwave. After concentration, the crude was diluted with 1 mL DMF and purified by preparative HPLC to afford 72 (11 mg, 20%) as a white solid.

LC/MS=770 (M$^+$+1)

BIOLOGICAL ASSAYS

HCV NS3 Protease IC50 Determination

HCV NS3 protease activity was monitored using a fluorescence resonance energy transfer (FRET) depsipeptide substrate (RET S1, Anaspec, San Jose, Calif.) based on the method of Taliani. Briefly, 2-10 nM of purified NS3 protease domains were pre-incubated at 37° C. for 10 minutes with 20 μM isogenic NS4A peptide cofactors (Sigma, St. Louis, Mo.), in 40% glycerol buffer with 50 mM HEPES pH 7.5 and 10 mM DTT. Compounds were diluted serially 1:3 in DMSO, incubated with the enzyme/cofactor mixture for 10 minutes and reactions were started by the addition of 2 μM RET S1 substrate (final concentration). Fluorescence increase was measured continuously over one hour using a Victor$^3$ V fluorescence plate reader (Perkin Elmer, Waltham, Mass.). Initial velocities were calculated for each inhibitor concentration using Workout 1.5 software (DAZDAQ, East Sussex, UK) with the maximal slope algorithm. Velocity data were converted into percentages relative to the untreated control (defined as 100%) and non-linear regression was performed to calculate 50% inhibitory concentrations (IC$_{50}$ values).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula 1:

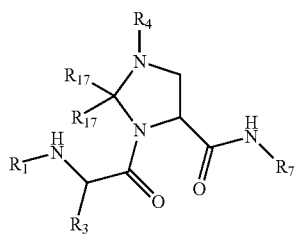

or a pharmaceutically acceptable salt thereof;
wherein:
$R_1$ is $R_2$—, $R_2$—C(O)—, $R_2$—O—C(O)— or $R_2$—N(H)—C(O)—

$R_2$ is optionally substituted $C_1$-$C_8$ alkyl, optionally substituted $C_3$-$C_{10}$ cycloalkyl, optionally substituted $C_7$-$C_{14}$ cycloalkylalkyl, optionally substituted aryl, optionally substituted arylalkyl, optionally substituted heterocycle or optionally substituted heterocyclylalkyl;

$R_3$ is optionally substituted $C_1$-$C_8$ alkyl, optionally substituted $C_3$-$C_{10}$ cycloalkyl, optionally substituted $C_7$-$C_{14}$ cycloalkylalkyl, optionally substituted heterocyclylalkyl, or optionally substituted heterocycle, or $R_3$ and $R_8$, along with the atoms that connect them, form a 12 to 18 membered saturated, partially unsaturated or unsaturated heterocycle wherein the 12 to 18 membered saturated, partially unsaturated or unsaturated heterocycle is optionally substituted with $C_1$-$C_6$ alkyl, $C_1$-$C_6$-haloalkyl, halo, oxo or cyano and wherein 0, 1, 2, or 3 carbon atoms of $R_3$ are optionally replaced by O, N, or S;

$R_4$ is $R_6$—, $R_6$—$R_5$—, $R_6$—W—, $R_6$—W—C(O)—, $R_6$—C(O)—, $R_6$—C(O)—W—, $R_6$—W—O—C(O)—, $R_6$—S(O)$_m$—, $R_6$—W—S(O)$_m$—, $R_6$—N(H)—C(O)—, $R_6$—N(H)—S(O)$_m$—, $R_6$—$R_5$—S(O)$_m$—, or $R_6$—N(H)—$R_5$—;

$R_5$ is optionally substituted arylene or optionally substituted heteroarylene;

$R_6$ is optionally substituted $C_3$-$C_{10}$ cycloalkyl, optionally substituted aryl or optionally substituted heterocycle;

m is 0, 1 or 2;

W is $C_1$-$C_4$ alkylene, $C_2$-$C_4$ alkenylene, or $C_2$-$C_4$alkynylene wherein the $C_1$-$C_4$ alkylene, $C_2$-$C_4$ alkenylene, or $C_2$-$C_4$ alkynylene is optionally substituted with $C_1$-$C_3$-alkyl, $C_1$-$C_3$-haloalkyl, cyano or halo;

$R_7$ is:

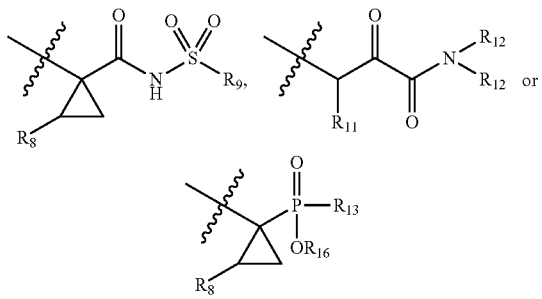

$R_8$ is $C_1$-$C_4$ alkyl, $C_2$-$C_4$ alkenyl or $C_2$-$C_4$-alkynyl wherein the $C_1$-$C_4$ alkyl, $C_2$-$C_4$ alkenyl or $C_2$-$C_4$-alkynyl is optionally substituted with halo or cyano;

$R_9$ is $R_{10}$, $R_{10}$—NH— or $R_{10}$—O—

$R_{10}$ is $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl is optionally substituted with $C_1$-$C_2$-alkyl, $C_1$-$C_2$-haloalkyl, cyano or halo;

$R_{11}$ is $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl is optionally substituted with $C_1$-$C_2$-alkyl, $C_1$-$C_2$-haloalkyl, $C_1$-$C_4$-alkylthio, cyano or halo;

each $R_{12}$ is independently H, $C_1$-$C_6$ alkyl, $C_3$-$C_7$ cycloalkyl or $C_4$-$C_9$ cycloalkylalkyl wherein the $C_1$-$C_6$ alkyl, $C_3$-$C_7$ cycloalkyl or $C_4$-$C_9$ cycloalkylalkyl is optionally substituted with $C_1$-$C_2$-alkyl, $C_1$-$C_2$-haloalkyl, cyano or halo;

$R_{13}$ is H, OH, OR$_{14}$, $C_1$-$C_4$ alkyl, $C_3$-$C_7$ cycloalkyl, $C_4$-$C_{12}$ cycloalkylalkyl, aryl, arylalkyl, heterocycle or heterocyclylalkyl wherein the $C_1$-$C_4$ alkyl, $C_3$-$C_7$ cycloalkyl, $C_4$-$C_{12}$ cycloalkylalkyl, aryl, arylalkyl, heterocycle or heterocyclylalkyl is optionally substituted with $C_1$-$C_2$-alkyl, $C_1$-$C_2$-haloalkyl cyano or halo;

$R_{14}$ is $R_{15}$—, $R_{15}$—C(O)—, $R_{15}$—O—C(O)—, or $R_{15}$O—C(O)—X—

$R_{15}$ is $C_1$-$C_6$ alkyl, $C_3$-$C_7$ cycloalkyl, $C_7$-$C_{12}$ cycloalkylalkyl, aryl, arylalkyl, heterocycle, or heterocyclylalkyl wherein the $C_1$-$C_6$ alkyl, $C_3$-$C_7$ cycloalkyl, or $C_7$-$C_{12}$ cycloalkylalkyl is optionally substituted with $C_1$-$C_2$-alkyl, $C_1$-$C_2$-haloalkyl, cyano or halo;

X is $C_1$-$C_5$ alkylene or $C_3$-$C_6$ spiroalkylene;

$R_{16}$ is H, $R_{17}$—C(O)—, $R_{17}$—O—C(O)— or $R_{17}$O—C(O)—X—;

each $R_{17}$ is independently H, $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl is optionally substituted with $C_1$-$C_2$-alkyl, $C_1$-$C_2$-haloalkyl, cyano or halo, or two $R_{17}$, along with the carbon to which they are attached, form a 3-6 membered spirocyclic carbocycle or heterocycle wherein any carbon of said carbocycle or heterocycle is optionally substituted with $C_1$-$C_2$-alkyl, $C_1$-$C_2$-haloalkyl, cyano or halo and any nitrogen of said heterocycle is optionally substituted with $C_1$-$C_2$-alkyl, $C_1$-$C_2$-haloalkyl, $C_3$-$C_5$ cycloalkyl or $C_1$-$C_3$ acyl, or, taken together, two instances of $R_{17}$ together with the carbon atom to which they are attached form a carbonyl group.

2. A compound according to claim 1 wherein $R_7$ is

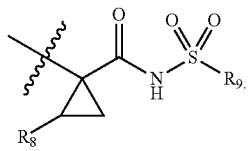

3. A compound according to claim 1 wherein $R_9$ is $R_{10}$.

4. A compound according to claim 3 wherein $R_1$ is $R_2$—O—C(O)—.

5. A compound according to claim 4 wherein $R_2$ is optionally substituted $C_1$-$C_8$ alkyl, optionally substituted $C_3$-$C_{10}$ cycloalkyl or optionally substituted $C_7$-$C_{14}$ cycloalkylalkyl.

6. A compound according to claim 1 wherein each $R_{17}$ is independently H or substituted alkyl.

7. A compound of claim 1 wherein $R_4$ is

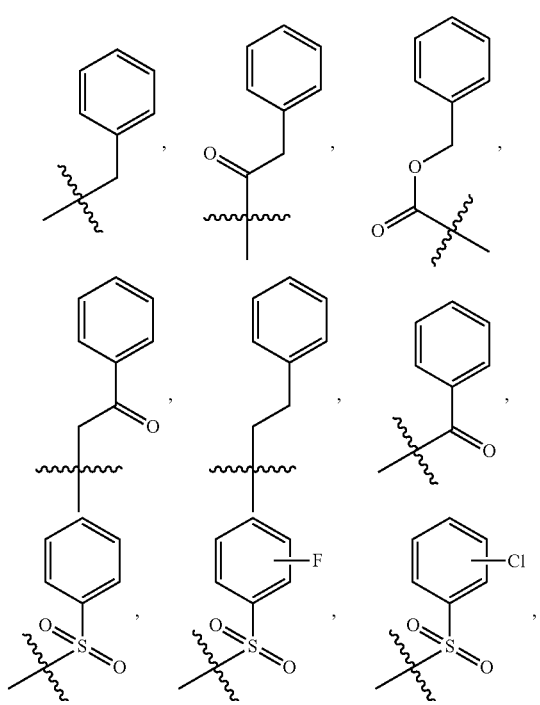

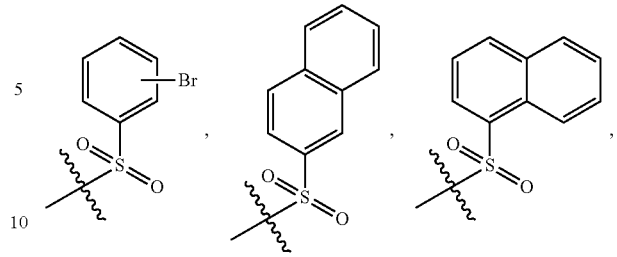

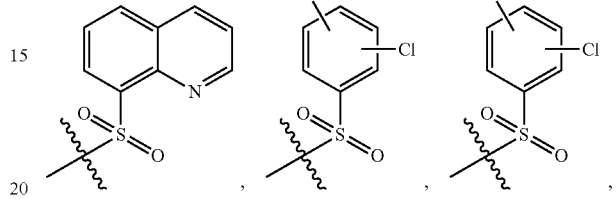

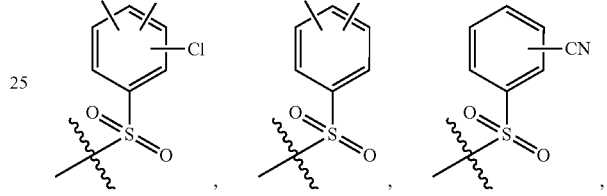

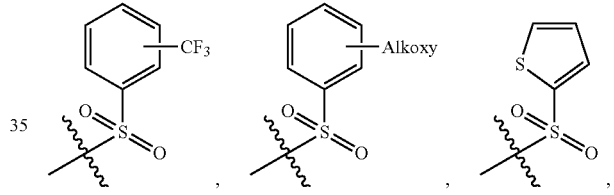

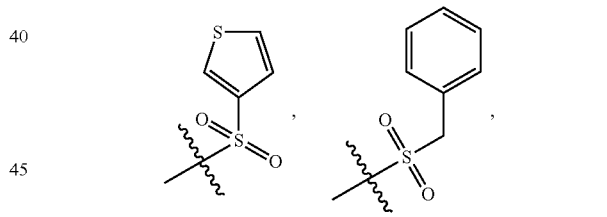

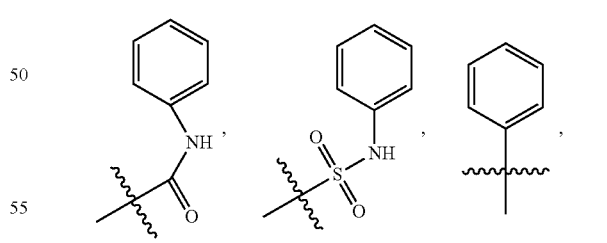

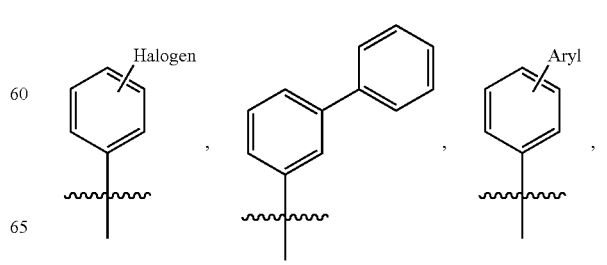

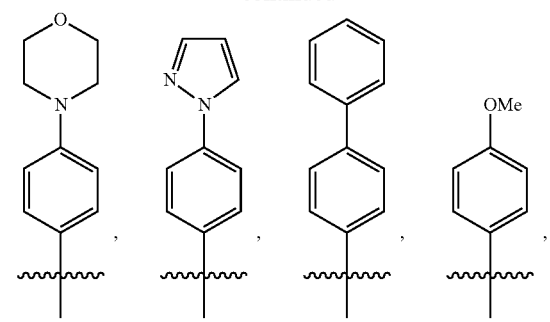
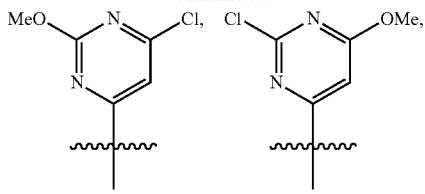
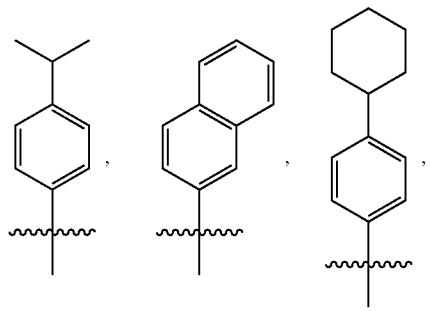
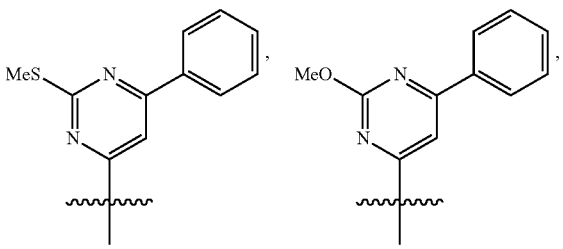
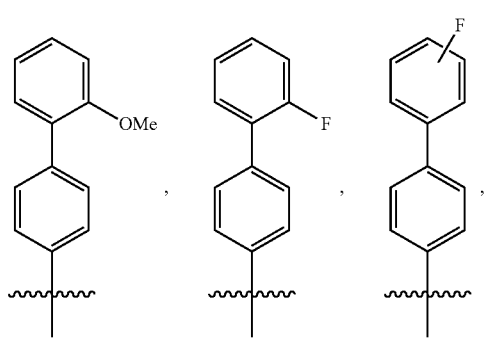
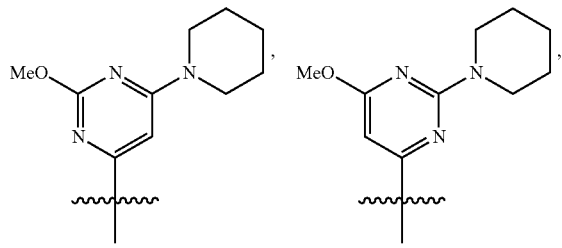
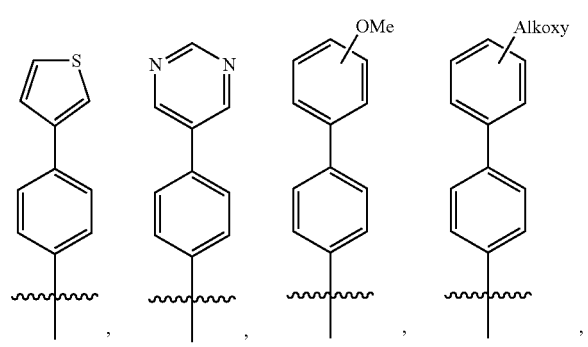
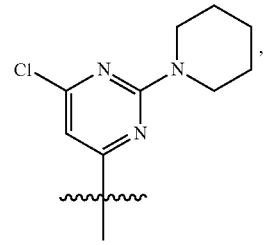
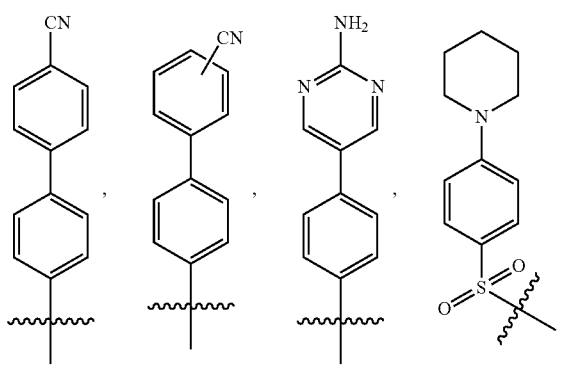
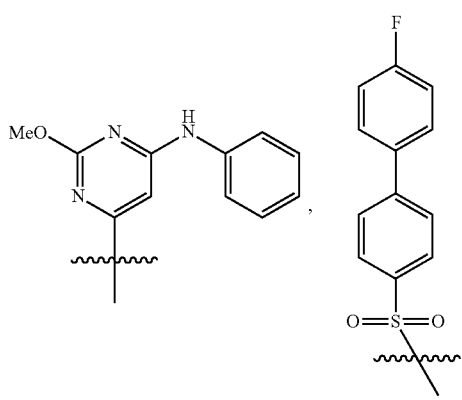
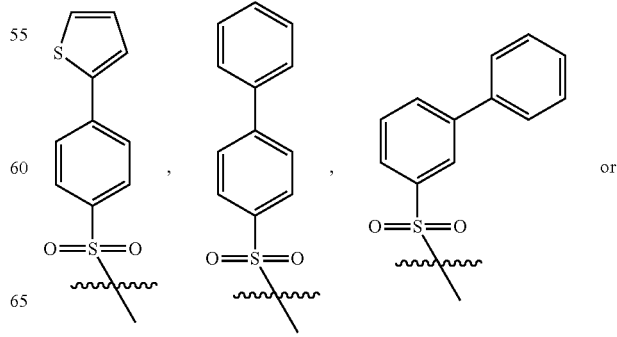

-continued

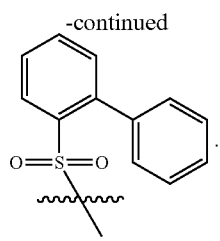

8. A compound according to claim 2 wherein $R_1$ is cyclopentyloxycarbonyl, t-butyloxycarbonyl, or 2,2,2-trifluoro-1,1-dimethylethyloxycarbonyl.

9. A compound according to claim 2 wherein $R_2$ is cyclopentyl, t-butyl or 2,2,2-trifluoro-1,1-dimethylethyl.

10. A compound according to claim 2 wherein $R_3$ is t-butyl.

11. A compound according to claim 2 wherein $R_3$ and $R_8$ together form

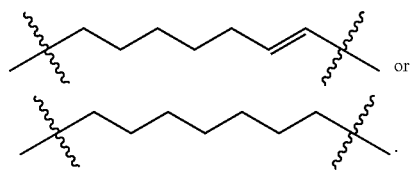 [SMILES: */C=C/CCCCC* ; *CCCCCCC*]

12. A compound according to claim 2 wherein $R_4$ is $R_6$-alkylene-, $R_6$-alkylene-C(O)—, $R_6$—C(O)-alkylene-, $R_6$—C(O)—, $R_6$—S(O)$_2$—, $R_6$-alkylene-S(O)$_2$—, $R_6$—NH—C(O)—, $R_6$—NH—S(O)$_2$—, $R_6$—, $R_6$—$R_5$—, $R_6$—$R_5$—S(O)$_2$—, or $R_6$—NH—$R_5$—.

13. A compound according to claim 2 wherein $R_5$ is

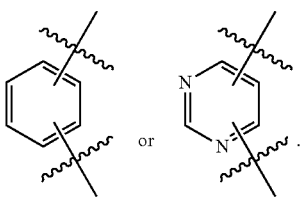

14. A compound according to claim 2 wherein $R_6$ is

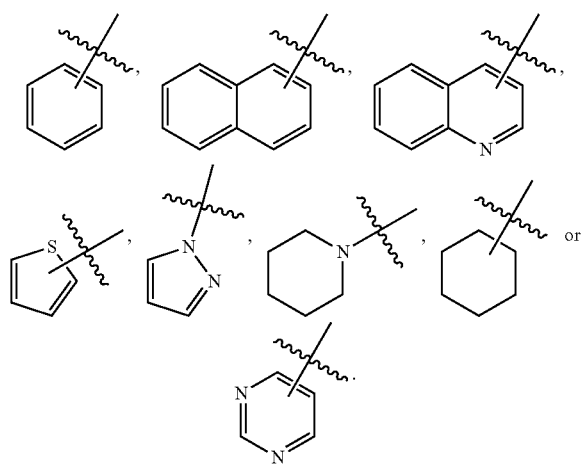

15. A compound according to claim 1 wherein $R_7$ is

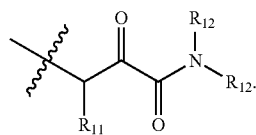

16. A compound according to claim 1 wherein $R_7$ is

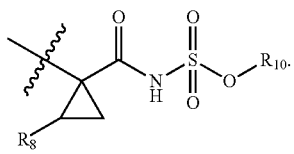

17. A compound according to claim 1 wherein $R_7$ is

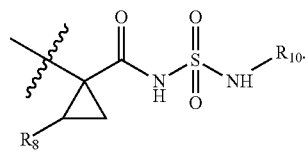

18. A compound according to claim 1 wherein $R_7$ is

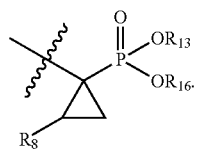

19. A compound according to claim 2 wherein $R_8$ is ethyl or ethylene.

20. A compound according to claim 2 wherein $R_9$ is $R_{10}$.

21. A compound according to claim 2 wherein $R_{10}$ is cyclopropyl or 1-methylcyclopropyl.

22. A compound according to claim 15 wherein $R_{11}$ is cyclobutylmethyl or n-propyl.

23. A compound according to claim 15 wherein each $R_{12}$ is independently H or cyclopropyl.

24. A compound according to claim 18 wherein $R_{13}$ is alkyl, optionally substituted alkyl, optionally substituted arylalkyl or optionally substituted heterocyclylalkyl.

25. A compound according to claim 24 wherein $R_{16}$ is H, $R_{17}$—C(O)—, $R_{17}$—O—C(O)— or $R_{17}$—O—C(O)—X—.

26. A compound according to claim 25 wherein $R_{17}$ is alkyl, optionally substituted alkyl, optionally substituted aryl, optionally substituted heterocycle, optionally substituted arylalkyl or optionally substituted heterocyclylalkyl.

27. A compound selected from the group consisting of
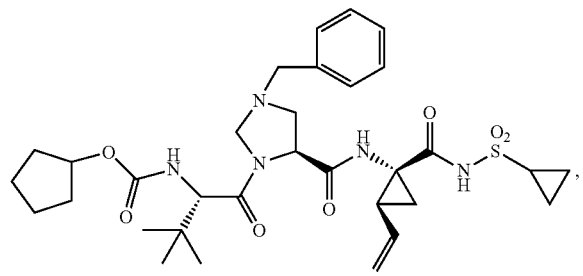
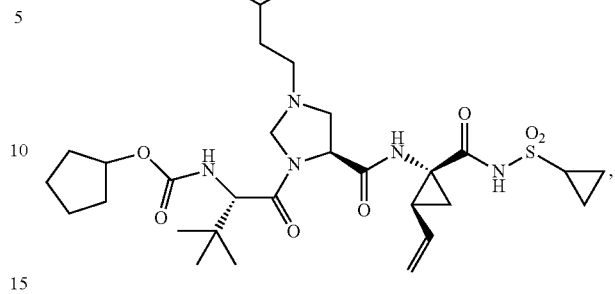
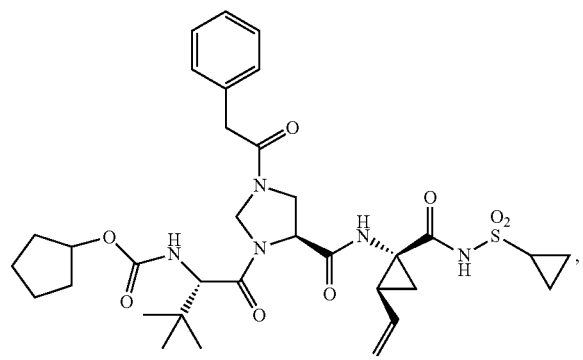
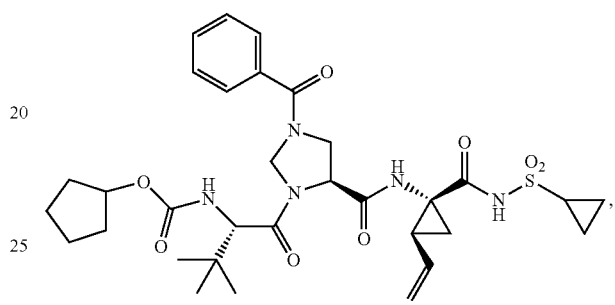
-continued
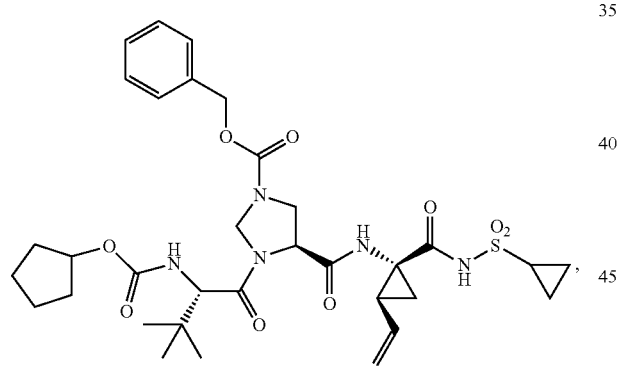
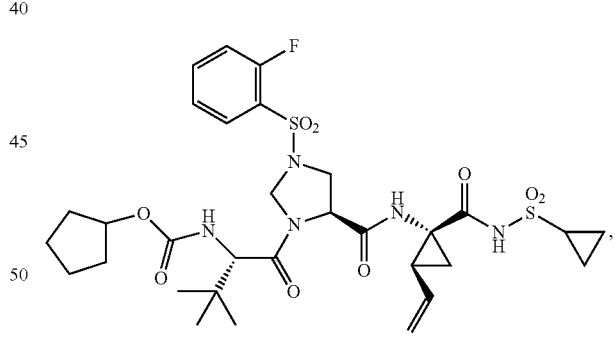
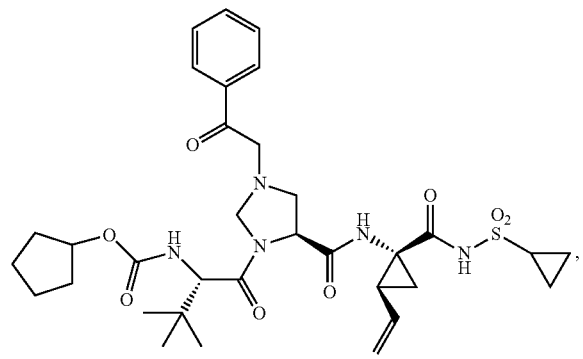
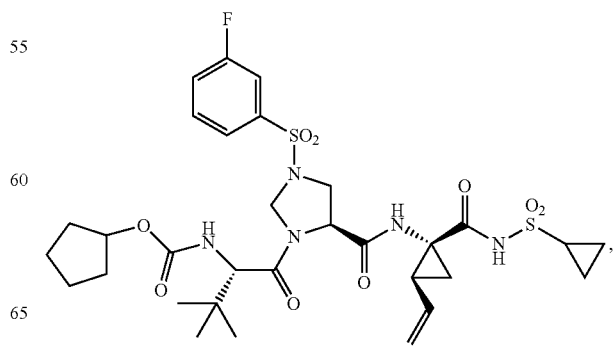

171
-continued
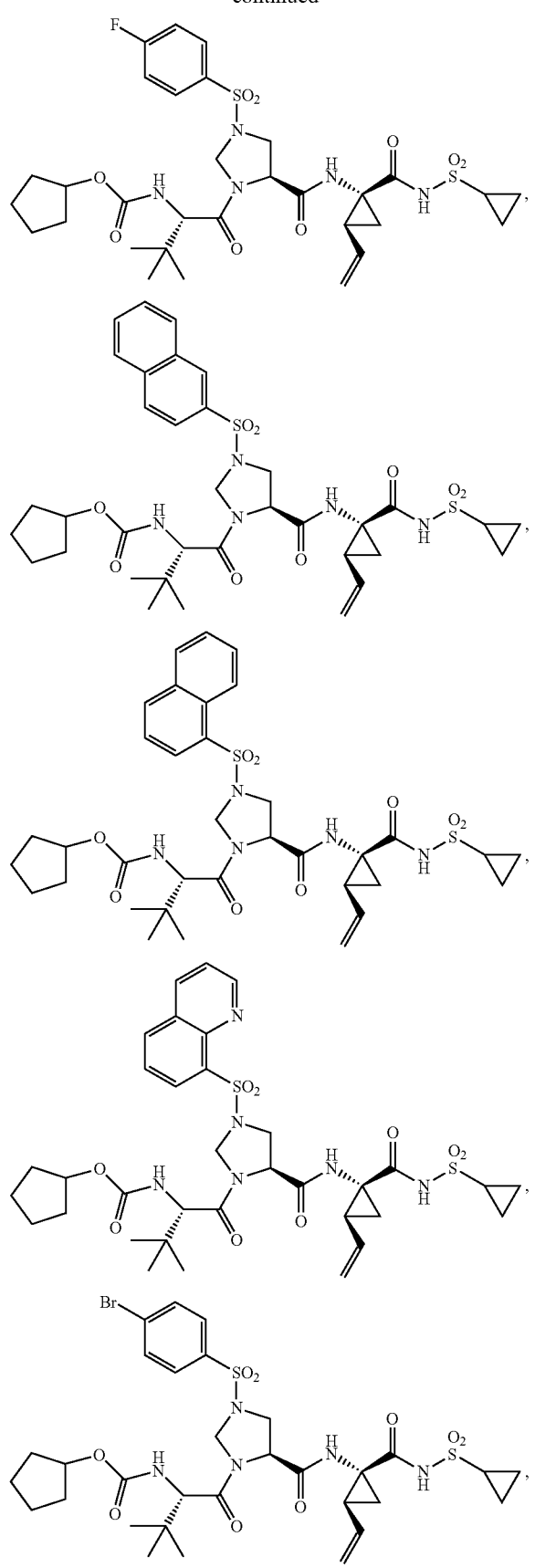
172
-continued
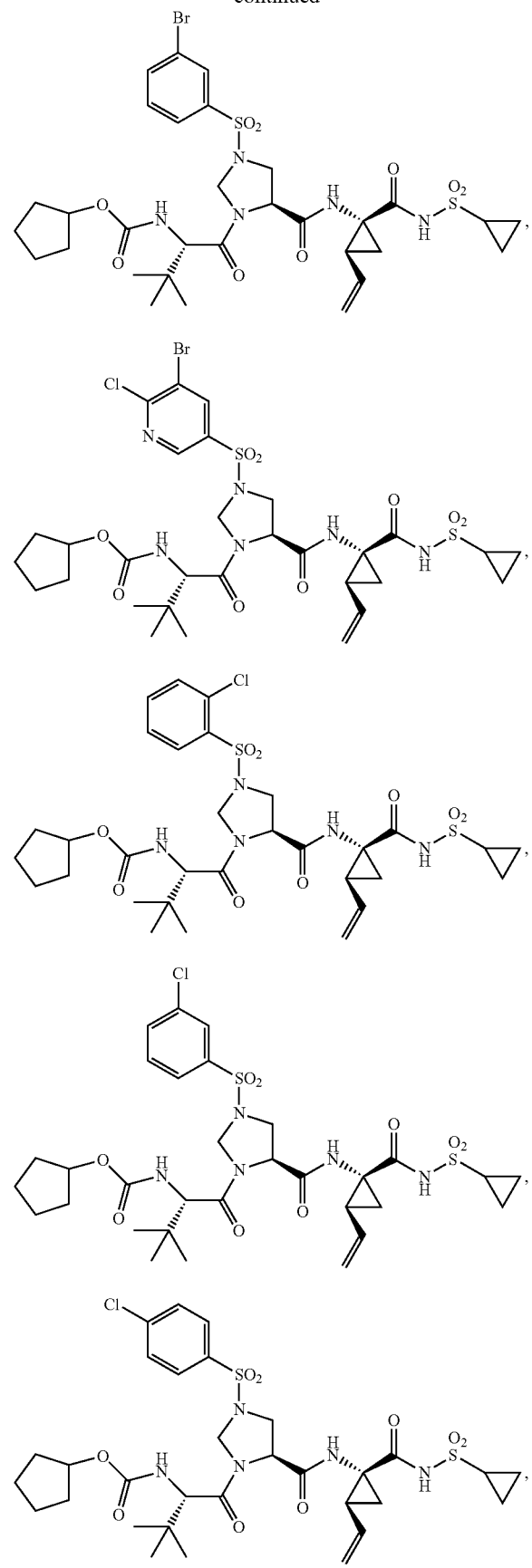

173
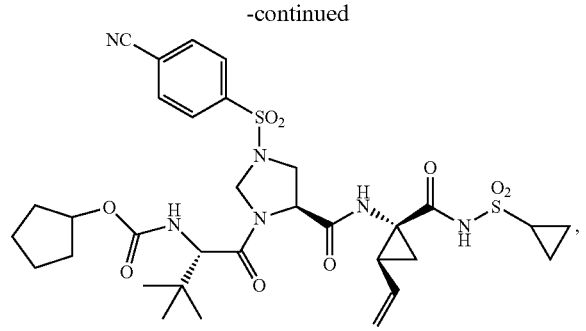
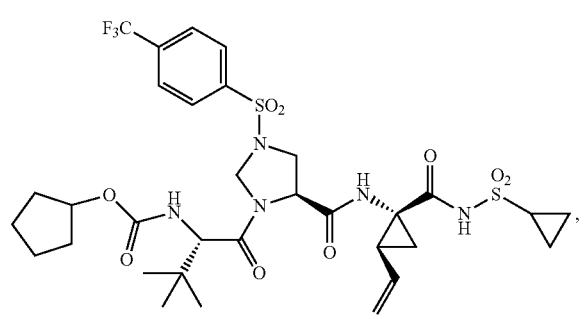
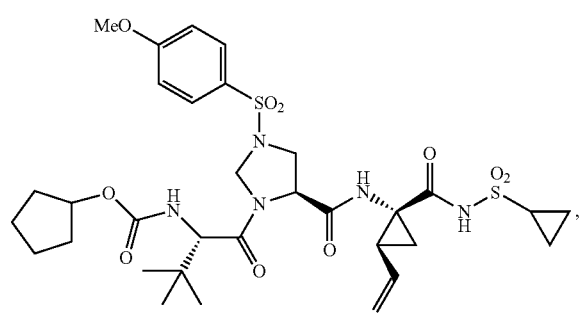
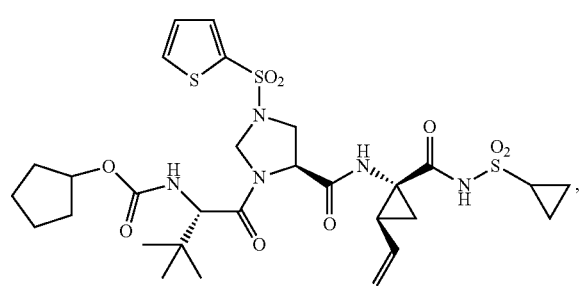
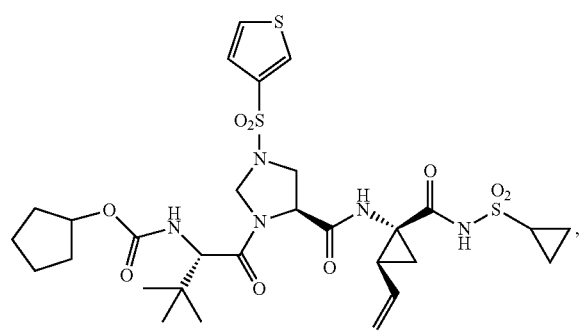
174
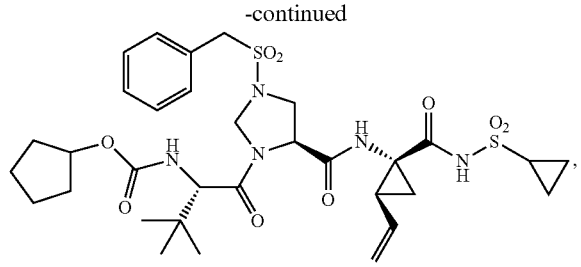
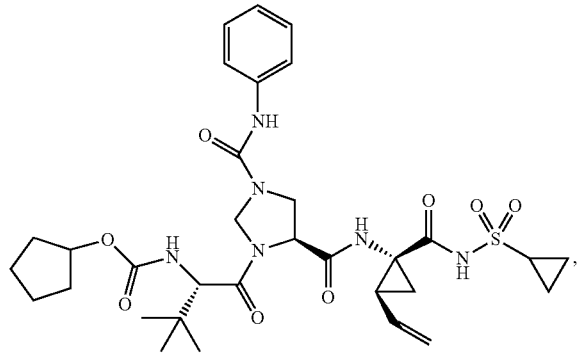
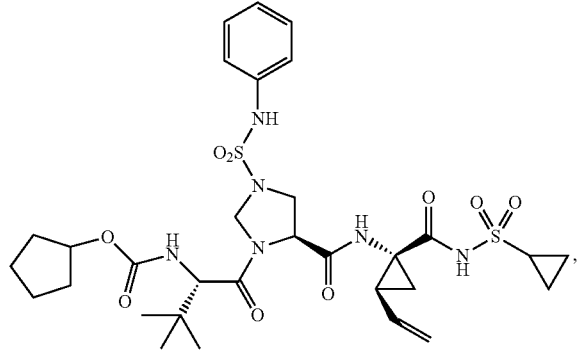
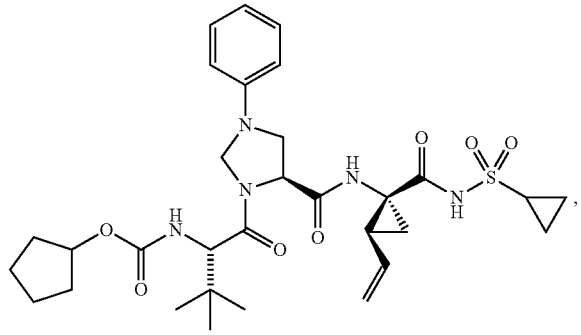
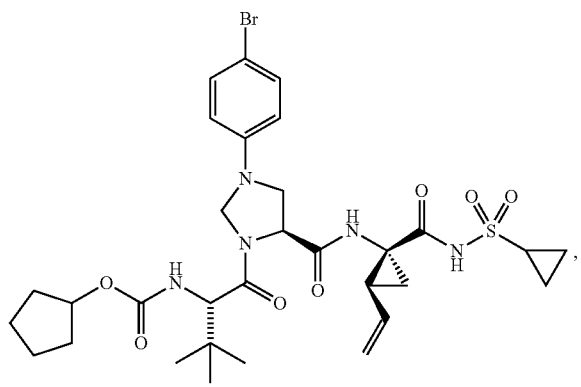

175
-continued
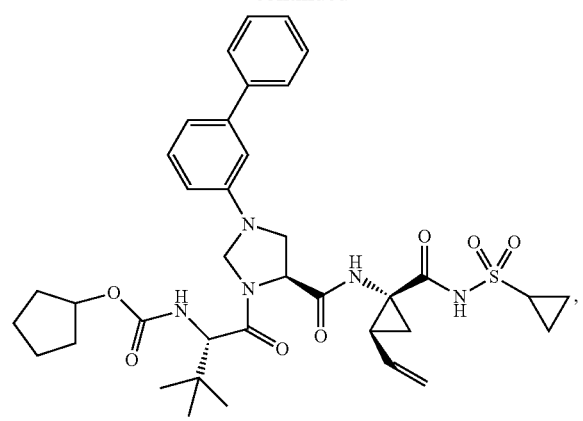
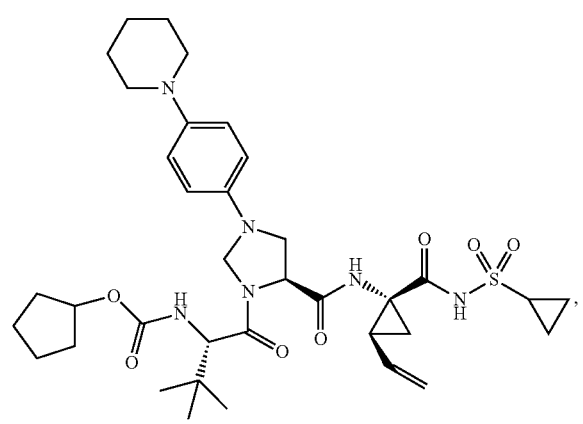
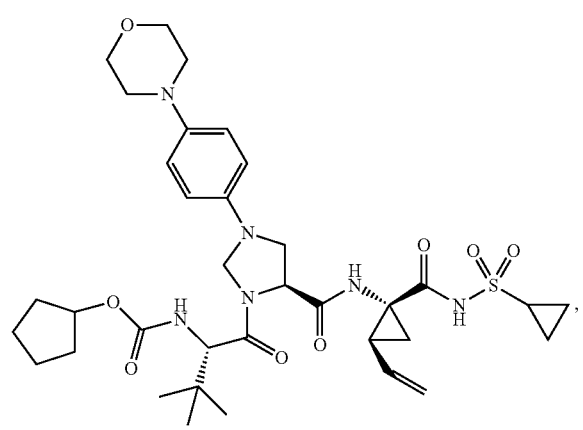
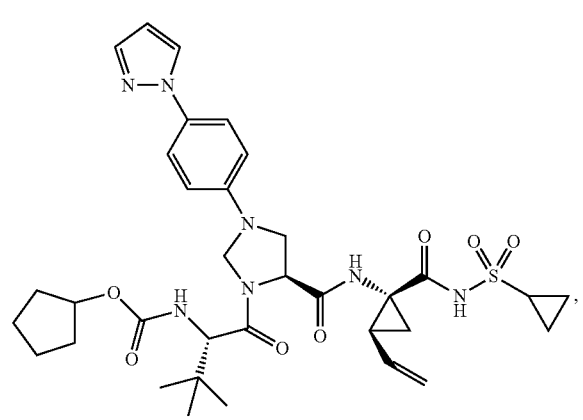
176
-continued
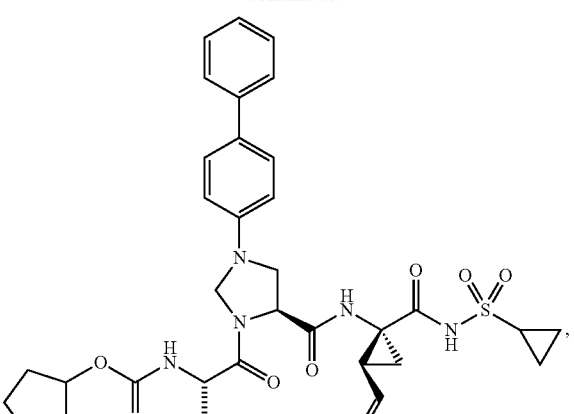
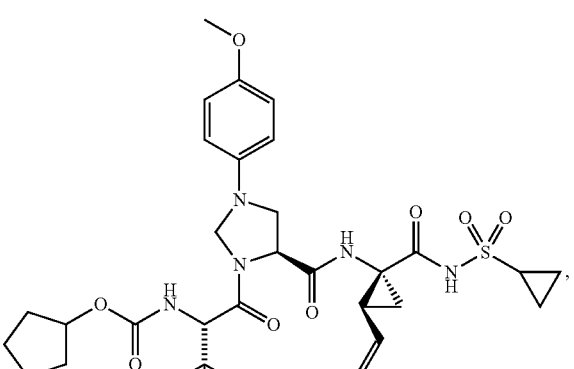
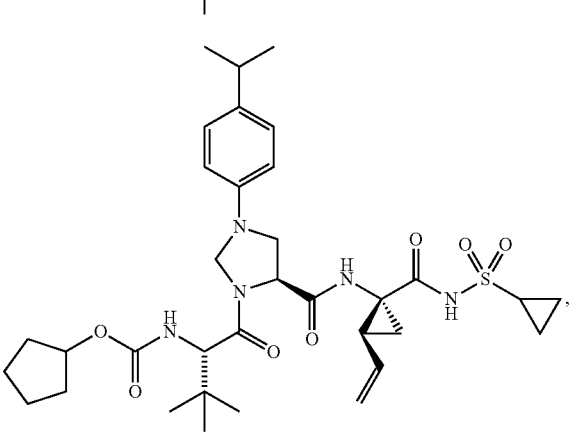
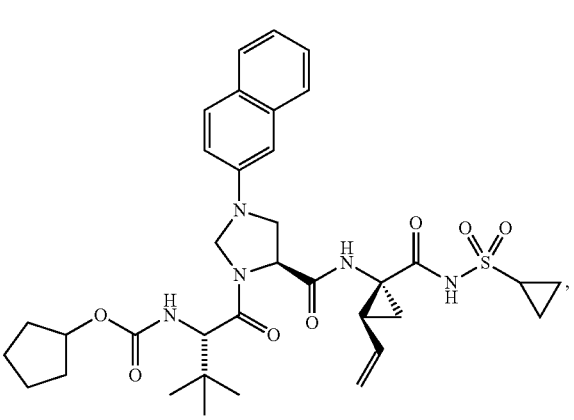

177
-continued
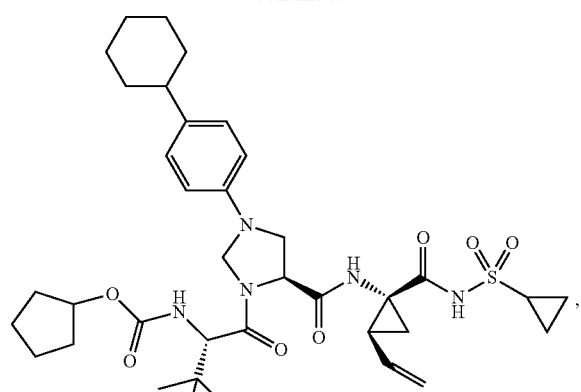
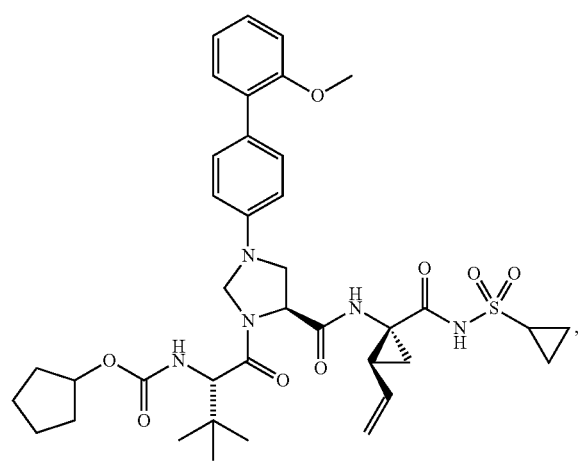
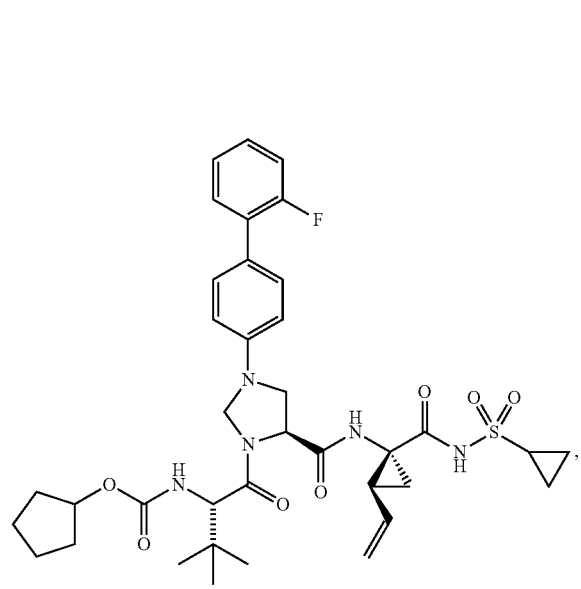
178
-continued
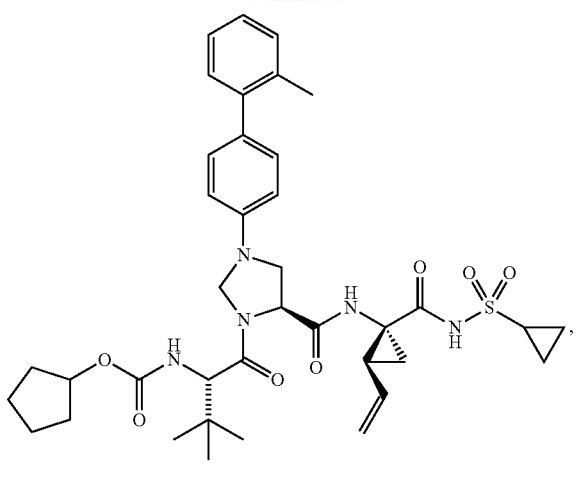
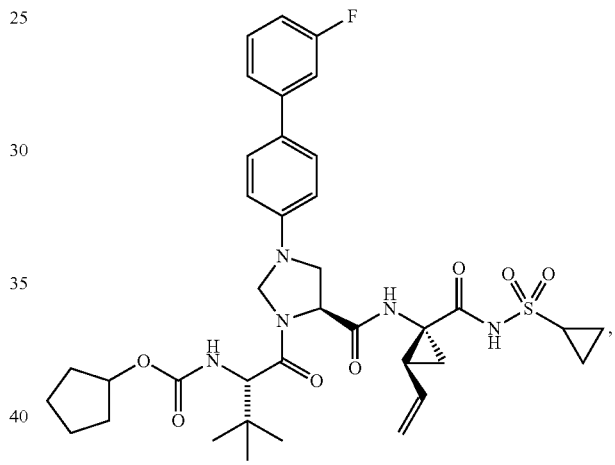
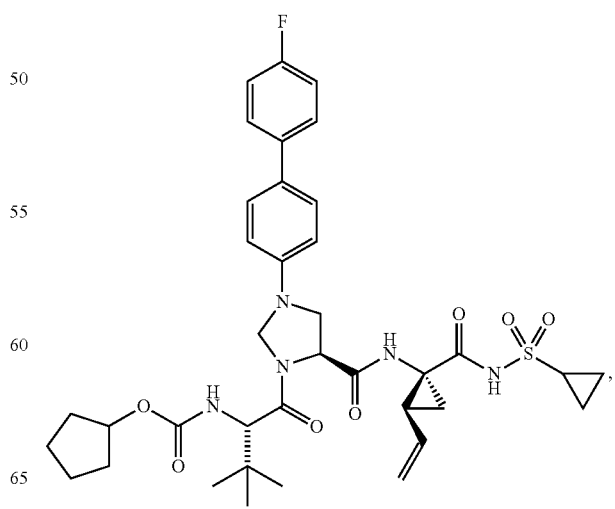

179
-continued
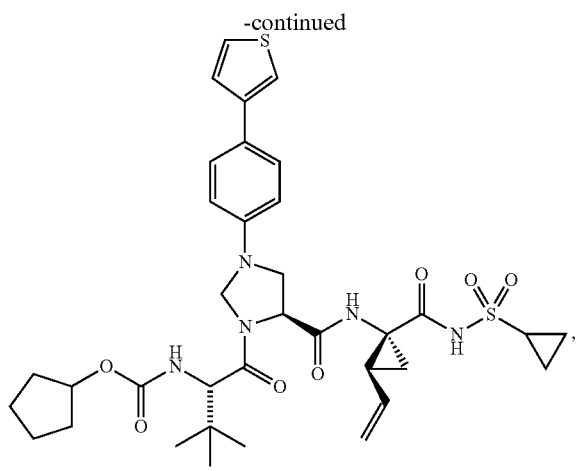
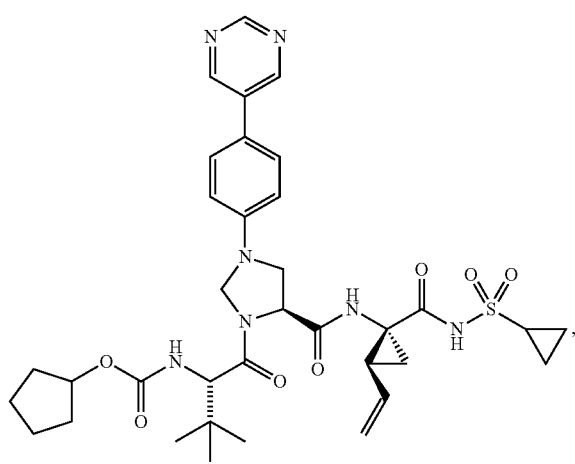
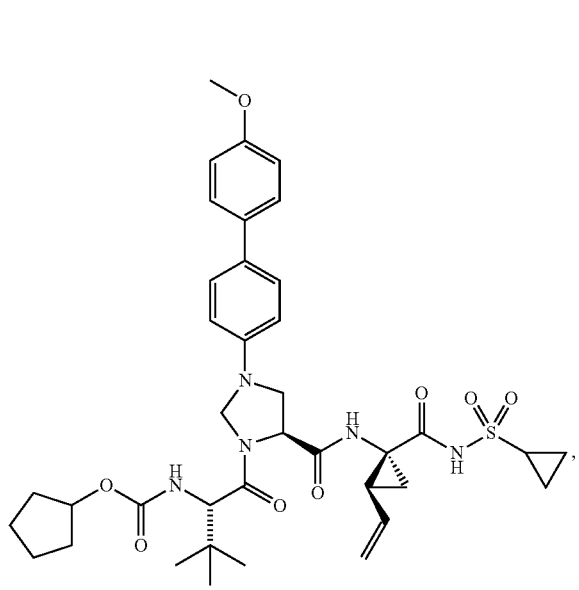
180
-continued
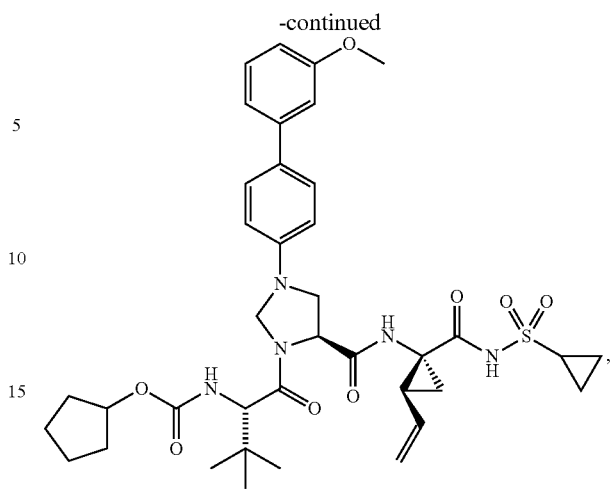
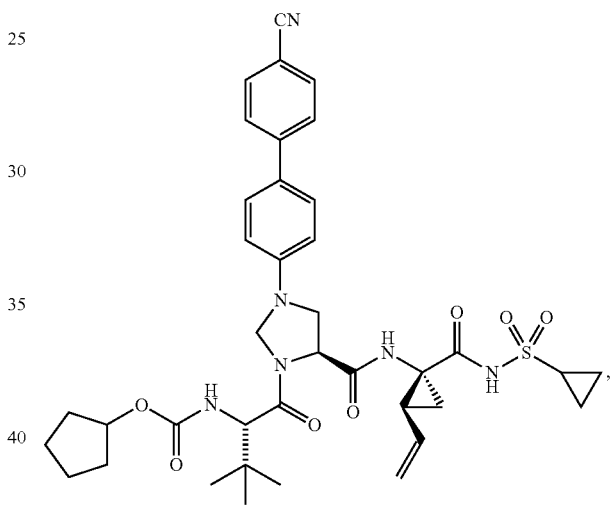
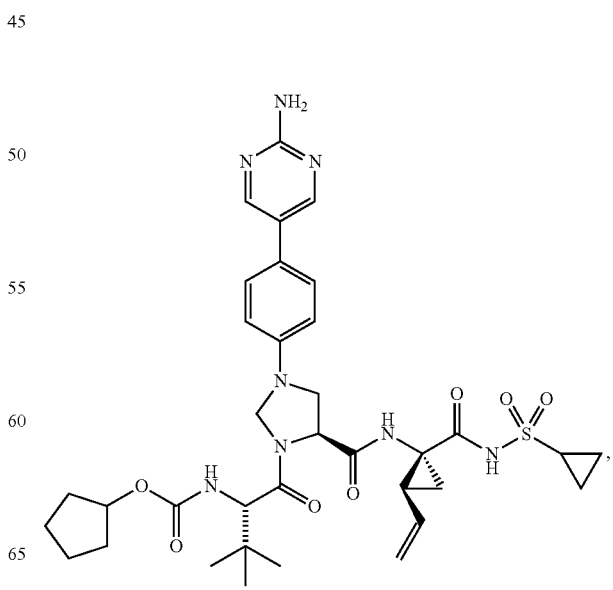

181
-continued
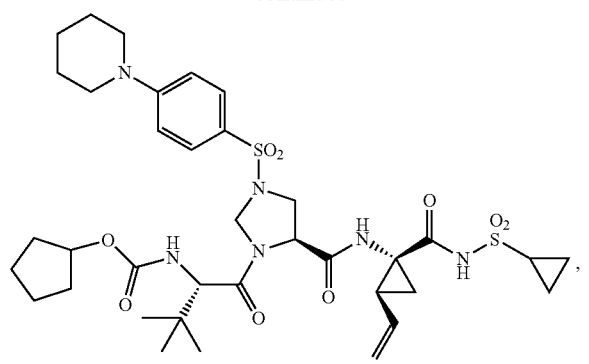
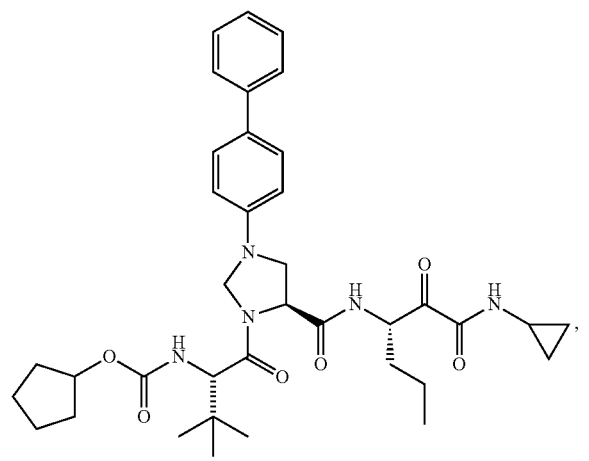
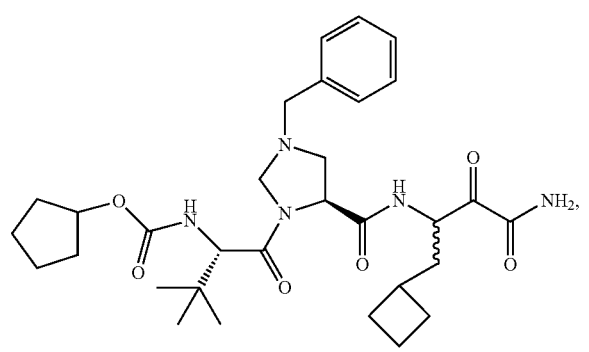
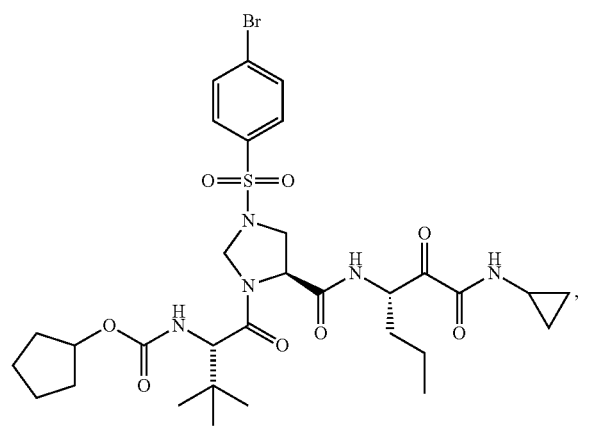
182
-continued
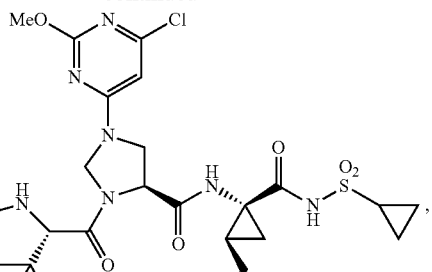
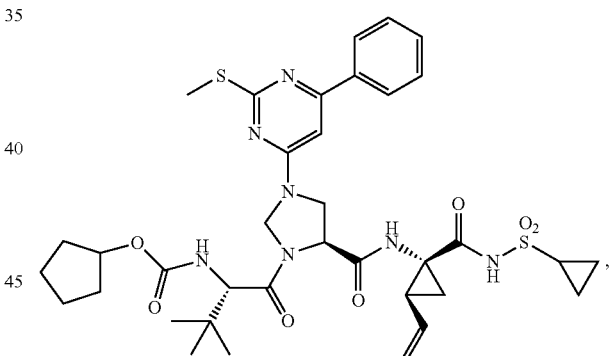
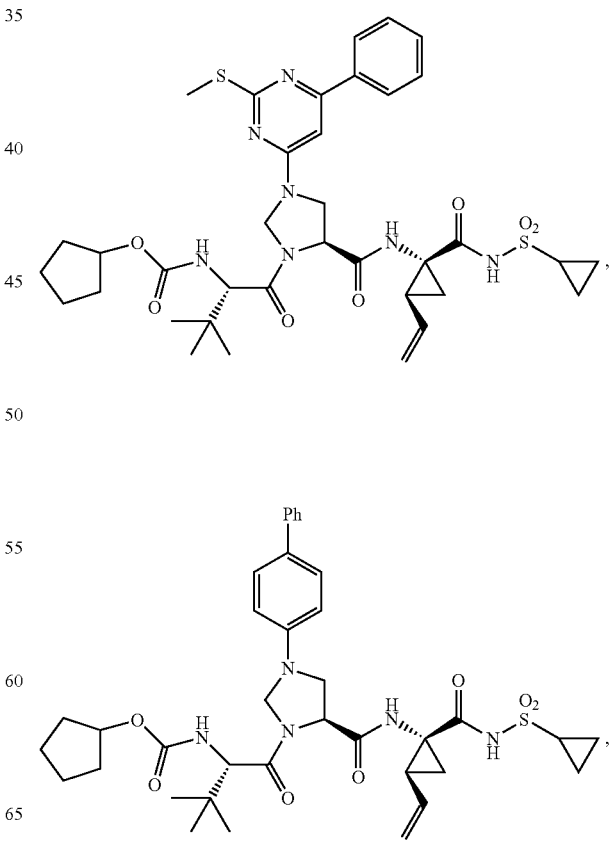

183
-continued
184
-continued
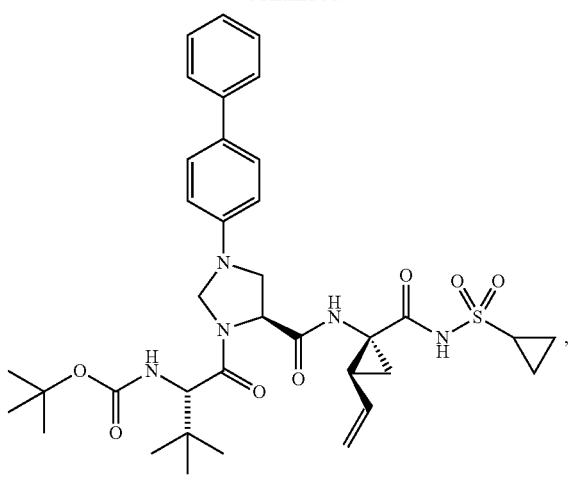
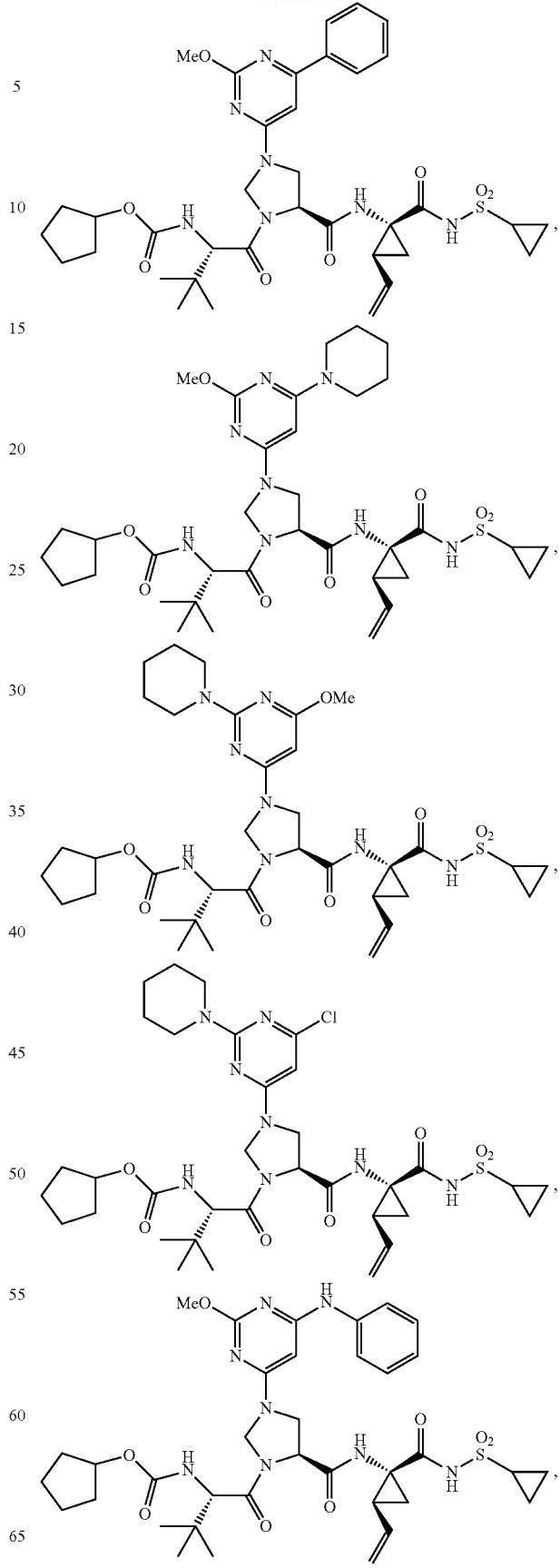

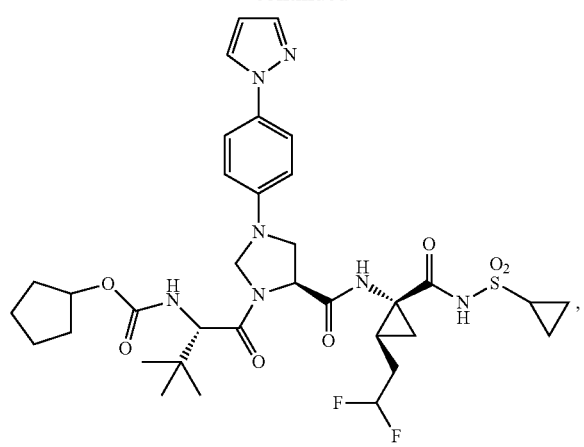

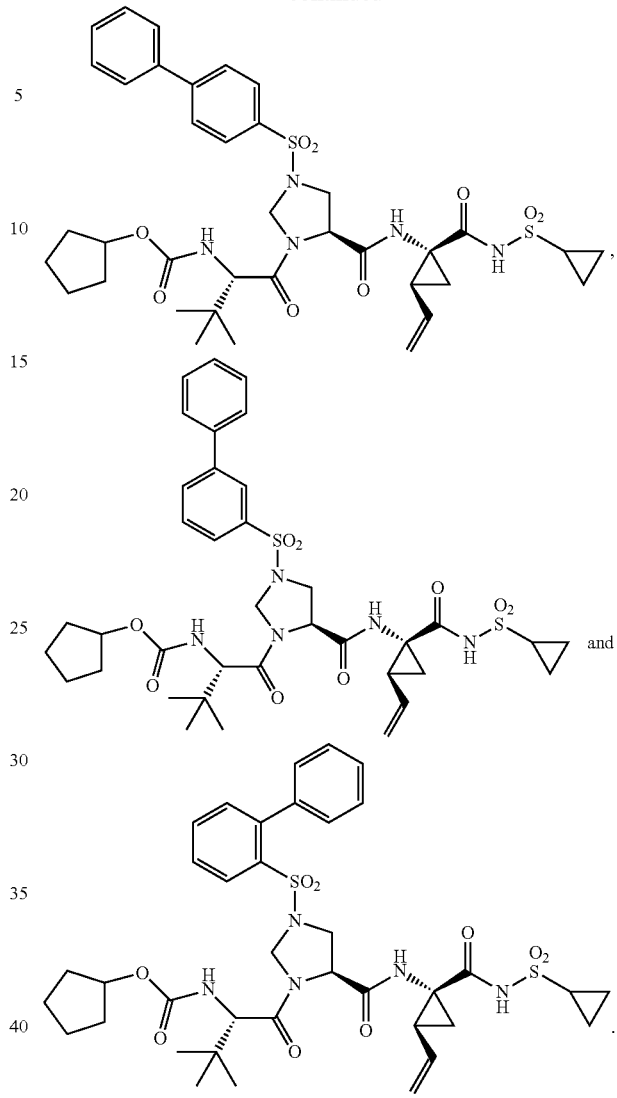

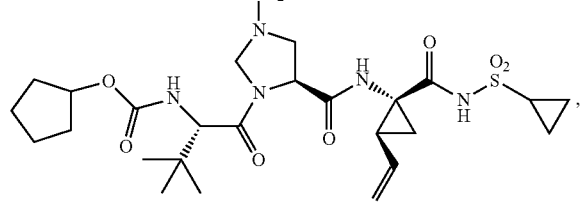

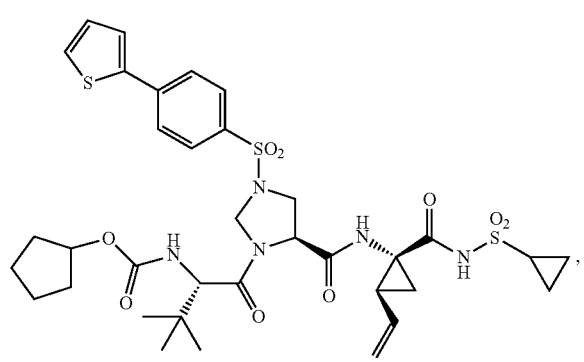

28. A pharmaceutical composition comprising the compound of claim 1 or a pharmaceutically acceptable salt thereof and at least one pharmaceutically acceptable carrier.

29. The pharmaceutical composition of claim 28, further comprising at least one additional therapeutic agent.

30. The pharmaceutical composition of claim 29, wherein said additional therapeutic agent is selected from the group consisting of interferons, ribavirin analogs, NS5a inhibitors, NS4b inhibitors, NS3 protease inhibitors, NS5b polymerase inhibitors, alpha-glucosidase 1 inhibitors, hepatoprotectants, and non-nucleoside inhibitors of HCV.

31. The pharmaceutical composition of claim 29, further comprising at least one additional therapeutic agent selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon.

32. The pharmaceutical composition of claim 28, further comprising at least one additional therapeutic agent selected from the group consisting of ribavirin (Rebetol, Copegus), and taribavirin (Viramidine).

33. The pharmaceutical composition of claim 29, further comprising at least one additional therapeutic agent selected from the group consisting of boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227).

34. The pharmaceutical composition of claim 29, further comprising at least one additional therapeutic agent selected from the group consisting of celgosivir (MX-3253), Miglitol, and UT-231B.

35. The pharmaceutical composition of claim 29, further comprising at least one additional therapeutic agent selected from the group consisting of emericasan (IDN-6556), ME-3738, GS-9450 (LB-84451), silibilin, and MitoQ, 6) nucleoside or nucleotide inhibitors of HCV NS5B polymerase, R1626, R7128 (R4048), IDX184, IDX-102, PSI-7851, BCX-4678, valopicitabine (NM-283), and MK-0608.

36. The pharmaceutical composition of claim 29, further comprising at least one additional therapeutic agent selected from the group consisting of filibuvir (PF-868554), ABT-333, ABT-072, BI-207127, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190.

37. The pharmaceutical composition of claim 29, further comprising at least one additional therapeutic agent selected from the group consisting of AZD-2836 (A-831), AZD-7295 (A-689), and BMS-790052.

38. The pharmaceutical composition of claim 29, further comprising at least one additional therapeutic agent selected from the group consisting of imiquimod, 852A, GS-9524, ANA-773, ANA-975, AZD-8848 (DSP-3025), PF-04878691, and SM-360320, cyclophillin inhibitors, e.g., DEBIO-025, SCY-635, and NIM811 and HCV IRES inhibitors, e.g., MCI-067.

39. The pharmaceutical composition of claim 29, further comprising at least one additional therapeutic agent selected from the group consisting of BAS-100, SPI-452, PF-4194477, TMC-41629, GS-9350, GS-9585, and roxythromycin.

40. The pharmaceutical composition of claim 29, further comprising at least one additional therapeutic agent selected from the group consisting of thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib).

41. The pharmaceutical composition according to claim 29, further comprising a nucleoside analogue.

42. The pharmaceutical composition according to claim 41, further comprising an interferon or pegylated interferon.

43. The pharmaceutical composition according to claim 42, wherein said nucleoside analogue is selected from ribavirin, viramidine, levovirin, a L-nucleoside, and isatoribine and wherein said interferon is α-interferon or pegylated interferon.

44. A method of treating HCV infection, said method comprising administering to an individual a pharmaceutical composition which comprises a therapeutically effective amount of a compound of claim 1 or a pharmaceutically acceptable salt thereof.

45. A compound of formula 1:

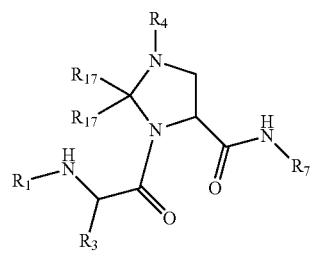

or a pharmaceutically acceptable salt thereof;

wherein:

$R_1$ is $R_2$—O—C(O)—;

$R_2$ is $C_1$-$C_8$ alkyl, $C_3$-$C_{10}$ cycloalkyl or $C_7$-$C_{14}$cycloalkylalkyl, wherein each $C_1$-$C_8$ alkyl, $C_3$-$C_{10}$ cycloalkyl and $C_7$-$C_{14}$ cycloalkylalkyl is optionally substituted with one or more F, Cl, Br, or I;

$R_3$ is t-butyl; or $R_3$ and $R_8$ together form:

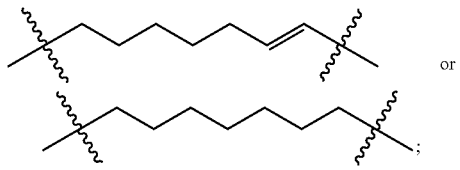

$R_4$ is $R_6$—, $R_6$—$R_5$—, $R_6$—W—, $R_6$—W—C(O)—, $R_6$—C(O)—, $R_6$—C(O)—W—, $R_6$—W—O—C(O)—, $R_6$—S(O)$_m$—, $R_6$—W—S(O)$_m$—, $R_6$—N(H)—C(O)—, $R_6$—N(H)—S(O)$_m$—, $R_6$—$R_5$—S(O)$_m$—, or $R_6$—N(H)—$R_5$—;

$R_5$ is optionally substituted arylene or optionally substituted heteroarylene, wherein said arylene or heteroarylene is optionally substituted with one or more alkyl, alkoxy, haloalkyl, cycloalkyl, cycloalkylalkyl, arylalkyl, heterocyclylalkyl, aryl, heterocycle, halogen, cyano, azido, amino, nitro, sulfonamide, alkylsulfonyl, or carboxamido;

$R_6$ is $C_3$-$C_{10}$ cycloalkyl, aryl or heterocycle, wherein said $C_3$-$C_{10}$ cycloalkyl, aryl or heterocycle is optionally substituted with one or more alkyl, alkoxy, haloalkyl, cycloalkyl, cycloalkylalkyl, arylalkyl, heterocyclylalkyl, aryl, heterocycle, halogen, cyano, azido, amino, nitro, sulfonamide, alkylsulfonyl, and carboxamido;

m is 0, 1 or 2;

W is $C_1$-$C_4$ alkylene, $C_2$-$C_4$ alkenylene, or $C_2$-$C_4$ alkynylene wherein the $C_1$-$C_4$ alkylene, $C_2$-$C_4$ alkenylene, or $C_2$-$C_4$ alkynylene is optionally substituted with $C_1$-$C_3$-alkyl, $C_1$-$C_3$-haloalkyl, cyano or halogen;

$R_7$ is:

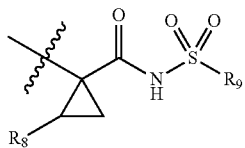

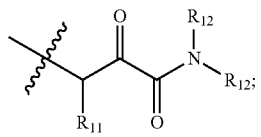

$R_8$ is $C_1$-$C_4$ alkyl, $C_2$-$C_4$ alkenyl or $C_2$-$C_4$-alkynyl wherein the $C_1$-$C_4$ alkyl, $C_2$-$C_4$ alkenyl or $C_2$-$C_4$-alkynyl is optionally substituted with halogen or cyano;

$R_9$ is $R_{10}$;

$R_{10}$ is $C_1$-$C_4$ alkyl, $C_3$-$C_7$ cycloalkyl or $C_4$-$C_9$ cycloalkylalkyl wherein the $C_1$-$C_4$ alkyl, $C_3$-$C_7$ cycloalkyl or $C_4$-$C_9$ cycloalkylalkyl is optionally substituted with $C_1$-$C_2$-alkyl, $C_1$-$C_2$-haloalkyl, cyano or halogen;

$R_{11}$ is cyclobutylmethyl or n-propyl;

each $R_{12}$ is independently H or cyclopropyl; and each $R_{17}$ is independently H or $C_1$-$C_4$ alkyl.

* * * * *